United States Patent
Wang et al.

(10) Patent No.: US 9,266,877 B2
(45) Date of Patent: *Feb. 23, 2016

(54) APOPTOSIS-INDUCING AGENTS FOR THE TREATMENT OF CANCER AND IMMUNE AND AUTOIMMUNE DISEASES

(71) Applicant: AbbVie Inc., North Chicago, IL (US)

(72) Inventors: Le Wang, Vernon Hills, IL (US); George Doherty, Libertyville, IL (US); Xilu Wang, Libertyville, IL (US); Zhi-Fu Tao, Gurnee, IL (US); Milan Bruncko, Green Oaks, IL (US); Aaron R. Kunzer, Arlington Heights, IL (US); Michael D. Wendt, Vernon Hills, IL (US); Xiaohong Song, Grayslake, IL (US); Robin Frey, Libertyville, IL (US); Todd M. Hansen, Grayslake, IL (US); Gerard M. Sullivan, Lake Villa, IL (US); Andrew Judd, Grayslake, IL (US); Andrew Souers, Evanston, IL (US)

(73) Assignee: ABBVIE INC., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/559,828

(22) Filed: Dec. 3, 2014

(65) Prior Publication Data

US 2015/0152097 A1 Jun. 4, 2015

Related U.S. Application Data

(63) Continuation of application No. 13/649,950, filed on Oct. 11, 2012, now Pat. No. 8,940,737.

(60) Provisional application No. 61/547,165, filed on Oct. 14, 2011.

(51) Int. Cl.
| | | |
|---|---|---|
| C07D 417/14 | (2006.01) | |
| A61K 31/4725 | (2006.01) | |
| A61K 31/5377 | (2006.01) | |
| A61K 45/06 | (2006.01) | |

(52) U.S. Cl.
CPC .......... *C07D 417/14* (2013.01); *A61K 31/4725* (2013.01); *A61K 31/5377* (2013.01); *A61K 45/06* (2013.01)

(58) Field of Classification Search
CPC ............. C07D 417/14; A61K 31/4725; A61K 31/5377; A61K 45/06
See application file for complete search history.

(56) References Cited

U.S. PATENT DOCUMENTS

| | | |
|---|---|---|
| 4,107,167 A | 8/1978 | Lorenz et al. |
| 6,699,857 B1 | 3/2004 | Stoltefuss et al. |
| 7,981,888 B2 | 7/2011 | Song et al. |
| 8,114,893 B2 | 2/2012 | Baell et al. |
| 8,232,273 B2 | 7/2012 | Baell et al. |
| 8,518,970 B2 | 8/2013 | Baell et al. |
| 8,883,784 B2 | 11/2014 | Judd et al. |
| 8,889,675 B2 | 11/2014 | Wang et al. |
| 9,067,928 B2 | 6/2015 | Baell et al. |
| 2004/0077643 A1 | 4/2004 | Ogawa et al. |
| 2005/0124614 A1 | 6/2005 | Gangloff et al. |
| 2007/0054892 A1 | 3/2007 | Isaacs et al. |
| 2014/0005190 A1 | 1/2014 | Baell et al. |

FOREIGN PATENT DOCUMENTS

| | | |
|---|---|---|
| WO | 2009039553 | 4/2009 |
| WO | 2010080478 A1 | 7/2010 |
| WO | 2010080503 A1 | 7/2010 |

OTHER PUBLICATIONS

Almerico, Anna Maria, et al., "In-silica screening of new potential Bcl-2/Bcl-xl inhibitors as apoptosis modulators," Journal of Molecular modeling, (2009), pp. 349-355, vol. 15, No. 4.

Barelier, Sarah, et al., "Fragment-based deconstruction of Bcl-xl inhibitors," Journal of Medicinal Chemistry, (201 0), pp. 2577-2588, vol. 53, No. 6.

Hunter, Allison, M., et al., "The inhibitors of apoptosis (IAPs) as cancer targets," Apoptosis, An International Journal on Programmed Cell Death, (Jun. 19, 2007), pp. 1543-1568, vol. 12, Issue 9.

International Searching Authority, "International Search Report and Written Opinion for International Application No. PCT/US2012/059717," (Dec. 4, 2012) 12 pages.

Juin, P. et al, Biochimica et Biophysica Acta; "Shooting at Survivors: Bcl-2 Family Members as Drug Targets for Cancer"; (2004), pp. 251-260, vol. 1644.

*Primary Examiner* — Wu-Cheng Winston Shen
*Assistant Examiner* — Jean Cornet
(74) *Attorney, Agent, or Firm* — Jones Day

(57) ABSTRACT

Disclosed are compounds which inhibit the activity of anti-apoptotic Bcl-xL proteins, compositions containing the compounds and methods of treating diseases during which is expressed anti-apoptotic Bcl-xL protein.

2 Claims, No Drawings

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: F-Bak Probe Peptide
<220> FEATURE:
<221> NAME/KEY: MOD_RES
<222> LOCATION: 1
<223> OTHER INFORMATION: Gly is modified with acetyl
<220> FEATURE:
<221> NAME/KEY: MOD_RES
<222> LOCATION: 13
<223> OTHER INFORMATION: Lys is modified with 6-FAM
<220> FEATURE:
<221> NAME/KEY: MOD_RES
<222> LOCATION: 16
<223> OTHER INFORMATION: Arg is modified with NH2

<400> SEQUENCE: 1

Gly Gln Val Gly Arg Gln Leu Ala Ile Ile Gly Asp Lys Ile Asn Arg
 1               5                  10                  15
```

APOPTOSIS-INDUCING AGENTS FOR THE TREATMENT OF CANCER AND IMMUNE AND AUTOIMMUNE DISEASES

CROSS-REFERENCE TO RELATED APPLICATION

This application is a continuation of U.S. application Ser. No. 13/649,950, filed Oct. 11, 2012, which claims priority to U.S. Provisional Application No. 61/547,165, filed Oct. 14, 2011, each of which are incorporated by reference in its entirety.

FIELD OF THE INVENTION

This invention pertains to compounds which inhibit the activity of Bcl-xL anti-apoptotic proteins, compositions containing the compounds, and methods of treating diseases during which anti-apoptotic Bcl-xL proteins are expressed.

BACKGROUND OF THE INVENTION

Apoptosis is recognized as an essential biological process for tissue homeostasis of all living species. In mammals in particular, it has been shown to regulate early embryonic development. Later in life, cell death is a default mechanism by which potentially dangerous cells (e.g., cells carrying cancerous defects) are removed. Several apoptotic pathways have been uncovered, and one of the most important involves the Bcl-2 family of proteins, which are key regulators of the mitochondrial (also called "intrinsic") pathway of apoptosis. See, Danial, N. N. and Korsmeyer, S. J. Cell (2004) 116, 205-219. The structural homology domains BH1, BH2, BH3 and BH4 are characteristic of this family of proteins. The Bcl-2 family of proteins can be further classified into three subfamilies depending on how many of the homology domains each protein contains and on its biological activity (i.e., whether it has pro- or anti-apoptotic function).

The first subgroup contains proteins having all 4 homology domains, i.e., BH1, BH2, BH3 and BH4. Their general effect is anti-apoptotic, that is to preserve a cell from starting a cell death process. Proteins such as, for example, Bcl-2, Bcl-w, Bcl-xL, Mcl-1 and Bfl-1/A1 are members of this first subgroup. Proteins belonging to the second subgroup contain the three homology domains BH1, BH2 and BH3, and have a pro-apoptotic effect. The two main representative proteins of this second subgroup are Bax and Bak. Finally, the third subgroup is composed of proteins containing only the BH3 domain and members of this subgroup are usually referred to as "BH3-only proteins." Their biological effect on the cell is pro-apoptotic. Bim, Bid, Bad, Bik, Noxa, Hrk, Bmf, and Puma are examples of this third subfamily of proteins. The exact mechanism by which the Bcl-2 family proteins regulate cell death is still not entirely known and understanding this mechanism is an active area of research in the science community. In one hypothesis of regulation of cell death by Bcl-2 family proteins, the BH3-only proteins are further categorized as either "activator" (e.g., Bim and Bid) or "sensitizer" (e.g., Bad, Bik, Noxa, Hrk, Bmf, and Puma) proteins depending on their regulatory function.

The key to tissue homeostasis is achieving the delicate balance in the interactions among the three subgroups of protein in cells. Recent studies have tried to elucidate the mechanisms by which pro-apoptotic and anti-apoptotic subgroups of Bcl-2 family proteins interact to allow a cell to undergo programmed cell death. After receiving intra- or extra-cellular signals in cells, post-translational or transcriptional activation of BH3-only proteins occurs. The BH3-only proteins are the primary inducers of an apoptotic cascade that includes, as one step, the activation of the pro-apoptotic proteins Bax and Bak on the mitochondrial membrane in cells. Upon activation of Bax and/or Bak that are either already anchored to the mitochondrial membrane or migrate to this membrane, Bax and/or Bak oligomerize to result in mitochondrial outer membrane permeabilization (MOMP), the release of cytochrome C, and downstream activation of effector caspases, to ultimately result in cell apoptosis. Some researchers hypothesize that certain BH3-only proteins (e.g., Puma, Bim, Bid) are "activators" in that these proteins directly engage pro-apoptotic proteins Bax and Bak to initiate MOMP, while other BH3-only proteins (e.g., Bad, Bik and Noxa) are "sensitizers" and induce Bax and Bak oligomerization indirectly by binding anti-apoptotic proteins (e.g., Bcl-2, Bcl-xL, Bcl-w, Mcl-1) and displacing and "freeing-up" the "activator" BH3-only proteins, which subsequently bind to and activate pro-apoptotic proteins (e.g., Bax, Bak) to induce cell death. Other researchers suggest that anti-apoptotic proteins engage and seqeuester Bax and Bak directly and all BH3-only proteins regulates this interaction by binding to anti-apoptotic proteins (e.g., Bcl-2, Bcl-xL, Bcl-w, Mcl-1) which results in the release Bax and Bak. See, Adams, J. M. and Cory S. Oncogene (2007) 26, 1324-1337; Willis, S. N. et al. Science (2007) 315, 856-859. Although the exact interactions through which the anti- and pro-apoptotic Bcl-2 family proteins regulate apoptosis remain under debate, there is a large body of scientific evidence to show that compounds which inhibit the binding of BH3-only proteins to anti-apoptotic Bcl-2 family proteins promote apoptosis in cells.

Dysregulated apoptotic pathways have been implicated in the pathology of many significant diseases such as neurodegenerative conditions (up-regulated apoptosis), such as for example, Alzheimer's disease; and proliferative diseases (down-regulated apoptosis) such as for example, cancer, autoimmune diseases and pro-thrombotic conditions.

In one aspect, the implication that down-regulated apoptosis (and more particularly the Bcl-2 family of proteins) is involved in the onset of cancerous malignancy has revealed a novel way of targeting this still elusive disease. Research has shown, for example, the anti-apoptotic proteins, Bcl-2 and Bcl-xL, are over-expressed in many cancer cell types. See, Zhang J. Y., Nature Reviews/Drug Discovery, (2002) 1, 101; Kirkin, V. et al. Biochimica et Biophysica Acta (2004) 1644, 229-249; and Amundson, S. A. et al. Cancer Research (2000) 60, 6101-6110. The effect of this deregulation is the survival of altered cells which would otherwise have undergone apoptosis in normal conditions. The repetition of these defects associated with unregulated proliferation is thought to be the starting point of cancerous evolution. Additionally, research has shown that BH3-only proteins can act as tumor suppressors when expressed in diseased animals.

These findings as well as numerous others have made possible the emergence of new strategies in drug discovery for targeting cancer. If a small molecule that could mimic the effect of BH3-only proteins were able to enter the cell and overcome the anti-apoptotic protein over-expression, then it could be possible to reset the apoptotic process. This strategy can have the advantage that it can alleviate the problem of drug resistance which is usually a consequence of apoptotic deregulation (abnormal survival).

Researchers also have demonstrated that platelets also contain the necessary apoptotic machinery (e.g., Bax, Bak, Bcl-xL, Bcl-2, cytochrome c, caspase-9, caspase-3 and APAF-1) to execute programmed cell death through the intrinsic apoptotic pathway. Although circulating platelet production is a normal physiological process, a number of diseases are caused or exacerbated by excess of, or undesired activation of, platelets. The above suggests that therapeutic agents capable of inhibiting anti-apoptotic proteins in platelets and reducing the number of platelets in mammals maybe useful in treating pro-thrombotic conditions and diseases that are characterized by an excess of, or undesired activation of, platelets.

We have developed a class of small molecule BH3-only protein mimetics, i.e., ABT-737 and ABT-263, that bind strongly to a subset of anti-apoptotic Bcl-2 proteins including Bcl-2, Bcl-w and Bcl-xL, but only weakly to Mcl-1 and A1, and exhibits mechanism-based cytotoxicity. These compounds were tested in animal studies and demonstrated cytotoxic activity in certain xenograft models as single agents, as well as enhanced the effects of a number of chemotherapeutic agents on other xenograft models when used in combination. See, Tse, C. et al. *Cancer Res* (2008) 68, 3421-3428; and van Delft, M. F. et al. *Cancer Cell* (2006) 10, 389-399. These in vivo studies suggest the potential utility of inhibitors of anti-apoptotic Bcl-2 family proteins for the treatment of diseases that involve a dysregulated apoptotic pathway.

The natural expression levels of anti-apoptotic Bcl-2 family proteins members vary in different cell types. For example, in young platelets, Bcl-xL protein is highly expressed and plays an important role in regulating cell death (life span) of platelets. Also, in certain cancer cell types, the cancer cell's survival is attributed to the dysregulation of the apoptotic pathway caused by the over-expression of one or more anti-apoptotic Bcl-2 protein family members. In view of the important role for Bcl-2 family of proteins in regulating apoptosis in both cancerous and normal (i.e., non-cancerous) cells, and the recognized inter-cell type variability of Bcl-2 family protein expression, it is advantageous to have a small molecule inhibitor that selectively targets and preferably binds to one type or a subset of anti-apoptotic Bcl-2 protein (s), for example, to an anti-apoptotic Bcl-2 family member that overexpressed in a certain cancer type. Such a selective compound also may confer certain advantages in the clinical setting, by providing, for example, the flexibility to select a dosing regimen, a reduced on-target toxic effect in normal cells, among others (e.g., lymphopenia has been observed in Bcl-2 deficient mice). See, Nakayama, K. et al. *PNAS* (1994) 91, 3700-3704.

In view of the above, there is a need in the art for small molecules therapeutics that can selectively inhibit the activity of one type or a subset of anti-apoptotic Bcl-2 proteins, for example, of a Bcl-xL anti-apoptotic protein. The present invention fulfills at least this need.

SUMMARY OF THE INVENTION

One embodiment of this invention, therefore, pertains to compounds or therapeutically acceptable salts thereof, which are useful as inhibitors of anti-apoptotic Bcl-xL proteins, the compounds having Formula (I)

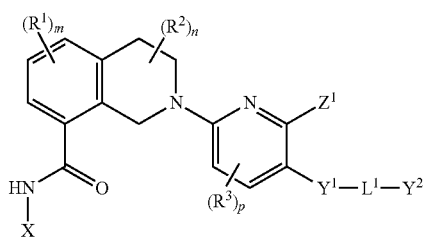

Formula (I)

or a therapeutically acceptable salt thereof, wherein

X is heteroaryl; wherein the heteroaryl represented by X is optionally substituted with one, two, three, or four $R^4$;

$Y^1$ is phenylene, or $C_{5-6}$ heteroarylene; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^1$ is optionally substituted with one, two, three, or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)$ $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, F, Cl, Br and I;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—$NR^{6A}C(O)$—$(CR^6R^7)_r$, $(CR^6R^7)_s$—C(O)$NR^{6A}$—$(CR^6R^7)_r$, $(CR^6R^7)_s$—$NR^{6A}$—$(CR^6R^7)_r$, $(CR^6R^7)_s$—S(O)$_2NR^{6A}$—$(CR^6R^7)_r$, and $(CR^6R^7)_s$—$NR^{6A}S$(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N$ $(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I; or $L^1$ is a bond; and $Y^2$ is selected from the group consisting of $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl represented by $Y^2$ are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein each $Y^2$ and each ring fused to $Y^2$ are optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR)^8$, $NH_2$, $NHR^8$, $N(R^8)_2$, $NHC(O)R^8$, $NR^8C(O)R^8$, $NHS(O)R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I;

$Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and $CN$; or $Z^1$ is selected from the group consisting of

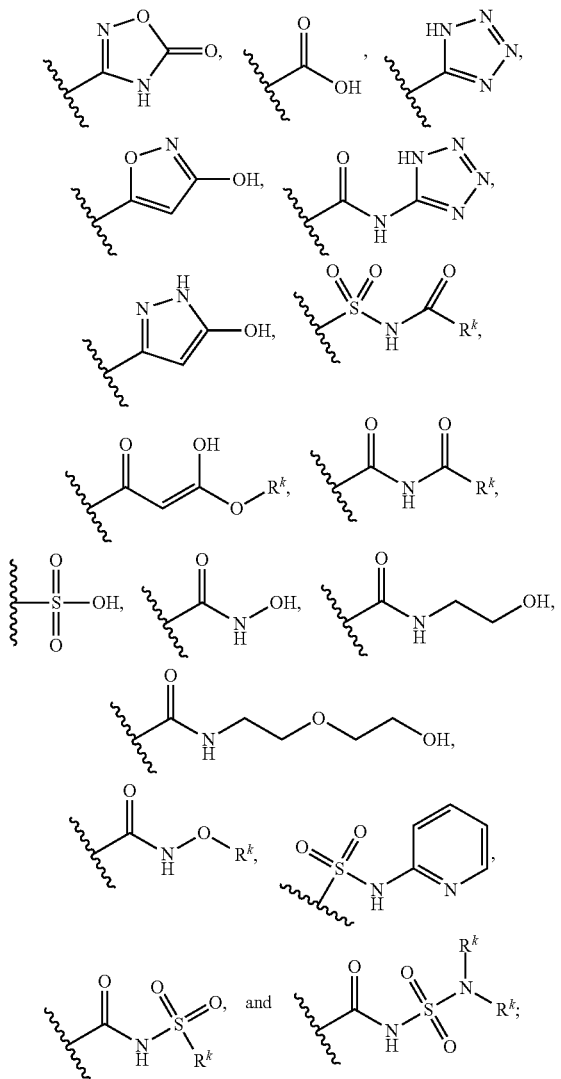

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^{12}R^{13}$, $OR^{12}$, CN, $NO_2$, halogen, $C(O)OR^{12}$, $C(O)NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^{14}$ and $R^{14}$;

$R^5$, at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

$R^6$ and $R^7$, at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $CO(O)H$, $C(O)H$, OH, CN, $N_3$, $NO_2$, F, Cl, Br and I;

$R^8$, at each occurrence, is independently selected from the group consisting of $C_{1-6}$ alkyl, $C_{2-6}$ alkenyl, $C_{2-6}$ alkynyl, $C_{1-6}$ haloalkyl, aryl, heterocyclyl, cycloalkyl, and cycloalkenyl; wherein the $R^8$ $C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^6$, $NR^{16}S(O)_2R^{16}$, $NHC(O)OR^{16}$, $NR^{16}C(O)OR^6$, $NHC(O)NH_2$, $NHC(O)NHR^{16}$, $NHC(O)N(R^{16})_2$, $NR^{16}C(O)NHR^{16}$, $NR^{16}C(O)N(R^{16})_2$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH_2$, $SO_2NHR^{16}$, $SO_2N(R^{16})_2$, $CO(O)H$, $C(O)H$, OH, CN, $N_3$, $NO_2$, F, Cl, Br and I; wherein the $R^8$ aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, $C(O)H$, (O), OH, CN, $NO_2$, $OCF_3$, $OCF_2CF_3$, F, Cl, Br and I;

$R^9$ is selected from the group consisting of $C_{1-6}$ alkyl, $C_{2-6}$ alkenyl, $C_{2-6}$ alkynyl, $C_{1-6}$ haloalkyl, cycloalkyl, phenyl and $(CH_2)_{1-4}$ phenyl; and $R^{10}$ and $R^{11}$, at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or $R^{10}$ and $R^{11}$, or $R^{10}$ and $R^9$, together with the atom to which each is attached are combined to form a heterocyclyl;

$R^k$, at each occurrence, is independently selected from the group consisting of $C_{1-4}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl; wherein the $R^k$ $C_{1-6}$ alkyl, $C_{2-6}$ alkenyl, and $C_{2-6}$ alkynyl are optionally substituted with aryl, heterocyclyl, cycloalkyl, or cycloalkenyl;

$R^{12}$ and $R^{13}$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^{14}$, at each occurrence, is independently selected from the group consisting of $C_{1-4}$ alkyl, $C_{2-4}$ alkenyl, $C_{2-4}$ alkynyl and $C_{1-4}$ haloalkyl;

$R^{12}$ and $R^{13}$, or $R^{12}$ and $R^{14}$, at each occurrence, together with the atom to which each is attached, are optionally combined to form a heterocyclyl;

$R^{15}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the $R^{15}$ $C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ alkoxy, aryl, heterocycloalkyl, heterocycloalkenyl, heteroaryl, cycloalkyl, and cycloalkenyl, $NH_2$, C(O)NH$_2$, SO$_2$NH$_2$, C(O)H, C(O)OH, (O), OH, CN, NO$_2$, OCF$_3$, OCF$_2$CF$_3$, F, Cl, Br and I;

R$^{16}$, at each occurrence, is independently selected from the group consisting of C$_{1-4}$ alkyl, C$_{2-4}$ alkenyl, C$_{2-4}$ alkynyl, C$_{1-4}$ haloalkyl, C$_{1-4}$ hydroxyalkyl, aryl, heterocycloalkyl, heterocycloalkenyl, heteroaryl, cycloalkyl, and cycloalkenyl; wherein the R$^{16}$C$_{1-4}$ alkyl, C$_{2-4}$ alkenyl, C$_{2-4}$ alkynyl, C$_{1-4}$ haloalkyl, and C$_{1-4}$ hydroxyalkyl are optionally substituted with one substituent independently selected from the group consisting of OCH$_3$, OCH$_2$CH$_2$OCH$_3$, and OCH$_2$CH$_2$NHCH$_3$;

q is 1, 2, or 3;
s is 0, 1, 2, or 3;
r is 0, 1, 2, or 3;
wherein the sum of s and r is 0, 1, or 2;
m is 0, 1, 2, or 3;
n is 0, 1, 2, 3, 4, 5, or 6; and
p is 0, 1, or 2.

In another embodiment of Formula (I), Y$^1$ is pyrrolyl, pyrazolyl, or triazolyl.

In another embodiment of Formula (I), Y$^1$ is pyridinyl or phenyl.

In another embodiment of Formula (I), X is benzo[d]thiazolyl; which is optionally substituted with one, two, three or four R$^4$. In another embodiment of Formula (I), Y$^1$ is pyrrolyl, pyrazolyl, or triazolyl, and X is benzo[d]thiazolyl; which is optionally substituted with one, two, three or four R$^4$. In another embodiment of Formula (I), Y$^1$ is pyridinyl or phenyl, and X is benzo[d]thiazolyl; which is optionally substituted with one, two, three or four R$^4$.

In another embodiment of Formula (I), Y$^1$ is pyrrolyl, pyrazolyl, or triazolyl; and Z$^1$ is

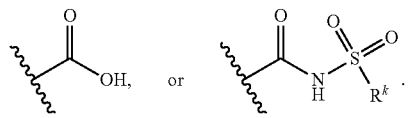

In another embodiment of Formula (I), Y$^1$ is pyridinyl or phenyl; and Z$^1$ is

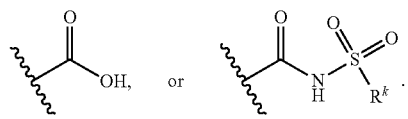

In another embodiment of Formula (I), Y$^1$ is pyrrolyl, pyrazolyl, or triazolyl; L$^1$ is (CR$^6$R$^7$)$_q$; and Y$^2$ is selected from the group consisting of C$_{3-7}$ cycloalkyl, C$_{4-7}$ cycloalkenyl, phenyl, C$_{5-6}$ heteroaryl, and C$_{3-7}$ heterocycloalkyl; wherein R$^6$ and R$^7$, at each occurrence, are R$^{15}$ or hydrogen; and q is 1, 2, or 3. In another embodiment of Formula (I), Y$^1$ is pyridinyl or phenyl; L$^1$ is (CR$^6$R$^7$)$_q$; and Y$^2$ is selected from the group consisting of C$_{3-7}$ cycloalkyl, C$_{4-7}$ cycloalkenyl, phenyl, C$_{5-6}$ heteroaryl, and C$_{3-7}$ heterocycloalkyl; wherein R$^6$ and R$^7$, at each occurrence, are R$^{15}$ or hydrogen; and q is 1, 2, or 3.

In another embodiment of Formula (I), Y$^1$ is pyrrolyl, pyrazolyl, or triazolyl; L$^1$ is selected from the group consisting of (CR$^6$R$^7$)$_s$—C(O)NR$^{6A}$—(CR$^6$R$^7$)$_r$, and (CR$^6$R$^7$)$_s$—S(O)$_2$NR$^{6A}$—(CR$^6$R$^7$)$_r$; s is 0; r is 0 or 1; R$^{6A}$ is independently selected from the group consisting of hydrogen, and C$_{1-6}$ alkyl; and R$^6$ and R$^7$, at each occurrence, are hydrogen. In another embodiment of Formula (I), Y$^1$ is pyridinyl or phenyl; L$^1$ is selected from the group consisting of (CR$^6$R$^7$)$_s$—NR$^{6A}$C(O)—(CR$^6$R$^7$)$_r$, (CR$^6$R$^7$)$_s$—C(O)NR$^{6A}$—(CR$^6$R$^7$)$_r$, (CR$^6$R$^7$)$_s$—NR$^{6A}$—(CR$^6$R$^7$)$_r$, (CR$^6$R$^7$)$_s$—S(O)$_2$NR$^{6A}$—(CR$^6$R$^7$)$_r$, and (CR$^6$R$^7$)$_s$—NR$^{6A}$S(O)$_2$—(CR$^6$R$^7$)$_r$; s is 0; r is 0 or 1; R$^{6A}$ is independently selected from the group consisting of hydrogen, and C$_{1-6}$ alkyl; and R$^6$ and R$^7$, at each occurrence, are hydrogen.

Still another embodiment pertains to a compound having Formula (I), selected from the group consisting of 6-[8-(1,3-benzothiazol-2-ylcarbamoyl)-3,4-dihydroisoquinolin-2(1H)-yl]-3-(1-benzyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(pyridin-4-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(pyridin-3-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-hydroxybenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(1-phenylethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{4-[2-(dimethylamino)ethoxy]benzyl}-1H-pyrazol-4-yl)pyridine-2-carboxylic acid;

3-(1-benzyl-1H-pyrazol-4-yl)-6-{8-[(5,6-difluoro-1,3-benzothiazol-2-yl)carbamoyl]-3,4-dihydroisoquinolin-2(1H)-yl}pyridine-2-carboxylic acid;

6-[8-(1,3-benzothiazol-2-ylcarbamoyl)-3,4-dihydroisoquinolin-2(1H)-yl]-3-{1-[2-(4-fluorophenyl)ethyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(3-chlorobenzyl)-1H-pyrazol-4-yl]pyridine-2-carboxylic acid;

3-(1-benzyl-1H-pyrazol-4-yl)-6-{8-[(6-fluoro-1,3-benzothiazol-2-yl)carbamoyl]-3,4-dihydroisoquinolin-2(1H)-yl}pyridine-2-carboxylic acid;

3-(1-benzyl-1H-pyrazol-4-yl)-6-{8-[(6-methoxy-1,3-benzothiazol-2-yl)carbamoyl]-3,4-dihydroisoquinolin-2(1H)-yl}pyridine-2-carboxylic acid;

6-[8-(1,3-benzothiazol-2-ylcarbamoyl)-3,4-dihydroisoquinolin-2(1H)-yl]-3-(1-benzyl-3,5-dimethyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(3-methylbenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3-methoxybenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-chlorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[3-(benzyloxy)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(3-hydroxybenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{3-[2-(dimethylamino)ethoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-benzyl-3-methyl-1H-pyrazol-4-yl)pyridine-2-carboxylic acid;

6-[8-(1,3-benzothiazol-2-ylcarbamoyl)-3,4-dihydroiso-
quinolin-2(1H)-yl]-3-(1-benzyl-5-methyl-1H-pyrazol-4-
yl)pyridine-2-carboxylic acid;
3-(1-benzyl-1H-pyrazol-4-yl)-6-{8-[(7-chloro-1,3-ben-
zothiazol-2-yl)carbamoyl]-3,4-dihydroisoquinolin-2
(1H)-yl}pyridine-2-carboxylic acid;
6-[8-(1,3-benzothiazol-2-ylcarbamoyl)-3,4-dihydroiso-
quinolin-2(1H)-yl]-3-(1-{[6-(pyrrolidin-1-yl)pyridin-2-
yl]methyl}-1H-pyrazol-4-yl)pyridine-2-carboxylic acid;
6-[8-(1,3-benzothiazol-2-ylcarbamoyl)-3,4-dihydroiso-
quinolin-2(1H)-yl]-3-(1-phenyl-1H-pyrazol-4-yl)pyri-
dine-2-carboxylic acid;
6-[8-(1,3-benzothiazol-2-ylcarbamoyl)-3,4-dihydroiso-
quinolin-2(1H)-yl]-3-[1-(3-cyanobenzyl)-1H-pyrazol-4-
yl]pyridine-2-carboxylic acid;
6-[8-(1,3-benzothiazol-2-ylcarbamoyl)-3,4-dihydroiso-
quinolin-2(1H)-yl]-3-[1-(2-chlorobenzyl)-1H-pyrazol-4-
yl]pyridine-2-carboxylic acid;
6-[8-(1,3-benzothiazol-2-ylcarbamoyl)-3,4-dihydroiso-
quinolin-2(1H)-yl]-3-[1-(pyridin-2-ylmethyl)-1H-pyra-
zol-4-yl]pyridine-2-carboxylic acid;
6-[8-(1,3-benzothiazol-2-ylcarbamoyl)-3,4-dihydroiso-
quinolin-2(1H)-yl]-3-[1-benzyl-3-cyano-1H-pyrazol-4-
yl]pyridine-2-carboxylic acid;
6-[8-(1,3-benzothiazol-2-ylcarbamoyl)-3,4-dihydroiso-
quinolin-2(1H)-yl]-3-[1-(naphthalen-2-ylmethyl)-1H-
pyrazol-4-yl]pyridine-2-carboxylic acid;
6-[8-(1,3-benzothiazol-2-ylcarbamoyl)-3,4-dihydroiso-
quinolin-2(1H)-yl]-3-{1-[3-(3-methyl-1,2,4-oxadiazol-5-
yl)benzyl]-1H-pyrazol-4-yl}pyridine-2-carboxylic acid;
6-[8-(1,3-benzothiazol-2-ylcarbamoyl)-3,4-dihydroiso-
quinolin-2(1H)-yl]-3-[1-benzyl-3-(hydroxymethyl)-5-
methyl-1H-pyrazol-4-yl]pyridine-2-carboxylic acid;
6-[8-(1,3-benzothiazol-2-ylcarbamoyl)-3,4-dihydroiso-
quinolin-2(1H)-yl]-3-{1-[2-(benzyloxy)benzyl]-1H-pyra-
zol-4-yl}pyridine-2-carboxylic acid;
6-[8-(1,3-benzothiazol-2-ylcarbamoyl)-3,4-dihydroiso-
quinolin-2(1H)-yl]-3-(5-methyl-1-{[6-(pyrrolidin-1-yl)
pyridin-2-yl]methyl}-1H-pyrazol-4-yl)pyridine-2-car-
boxylic acid;
6-[8-(1,3-benzothiazol-2-ylcarbamoyl)-3,4-dihydroiso-
quinolin-2(1H)-yl]-3-[1-benzyl-3-(ethoxycarbonyl)-5-
methyl-1H-pyrazol-4-yl]pyridine-2-carboxylic acid;
6-[8-(1,3-benzothiazol-2-ylcarbamoyl)-3,4-dihydroiso-
quinolin-2(1H)-yl]-3-{1-[3-(dimethylamino)benzyl]-1H-
pyrazol-4-yl}pyridine-2-carboxylic acid;
6-[8-(1,3-benzothiazol-2-ylcarbamoyl)-3,4-dihydroiso-
quinolin-2(1H)-yl]-3-(1-benzyl-3-carboxy-5-methyl-1H-
pyrazol-4-yl)pyridine-2-carboxylic acid;
6-[8-(1,3-benzothiazol-2-ylcarbamoyl)-3,4-dihydroiso-
quinolin-2(1H)-yl]-3-[1-(2-hydroxybenzyl)-1H-pyrazol-
4-yl]pyridine-2-carboxylic acid;
6-[8-(1,3-benzothiazol-2-ylcarbamoyl)-3,4-dihydroiso-
quinolin-2(1H)-yl]-3-[1-(2,3-dihydro-1H-inden-1-yl)-
1H-pyrazol-4-yl]pyridine-2-carboxylic acid;
6-[8-(1,3-benzothiazol-2-ylcarbamoyl)-3,4-dihydroiso-
quinolin-2(1H)-yl]-3-[1-(2-phenylethyl)-1H-pyrazol-4-
yl]pyridine-2-carboxylic acid;
6-[8-(1,3-benzothiazol-2-ylcarbamoyl)-3,4-dihydroiso-
quinolin-2(1H)-yl]-3-[1-(3,4-dihydro-2H-chromen-4-yl)-
1H-pyrazol-4-yl]pyridine-2-carboxylic acid;
6-[8-(1,3-benzothiazol-2-ylcarbamoyl)-3,4-dihydroiso-
quinolin-2(1H)-yl]-3-(1-{2-[2-(dimethylamino)ethoxy]
benzyl}-1H-pyrazol-4-yl)pyridine-2-carboxylic acid;
6-[8-(1,3-benzothiazol-2-ylcarbamoyl)-3,4-dihydroiso-
quinolin-2(1H)-yl]-3-[1-(2-fluorobenzyl)-5-methyl-1H-
pyrazol-4-yl]pyridine-2-carboxylic acid;
6-[8-(1,3-benzothiazol-2-ylcarbamoyl)-3,4-dihydroiso-
quinolin-2(1H)-yl]-3-[1-(cyclohexylmethyl)-1H-pyrazol-
4-yl]pyridine-2-carboxylic acid;
6-[8-(1,3-benzothiazol-2-ylcarbamoyl)-3,4-dihydroiso-
quinolin-2(1H)-yl]-3-[1-(cyclohexylmethyl)-5-methyl-
1H-pyrazol-4-yl]pyridine-2-carboxylic acid;
6-[8-(1,3-benzothiazol-2-ylcarbamoyl)-3,4-dihydroiso-
quinolin-2(1H)-yl]-3-[1-(4-{[3-(dimethylamino)propyl]
amino}-3-nitrobenzyl)-1H-pyrazol-4-yl]pyridine-2-car-
boxylic acid;
6-[8-(1,3-benzothiazol-2-ylcarbamoyl)-3,4-dihydroiso-
quinolin-2(1H)-yl]-3-[1-(4-fluoro-3-nitrobenzyl)-1H-
pyrazol-4-yl]pyridine-2-carboxylic acid;
6-[8-(1,3-benzothiazol-2-ylcarbamoyl)-3,4-dihydroiso-
quinolin-2(1H)-yl]-3-(1-{2-[2-(morpholin-4-yl)ethoxy]
benzyl}-1H-pyrazol-4-yl)pyridine-2-carboxylic acid;
6-[8-(1,3-benzothiazol-2-ylcarbamoyl)-3,4-dihydroiso-
quinolin-2(1H)-yl]-3-(1-{2-[3-(dimethylamino)propoxy]
benzyl}-1H-pyrazol-4-yl)pyridine-2-carboxylic acid;
6-[8-(1,3-benzothiazol-2-ylcarbamoyl)-3,4-dihydroiso-
quinolin-2(1H)-yl]-3-{1-[2-(pyridin-4-ylmethoxy)ben-
zyl]-1H-pyrazol-4-yl}pyridine-2-carboxylic acid;
6-[8-(1,3-benzothiazol-2-ylcarbamoyl)-3,4-dihydroiso-
quinolin-2(1H)-yl]-3-(1-{2-[2-(dimethylamino)ethoxy]
benzyl}-5-methyl-1H-pyrazol-4-yl)pyridine-2-carboxylic
acid;
6-[8-(1,3-benzothiazol-2-ylcarbamoyl)-3,4-dihydroiso-
quinolin-2(1H)-yl]-3-[1-(tetrahydro-2H-pyran-4-ylm-
ethyl)-1H-pyrazol-4-yl]pyridine-2-carboxylic acid;
6-[8-(1,3-benzothiazol-2-ylcarbamoyl)-3,4-dihydroiso-
quinolin-2(1H)-yl]-3-(1-{2-[3-(dimethylamino)prop-1-
yn-1-yl]benzyl}-1H-pyrazol-4-yl)pyridine-2-carboxylic
acid;
6-[8-(1,3-benzothiazol-2-ylcarbamoyl)-3,4-dihydroiso-
quinolin-2(1H)-yl]-3-[1-(2,3-difluorobenzyl)-1H-pyra-
zol-4-yl]pyridine-2-carboxylic acid;
6-[8-(1,3-benzothiazol-2-ylcarbamoyl)-3,4-dihydroiso-
quinolin-2(1H)-yl]-3-[1-(3,5-difluorobenzyl)-1H-pyra-
zol-4-yl]pyridine-2-carboxylic acid;
6-[8-(1,33-benzothiazol-2-ylcarbamoyl)-3,4-dihydroiso-
quinolin-2(1H)-yl]-3-[1-(2,5-difluorobenzyl)-1H-pyra-
zol-4-yl]pyridine-2-carboxylic acid;
6-[8-(1,3-benzothiazol-2-ylcarbamoyl)-3,4-dihydroiso-
quinolin-2(1H)-yl]-3-[1-(2,6-difluorobenzyl)-1H-pyra-
zol-4-yl]pyridine-2-carboxylic acid;
6-[8-(1,3-benzothiazol-2-ylcarbamoyl)-3,4-dihydroiso-
quinolin-2(1H)-yl]-3-[1-(tetrahydro-2H-pyran-3-ylm-
ethyl)-1H-pyrazol-4-yl]pyridine-2-carboxylic acid;
6-[8-(1,3-benzothiazol-2-ylcarbamoyl)-3,4-dihydroiso-
quinolin-2(1H)-yl]-3-[1-(2-nitrobenzyl)-1H-pyrazol-4-
yl]pyridine-2-carboxylic acid;
6-[8-(1,3-benzothiazol-2-ylcarbamoyl)-3,4-dihydroiso-
quinolin-2(1H)-yl]-3-[1-(biphenyl-3-ylmethyl)-1H-pyra-
zol-4-yl]pyridine-2-carboxylic acid;
6-[8-(1,33-benzothiazol-2-ylcarbamoyl)-3,4-dihydroiso-
quinolin-2(1H)-yl]-3-[1-(2,2-dimethylpropyl)-1H-pyra-
zol-4-yl]pyridine-2-carboxylic acid;
6-[8-(1,3-benzothiazol-2-ylcarbamoyl)-3,4-dihydroiso-
quinolin-2(1H)-yl]-3-[1-(2-cyclohexylethyl)-1H-pyrazol-
4-yl]pyridine-2-carboxylic acid;
6-[8-(1,3-benzothiazol-2-ylcarbamoyl)-3,4-dihydroiso-
quinolin-2(1H)-yl]-3-{1-[3-(trifluoromethyl)benzyl]-1H-
pyrazol-4-yl}pyridine-2-carboxylic acid;
6-[8-(1,3-benzothiazol-2-ylcarbamoyl)-3,4-dihydroiso-
quinolin-2(1H)-yl]-3-[1-(biphenyl-2-ylmethyl)-1H-pyra-
zol-4-yl]pyridine-2-carboxylic acid;

6-[8-(1,3-benzothiazol-2-ylcarbamoyl)-3,4-dihydroisoquinolin-2(1H)-yl]-3-[1-(cyclopentylmethyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3-formylbenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-benzyl-5-phenyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[5-methyl-1-(tetrahydro-2H-pyran-3-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[(1-phenylcyclohexyl)methyl]-1H-pyrazol-4-yl}pyridine-2-carboxylic acid;

6-[8-(1,3-benzothiazol-2-ylcarbamoyl)-3,4-dihydro isoquinolin-2(1H)-yl]-3-(1-{3-[(dimethylamino)methyl]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[3-(methylsulfonyl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(cyclohexylmethyl)-5-cyclopropyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3,5-di-tert-butylbenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[2-(morpholin-4-ylsulfonyl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(4,4-difluorocyclohexyl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[1-(trifluoromethyl)cyclohexyl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(diphenylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[2-(morpholin-4-yl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[3-(morpholin-4-yl)-1-phenylpropyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[1-(tert-butoxycarbonyl)piperidin-4-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(5-methyl-1-{2-[2-(morpholin-4-yl)ethoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[2-(dimethylamino)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(5-methyl-1-{2-[3-(morpholin-4-yl)propoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{5-methyl-1-[(1-methylcyclohexyl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[2-(4-chlorophenyl)-4,4-dimethylcyclohex-1-en-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(cyclohexylmethyl)-5-ethyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[(1R,2R,5R)-6,6-dimethylbicyclo[3.1.1]hept-2-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[(1S,2R,5S)-6,6-dimethylbicyclo[3.1.1]hept-2-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methylpropyl)cyclohexyl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)cyclohexyl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[2-(2-methoxyethoxy)benzyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[(1R,2R,4R)-bicyclo[2.2.1]hept-5-en-2-ylmethyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,3-dimethylcyclohexyl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(3-methoxy-1-phenylpropyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-methoxy-1-phenylbutyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2-methoxy-2-oxo-1-phenylethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2-cyclohexyl-1-phenylethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[1-(3-methoxypropyl)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{2-[3-hydroxy-2-(hydroxymethyl)-2-methylpropoxy]benzyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{5-methyl-1-[2-(tetrahydro-2H-pyran-4-ylmethoxy)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[2-(1,4-dioxan-2-ylmethoxy)benzyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[1-(2-methoxyethoxy)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(4-phenoxyphenyl)pyridine-2-carboxylic acid;

6-[8-(1,3-benzothiazol-2-ylcarbamoyl)-3,4-dihydroisoquinolin-2(1H)-yl]-3-(3-phenoxyphenyl)pyridine-2-carboxylic acid;

6-[8-(1,3-benzothiazol-2-ylcarbamoyl)-3,4-dihydroisoquinolin-2(1H)-yl]-3-[3-(4-nitrophenoxy)phenyl]pyridine-2-carboxylic acid;

6-[8-(1,3-benzothiazol-2-ylcarbamoyl)-3,4-dihydroisoquinolin-2(1H)-yl]-3-[3-(4-chlorophenoxy)phenyl]pyridine-2-carboxylic acid;

6-[8-(1,3-benzothiazol-2-ylcarbamoyl)-3,4-dihydroisoquinolin-2(1H)-yl]-3-(3-benzylphenyl)pyridine-2-carboxylic acid;

6-[8-(1,3-benzothiazol-2-ylcarbamoyl)-3,4-dihydroisoquinolin-2(1H)-yl]-3-[3-(cyclohexylmethyl)-2-methylphenyl]pyridine-2-carboxylic acid;

6-[8-(1,3-benzothiazol-2-ylcarbamoyl)-3,4-dihydroisoquinolin-2(1H)-yl]-3-(4-methyl-3-phenoxyphenyl)pyridine-2-carboxylic acid;

6-[8-(1,3-benzothiazol-2-ylcarbamoyl)-3,4-dihydroisoquinolin-2(1H)-yl]-3-(2-methyl-5-phenoxyphenyl)pyridine-2-carboxylic acid;

6-[8-(1,3-benzothiazol-2-ylcarbamoyl)-3,4-dihydroisoquinolin-2(1H)-yl]-3-(2-methyl-3-phenoxyphenyl)pyridine-2-carboxylic acid;

6-[8-(1,3-benzothiazol-2-ylcarbamoyl)-3,4-dihydroisoquinolin-2(1H)-yl]-3-(2-methyl-4-phenoxyphenyl)pyridine-2-carboxylic acid;

6-[8-(1,3-benzothiazol-2-ylcarbamoyl)-3,4-dihydroisoquinolin-2(1H)-yl]-3-[3-(cyclohexylmethoxy)-2-methylphenyl]pyridine-2-carboxylic acid;

6-[8-(1,3-benzothiazol-2-ylcarbamoyl)-3,4-dihydroisoquinolin-2(1H)-yl]-3-[4-(cyclohexyloxy)-2-methylphenyl]pyridine-2-carboxylic acid;

6-[8-(1,3-benzothiazol-2-ylcarbamoyl)-3,4-dihydroisoquinolin-2(1H)-yl]-3-[3-(cyclohexyloxy)-2-methylphenyl]pyridine-2-carboxylic acid;

6-[8-(1,3-benzothiazol-2-ylcarbamoyl)-3,4-dihydroisoquinolin-2(1H)-yl]-3-[4-(cyclohexylmethoxy)-2-methylphenyl]pyridine-2-carboxylic acid;

6-[8-(1,3-benzothiazol-2-ylcarbamoyl)-3,4-dihydroisoquinolin-2(1H)-yl]-3-[2-cyano-3-(cyclohexyloxy)phenyl]pyridine-2-carboxylic acid;

6-[8-(1,3-benzothiazol-2-ylcarbamoyl)-3,4-dihydroisoquinolin-2(1H)-yl]-3-[2-chloro-3-(cyclohexyloxy)phenyl]pyridine-2-carboxylic acid;

6-[8-(1,3-benzothiazol-2-ylcarbamoyl)-3,4-dihydroisoquinolin-2(1H)-yl]-3-[3-(cyclohexylamino)-2-methylphenyl]pyridine-2-carboxylic acid;

6-[8-(1,3-benzothiazol-2-ylcarbamoyl)-3,4-dihydroisoquinolin-2(1H)-yl]-3-[3-(cyclohexyloxy)-2-fluorophenyl]pyridine-2-carboxylic acid;

6-[8-(1,3-benzothiazol-2-ylcarbamoyl)-3,4-dihydroisoquinolin-2(1H)-yl]-3-[3-(cyclohexyloxy)-2-(trifluoromethyl)phenyl]pyridine-2-carboxylic acid;

6-[8-(1,3-benzothiazol-2-ylcarbamoyl)-3,4-dihydroisoquinolin-2(1H)-yl]-3-{3-[(3,3-dimethylcyclohexyl)oxy]-2-methylphenyl}pyridine-2-carboxylic acid;

6-[8-(1,3-benzothiazol-2-ylcarbamoyl)-3,4-dihydroisoquinolin-2(1H)-yl]-3-(1-benzyl-1H-1,2,3-triazol-4-yl)pyridine-2-carboxylic acid;

6-[8-(1,3-benzothiazol-2-ylcarbamoyl)-3,4-dihydroisoquinolin-2(1H)-yl]-3-[1-benzyl-5-(ethoxycarbonyl)-2-methyl-1H-pyrrol-3-yl]pyridine-2-carboxylic acid;

6-[8-(1,3-benzothiazol-2-ylcarbamoyl)-3,4-dihydroisoquinolin-2(1H)-yl]-3-(1-benzyl-5-carboxy-2-methyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-(1-benzyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-{1-[(4-methylphenyl)sulfonyl]-1H-pyrrol-3-yl}pyridine-2-carboxylic acid;

6-[8-(1,3-benzothiazol-2-ylcarbamoyl)-3,4-dihydroisoquinolin-2(1H)-yl]-3-(1-benzoyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-[1-(phenylsulfonyl)-1H-pyrrol-3-yl]pyridine-2-carboxylic acid;

6-[8-(1,3-benzothiazol-2-ylcarbamoyl)-3,4-dihydroisoquinolin-2(1H)-yl]-3-(1-benzyl-5-cyano-2-methyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-[5-cyano-1-(cyclohexylmethyl)-2-methyl-1H-pyrrol-3-yl]pyridine-2-carboxylic acid;

6-[8-(1,3-benzothiazol-2-ylcarbamoyl)-3,4-dihydroisoquinolin-2(1H)-yl]-3-(5-cyano-2-methyl-1-{[1-(piperidin-1-yl)cyclohexyl]methyl}-1H-pyrrol-3-yl)pyridine-2-carboxylic acid;

6,6'-bis[8-(1,3-benzothiazol-2-ylcarbamoyl)-3,4-dihydroisoquinolin-2(1H)-yl]-3,3'-bipyridine-2,2'-dicarboxylic acid;

6-[8-(1,3-benzothiazol-2-ylcarbamoyl)-3,4-dihydroisoquinolin-2(1H)-yl]-3-(2-benzyl-1,2,3,4-tetrahydroisoquinolin-6-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)cycloheptyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(piperidin-4-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[2-(pyridin-2-ylmethyl)-1,2,3,4-tetrahydroisoquinolin-6-yl]pyridine-2-carboxylic acid;

6-[8-(1,3-benzothiazol-2-ylcarbamoyl)-3,4-dihydroisoquinolin-2(1H)-yl]-3-[2-(cyclohexylmethyl)-1,2,3,4-tetrahydroisoquinolin-6-yl]pyridine-2-carboxylic acid;

6-[8-(1,3-benzothiazol-2-ylcarbamoyl)-3,4-dihydroisoquinolin-2(1H)-yl]-2'-(cyclohexyloxy)-3'-methyl-3,4'-bipyridine-2-carboxylic acid;

6-[8-(1,3-benzothiazol-2-ylcarbamoyl)-3,4-dihydroisoquinolin-2(1H)-yl]-2'-(cyclohexyloxy)-3,4'-bipyridine-2-carboxylic acid;

6-[8-(1,3-benzothiazol-2-ylcarbamoyl)-3,4-dihydroisoquinolin-2(1H)-yl]-2'-phenoxy-3,4'-bipyridine-2-carboxylic acid;

6-[8-(1,3-benzothiazol-2-ylcarbamoyl)-3,4-dihydroisoquinolin-2(1H)-yl]-3-(1-benzyl-1H-pyrrolo[2,3-b]pyridin-3-yl)pyridine-2-carboxylic acid;

6-[8-(1,3-benzothiazol-2-ylcarbamoyl)-3,4-dihydroisoquinolin-2(1H)-yl]-3'-methyl-2'-phenoxy-3,4'-bipyridine-2-carboxylic acid;

6-[8-(1,3-benzothiazol-2-ylcarbamoyl)-3,4-dihydroisoquinolin-2(1H)-yl]-3'-methyl-2'-[methyl(phenyl)amino]-3,4'-bipyridine-2-carboxylic acid;

6-[8-(1,3-benzothiazol-2-ylcarbamoyl)-3,4-dihydroisoquinolin-2(1H)-yl]-3-(1-{[1-methoxymethyl)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3,3-dimethyl-1-(morpholin-4-yl)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)-3,3-dimethylcyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(3-methoxypropyl)cycloheptyl]methyl}-5-methyl-1H-pyrazol-4-yl)pyridine-2-carboxylic acid;

N-(1,3-benzothiazol-2-yl)-2-{5-(1-{[1-(2-methoxyethyl)cycloheptyl]methyl}-5-methyl-1H-pyrazol-4-yl)-6-[(methylsulfonyl)carbamoyl]pyridin-2-yl}-1,2,3,4-tetrahydroisoquinoline-8-carboxamide;

6-[8-(1,3-benzothiazol-2-ylcarbamoyl)-3,4-dihydroisoquinolin-2(1H)-yl]-3-[1-(tetrahydro-2H-pyran-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[(1R,2R,3R,5S)-2-(2-methoxyethyl)-6,6-dimethylbicyclo[3.1.1]hept-3-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethoxy)cycloheptyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[1-cyclohexyl-3-(morpholin-4-yl)propyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-benzyl-1H-indazol-5-yl)pyridine-2-carboxylic acid;

6-[8-(1,3-benzothiazol-2-ylcarbamoyl)-3,4-dihydroisoquinolin-2(1H)-yl]-3-[5-methyl-1-(tetrahydro-2H-pyran-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[5-methyl-1-({1-[3-(morpholin-4-yl)propoxy]cycloheptyl}methyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{2-methyl-3-[methyl(phenyl)amino]phenyl}pyridine-2-carboxylic acid;

6-[8-(1,3-benzothiazol-2-ylcarbamoyl)-3,4-dihydroisoquinolin-2(1H)-yl]-3-{1-[(1-methoxy-3,3-dimethylcyclohexyl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[(1S,2R,5S)-6,6-dimethylbicyclo[3.1.1]hept-2-yl]methyl}-5-methyl-1H-1,2,3-triazol-4-yl)pyridine-2-carboxylic acid;

6-[8-(1,3-benzothiazol-2-ylcarbamoyl)-3,4-dihydroisoquinolin-2(1H)-yl]-3-{3-[(3,3-dimethylcyclohexyl)(methyl)amino]-2-methylphenyl}pyridine-2-carboxylic acid;

6-[8-(1,3-benzothiazol-2-ylcarbamoyl)-3,4-dihydroisoquinolin-2(1H)-yl]-3-(5-methyl-1-{[1-(morpholin-4-yl)cyclohexyl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-2'-[cyclohexyl(methyl)amino]-3'-methyl-3,4'-bipyridine-2-carboxylic acid;

N-1,3-benzothiazol-2-yl)-2-(5-{1-[(1-methoxy-3,3-dimethylcyclohexyl)methyl]-5-methyl-1H-pyrazol-4-yl}-6-[(methylsulfonyl)carbamoyl]pyridin-2-yl)-1,2,3,4-tetrahydroisoquinoline-8-carboxamide;

6-[8-(1,3-benzothiazol-2-ylcarbamoyl)-1-methyl-3,4-dihydroisoquinolin-2(1H)-yl]-3-{5-methyl-1-[(1-methylcyclohexyl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3'-cyano-2'-[cyclohexyl(methyl)amino]-3,4'-bipyridine-2-carboxylic acid;

6-[8-(1,3-benzothiazol-2-ylcarbamoyl)-3,4-dihydroisoquinolin-2(1H)-yl]-3-{1-[(1-methoxycyclohexyl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(1-methoxy-3,3-dimethylcyclohexyl)methyl]-5-methyl-1H-1,2,3-triazol-4-yl}pyridine-2-carboxylic acid;

6-[8-(1,3-benzothiazol-2-ylcarbamoyl)-3,4-dihydroisoquinolin-2(1H)-yl]-3-[1-({1-[2-(1,1-dioxidothiomorpholin-4-yl)ethoxy]cyclohexyl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-(5-cyano-2-methyl-1-{[1-(morpholin-4-yl)cyclohexyl]methyl}-1H-pyrrol-3-yl)pyridine-2-carboxylic acid;

6-[8-(1,3-benzothiazol-2-ylcarbamoyl)-3,4-dihydroisoquinolin-2(1H)-yl]-3-(1-{[1-(2-hydroxyethoxy)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2,3-dimethoxypropoxy)cycloheptyl]methyl}-5-methyl-1H-pyrazol-4-yl)pyridine-2-carboxylic acid;

N-(1,3-benzothiazol-2-yl)-2-{5-[5-cyano-1-(cyclohexylmethyl)-2-methyl-1H-pyrrol-3-yl]-6-[(methylsulfonyl)carbamoyl]pyridin-2-yl}-1,2,3,4-tetrahydroisoquinoline-8-carboxamide;

6-[8-(1,3-benzothiazol-2-ylcarbamoyl)-3,4-dihydroisoquinolin-2(1H)-yl]-3-(5-cyano-1-{[1-(2-methoxyethoxy)cycloheptyl]methyl}-2-methyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-(1-{[(1-(1,4-dioxan-2-ylmethoxy)cycloheptyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[5-methyl-1-({1-[2-(morpholin-4-yl)-2-oxoethoxy]cyclohexyl}methyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[1-(2,3-dihydroxypropoxy)cycloheptyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(5-cyano-1-{[1-(dimethylamino)cyclohexyl]methyl}-2-methyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-{3-[(cyclohexylcarbonyl)(methyl)amino]-2-methylphenyl}pyridine-2-carboxylic acid;

6-[8-(1,3-benzothiazol-2-ylcarbamoyl)-3,4-dihydroisoquinolin-2(1H)-yl]-3-[1-({3,3-dimethyl-1-[2-(methylsulfonyl)ethoxy]cyclohexyl}methyl)-5-methyl-1H-pyrazol-4-yl]pyridine-2-carboxylic acid;

6-[8-(1,3-benzothiazol-2-ylcarbamoyl)-3,4-dihydroiso-quinolin-2(1H)-yl]-3-(2-methyl-3-{methyl[(1-methylcyclohexyl)carbonyl]amino}phenyl)pyridine-2-carboxylic acid;

6-[8-(1,3-benzothiazol-2-ylcarbamoyl)-3,4-dihydroiso-quinolin-2(1H)-yl]-3-({1-[1-(2-methoxyethoxy)-3,3-dimethylcyclohexyl]methyl}-5-methyl-1H-pyrazol-4-yl)pyridine-2-carboxylic acid;

6-[8-(1,3-benzothiazol-2-ylcarbamoyl)-3,4-dihydroiso-quinolin-2(1H)-yl]-3-{2-cyano-3-[(cyclohexylsulfonyl)(methyl)amino]phenyl}pyridine-2-carboxylic acid;

6-[8-(1,3-benzothiazol-2-ylcarbamoyl)-3,4-dihydroiso-quinolin-2(1H)-yl]-3-{2-cyano-3-[2-(tricyclo[3.3.1.1$^{3,7}$]dec-1-yl)pyrrolidin-1-yl]phenyl}pyridine-2-carboxylic acid;

6-[8-(1,3-benzothiazol-2-ylcarbamoyl)-3,4-dihydroiso-quinolin-2(1H)-yl]-3'-methyl-2'-(piperidin-1-yl)-3,4'-bipyridine-2-carboxylic acid;

6-[8-(1,3-benzothiazol-2-ylcarbamoyl)-3,4-dihydroiso-quinolin-2(1H)-yl]-3-[1-(1-cyclohexyl-3-methoxypropyl)-5-methyl-1H-pyrazol-4-yl]pyridine-2-carboxylic acid;

6-[8-(1,3-benzothiazol-2-ylcarbamoyl)-3,4-dihydroiso-quinolin-2(1H)-yl]-3-[1-({3,3-dimethyl-1-[2-(methylamino)ethoxy]cyclohexyl}methyl)-5-methyl-1H-pyrazol-4-yl]pyridine-2-carboxylic acid;

6-[8-(1,3-benzothiazol-2-ylcarbamoyl)-3,4-dihydroiso-quinolin-2(1H)-yl]-3-{5-methyl-1-[(2,6,6-trimethyltetrahydro-2H-pyran-2-yl)methyl]-1H-pyrazol-4-yl}pyridine-2-carboxylic acid;

6-[8-(1,3-benzothiazol-2-ylcarbamoyl)-3,4-dihydroiso-quinolin-2(1H)-yl]-3-(1-benzyl-1H-indazol-4-yl)pyridine-2-carboxylic acid;

6-[8-(1,3-benzothiazol-2-ylcarbamoyl)-3,4-dihydroiso-quinolin-2(1H)-yl]-3-(1-benzyl-1H-pyrrolo[2,3-c]pyridin-3-yl)pyridine-2-carboxylic acid; and therapeutically acceptable salts, metabolites, prodrugs, salts of metabolites, and salts of prodrugs thereof.

Another embodiment pertains to a composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said composition comprising an excipient and a therapeutically effective amount of a compound of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient a therapeutically effective amount of a compound of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient therapeutically effective amount of the compound of Formula (I) and a therapeutically effective amount of one additional therapeutic agent or more than one additional therapeutic agent.

DETAILED DESCRIPTION OF THE INVENTION

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, cyclooctanyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. Examples of spirocyclic carbocyclyls include spiropentanyl, spiro[3.5]nonanyl, and spiro[2.5]octanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl (tricyclo[3.3.1.1$^{3,7}$]decanyl). In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, cyclohexyl, cycloheptanyl, and cyclooctanyl. A cycloalkyl may alternatively be polycyclic or contain more than one ring. Examples of polycyclic cycloalkyls include bridged, fused, and spirocyclic carbocyclyls. Examples of bridged cycloalkyls include adamantanyl(tricyclo[3.3.1.1$^{3,7}$]decanyl), and bicyclo[3.1.1]heptanyl.

The term "$C_x$-$C_y$ cycloalkyl" means a cycloalkyl ring system containing from x to y carbon atoms. For example "$C_3$-$C_7$ cycloalkyl" means a cycloalkyl ring system containing from 3 to 7 carbon atoms.

The term "cycloalkenyl" (alone or in combination with another term(s)) means a partially saturated cyclic hydrocarbyl substituent containing from 3 to 14 carbon ring atoms. A cycloalkenyl may be a single carbon ring, which typically contains from 3 to 8 carbon ring atoms and more typically from 4 to 6 ring atoms. Examples of single-ring cycloalkenyls include cyclopentenyl, and cyclohexenyl. A cycloalkenyl may alternatively be polycyclic or contain more than one ring. Examples of polycyclic cycloalkenyls include bridged, fused, and spirocyclic carbocyclyls. Examples of bridged cycloalkenyls include bicyclo[2.2.1]hept-2-enyl.

The term "$C_x$-$C_y$ cycloalkenyl" means a cycloalkenyl ring system containing from x to y carbon atoms. For example "$C_4$-$C_7$ cycloalkenyl" means a cycloalkenyl ring system containing from 4 to 7 carbon atoms.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronaphthyl.

The term "heteroarylene" means a divalent heteroarene.

The term "arylene" means a divalent arene.

The term "phenylene" means a divalent benzene.

In some instances, the number of carbon atoms in a substituent (e.g., alkyl, alkenyl, alkynyl, cycloalkyl, heterocyclyl, heteroaryl, and aryl) is indicated by the prefix "$C_x$-$C_y$-", wherein x is the minimum and y is the maximum number of carbon atoms. Thus, for example, "$C_1$-$C_6$-alkyl" refers to an alkyl containing from 1 to 6 carbon atoms. Illustrating further, "$C_3$-$C_8$-cycloalkyl" means a saturated hydrocarbyl ring containing from 3 to 8 carbon ring atoms.

The term "$C_{x-y}$ branched chain alkyl" means a saturated hydrocarbyl substituent containing from x to y carbons wherein attachment occurs through a dialkyl trivalent- or trialkyl tetravalent-carbon radical. Examples of such substituents include isopentanyl (pentan-3-yl), neopentanyl(2,2-dimethylpropan-2-yl), heptan-4-yl, and 2,6-dimethylheptan-4-yl.

The term, "$C_{3-11}$ branched chain alkyl" means a saturated hydrocarbyl substituent containing from 3 to 11 carbons wherein attachment occurs through a dialkyl trivalent- or trialkyl tetravalent-carbon radical.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "hydroxyalkyl" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means replacement by a sulfur radical, i.e. a thiaether substituent means an ether substituent wherein a divalent sulfur atom is in the place of the ether oxygen atom. Such a substituent may be depicted as —S—. For example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, tetrahydropyranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), 1,4-dioxanyl, dioxothiomorpholinyl, oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, diazepinyl, pyridonyl (including pyrid-2(1H)-onyl and pyrid-4(1H)-onyl), furan-2(5H)-onyl, pyrimidinyl (including pyramid-2(1H)- onyl and pyramid-4(3H)-onyl), oxazol-2(3H)-onyl, 1H-imidazol-2(3H)-onyl, pyridazin-3(2H)-onyl, and pyrazin-2(1H)-onyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. Examples of bridged heterocyclyls include 2-oxatricyclo[3.3.1.1$^{3,7}$]decane. In a fused-ring heterocyclyl, two or more rings may be fused together, such that two rings share one common bond. Examples of fused ring heterocyclyls containing two or three rings include imidazopyrazinyl (including imidazo[1,2-a]pyrazinyl), imidazopyridinyl (including imidazo[1,2-a]pyridinyl), imidazopyridazinyl (including imidazo[1,2-b]pyridazinyl), thiazolopyridinyl (including thiazolo[5,4-c]pyridinyl, thiazolo[5,4-b]pyridinyl, thiazolo[4,5-b]pyridinyl, and thiazolo[4,5-c]pyridinyl), indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as dihydrochromenyl, tetrahydroisoquinolinyl, indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzxodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), benzo[d]thiazolyl, and benzisoxazinyl (including 1,2-benzisoxazinyl or 1,4-benzisoxazinyl).

The term "heterocycloalkyl" (alone or in combination with another term(s)) means a saturated heterocyclyl.

The term "$C_x$-$C_y$ heterocycloalkyl" means a heterocycloalkyl ring system containing from x to y ring atoms. For example "$C_3$-$C_7$ heterocycloalkyl" means a heterocycloalkyl ring system containing 3 to 7 ring atoms.

The term "heterocycloalkenyl" (alone or in combination with another term(s)) means a partially saturated heterocyclyl.

The term "$C_x$-$C_y$ heterocycloalkenyl" means a heterocycloalkenyl ring system containing from x to y ring atoms. For example "$C_3$-$C_7$ heterocycloalkenyl" means a heterocycloalkenyl ring system containing from 3 to 7 ring atoms.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryls include 6-membered ring substituents such as pyridyl, pyrazyl, pyrimidinyl, pyridazinyl, and 1,3,5-, 1,2,4- or 1,2,3-triazinyl; 5-membered ring substituents such as triazolyl, pyrrolyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl: 6/5-membered fused ring substituents such as imidazopyrazinyl (including imidazo[1,2-a]pyrazinyl)imidazopyridinyl (including imidazo[1,2-a]pyridinyl), imidazopyridazinyl (including imidazo[1,2-b]pyridazinyl), thiazolopyridinyl (including thiazolo[5,4-c]pyridinyl, thiazolo[5,4-b]pyridinyl, thiazolo[4,5-b]pyridinyl, and thiazolo[4,5-c]pyridinyl), benzo[d]thiazolyl, benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl. Heteroaryls may also be heterocycles having aromatic (4N+2 pi electron) resonance contributors such as pyridonyl (including pyrid-2(1H)-onyl and pyrid-4(1H)-onyl), pyrimidonyl (including pyramid-2(1H)-onyl and pyramid-4(3H)-onyl), pyridazin-3(2H)-onyl and pyrazin-2(1H)-onyl.

The term "$C_x$-$C_y$ heteroaryl" means a heteroaryl ring system containing from x to y ring atoms. For example "$C_5$-$C_6$ heteroaryl" means a heteroaryl ring system containing from 5 to 6 ring atoms.

The term "heteroarylene" means a divalent heteroaryl group.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "NH protecting group," as used herein, means trichloroethoxycarbonyl, tribromoethoxycarbonyl, benzyloxycarbonyl, para-nitrobenzylcarbonmyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydrofuranyl, 2,2,2-trichloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl) ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio) ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are sometimes designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry. Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4D_2O$. In addition to the above, relevant procedures and intermediates are disclosed, for instance, in Lizondo, J et al., *Drugs Fat*, 21(11), 1116 (1996); Brickner, S J et al., *J Med Chem*, 39(3), 673 (1996); Mallesham, B et al., *Org Lett*, 5(7), 963 (200(3); PCT publications WO1997010223, WO2005099353, WO1995007271, WO2006008754; U.S. Pat. Nos. 7,538,189; 7,534,814; 7,531,685; 7,528,131; 7,521, 421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-xL inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al. Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999)).

In addition, non-radio active isotope containing drugs, such as deuterated drugs called "heavy drugs," can be used for the treatment of diseases and conditions related to Bcl-xL activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J. Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Suitable groups for $X, Y^1, L^1, Y^2, Z^1, R^1, R^2, R^3, m, n$, and p in compounds of Formula (I) are independently selected. The described embodiments of the present invention may be combined. Such combination is contemplated and within the scope of the present invention. For example, it is contemplated that embodiments for any of $X, Y^1, L^1, Y^2, Z^1, R^1, R^2, R^3, m, n$, and p can be combined with embodiments defined for any other of $X, Y^1, L^1, Y^2, Z^1, R^1, R^2, R^3, m, n$, and p.

One embodiment of this invention, therefore, pertains to compounds or and therapeutically acceptable salts thereof, metabolites, prodrugs, salts of metabolites, and salts of prodrugs thereof, which are useful as inhibitors of anti-apoptotic Bcl-xL proteins, the compounds having Formula (I)

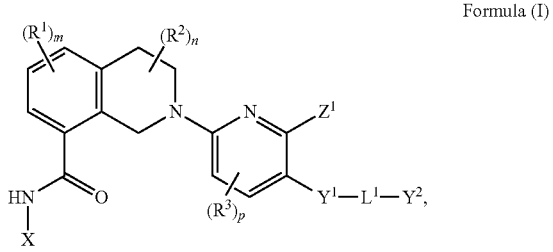

Formula (I)

wherein

X is heteroaryl; wherein the heteroaryl represented by X is optionally substituted with one, two, three, or four $R^4$;

$Y^1$ is phenylene, or $C_{5-6}$ heteroarylene; optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^1$ is optionally substituted with one, two, three, or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, F, Cl, Br and I;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—$S(O)_2$—$(CR^6R^7)_r$, $(CR^6R^7)_s$—$NR^{6A}C(O)$—$(CR^6R^7)_r$, $(CR^6R^7)_s$—$C(O)NR^{6A}$—$(CR^6R^7)_r$, $(CR^6R^7)_s$—$NR^{6A}$—$(CR^6R^7)_r$, $(CR^6R^7)_s$—$S(O)_2NR^{6A}$—$(CR^6R^7)_r$, and $(CR^6R^7)_s$—$NR^{6A}S(O)_2$—$(CR^7R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I; or $L^1$ is a bond; and $Y^2$ is selected from the group consisting of $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl represented by $Y^2$ are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein each $Y^2$ and each ring fused to $Y^2$ are optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I;

$Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and CN; or $Z^1$ is selected from the group consisting of

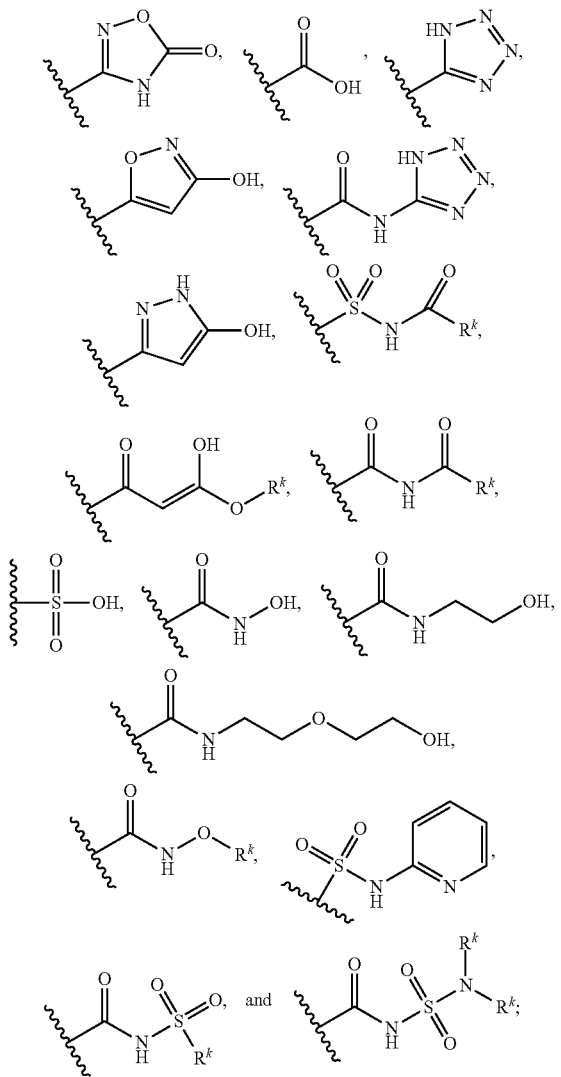

$R^1$, at each occurrence, is independently selected from the group consisting of halo, $C_{1-4}$ alkyl, $C_{2-4}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{2-6}$ haloalkyl;

$R^4$, at each occurrence, is independently selected from the group consisting of $NR^{12}R^{13}$, $OR^{12}$, CN, $NO_2$, halogen, $C(O)OR^{12}$, $C(O)NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^{14}$ and $R^{14}$;

$R^5$, at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

$R^6$ and $R^7$, at each occurrence, are each independently selected from the group consisting of hydrogen, $R^{15}$, $OR^{15}$, $SR^{15}S$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{14})$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $CO(O)H$, $C(O)H$, OH, CN, $N_3$, $NO_2$, F, Cl, Br and I;

$R^8$, at each occurrence, is independently selected from the group consisting of $C_{1-6}$ alkyl, $C_{2-6}$ alkenyl, $C_{2-6}$ alkynyl, $C_{1-6}$ haloalkyl, aryl, heterocyclyl, cycloalkyl, and cycloalkenyl; wherein the $R^8 C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^{16}$, $NR^{16}S(O)_2R^{16}$, $NHC(O)OR^{16}$, $NR^{16}C(O)OR^{16}$, $NHC(O)NH_2$, $NHC(O)NHR^{16}$, $NHC(O)N(R^{16})_2$, $NR^{16}C(O)NHR^{16}$, $NR^{16}C(O)N(R^{16})_2$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH$, $SO_2NHR^{16}$, $SO_2N(R^{16})_2$, $CO(O)H$, $C(O)H$, OH, CN, $N_3$, $NO_2$, F, Cl, Br and I; wherein the $R^8$ aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, $C(O)H$, (O), OH, CN, $NO_2$, $OCF_3$, $OCF_2CF_3$, F, Cl, Br and I;

$R^9$ is selected from the group consisting of $C_{1-6}$ alkyl, $C_{2-6}$ alkenyl, $C_{2-6}$ alkynyl, $C_{1-4}$ haloalkyl, cycloalkyl, phenyl and $(CH_2)_{1-4}$ phenyl; and $R^{10}$ and $R^{11}$, at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or $R^{10}$ and $R^{11}$, or $R^{10}$ and $R^9$, together with the atom to which each is attached are combined to form a heterocyclyl;

$R^k$, at each occurrence, is independently selected from the group consisting of $C_{1-6}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl; wherein the $R^k C_{1-6}$ alkyl, $C_{2-6}$ alkenyl, and $C_{2-6}$ alkynyl are optionally substituted with aryl, heterocyclyl, cycloalkyl, or cycloalkenyl;

$R^{12}$ and $R^{13}$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^{14}$, at each occurrence, is independently selected from the group consisting of $C_{1-4}$ alkyl, $C_{2-4}$ alkenyl, $C_{2-4}$ alkynyl and $C_{1-4}$ haloalkyl;

$R^{12}$ and $R^{13}$, or $R^{12}$ and $R^{14}$, at each occurrence, together with the atom to which each is attached, are optionally combined to form a heterocyclyl;

$R^{15}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the $R^{15} C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ alkoxy, aryl, heterocycloalkyl, heterocycloalkenyl, heteroaryl, cycloalkyl, and cycloalkenyl, $NH_2$, C(O)NH$_2$, SO$_2$NH$_2$, C(O)H, C(O)OH, (O), OH, CN, NO$_2$, OCF$_3$, OCF$_2$CF$_3$, F, Cl, Br and I;

R$^{16}$, at each occurrence, is independently selected from the group consisting of C$_{1-4}$ alkyl, C$_{2-4}$ alkenyl, C$_{2-4}$ alkynyl, C$_{1-4}$ haloalkyl, C$_{1-4}$ hydroxyalkyl, aryl, heterocycloalkyl, heterocycloalkenyl, heteroaryl, cycloalkyl, and cycloalkenyl; wherein the R$^{16}$C$_{1-4}$ alkyl, C$_{2-4}$ alkenyl, C$_{2-4}$ alkynyl, C$_{1-4}$ haloalkyl, and C$_{1-4}$ hydroxyalkyl are optionally substituted with one substituent independently selected from the group consisting of OCH$_3$, OCH$_2$CH$_2$OCH$_3$, and OCH$_2$CH$_2$NHCH$_3$;

q is 1, 2, or 3;
s is 0, 1, 2, or 3;
r is 0, 1, 2, or 3;
wherein the sum of s and r is 0, 1, or 2;
m is 0, 1, 2, or 3;
n is 0, 1, 2, 3, 4, 5, or 6; and
p is 0, 1, or 2.

In one embodiment of Formula (I), m is 0, 1, 2, or 3; n is 0, 1, 2, 3, 4, 5, or 6; and p is 0, 1, or 2. In another embodiment of Formula (I), n is 0 or 1. In another embodiment of Formula (I), n is 0 or 1; and each R$^2$ is independently deuterium or C$_{1-6}$ alkyl. In another embodiment of Formula (I), m, n, and p are 0.

In one embodiment of Formula (I), X is heteroaryl, which is optionally substituted with one, two, three or four R$^4$. In another embodiment of Formula (I), X is heteroaryl, which is unsubstituted. In another embodiment of Formula (I), X is heteroaryl, which is substituted with one R$^4$. In another embodiment of Formula (I), X is heteroaryl, which is substituted with two R$^4$. In another embodiment of Formula (I), X is heteroaryl, which is substituted with one R$^4$, and R$^4$ is OR$^{12}$ or halogen. In another embodiment of Formula (I), X is heteroaryl, which is substituted with two R$^4$, and each R$^4$ is independently OR$^{12}$ or halogen. In another embodiment of Formula (I), X is heteroaryl, which is substituted with one R$^4$, and R$^4$ is Cl, F, or methoxy. In another embodiment of Formula (I), X is heteroaryl, which is substituted with two R$^4$, and each R$^4$ is independently F.

In one embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four R$^4$. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R$^4$. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two R$^4$. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R$^4$, and R$^4$ is OR$^{12}$ or halogen. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two R$^4$, and each R$^4$ is independently OR$^{12}$ or halogen. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R$^4$, and R$^4$ is Cl, F, or methoxy. In another embodiment of Formula (I), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two R$^4$, and each R$^4$ is independently F.

In one embodiment of Formula (I), X is benzo[d]thiazolyl, which is optionally substituted with one, two, three or four R$^4$. In another embodiment of Formula (I), X is benzo[d]thiazolyl, which is unsubstituted. In another embodiment of Formula (I), X is benzo[d]thiazolyl, which is substituted with one R$^4$. In another embodiment of Formula (I), X is benzo[d]thiazolyl, which is substituted with two R$^4$. In another embodiment of Formula (I), X is benzo[d]thiazolyl, which is substituted with one R$^4$, and R$^4$ is OR$^{12}$ or halogen. In another embodiment of Formula (I), X is benzo[d]thiazolyl, which is substituted with two R$^4$, and each R$^4$ is independently OR$^{12}$ or halogen. In another embodiment of Formula (I), X is benzo[d]thiazolyl, which is substituted with one R$^4$, and R$^4$ is Cl, F, or methoxy. In another embodiment of Formula (I), X is benzo[d]thiazolyl, which is substituted with two R$^4$, and each R$^4$ is independently F.

In one embodiment of Formula (I), Z$^1$ is selected from the group consisting of C(O)OR$^9$, C(O)NR$^{10}$R$^{11}$, C(O)R$^{11}$, NR$^{10}$C(O)R$^{11}$, NR$^{10}$C(O)NR$^{10}$R$^{11}$, OC(O)NR$^{10}$R$^{11}$, NR$^{10}$C(O)OR$^9$, C(=NOR$^{10}$)NR$^{10}$R$^{11}$, NR$^{10}$C(=NCN)NR$^{10}$R$^{11}$, NR$^{10}$S(O)$_2$NR$^{10}$R$^{11}$, S(O)$_2$R$^9$, S(O)$_2$NR$^{10}$R$^{11}$, N(R$^{10}$)S(O)$_2$R$^{11}$, NR$^{10}$C(=NR$^{11}$)NR$^{10}$R$^{11}$, C(=S)NR$^{10}$R$^{11}$, C(=NR$^{10}$)NR$^{10}$R$^{11}$, halogen, NO$_2$, and CN; or Z$^1$ is selected from the group consisting of

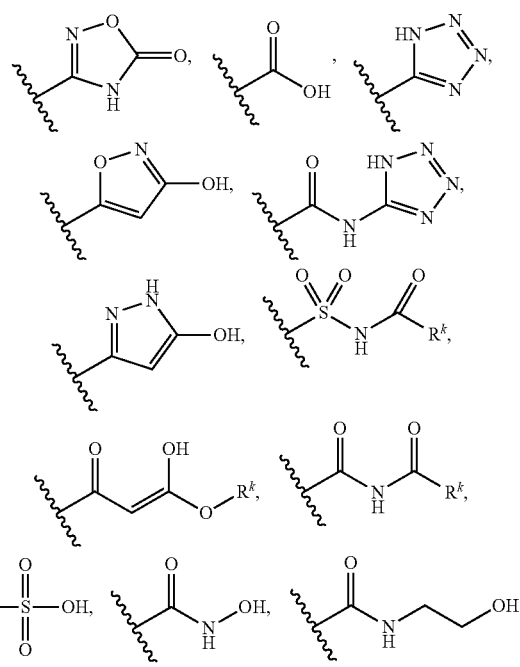

-continued

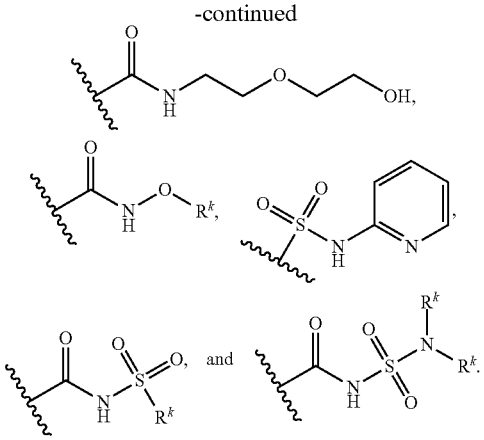

In another embodiment of Formula (I), $Z^1$ is

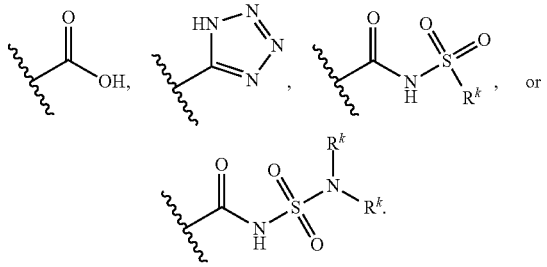

In another embodiment of Formula (I), $Z^1$ is

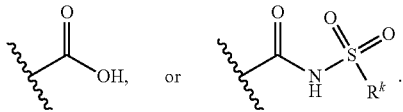

In another embodiment of Formula (I), $Z^1$ is

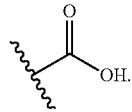

In one embodiment of Formula (I), $Y^1$ is phenylene, or $C_{5-6}$ heteroarylene; optionally fused to one or two rings selected from the group consisting of $C_{3-8}$ cycloalkane, $C_{3-8}$ cycloalkene, benzene. $C_{5-6}$ heteroarene, $C_{3-8}$ heterocycloalkane, and $C_{3-8}$ heterocycloalkene; wherein $Y^1$ is optionally substituted with one, two, three, or four substituents independently selected from the group consisting of $R^5$, $OR^5$ $SR^5$ $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, $F$, $Cl$, $Br$ and $I$. In another embodiment of Formula (I), $Y^1$ is phenylene or $C_{5-6}$ heteroarylene; optionally fused to one or two rings selected from the group consisting of $C_{5-6}$ heteroarene and $C_{3-8}$ heterocycloalkane; wherein $Y^1$ is optionally substituted with one or two substituents independently selected from the group consisting of $R^5$, $CO(O)R^5$, $CO(O)H$, $CN$, $F$, $Cl$, $Br$ and $I$. In another embodiment of Formula (I), $Y^1$ is pyrrolyl, pyrazolyl, triazolyl, pyridinyl, or phenyl. In another embodiment of Formula (I), $Y^1$ is pyrrolyl, pyrazolyl, or triazolyl. In another embodiment of Formula (I), $Y^1$ is pyridinyl or phenyl. In another embodiment of Formula (I), $Y^1$ is pyrrolyl. In another embodiment of Formula (I), $Y^1$ is pyrazolyl. In another embodiment of Formula (I), $Y^1$ is triazolyl. In another embodiment of Formula (I), $Y^1$ is pyridinyl. In another embodiment of Formula (I), $Y^1$ is phenyl. In another embodiment of Formula (I), $Y^1$ is pyrrolyl, pyrazolyl, triazolyl, pyridinyl, or phenyl; wherein the pyrrolyl, pyrazolyl, triazolyl, pyridinyl, and phenyl represented by $Y^1$ are optionally substituted with one, or two substituents independently selected from the group consisting of $R^5$, $CO(O)R^5$, $CO(O)H$, $CN$, $F$, $Cl$, $Br$ and $I$.

In one embodiment of Formula (I), $L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—$NR^{6A}$C(O)—$(CR^6R^7)_r$, $(CR^6R^7)_s$—C(O)$NR^{6A}$—$(CR^6R^7)_r$, $(CR^6R^7)_s$—$NR^{6A}$—$(CR^6R^7)_r$, $(CR^6R^7)_s$—S(O)$_2$$NR^{6A}$—$(CR^6R^7)_r$, and $(CR^6R^7)_s$—$NR^{6A}$S(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two rings selected from the group consisting of $C_{3-7}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, $F$, $Cl$, $Br$ and $I$; or $L^1$ is a bond; and $Y^2$ is selected from the group consisting of $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl represented by $Y^2$ are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein each $Y^2$ and each ring fused to $Y^2$ are optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, $F$, $Cl$, $Br$ and $I$.

In another embodiment of Formula (I), $L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S(O)$_2$—$(CR^6R^7)_r$, $(CR^6R^7)_s$—$NR^{6A}$C(O)—$NR^{6A}$—$(CR^6R^7)_r$, and $(CR^6R^7)_s$—$NR^{6A}$S(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two benzene rings; wherein $Y^2$ is optionally substituted with one, two, or three substituents independently selected from the group consisting of $R^8$, $OR^8$, $SO_2R^8$, $CO(O)R^8$, $NHR^8$, $N(R^8)_2$, $C(O)H$, $OH$, $CN$, $NO_2$, F, Cl, Br and I; or $L^1$ is a bond; and $Y^2$ is selected from the group consisting of $C_{3-7}$ cycloalkyl, phenyl, and $C_{3-7}$ heterocyclyl; wherein the $C_{3-7}$ cycloalkyl, phenyl, and $C_{3-7}$ heterocyclyl represented by $Y^2$ are optionally fused to one benzene ring; wherein each $Y^2$ and each ring fused to $Y^2$ are optionally substituted with one substituent independently selected from the group consisting of $R^8$, $C(O)NHR^8$, F, Cl, Br and I.

In another embodiment of Formula (I), $L^1$ is $(CR^6R^7)_q$; and $Y^2$ is selected from the group consisting of $C_{3-7}$ cycloalkyl, $C_{4-7}$ cycloalkenyl, phenyl, and $C_{3-7}$ heterocyclyl; wherein $R^6$ and $R^7$, at each occurrence, are $R^{15}$ or hydrogen; and q is 1, 2, or 3.

In another embodiment of Formula (I), $L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S(O)$_2$—$(CR^6R^7)_r$, $(CR^6R^7)_s$—$NR^{6A}C(O)$—$(CR^6R^7)_r$, $(CR^6R^7)_s$—$NR^{6A}$—$(CR^6R^7)_r$, and $(CR^6R^7)_s$—$NR^{6A}S(O)_2$—$(CR^6R^7)_r$; q is 1, 2, or 3; s is 0; r is 0 or 1; $R^{6A}$ is independently selected from the group consisting of hydrogen, and $C_{1-6}$ alkyl; and $R^6$ and $R^7$, at each occurrence, are hydrogen.

In one embodiment of Formula (I), X is heteroaryl; wherein the heteroaryl represented by X is optionally substituted with one or two $R^4$;

$Y^1$ is phenylene or $C_{5-6}$ heteroarylene; optionally fused to one ring selected from the group consisting of $C_{5-6}$ heteroarene and $C_{3-8}$ heterocycloalkane; wherein $Y^1$ is optionally substituted with one or two substituents independently selected from the group consisting of $R^5$, $CO(O)R^5$, $CO(O)H$, CN, F, Cl, Br and I;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S(O)$_2$—$(CR^6R^7)_r$, $(CR^6R^7)_s$—$NR^{6A}C(O)$—$(CR^6R^7)_r$, $(CR^6R^7)_s$—$NR^{6A}$—$(CR^6R^7)_r$, and $(CR^6R^7)_s$—$NR^{6A}S(O)_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one benzene ring; wherein $Y^2$ is optionally substituted with one, two, or three substituents independently selected from the group consisting of $R^8$, $OR^8$, $SO_2R^8$, $CO(O)R^8$, $NHR^8$, $N(R^8)_2$, $C(O)H$, $OH$, $CN$, $NO_2$, F, Cl, Br and I; or $L^1$ is a bond; and $Y^2$ is selected from the group consisting of $C_{3-7}$ cycloalkyl, phenyl, and $C_{3-7}$ heterocyclyl; wherein the $C_{3-7}$ cycloalkyl, phenyl, and $C_{3-7}$ heterocyclyl represented by $Y^2$ are optionally fused to one benzene ring, wherein each $Y^2$ and each ring fused to $Y^2$ are optionally substituted with one substituent independently selected from the group consisting of $R^8$ and $C(O)NHR^8$;

$Z^1$ is selected from the group consisting of

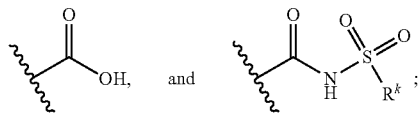

$R^2$, at each occurrence, is independently $C_{1-6}$ alkyl;

$R^4$, at each occurrence, is independently selected from the group consisting of $OR^{12}$ and halogen;

$R^5$, at each occurrence, is independently selected from the group consisting of $C_{1-6}$ alkyl, $C_{1-6}$ haloalkyl, $C_{1-6}$ hydroxyalkyl, aryl, and cycloalkyl;

$R^{6A}$ is independently selected from the group consisting of hydrogen and $C_{1-6}$ alkyl;

$R^6$ and $R^7$, at each occurrence, are each independently selected from the group consisting of hydrogen, $R^{15}$, and $CO(O)R^{15}$;

$R^8$, at each occurrence, is independently selected from the group consisting of $C_{1-6}$ alkyl, $C_{2-4}$ alkynyl, aryl, heterocyclyl, and cycloalkyl; wherein the $R^8 C_{1-6}$ alkyl, and $C_{2-6}$ alkynyl are optionally substituted with one, two, or three substituents independently selected from the group consisting of $R^{16}$, $OR^{16}$, $SO_2R^{16}$, $C(O)R^{16}$, $N(R^{16})_2$, OH, F, Cl, Br and I; wherein the $R^8$ aryl and heterocyclyl are optionally substituted with one substituent independently selected from the group consisting of $C_{1-6}$ alkyl, F, Cl, Br and I;

$R^k$, at each occurrence, is independently $C_{1-6}$ alkyl;

$R^{12}$ and $R^{13}$, at each occurrence, are each independently $C_{1-4}$ alkyl;

$R^{15}$, at each occurrence, is independently selected from the group consisting of $C_{1-4}$ alkyl, and aryl; wherein the $R^{15}C_{1-4}$ alkyl is optionally substituted with one substituent independently selected from the group consisting $C_{1-4}$ alkoxy, and heterocycloalkyl;

$R^{16}$, at each occurrence, is independently selected from the group consisting of $C_{1-4}$ alkyl, aryl, heterocycloalkyl, and heteroaryl;

q is 1, 2, or 3;

s is 0;

r is 0, or 1;

m is 0;

n is 0, or 1; and p is 0.

Still another embodiment pertains to a compound having Formula (I) selected from the group consisting of 6-[8-(1,3-benzothiazol-2-ylcarbamoyl)-3,4-dihydroisoquinolin-2(1H)-yl]-3-(1-benzyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(pyridin-4-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(pyridin-3-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-hydroxybenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(1-phenylethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{4-[2-(dimethylamino)ethoxy]benzyl}-1H-pyrazol-4-yl)pyridine-2-carboxylic acid;

3-(1-benzyl-1H-pyrazol-4-yl)-6-{8-[(5,6-difluoro-1,3-benzothiazol-2-yl)carbamoyl]-3,4-dihydroisoquinolin-2(1H)-yl}pyridine-2-carboxylic acid;

6-[8-(1,3-benzothiazol-2-ylcarbamoyl)-3,4-dihydroisoquinolin-2(1H)-yl]-3-{1-[2-(4-fluorophenyl)ethyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(3-chlorobenzyl)-1H-pyrazol-4-yl]pyridine-2-carboxylic acid;

3-(1-benzyl-1H-pyrazol-4-yl)-6-{8-[(6-fluoro-1,3-benzothiazol-2-yl)carbamoyl]-3,4-dihydroisoquinolin-2(1H)-yl}pyridine-2-carboxylic acid;

3-(1-benzyl-1H-pyrazol-4-yl)-6-{8-[(6-methoxy-1,3-benzothiazol-2-yl)carbamoyl]-3,4-dihydroisoquinolin-2(1H)-yl}pyridine-2-carboxylic acid;

6-[8-(1,3-benzothiazol-2-ylcarbamoyl)-3,4-dihydroisoquinolin-2(1H)-yl]-3-(1-benzyl-3,5-dimethyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(3-methylbenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3-methoxybenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-chlorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[3-(benzyloxy)benzyl]-1H-pyrazol-1-yl}pyridine-2-carboxylic acid;

6-[8-(1,3-benzothiazol-2-ylcarbamoyl)-3,4-dihydroisoquinolin-2(1H)-yl]-3-[1-(3-hydroxybenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{3-[2-(dimethylamino)ethoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-benzyl-3-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-benzyl-5-methyl-1H-pyrazol-4-yl)pyridine-2-carboxylic acid;

3-(1-benzyl-1H-pyrazol-4-yl)-6-{8-[(7-chloro-1,3-benzothiazol-2-yl)carbamoyl]-3,4-dihydroisoquinolin-2(1H)-yl}pyridine-2-carboxylic acid;

6-[8-(1,3-benzothiazol-2-ylcarbamoyl)-3,4-dihydroisoquinolin-2(1H)-yl]-3-(1-{[6-(pyrrolidin-1-yl)pyridin-2-yl]methyl}-1-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-phenyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(3-cyanobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2-chlorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(pyridin-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-benzyl-3-cyano-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(naphthalen-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[3-(3-methyl-1,2,4-oxadiazol-5-yl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-benzyl-3-(hydroxymethyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[2-(benzyloxy)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(5-methyl-1-{[6-(pyrrolidin-1-yl)pyridin-2-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-benzyl-3-(ethoxycarbonyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[3-(dimethylamino)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-benzyl-3-carboxy-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(2-hydroxybenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2,3-dihydro-1H-inden-1-yl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2-phenylethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3,4-dihydro)-2H-chromen-4-yl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{2-[2-(dimethylamino)ethoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(2-fluorobenzyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(cyclohexylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(cyclohexylmethyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-{[3-(dimethylamino)propyl]amino}-3-nitrobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-fluoro-3-nitrobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{2-[2-(morpholin-4-yl)ethoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{2-[3-(dimethylamino)propoxy]benzyl)-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[2-(pyridin-4-yl-methoxy)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{2-[2-(dimethylamino)ethoxy]benzyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(tetrahydro-2H-pyran-4-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{2-[3-(dimethylamino)prop-1-yn-1-yl]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(2,3-difluorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3,5-difluorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2,5-difluorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2,6-difluorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(tetrahydro-2H-pyran-3-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2-nitrobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(biphenyl-3-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2,2-dimethylpropyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2-cyclohexylethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[3-(trifluoromethyl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(biphenyl-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(cyclopentylmethyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3-formylbenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-benzyl-5-phenyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[5-methyl-1-(tetrahydro-2H-pyran-3-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[(1-phenylcyclohexyl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{3-[(dimethylamino)methyl]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[3-(methylsulfonyl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(cyclohexylmethyl)-5-cyclopropyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3,5-di-tert-butylbenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[2-morpholin-4-ylsulfonyl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(4,4-difluoro)cyclohexyl)methyl]-5-methyl-1H-pyrazol-4-yl}pyridine-2-carboxylic acid;

6-[8-(1,3-benzo thiazol-2-ylcarbamoyl)-3,4-dihydroisoquinolin-2(1H)-yl]-3-(1-{[1-(trifluoromethyl)cyclohexyl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(diphenylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[2-(morpholin-4-yl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[3-(morpholin-4-yl)-1-phenylpropyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[1-(tert-butoxycarbonyl)piperidin-4-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(5-methyl-1-{2-[2-(morpholin-4-yl)ethoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[2-(dimethylamino)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(5-methyl-1-{2-[3-(morpholin-4-yl)propoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{5-methyl-1-[(1-methylcyclohexyl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[2-(4-chlorophenyl)-4,4-dimethylcyclohex-1-en-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(cyclohexylmethyl)-5-ethyl-1H-pyrazol-4-yl]pyridine-2-carboxylic acid;

6-[8-(1,3-benzo thiazol-2-ylcarbamoyl)-3,4-dihydroisoquinolin-2(1H)-yl]-3-(1-{[(1R,2R,5R)-6,6-dimethylbicyclo[3.1.1]hept-2-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[(1S,2R,5S)-6,6-dimethylbicyclo[3.1.1]hept-2-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methylpropyl)cyclohexyl]methyl}-1H-pyrazol)-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)cyclohexyl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[2-(2-methoxyethoxy)benzyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[(1R,2R,4R)-bicyclo[2.2.1]hept-5-en-2-ylmethyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,3-dimethylcyclohexyl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(3-methoxy-1-phenylpropyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-methoxy-1-phenylbutyl)-1H-pyrazol-4-yl]pyridine-2-carboxylic acid;
6-[8-(1,3-benzothiazol-2-ylcarbamoyl)-3,4-dihydroisoquinolin-2(1H)-yl]-3-[1-(2-methoxy-2-oxo-1-phenylethyl)-1H-pyrazol-4-yl]pyridine-2-carboxylic acid;
6-[8-(1,3-benzothiazol-2-ylcarbamoyl)-3,4-dihydroisoquinolin-2(1H)-yl]-3-[1-(2-cyclohexyl-1-phenylethyl)-1H-pyrazol-4-yl]pyridine-2-carboxylic acid;
6-[8-(1,3-benzothiazol-2-ylcarbamoyl)-3,4-dihydroisoquinolin-2(1H)-yl]-3-(1-{[1-(3-methoxypropyl)cyclohexyl]methyl}-5-methyl-1H-pyrazol-4-yl)pyridine-2-carboxylic acid;
6-[8-(1,3-benzothiazol-2-ylcarbamoyl)-3,4-dihydroisoquinolin-2(1H)-yl]-3-(1-{2-[3-hydroxy-2-(hydroxymethyl)-2-methylpropoxy]benzyl}-5-methyl-1H-pyrazol-4-yl)pyridine-2-carboxylic acid;
6-[8-(1,3-benzothiazol-2-ylcarbamoyl)-3,4-dihydroisoquinolin-2(1H)-yl]-3-{5-methyl-1-[2-(tetrahydro-2H-pyran-4-ylmethoxy)benzyl]-1H-pyrazol-4-yl}pyridine-2-carboxylic acid;
6-[8-(1,3-benzothiazol-2-ylcarbamoyl)-3,4-dihydroisoquinolin-2(1H)-yl]-3-{1-[2-(1,4-dioxan-2-ylmethoxy)benzyl]-5-methyl-1H-pyrazol-4-yl}pyridine-2-carboxylic acid;
6-[8-(1,3-benzothiazol-2-ylcarbamoyl)-3,4-dihydroisoquinolin-2(1H)-yl]-3-(1-{[1-(2-methoxyethoxy)cyclohexyl]methyl}-5-methyl-1H-pyrazol-4-yl)pyridine-2-carboxylic acid;
6-[8-(1,3-benzothiazol-2-ylcarbamoyl)-3,4-dihydroisoquinolin-2(1H)-yl]-3-(4-phenoxyphenyl)pyridine-2-carboxylic acid;
6-[8-(1,3-benzothiazol-2-ylcarbamoyl)-3,4-dihydroisoquinolin-2(1H)-yl]-3-(3-phenoxyphenyl)pyridine-2-carboxylic acid;
6-[8-(1,3-benzothiazol-2-ylcarbamoyl)-3,4-dihydroisoquinolin-2(1H)-yl]-3-[3-(4-nitrophenoxy)phenyl]pyridine-2-carboxylic acid;
6-[8-(1,3-benzothiazol-2-ylcarbamoyl)-3,4-dihydroisoquinolin-2(1H)-yl]-3-[3-(4-chlorophenoxy)phenyl]pyridine-2-carboxylic acid;
6-[8-(1,3-benzothiazol-2-ylcarbamoyl)-3,4-dihydroisoquinolin-2(1H)-yl]-3-(3-benzylphenyl)pyridine-2-carboxylic acid;
6-[8-(1,3-benzothiazol-2-ylcarbamoyl)-3,4-dihydroisoquinolin-2(1H)-yl]-3-[3-(cyclohexylmethyl)-2-methylphenyl]pyridine-2-carboxylic acid;
6-[8-(1,3-benzothiazol-2-ylcarbamoyl)-3,4-dihydroisoquinolin-2(1H)-yl]-3-(4-methyl-3-phenoxyphenyl)pyridine-2-carboxylic acid;
6-[8-(1,3-benzothiazol-2-ylcarbamoyl)-3,4-dihydroisoquinolin-2(1H)-yl]-3-(2-methyl-5-phenoxyphenyl)pyridine-2-carboxylic acid;
6-[8-(1,3-benzothiazol-2-ylcarbamoyl)-3,4-dihydroisoquinolin-2(1H)-yl]-3-(2-methyl-3-phenoxyphenyl)pyridine-2-carboxylic acid;
6-[8-(1,3-benzothiazol-2-ylcarbamoyl)-3,4-dihydroisoquinolin-2(1H)-yl]-3-(2-methyl-4-phenoxyphenyl)pyridine-2-carboxylic acid;
6-[8-(1,3-benzothiazol-2-ylcarbamoyl)-3,4-dihydroisoquinolin-2(1H)-yl]-3-[3-(cyclohexylethoxy)-2-methylphenyl]pyridine-2-carboxylic acid;
6-[8-(1,3-benzothiazol-2-ylcarbamoyl)-3,4-dihydroisoquinolin-2(1H)-yl]-3-[4-(cyclohexyloxy)-2-methylphenyl]pyridine-2-carboxylic acid;
6-[8-(1,3-benzothiazol-2-ylcarbamoyl)-3,4-dihydroisoquinolin-2(1H)-yl]-3-[3-(cyclohexyloxy)-2-methylphenyl]pyridine-2-carboxylic acid;
6-[8-(1,3-benzothiazol-2-ylcarbamoyl)-3,4-dihydroisoquinolin-2(1H)-yl]-3-[4-(cyclohexylmethoxy)-2-methylphenyl]pyridine-2-carboxylic acid;
6-[8-(1,3-benzothiazol-2-ylcarbamoyl)-3,4-dihydroisoquinolin-2(1H)-yl]-3-[2-cyano-3-(cyclohexyloxy)phenyl]pyridine-2-carboxylic acid;
6-[8-(1,3-benzothiazol-2-ylcarbamoyl)-3,4-dihydroisoquinolin-2(1H)-yl]-3-[2-chloro-3-(cyclohexyloxy)phenyl]pyridine-2-carboxylic acid;
6-[8-(1,3-benzothiazol-2-ylcarbamoyl)-3,4-dihydroisoquinolin-2(1H)-yl]-3-[3-(cyclohexylamino)-2-methylphenyl]pyridine-2-carboxylic acid;
6-[8-(1,3-benzothiazol-2-ylcarbamoyl)-3,4-dihydroisoquinolin-2(1H)-yl]-3-[3-(cyclohexyloxy)-2-fluorophenyl]pyridine-2-carboxylic acid;
6-[8-(1,3-benzothiazol-2-ylcarbamoyl)-3,4-dihydroisoquinolin-2(1H)-yl]-3-[3-(cyclohexyloxy)-2-(trifluoromethyl)phenyl]pyridine-2-carboxylic acid;
6-[8-(1,3-benzothiazol-2-ylcarbamoyl)-3,4-dihydroisoquinolin-2(1H)-yl]-3-{3-[(3,3-dimethylcyclohexyl)oxy]-2-methyphenyl}pyridine-2-carboxylic acid;
6-[8-(1,3-benzothiazol-2-ylcarbamoyl)-3,4-dihydroisoquinolin-2(1H)-yl]-3-(1-benzyl-1H-1,2,3-triazol-4-yl)pyridine-2-carboxylic acid;
6-[8-(1,3-benzothiazol-2-ylcarbamoyl)-3,4-dihydroisoquinolin-2(1H)-yl]-3-[1-benzyl-5-(ethoxycarbonyl)-2-methyl-1H-pyrrol-3-yl]pyridine-2-carboxylic acid;
6-[8-(1,3-benzothiazol-2-ylcarbamoyl)-3,4-dihydroisoquinolin-2(1H)-yl]-3-(1-benzyl-5-carboxy-2-methyl-1H-pyrrol-3-yl)pyridine-2-carboxylic acid;
6-[8-(1,3-benzothiazol-2-ylcarbamoyl)-3,4-dihydroisoquinolin-2(1H)-yl]-3-(1-benzyl-1H-pyrrol-3-yl)pyridine-2-carboxylic acid;
6-[8-(1,3-benzothiazol-2-ylcarbamoyl)-3,4-dihydroisoquinolin-2(1H)-yl]-3-{1-[(4-methylphenyl)sulfonyl]-1H-pyrrol-3-yl}pyridine-2-carboxylic acid;
6-[8-(1,3-benzothiazol-2-ylcarbamoyl)-3,4-dihydroisoquinolin-2(1H)-yl]-3-(1-benzoyl-1H-pyrrol-3-yl)pyridine-2-carboxylic acid;
6-[8-(1,3-benzothiazol-2-ylcarbamoyl)-3,4-dihydroisoquinolin-2(1H)-yl]-3-[1-(phenylsulfonyl)-1H-pyrrol-3-yl]pyridine-2-carboxylic acid;
6-[8-(1,3-benzothiazol-2-ylcarbamoyl)-3,4-dihydroisoquinolin-2(1H)-yl]-3-(1-benzyl-5-cyano-2-methyl-1H-pyrrol-3-yl)pyridine-2-carboxylic acid;
6-[8-(1,3-benzothiazol-2-ylcarbamoyl)-3,4-dihydroisoquinolin-2(1H)-yl]-3-[5-cyano-1-(cyclohexylmethyl)-2-methyl-1H-pyrrol-3-yl]pyridine-2-carboxylic acid;
6-[8-(1,3-benzothiazol-2-ylcarbamoyl)-3,4-dihydroisoquinolin-2(1H)-yl]-3-(5-cyano-2-methyl-1-{[1-(piperidin-1-yl)cyclohexyl]methyl}-1H-pyrrol-3-yl)pyridine-2-carboxylic acid;
6,6'-bis[8-(1,3-benzothiazol-2-ylcarbamoyl)-3,4-dihydroisoquinolin-2(1H)-yl]-3,3'-bipyridine-2,2'-dicarboxylic acid;
6-[8-(1,3-benzothiazol-2-ylcarbamoyl)-3,4-dihydroisoquinolin-2(1H)-yl]-3-(2-benzyl-1,2,3,4-tetrahydroisoquinolin-6-yl)pyridine-2-carboxylic acid;
6-[8-(1,3-benzothiazol-2-ylcarbamoyl)-3,4-dihydroisoquinolin-2(1H)-yl]-3-(1-{[1-(2-methoxyethyl)cycloheptyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(piperidin-4-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[2-(pyridin-2-ylmethyl)-1,2,3,4-tetrahydroisoquinolin-6-yl]pyridine-2-carboxylic acid;

6-[8-(1,3-benzothiazol-2-ylcarbamoyl)-3,4-dihydroisoquinolin-2(1H)-yl]-3-[2-(cyclohexylmethyl)-1,2,3,4-tetrahydroisoquinolin-6-yl]pyridine-2-carboxylic acid;

6-[8-(1,3-benzothiazol-2-ylcarbamoyl)-3,4-dihydroisoquinolin-2(1H)-yl]-2'-(cyclohexyloxy)-3'-methyl-3,4'-bipyridine-2-carboxylic acid;

6-[8-(1,3-benzothiazol-2-ylcarbamoyl)-3,4-dihydroisoquinolin-2(1H)-yl]-2'-(cyclohexyloxy)-3,4'-bipyridine-2-carboxylic acid;

6-[8-(1,3-benzothiazol-2-ylcarbamoyl)-3,4-dihydroisoquinolin-2(1H)-yl]-2'-phenoxy-3,4'-bipyridine-2-carboxylic acid;

6-[8-(1,3-benzothiazol-2-ylcarbamoyl)-3,4-dihydroisoquinolin-2(1H)-yl]-3-(1-benzyl-1H-pyrrolo[2,3-b]pyridin-3-yl)pyridine-2-carboxylic acid;

6-[8-(1,3-benzothiazol-2-ylcarbamoyl)-3,4-dihydroisoquinolin-2(1H)-yl]-3'-methyl-2'-phenoxy-3,4'-bipyridine-2-carboxylic acid;

6-[8-(1,3-benzothiazol-2-ylcarbamoyl)-3,4-dihydroisoquinolin-2(1H)-yl]-3'-methyl-2'-[methyl(phenyl)amino]-3,4'-bipyridine-2-carboxylic acid;

6-[8-(1,3-benzothiazol-2-ylcarbamoyl)-3,4-dihydroisoquinolin-2(1H)-yl]-3-(1-{[1-(methoxymethyl)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3,3-dimethyl-1-(morpholin-4-yl)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)-3,3-dimethylcyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(3-methoxypropyl)cycloheptyl]methyl}-5-methyl-1H-pyrazol-4-yl)pyridine-2-carboxylic acid;

N-(1,3-benzothiazol-2-yl)-2-{5-(1-{[1-(2-methoxyethyl)cycloheptyl]methyl}-5-methyl-1H-pyrazol-4-yl)-6-[(methylsulfonyl)carbamoyl]pyridin-2-yl}-1,2,3,4-tetrahydroisoquinoline-8-carboxamide;

6-[8-(1,3-benzothiazol-2-ylcarbamoyl)-3,4-dihydroisoquinolin-2(1H)-yl]-3-[1-(tetrahydro-2H-pyran-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[(1R,2R,3R,5S)-2-(2-methoxyethyl)-6,6-dimethylbicyclo[3.1.1]hept-3-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethoxy)cycloheptyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[1-cyclohexyl-3-(morpholin-4-yl)propyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-benzyl-1H-indazol-5-yl)pyridine-2-carboxylic acid;

6-[8-(1,3-benzothiazol-2-ylcarbamoyl)-3,4-dihydroisoquinolin-2(1H)-yl]-3-[5-methyl-1-(tetrahydro-2H-pyran-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[5-methyl-1-({1-[3-(morpholin-4-yl)propoxy]cycloheptyl}-methyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{2-methyl-3-[methyl(phenyl)amino]phenyl}pyridine-2-carboxylic acid;

6-[8-(1,33-benzothiazol-2-ylcarbamoyl)-3,4-dihydroisoquinolin-2(1H)-yl]-3-{1-[(1-methoxy-3,3-dimethylcyclohexyl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[(1S,2R,5S)-6,6-dimethylbicyclo[3.1.1]hept-2-yl]methyl}-5-methyl-1H-1,2,3-triazol-4-yl)pyridine-2-carboxylic acid;

6-[8-(1,3-benzothiazol-2-ylcarbamoyl)-3,4-dihydroisoquinolin-2(1H)-yl]-3-{3-[(3,3-dimethylcyclohexyl)(methyl)amino]-2-methylphenyl}pyridine-2-carboxylic acid;

6-[8-(1,3-benzothiazol-2-ylcarbamoyl)-3,4-dihydroisoquinolin-2(1H)-yl]-3-(5-methyl-1-{[1-(morpholin-4-yl)cyclohexyl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-2'-[cyclohexyl(methyl)amino]-3'-methyl-3,4'-bipyridine-2-carboxylic acid;

N-(1,3-benzothiazol-2-yl)-2-(5-{1-[(1-methoxy-3,3-dimethylcyclohexyl)methyl]-5-methyl-1H-pyrazol-4-yl}-6-[(methylsulfonyl)carbamoyl]pyridin-2-yl)-1,2,3,4-tetrahydroisoquinoline-8-carboxamide;

6-[8-(1,3-benzothiazol-2-ylcarbamoyl)-1-methyl-3,4-dihydroisoquinolin-2(1H)-yl]-3-{5-methyl-1-[(1-methylcyclohexyl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3'-cyano-2'-[cyclohexyl(methyl)amino]-3,4'-bipyridine-2-carboxylic acid;

6-[8-(1,3-benzothiazol-2-ylcarbamoyl)-3,4-dihydroisoquinolin-2(1H)-yl]-3-{1-[(1-methoxycyclohexyl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(1-methoxy-3,3-dimethylcyclohexyl)methyl]-5-methyl-1H-1,2,3-triazol-4-yl}pyridine-2-carboxylic acid;

6-[8-(1,3-benzothiazol-2-ylcarbamoyl)-3,4-dihydroisoquinolin-2(1H)-yl]-3-[1-({1-[2-(1,1-dioxidothiomorpholin-4-yl)ethoxy]cyclohexyl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-(5-cyano-2-methyl-1-{[1-(morpholin-4-yl)cyclohexyl]methyl}-1H-pyrrol-3-yl)pyridine-2-carboxylic acid;

6-[8-(1,3-benzothiazol-2-ylcarbamoyl)-3,4-dihydroisoquinolin-2(1H)-yl]-3-(1-{[1-(2-hydroxyethoxy)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2,3-dimethoxypropoxy)cycloheptyl]methyl}-5-methyl-1H-pyrazol-4-yl)pyridine-2-carboxylic acid;

N-(1,3-benzothiazol-2-yl)-2-{5-[5-cyano-1-(cyclohexylmethyl)-2-methyl-1H-pyrrol-3-yl]-6-[(methylsulfonyl)carbamoyl]pyridin-2-yl}-1,2,3,4-tetrahydroisoquinoline-8-carboxamide;

6-[8-(1,3-benzothiazol-2-ylcarbamoyl)-3,4-dihydroiso-quinolin-2(1H)-yl]-3-(5-cyano-1-{[1-(2-methoxyethoxy)cycloheptyl]methyl}-2-methyl-1H-pyrrol-3-yl)pyridine-2-carboxylic acid;

6-[8-(1,3-benzothiazol-2-ylcarbamoyl)-3,4-dihydroiso-quinolin-2(1H)-yl]-3-(1-{[1-(1,4-dioxan-2-ylmethoxy)cycloheptyl]methyl}-5-methyl-1H-pyrazol-4-yl)pyridine-2-carboxylic acid;

6-[8-(1,3-benzothiazol-2-ylcarbamoyl)-3,4-dihydroiso-quinolin-2(1H)-yl]-3-[5-methyl-1-({1-[2-(morpholin-4-yl)-2-oxoethoxy]cyclohexyl}methyl)-1H-pyrazol-4-yl]pyridine-2-carboxylic acid;

6-[8-(1,3-benzothiazol-2-ylcarbamoyl)-3,4-dihydroiso-quinolin-2(1H)-yl]-3-(1-{[1-(2,3-dihydroxypropoxy)cycloheptyl]methyl}-5-methyl-1H-pyrazol-4-yl)pyridine-2-carboxylic acid;

6-[8-(1,3-benzothiazol-2-ylcarbamoyl)-3,4-dihydroiso-quinolin-2(1H)-yl]-3-(5-cyano-1-{[1-(dimethylamino)cyclohexyl]methyl}-2-methyl-1H-pyrrol-3-yl)pyridine-2-carboxylic acid;

6-[8-(1,3-benzothiazol-2-ylcarbamoyl)-3,4-dihydroiso-quinolin-2(1H)-yl]-3-{3-[(cyclohexylcarbonyl)(methyl)amino]-2-methylphenyl}pyridine-2-carboxylic acid;

6-[8-(1,3-benzothiazol-2-ylcarbamoyl)-3,4-dihydroiso-quinolin-2(1H)-yl]-3-[1-({3,3-dimethyl-1-[2-(methylsulfonyl)ethoxy]cyclohexyl}methyl)-5-methyl-1H-pyrazol-4-yl]pyridine-2-carboxylic acid;

6-[8-(1,3-benzothiazol-2-ylcarbamoyl)-3,4-dihydroiso-quinolin-2(1H)-yl]-3-(2-methyl-3-{methyl[(1-methylcyclohexyl)carbonyl]amino}phenyl)pyridine-2-carboxylic acid;

6-[8-(1,3-benzothiazol-2-ylcarbamoyl)-3,4-dihydroiso-quinolin-2(1H)-yl]-3-(1-{[1-(2-methoxyethoxy)-3,3-dimethylcyclohexyl]methyl}-5-methyl-1H-pyrazol-4-yl)pyridine-2-carboxylic acid;

6-[8-(1,3-benzothiazol-2-ylcarbamoyl)-3,4-dihydroiso-quinolin-2(1H)-yl]-3-{2-cyano-3-[(cyclohexylsulfonyl)(methyl)amino]phenyl}pyridine-2-carboxylic acid;

6-[8-(1,3-benzothiazol-2-ylcarbamoyl)-3,4-dihydroiso-quinolin-2(1H)-yl]-3-{2-cyano-3-[2-(tricyclo[3.3.1.1$^{3,7}$]dec-1-yl)pyrrolidin-1-yl]phenyl}pyridine-2-carboxylic acid;

6-[8-(1,3-benzothiazol-2-ylcarbamoyl)-3,4-dihydroiso-quinolin-2(1H)-yl]-3'-methyl-2'-(piperidin-1-yl)-3,4'-bipyridine-2-carboxylic acid;

6-[8-(1,3-benzothiazol-2-ylcarbamoyl)-3,4-dihydroiso-quinolin-2(1H)-yl]-3-[1-(1-cyclohexyl-3-methoxypropyl)-5-methyl-1H-pyrazol-4-yl]pyridine-2-carboxylic acid;

6-[8-(1,3-benzothiazol-2-ylcarbamoyl)-3,4-dihydroiso-quinolin-2(1H)-yl]-3-[4-{3,3-dimethyl-1-[2-(methylamino)ethoxy]cyclohexyl}methyl)-5-methyl-1H-pyrazol-4-yl]pyridine-2-carboxylic acid;

6-[8-(1,3-benzothiazol-2-ylcarbamoyl)-3,4-dihydroiso-quinolin-2(1H)-yl]-3-{5-methyl-1-[(2,6,6-trimethyltetrahydro-2H-pyran-2-yl)methyl]-1H-pyrazol-4-yl}pyridine-2-carboxylic acid;

6-[8-(1,3-benzothiazol-2-ylcarbamoyl)-3,4-dihydroiso-quinolin-2(1H)-yl]-3-(1-benzyl-1H-indazol-4-yl)pyridine-2-carboxylic acid;

6-[8-(1,3-benzothiazol-2-ylcarbamoyl)-3,4-dihydroiso-quinolin-2(1H)-yl]-3-(1-benzyl-1H-pyrrolo[2,3-c]pyridin-3-yl)pyridine-2-carboxylic acid; and therapeutically acceptable salts, metabolites, prodrugs, salts of metabolites, and salts of prodrugs thereof.

In another aspect, the present invention provides compounds of Formula (II)

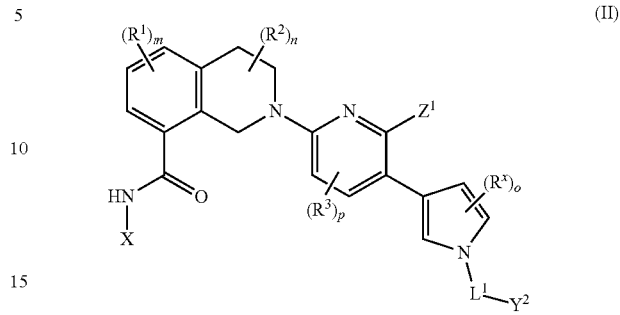

and therapeutically acceptable salts, metabolites, prodrugs, salts of metabolites, and salts of prodrugs thereof, wherein X, $L^1$, $Y^2$, $Z^1$, $R^1$, $R^2$, $R^3$, n, n, and p are as described herein for Formula (I); $R^x$ is as described herein for substituents on $Y^1$, and o is 0, 1, 2, or 3.

One embodiment of this invention pertains to compounds or therapeutically acceptable salts thereof, which are useful as inhibitors of anti-apoptotic Bcl-xL proteins, the compounds having Formula (II)

Formula (II)

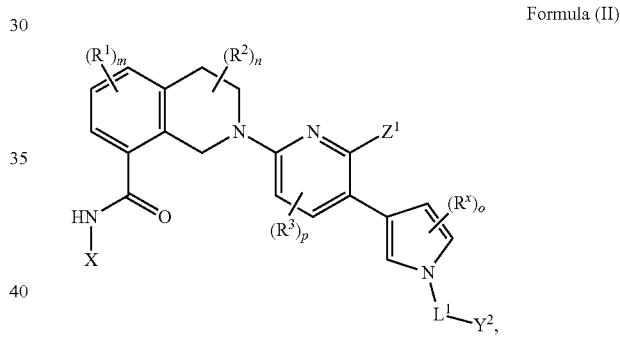

wherein

X is heteroaryl; wherein the heteroaryl represented by X is optionally substituted with one, two, three, or four $R^4$;

$R^x$, at each occurrence, is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, $F$, $Cl$, $Br$ and $I$;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—$NR^{6A}$C(O)—$(CR^6R^7)_r$, $(CR^6R^7)_s$—C(O)$NR^{6A}$—$(CR^6R^7)_r$, $(CR^6R^7)_s$—$NR^{6A}$—$(CR^6R^7)_r$, $(CR^6R^7)_s$—S(O)$_2$$NR^{6A}$—$(CR^6R^7)_r$, and $(CR^6R^7)_s$—$NR^{6A}$(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, $F$, $Cl$, $Br$ and $I$; or $L^1$ is a bond; and $Y^2$ is selected from the group consisting of $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl represented by $Y^2$ are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein each $Y^2$ and each ring fused to $Y^2$ are optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, $F$, $Cl$, $Br$ and $I$;

$Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and $CN$; or $Z^1$ is selected from the group consisting of

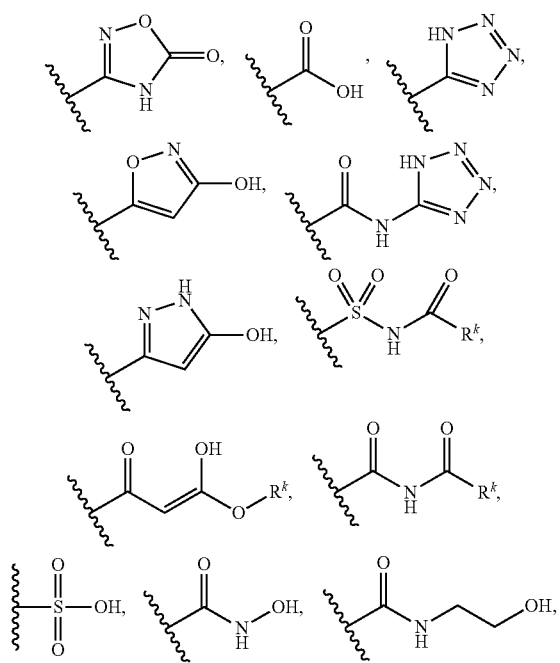

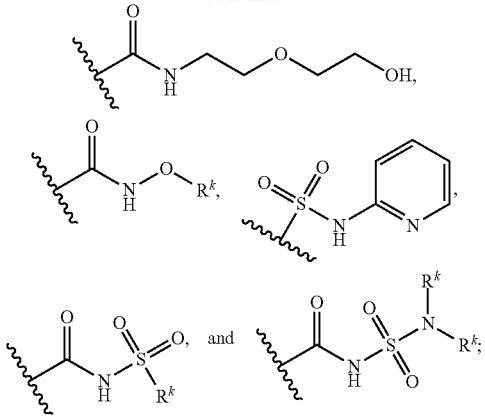

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^{12}R^{13}$, $OR^{12}$, $CN$, $NO_2$, halogen, $C(O)OR^{12}$, $C(O)NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^4$ and $R^{14}$;

$R^5$, at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

$R^6$ and $R^7$, at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^5)_2$, $CO(O)H$, $C(O)H$, $OH$, $CN$, $N_3$, $NO_2$, $F$, $Cl$, $Br$ and $I$;

$R^8$, at each occurrence, is independently selected from the group consisting of $C_{1-6}$ alkyl, $C_{2-6}$ alkenyl, $C_{2-6}$ alkynyl, $C_{1-6}$ haloalkyl, aryl, heterocyclyl, cycloalkyl, and cycloalkenyl; wherein the $R^8$ $C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^{16}$, $NR^{16}S(O)_2R^{16}$, $NHC(O)OR^{16}$, $NR^{16}C(O)OR^{16}$, $NHC(O)NH_2$, $NHC(O)NHR^{16}$, $NHC(O)N(R^{16})_2$, $NR^{16}C(O)NHR^{16}$, $NR^{16}C(O)N(R^6)_2$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH_2$, $SO_2NHR^{16}$, $SO_2N(R^{16})_2$, $CO(O)H$, C(O)H, OH, CN, $N_3$, $NO_2$, F, Cl, Br and I; wherein the $R^8$ aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, $C(O)$H, (O), OH, CN, $NO_2$, $OCF_3$, $OCF_2CF_3$, F, Cl, Br and I;

$R^9$ is selected from the group consisting of $C_{1-6}$ alkyl, $C_{2-6}$ alkenyl, $C_{2-6}$ alkynyl, $C_{1-6}$ haloalkyl, cycloalkyl, phenyl and $(CH_2)_{1-4}$ phenyl; and $R^{10}$ and $R^{11}$, at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or $R^{10}$ and $R^{11}$, or $R^{10}$ and $R^9$, together with the atom to which each is attached are combined to form a heterocyclyl;

$R^k$, at each occurrence, is independently selected from the group consisting of $C_{1-6}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl; wherein the $R^k C_{1-6}$ alkyl, $C_{2-6}$ alkenyl, and $C_{2-6}$ alkynyl are optionally substituted with aryl, heterocyclyl, cycloalkyl, or cycloalkenyl;

$R^{12}$ and $R^{13}$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^{14}$, at each occurrence, is independently selected from the group consisting of $C_{1-4}$ alkyl, $C_{2-4}$ alkenyl, $C_{2-4}$ alkynyl and $C_{1-4}$ haloalkyl;

$R^{12}$ and $R^{13}$, or $R^{12}$ and $R^{14}$, at each occurrence, together with the atom to which each is attached, are optionally combined to form a heterocyclyl;

$R^{15}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the $R^{15} C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ alkoxy, aryl, heterocycloalkyl, heterocycloalkenyl, heteroaryl, cycloalkyl, and cycloalkenyl, $NH_2$, $C(O)NH_2$, $SO_2NH_2$, $C(O)H$, $C(O)OH$, (O), OH, CN, $NO_2$, $OCF_3$, $OCF_2CF_3$, F, Cl, Br and I;

$R^{16}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocycloalkyl heterocycloalkenyl, heteroaryl, cycloalkyl, and cycloalkenyl; wherein the $R^{16} C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one substituent independently selected from the group consisting of $OCH_3$, $OCH_2CH_2OCH_3$, and $OCH_2CH_2NHCH_3$;

q is 1, 2, or 3;
s is 0, 1, 2, or 3;
r is 0, 1, 2, or 3;
wherein the sum of s and r is 0, 1, or 2;
m is 0, 1, 2, or 3;
n is 0, 1, 2, 3, 4, 5, or 6;
o is 0, 1, 2, or 3; and
p is 0, 1, or 2.

In one embodiment of Formula (II), m is 0, 1, 2, or 3; n is 0, 1, 2, 3, 4, 5, or 6; and p is 0, 1, or 2. In another embodiment of Formula (II), n is 0 or 1. In another embodiment of Formula (II), n is 0 or 1; and each $R^2$ is independently deuterium or $C_{1-6}$ alkyl. In another embodiment of Formula (II), m, n, and p are 0.

In one embodiment of Formula (II), X is heteroaryl, which is optionally substituted with one, two, three or four $R^4$. In another embodiment of Formula (II), X is heteroaryl, which is unsubstituted. In another embodiment of Formula (II). X is heteroaryl, which is substituted with one $R^4$. In another embodiment of Formula (II), X is heteroaryl, which is substituted with two $R^4$. In another embodiment of Formula (II), X is heteroaryl, which is substituted with one $R^4$, and $R^4$ is $OR^{12}$ or halogen. In another embodiment of Formula (II), X is heteroaryl, which is substituted with two $R^4$, and each $R^4$ is independently $OR^{12}$ or halogen. In another embodiment of Formula (II), X is heteroaryl, which is substituted with one $R^4$, and $R^4$ is Cl, F, or methoxy. In another embodiment of Formula (II), X is heteroaryl, which is substituted with two $R^4$, and each $R^4$ is independently F.

In one embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is $OR^{12}$ or halogen. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently $OR^{12}$ or halogen. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is Cl, F, or methoxy. In another embodiment of Formula (II), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently F.

In one embodiment of Formula (II), X is benzo[d]thiazolyl, which is optionally substituted with one, two, three or four $R^4$. In another embodiment of Formula (II), X is benzo[d]thiazolyl, which is unsubstituted. In another embodiment of Formula (II), X is benzo[d]thiazolyl, which is substituted with one $R^4$. In another embodiment of Formula (II), X is benzo[d]thiazolyl, which is substituted with two $R^4$. In another embodiment of Formula (II), X is benzo[d]thiazolyl, which is substituted with one $R^4$, and $R^4$ is $OR^{12}$ or halogen. In another embodiment of Formula (II), X is benzo[d]thiazolyl, which is substituted with two $R^4$, and each $R^4$ is independently OR$^{12}$ or halogen. In another embodiment of Formula (II), X is benzo[d]thiazolyl, which is substituted with one R$^4$, and R$^4$ is Cl, F, or methoxy. In another embodiment of Formula (II), X is benzo[d]thiazolyl, which is substituted with two R$^4$, and each R$^4$ is independently F.

In one embodiment of Formula (II), Z$^1$ is selected from the group consisting of C(O)OR$^9$, C(O)NR$^{10}$R$^{11}$, C(O)R$^{11}$, NR$^{10}$C(O)R$^{11}$, NR$^{10}$C(O)NR$^{10}$R$^{11}$, OC(O)NR$^{10}$R$^{11}$, NR$^{10}$C(O)OR$^9$, C(=NOR$^{10}$)NR$^{10}$R$^{11}$, NR$^{10}$C(=NCN)NR$^{10}$R$^{11}$, NR$^{11}$S(O)$_2$NR$^{10}$R$^{11}$, S(O)$_2$R$^9$, S(O)$_2$NR$^{10}$R$^{11}$, N(R$^{10}$)S(O)$_2$R$^{11}$, NR$^{10}$C(=NR$^{11}$)NR$^{10}$R$^{11}$, C(=S)NR$^{10}$R$^{11}$, C(=NR)NR$^{10}$R$^{11}$, halogen, NO$_2$, and CN; or Z$^1$ is selected from the group consisting of

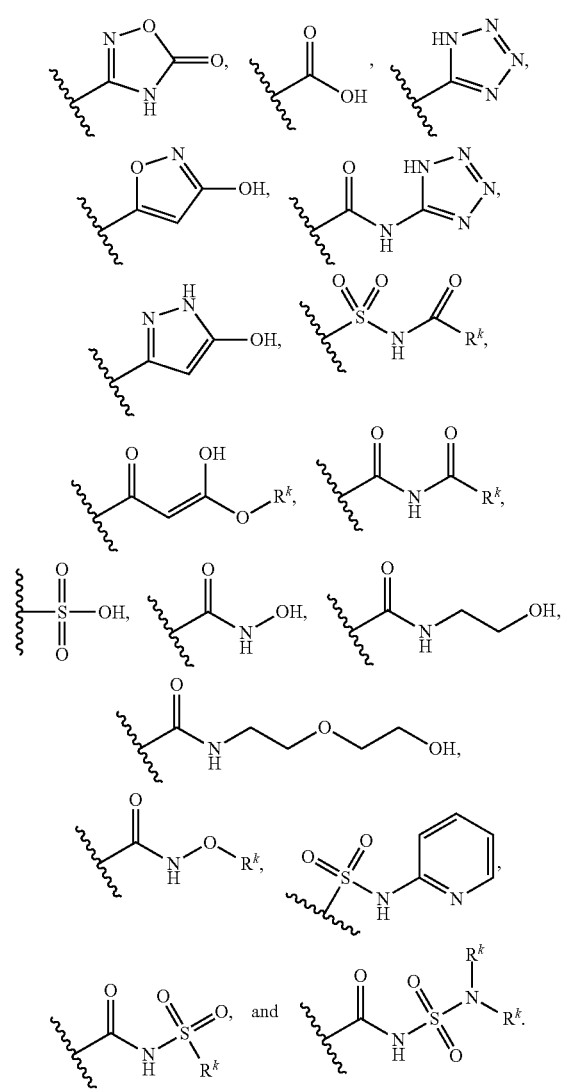

In another embodiment of Formula (II), Z$^1$ is

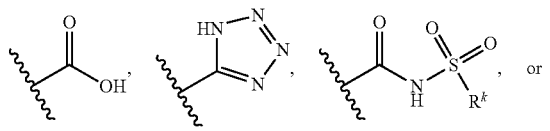

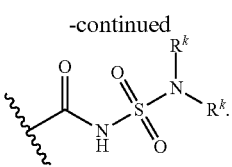

In another embodiment of Formula (II), Z$^1$ is

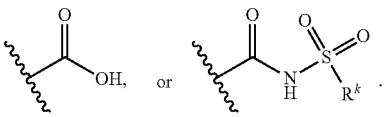

In another embodiment of Formula (II), Z$^1$ is

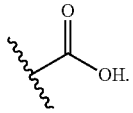

In one embodiment of Formula (II), L$^1$ is selected from the group consisting of (CR$^6$R$^7$)$_q$, (CR$^6$R$^7$)$_s$—O—(CR$^6$R$^7$)$_r$, (CR$^6$R$^7$)$_s$—C(O)—(CR$^6$R$^7$)$_r$, (CR$^6$R$^7$)$_s$—S—(CR$^6$R$^7$)$_r$, (CR$^6$R$^7$)$_s$—S(O)$_2$—(CR$^6$R$^7$)$_r$, (CR$^6$R$^7$)$_s$—NR$^{6A}$C(O)—(CR$^6$R$^7$)$_r$, (CR$^6$R$^7$)$_s$—C(O)NR$^{6A}$—(CR$^6$R$^7$)$_r$, (CR$^6$R$^7$)$_s$—NR$^{6A}$—(CR$^6$R$^7$)$_r$, (CR$^6$R$^7$)$_s$—S(O)$_2$NR$^{6A}$—(CR$^6$R$^7$)$_r$, and (CR$^6$R$^7$)$_s$—NR$^{6A}$S(O)$_2$—(CR$^6$R$^7$)$_r$; and Y$^2$ is selected from the group consisting of C$_{3-11}$ branched chain alkyl, C$_{3-7}$ cycloalkyl, C$_{4-7}$ cycloalkenyl, phenyl, and C$_{3-7}$ heterocyclyl; wherein the C$_{3-7}$ cycloalkyl, C$_{4-7}$ cycloalkenyl, phenyl, and C$_{3-7}$ heterocyclyl are optionally fused to one or two rings selected from the group consisting of C$_{3-8}$ cycloalkane, C$_{3-8}$ cycloalkene, benzene, C$_{5-6}$ heteroarene, C$_{3-8}$ heterocycloalkane, and C$_{3-8}$ heterocycloalkene; wherein Y$^2$ is optionally substituted with one, two, three, four, or five substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, CO(O)H, C(O)H, OH, CN, N$_3$, NO$_2$, F, Cl, Br and I; or L$^1$ is a bond; and Y$^2$ is selected from the group consisting of C$_{3-7}$ cycloalkyl, C$_{4-7}$ cycloalkenyl, phenyl, and C$_{3-7}$ heterocyclyl; wherein the C$_{3-7}$ cycloalkyl, C$_{4-7}$ cycloalkenyl, phenyl, and C$_{3-7}$ heterocyclyl represented by Y$^2$ are optionally fused to one or two rings selected from the group consisting of C$_{3-8}$ cycloalkane, C$_{3-8}$ cycloalkene, benzene, C$_{5-6}$ heteroarene, C$_{3-8}$ heterocycloalkane, and C$_{3-8}$ heterocycloalkene; wherein each Y$^2$ and each ring fused to Y$^2$ are optionally substituted with one, two, three, four, or five substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, CO(O)H, C(O)H, OH, CN, N$_3$, NO$_2$, F, Cl, Br and I.

In another embodiment of Formula (II), $L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S(O)$_2$—$(CR^6R^7)_r$, $(CR^6R^7)_s$—NR$^{6A}$C(O)—$(CR^6R^7)_r$, $(CR^6R^7)_s$—NR$^{6A}$—$(CR^6R^7)_r$, and $(CR^6R^7)_s$—NR$^{6A}$S(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two benzene rings; wherein $Y^2$ is optionally substituted with one, two, or three substituents independently selected from the group consisting of $R^8$, $OR^8$, $SO_2R^8$, $CO(O)R^8$, $NHR^8$, $N(R^8)_2$, C(O)H, OH, CN, NO$_2$, F, Cl, Br and I; or $L^1$ is a bond; and $Y^2$ is selected from the group consisting of $C_{3-7}$ cycloalkyl, phenyl, and $C_{3-7}$ heterocyclyl; wherein the $C_{3-7}$ cycloalkyl, phenyl, and $C_{3-7}$ heterocyclyl represented by $Y^2$ are optionally fused to one benzene ring; wherein each $Y^2$ and each ring fused to $Y^2$ are optionally substituted with one substituent independently selected from the group consisting of $R^8$, C(O)NHR$^8$, F, Cl, Br and I.

In another embodiment of Formula (II), $L^1$ is $(CR^6R^7)_q$; and $Y^2$ is selected from the group consisting of $C_{3-7}$ cycloalkyl, $C_{4-7}$ cycloalkenyl, phenyl, and $C_{3-7}$ heterocyclyl; wherein $R^6$ and $R^7$, at each occurrence, are $R^{15}$ or hydrogen; and q is 1, 2, or 3.

In another embodiment of Formula (II), $L^1$ is selected from the group consisting of $(CR^6R^7)_q$, $(CR^6R^7)_s$—C(O)—$(CR^6R^7)_r$, and $(CR^6R^7)_s$—S(O)$_2$—$(CR^6R^7)_r$; q is 1, 2, or 3; s is 0; r is 0 or 1; $R^{6A}$ is independently selected from the group consisting of hydrogen, and $C_{1-6}$ alkyl; and $R^6$ and $R^7$, at each occurrence, are hydrogen.

In one embodiment of Formula (II), o is 0. In another embodiment of Formula (II), o is 2. In another embodiment of Formula (II), o is 0, 1, 2, or 3. In another embodiment of Formula (II), o is 1, 2, or 3; and $R^x$, at each occurrence, is independently selected from the group consisting of, $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, C(O)NHOH, C(O)NHOR$^5$, C(O)NHSO$_2R^5$, C(O)NR$^5$SO$_2R^5$, SO$_2$NH$_2$, SO$_2$NHR$^5$, SO$_2$N(R$^5$)$_2$, C(O)H, C(O)OH, OH, CN, N$_3$, NO$_2$, F, Cl, Br and I. In another embodiment of Formula (II), o is 1, 2, or 3; and $R^x$, at each occurrence, is independently selected from the group consisting of $R^5$, CO(O)R$^5$, CO(O)H, CN, F, Cl, Br and I. In another embodiment of Formula (II), o is 1 or 2; $R^x$, at each occurrence, is independently selected from the group consisting of $R^5$, CO(O)R$^5$, CO(O)H, CN, F, Cl, Br and I; and $R^5$, at each occurrence, is independently selected from the group consisting of $C_{1-6}$ alkyl, $C_{2-6}$ alkenyl, $C_{1-6}$ haloalkyl, $C_{1-6}$ hydroxyalkyl, aryl, and cycloalkyl. In another embodiment of Formula (II), o is 1 or 2; $R^x$, at each occurrence, is independently selected from the group consisting of $R^5$, CN, F, Cl, Br and I; and $R^5$, at each occurrence, is independently selected from the group consisting of $C_{1-2}$ alkyl, and $C_1$ haloalkyl. In another embodiment of Formula (II), o is 1 or 2; $R^x$ is $R^5$ or CN; and $R^5$ is CH$_3$. In another embodiment of Formula (II), o is 1; and $R^x$ is CN.

In one embodiment of Formula (II), X is heteroaryl; wherein the heteroaryl represented by X is optionally substituted with one or two $R^4$;

$R^x$, at each occurrence, is independently selected from the group consisting of $R^5$, CO(O)R$^5$, CO(O)H, CN, F, Cl, Br and I;

$L^1$ is selected from the group consisting of $(CR^6R^7)_q$, $(CR^6R^7)_s$—C(O)—$(CR^6R^7)_r$, and $(CR^6R^7)_s$—S(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one benzene ring; wherein $Y^2$ is optionally substituted with one, two, or three substituents independently selected from the group consisting of $R^8$, $OR^8$, $SO_2R^8$, $CO(O)R^8$, $NHR^8$, $N(R^8)_2$, C(O)H, OH, CN, NO$_2$, F, Cl, Br and I; or $L^1$ is a bond; and $Y^2$ is selected from the group consisting of $C_{3-7}$ cycloalkyl, phenyl, and $C_{3-7}$ heterocyclyl; wherein the $C_{3-7}$ cycloalkyl, phenyl, and $C_{3-7}$ heterocyclyl represented by $Y^2$ are optionally fused to one benzene ring; wherein each $Y^2$ and each ring fused to $Y^2$ are optionally substituted with one substituent independently selected from the group consisting of $R^8$ and C(O)NHR$^8$;

$Z^1$ is selected from the group consisting of

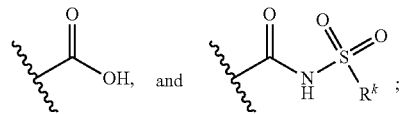

$R^2$, at each occurrence, is independently $C_{1-6}$ alkyl;

$R^4$, at each occurrence, is independently selected from the group consisting of $OR^{12}$ and halogen;

$R^5$, at each occurrence, is independently selected from the group consisting of $C_{1-6}$ alkyl, $C_{1-6}$ haloalkyl, $C_{1-6}$ hydroxyalkyl, aryl, and cycloalkyl;

$R^{6A}$ is independently selected from the group consisting of hydrogen and $C_{1-6}$ alkyl;

$R^6$ and $R^7$, at each occurrence, are each independently selected from the group consisting of hydrogen, $R^{15}$, and CO(O)R$^{15}$;

$R^8$, at each occurrence, is independently selected from the group consisting of $C_{1-6}$ alkyl, $C_{2-6}$ alkynyl, aryl, heterocyclyl, and cycloalkyl; wherein the $R^8C_{1-6}$ alkyl, and $C_{2-4}$ alkynyl are optionally substituted with one, two, or three substituents independently selected from the group consisting of $R^{16}$, $OR^{16}$, $SO_2R^{16}$, $C(O)R^{16}$, $N(R^{16})_2$, OH, F, Cl, Br and I; wherein the $R^8$ aryl and heterocyclyl are optionally substituted with one substituent independently selected from the group consisting of $C_{1-6}$ alkyl, F, Cl, Br and I;

$R^k$, at each occurrence, is independently $C_{1-4}$ alkyl;

$R^{12}$ and $R^{13}$, at each occurrence, are each independently $C_{1-4}$ alkyl;

$R^{15}$, at each occurrence, is independently selected from the group consisting of $C_{1-4}$ alkyl, and aryl; wherein the $R^{15} C_{1-4}$ alkyl is optionally substituted with one substituent independently selected from the group consisting $C_{1-4}$ alkoxy, and heterocycloalkyl;

$R^{16}$, at each occurrence, is independently selected from the group consisting of $C_{1-4}$ alkyl, aryl, heterocycloalkyl, and heteroaryl;

q is 1, 2, or 3;

s is 0;

r is 0, or 1;

m is 0;

n is 0, or 1;

o is 0, 1, 2, or 3; and p is 0.

Still another embodiment pertains to a compound having Formula (II) selected from the group consisting of 6-[8-(1,3-benzothiazol-2-ylcarbamoyl)-3,4-dihydroisoquinolin-2(1H)-yl]-3-[1-benzyl-5-(ethoxycarbonyl)-2-methyl-1H-pyrrol-3-yl]pyridine-2-carboxylic acid;

6-[8-(1,3-benzothiazol-2-ylcarbamoyl)-3,4-dihydroisoquinolin-2(1H)-yl]-3-(1-benzyl-5-carboxy-2-methyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-(1-benzyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-{1-[(4-methylphenyl)sulfonyl]-1H-pyrrol-3-yl}pyridine-2-carboxylic acid;

6-[8-(1,3-benzothiazol-2-ylcarbamoyl)-3,4-dihydroisoquinolin-2(1H)-yl]-3-(1-benzoyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-[1-(phenylsulfonyl)-1H-pyrrol-3-yl]pyridine-2-carboxylic acid;

6-[8-(1,3-benzothiazol-2-ylcarbamoyl)-3,4-dihydroisoquinolin-2(1H)-yl]-3-(1-benzyl-5-cyano-2-methyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-[5-cyano-1-(cyclohexylmethyl)-2-methyl-1H-pyrrol-3-yl]pyridine-2-carboxylic acid;

6-[8-(1,3-benzothiazol-2-ylcarbamoyl)-3,4-dihydroisoquinolin-2(1H)-yl]-3-(5-cyano-2-methyl-1-{[1-(piperidin-1-yl)cyclohexyl]methyl}-1H-pyrrol-3-yl)pyridine-2-carboxylic acid;

6-[8-(1,3-benzothiazol-2-ylcarbamoyl)-3,4-dihydroisoquinolin-2(1H)-yl]-3-(1-benzyl-1H-pyrrolo[2,3-b]pyridin-3-yl)pyridine-2-carboxylic acid;

6-[8-(1,3-benzothiazol-2-ylcarbamoyl)-3,4-dihydroisoquinolin-2(1H)-yl]-3-(5-cyano-2-methyl-1-{[1-(morpholin-4-yl)cyclohexyl]methyl}-1H-pyrrol-3-yl)pyridine-2-carboxylic acid;

N-(1,3-benzothiazol-2-yl)-2-yl)-2-{5-[5-cyano-1-(cyclohexylmethyl)-2-methyl-1H-pyrrol-3-yl]-6-[(methylsulfonyl)carbamoyl]pyridin-2-yl}-1,2,3,4-tetrahydroisoquinoline-8-carboxamide;

6-[8-(1,3-benzothiazol-2-ylcarbamoyl)-3,4-dihydroisoquinolin-2(1H)-yl]-3-(5-cyano-1-{[1-(2-methoxyethoxy)cycloheptyl]methyl}-2-methyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-(5-cyano-1-{[1-(dimethylamino)cyclohexyl]methyl)-2-methyl}-1H-pyrrol-3-yl)pyridine-2-carboxylic acid 6-[8-(1,3-benzothiazol-2-ylcarbamoyl)-3,4-dihydroisoquinolin-2(1H)-yl]-3-(1-benzyl-1H-pyrrolo[2,3-c]pyridin-3-yl)pyridine-2-carboxylic acid; and therapeutically acceptable salts, prodrugs, salts of metabolites, and salts of prodrugs thereof.

In another aspect, the present invention provides compounds of Formula (III)

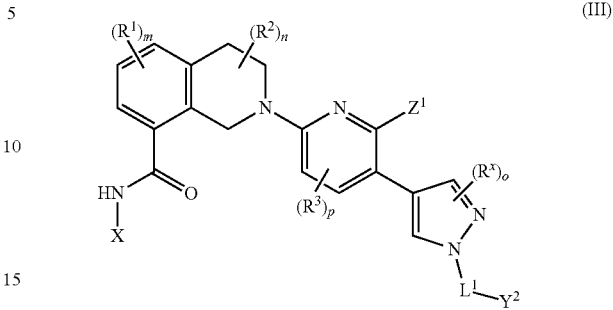

and therapeutically acceptable salts, metabolites, prodrugs, salts of metabolites, and salts of prodrugs thereof, wherein X, $L^1$, $Y^2$, $Z^1$, $R^1$, $R^2$, $R^3$, m, n, and p are as described herein for Formula (I); $R^x$ is as described herein for substituents on $Y^1$, and o is 0, 1, or 2.

One embodiment of this invention pertains to compounds or therapeutically acceptable salts thereof, which are useful as inhibitors of anti-apoptotic Bcl-xL proteins, the compounds having Formula (III)

Formula (III)

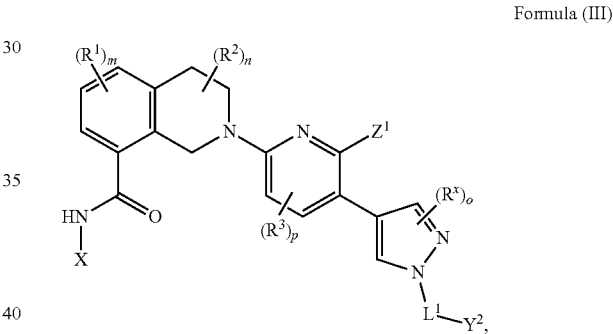

wherein

X is heteroaryl; wherein the heteroaryl represented by X is optionally substituted with one, two, three, or four $R^4$;

$R^x$, at each occurrence, is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)ORS$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, F, Cl, Br and I;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—$NR^{6A}C(O)$—$(CR^6R^7)_r$, $(CR^6R^7)_s$—C(O)$NR^{6A}$—$(CR^6R^7)_r$, $(CR^6R^7)_s$—$NR^{6A}$—$(CR^6R^7)_r$, $(CR^6R^7)_s$—$S(O)_2NR^{6A}$—$(CR^6R^7)_r$, and $(CR^6R^7)_s$—$NR^{6A}S(O)_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, $F$, $Cl$, $Br$ and $I$; or $L^1$ is a bond; and $Y^2$ is selected from the group consisting of $C_{3-7}$ cycloalkyl, $C_{4-7}$ cycloalkenyl, phenyl, and $C_{3-7}$, heterocyclyl; wherein the $C_{3-7}$ cycloalkyl, $C_{4-7}$ cycloalkenyl, phenyl, and $C_{3-7}$ heterocyclyl represented by $Y^2$ are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein each $Y^2$ and each ring fused to $Y^2$ are optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, $F$, $Cl$, $Br$ and $I$;

$Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and $CN$; or $Z^1$ is selected from the group consisting of

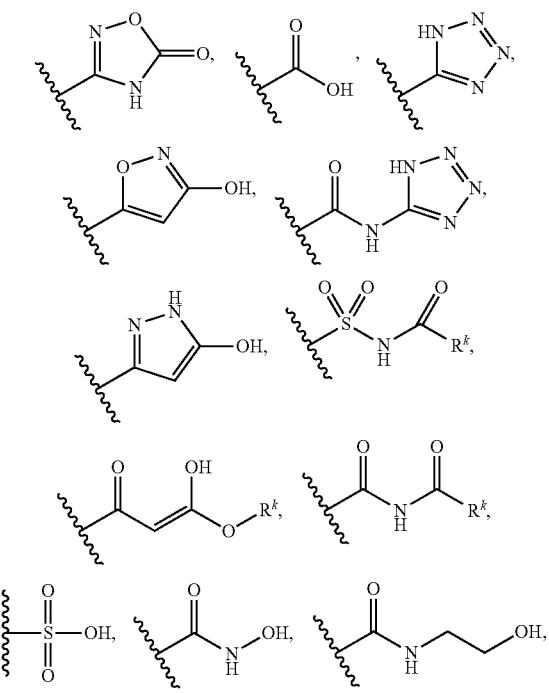

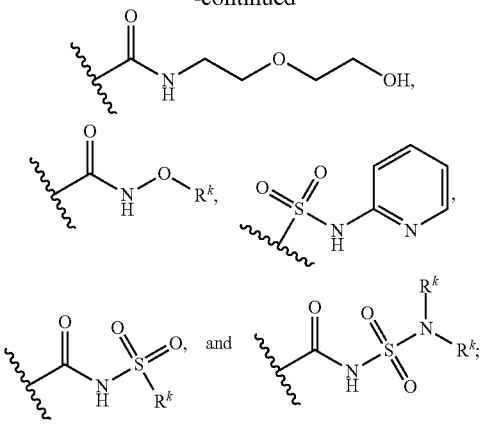

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-4}$ alkenyl, $C_{2-4}$ alkynyl, and $C_{1-6}$ haloalkyl;

$R^4$, at each occurrence, is independently selected from the group consisting of $NR^{12}R^{13}$, $OR^{12}$, $CN$, $NO_2$, halogen, $C(O)OR^{12}$, $C(O)NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^{14}$ and $R^{14}$;

$R^5$, at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

$R^6$ and $R^7$, at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $CO(O)H$, $C(O)H$, $OH$, $CN$, $N_3$, $NO_2$, $F$, $Cl$, $Br$ and $I$;

$R^8$, at each occurrence, is independently selected from the group consisting of $C_{1-6}$ alkyl, $C_{2-6}$ alkenyl, $C_{2-6}$ alkynyl, $C_{1-6}$ haloalkyl, aryl, heterocyclyl, cycloalkyl, and cycloalkenyl; wherein the $R^8$ $C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^{16}$, $NR^{16}S(O)_2R^{16}$, $NHC(O)OR^{16}$, $NR^{16}C(O)OR^{16}$, $NHC(O)NH_2$, $NHC(O)NHR^{16}$, $NHC(O)N(R^6)_2$, $NR^{16}C(O)NHR^{16}$, $NR^{16}C(O)N(R^{16})_2$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH_2$, $SO_2NHR^{16}$, $SO_2N(R^{16})_2$, $CO(O)H$, $C(O)H$, $OH$, $CN$, $N_3$, $NO_2$, F, Cl, Br and I; wherein the $R^8$ aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, $C(O)H$, (O), OH, CN, $NO_2$, $OCF_3$, $OCF_2CF_3$, F, Cl, Br and I;

$R^9$ is selected from the group consisting of $C_{1-6}$ alkyl, $C_{2-6}$ alkenyl, $C_{2-6}$ alkynyl, $C_{1-6}$ haloalkyl, cycloalkyl, phenyl and $(CH_2)_{1-4}$ phenyl; and $R^{10}$ and $R^{11}$, at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or $R^{10}$ and $R^{11}$, or $R^{10}$ and $R^9$, together with the atom to which each is attached are combined to form a heterocyclyl;

$R^k$, at each occurrence, is independently selected from the group consisting of $C_{1-6}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl; wherein the $R^k C_{1-6}$ alkyl, $C_{2-6}$ alkenyl, and $C_{2-6}$ alkynyl are optionally substituted with aryl, heterocyclyl, cycloalkyl, or cycloalkenyl;

$R^{12}$ and $R^{13}$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^{14}$, at each occurrence, is independently selected from the group consisting of $C_{1-4}$ alkyl, $C_{2-4}$ alkenyl, $C_{2-4}$ alkynyl and $C_{1-4}$ haloalkyl;

$R^{12}$ and $R^{13}$, or $R^{12}$ and $R^{14}$, at each occurrence, together with the atom to which each is attached, are optionally combined to form a heterocyclyl;

$R^{15}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the $R^{15}C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ alkoxy, aryl, heterocycloalkyl, heterocycloalkenyl, heteroaryl, cycloalkyl, and cycloalkenyl, $NH_2$, $C(O)NH_2$, $SO_2NH_2$, $C(O)H$, $C(O)OH$, (O), OH, CN, $NO_2$, $OCF_3$, $OCF_2CF_3$, F, Cl, Br and I;

$R^{16}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocycloalkyl, heterocycloalkenyl, heteroaryl, cycloalkyl, and cycloalkenyl; wherein the $R^{16}C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one substituent independently selected from the group consisting of $OCH_3$, $OCH_2CH_2OCH_3$, and $OCH_2CH_2NHCH_3$;

q is 1, 2, or 3;
s is 0, 1, 2, or 3;
r is 0, 1, 2, or 3;
wherein the sum of s and r is 0, 1, or 2;
m is 0, 1, 2, or 3;
n is 0, 1, 2, 3, 4, 5, or 6;
o is 0, 1, or 2; and
p is 0, 1, or 2.

In one embodiment of Formula (III), m is 0, 1, 2, or 3; n is 0, 1, 2, 3, 4, 5, or 6; and p is 0, 1, or 2. In another embodiment of Formula (III), n is 0 or 1. In another embodiment of Formula (III), n is 0 or 1; and each $R^2$ is independently deuterium or $C_{1-6}$ alkyl. In another embodiment of Formula (III), m, n, and p are 0.

In one embodiment of Formula (III), X is heteroaryl, which is optionally substituted with one, two, three or four $R^4$. In another embodiment of Formula (III), X is heteroaryl, which is unsubstituted. In another embodiment of Formula (III), X is heteroaryl, which is substituted with one $R^4$. In another embodiment of Formula (III), X is heteroaryl, which is substituted with two $R^4$. In another embodiment of Formula (III), X is heteroaryl, which is substituted with one $R^4$, and $R^4$ is $OR^{12}$ or halogen. In another embodiment of Formula (III), X is heteroaryl, which is substituted with two $R^4$, and each $R^4$ is independently $OR^{12}$ or halogen. In another embodiment of Formula (III), X is heteroaryl, which is substituted with one $R^4$, and $R^4$ is Cl, F, or methoxy. In another embodiment of Formula (III), X is heteroaryl, which is substituted with two $R^4$, and each $R^4$ is independently F.

In one embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is $OR^{12}$ or halogen. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently $OR^{12}$ or halogen. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is Cl, F, or methoxy. In another embodiment of Formula (III), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently F.

In one embodiment of Formula (III), X is benzo[d]thiazolyl, which is optionally substituted with one, two, three or four $R^4$. In another embodiment of Formula (III), X is benzo[d]thiazolyl, which is unsubstituted. In another embodiment of Formula (III), X is benzo[d]thiazolyl, which is substituted with one $R^4$. In another embodiment of Formula (III), X is benzo[d]thiazolyl, which is substituted with two $R^4$. In another embodiment of Formula (III), X is benzo[d]thiazolyl, which is substituted with one $R^4$, and $R^4$ is $OR^{12}$ or halogen. In another embodiment of Formula (III), X is benzo[d]thiazolyl, which is substituted with two $R^4$, and each $R^4$ is independently $OR^{12}$ or halogen. In another embodiment of Formula (III), X is benzo[d]thiazolyl, which is substituted with one $R^4$, and $R^4$ is Cl, F, or methoxy. In another embodiment of Formula (III), X is benzo[d]thiazolyl, which is substituted with two $R^4$, and each $R^4$ is independently F.

In one embodiment of Formula (III), $Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{10}$, $OC(O)NR^{10}R^{11}$, $NR^{10}C(O)OR^9$, $C(=NOR^{10})NR^{10}R^{11}$, $NR^{11}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and CN; or $Z^1$ is selected from the group consisting of

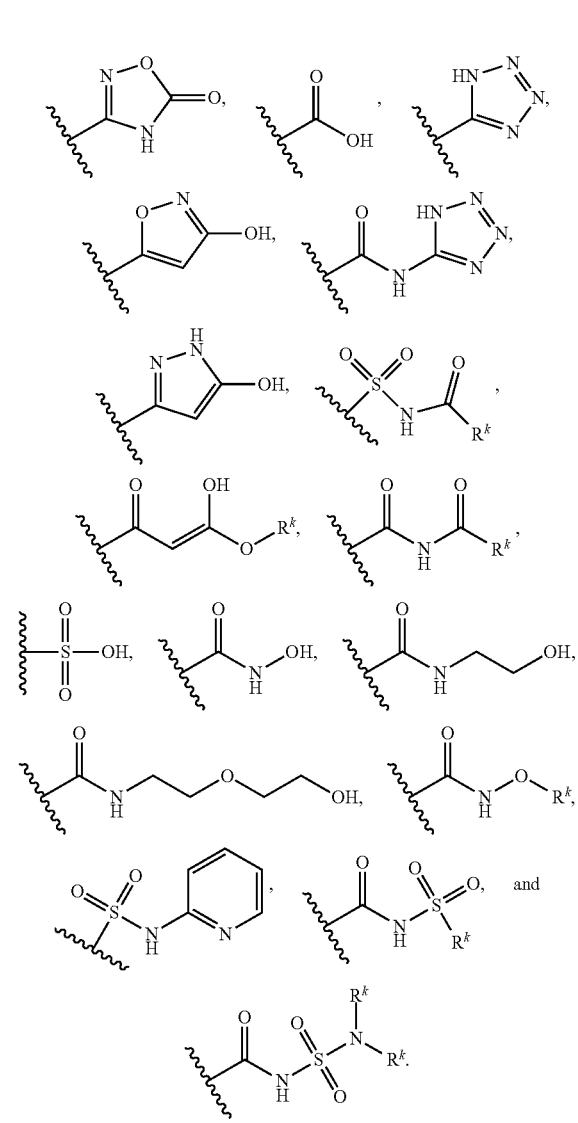

In another embodiment of Formula (III), $Z^1$ is

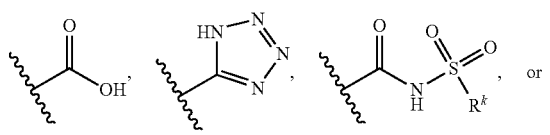

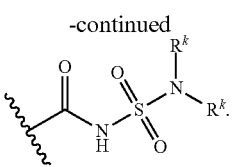

In another embodiment of Formula (III), $Z^1$ is

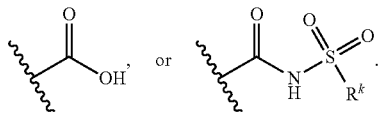

In another embodiment of Formula (III), $Z^1$ is

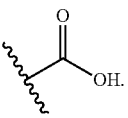

In one embodiment of Formula (III), $L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—$NR^{6A}C(O)$—$(CR^6R^7)_r$, $(CR^6R^7)_s$—C(O)$NR^{6A}$—$(CR^6R^7)_r$, $(CR^6R^7)_s$—$NR^{6A}$—$(CR^6R^7)_r$, $(CR^6R^7)_s$—S(O)$_2NR^{6A}$—$(CR^6R^7)_r$, and $(CR^6R^7)_s$—$NR^{6A}S(O)_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8SO_2NH_2$, $SO_2NHR^8$, $SO_2N(R^8)_2$, $CO(O)H$, $C(O)H$, $OH$, $CN$, $N_3$, $NO_2$, F, Cl, Br and I; or $L^1$ is a bond; and $Y^2$ is selected from the group consisting of $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl represented by $Y^2$ are optionally fused to one or two rings selected from the group consisting of $C_{3-8}$ cycloalkane, $C_{3-7}$ cycloalkene, benzene, $C_{5-8}$ heteroarene, $C_{3-8}$ heterocycloalkane, and $C_{3-8}$ heterocycloalkene; wherein each $Y^2$ and each ring fused to $Y^2$ are optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, OH, CN, $N_3$, $NO_2$, F, Cl, Br and I.

In another embodiment of Formula (III), $L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S(O)—$(CR^6R^7)_r$, $(CR^6R^7)_s$—$NR^{6A}$C(O)—$(CR^6R^7)_r$, $(CR^6R^7)_s$—$NR^{6A}$—$(CR^6R^7)_r$, and $(CR^6R^7)_s$—$NR^{6A}$S(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two benzene rings; wherein $Y^2$ is optionally substituted with one, two, or three substituents independently selected from the group consisting of $R^8$, $OR^8$, $SO_2R^8$, $CO(O)R^8$, $NHR^8$, $N(R^8)_2$, C(O)H, OH, CN, $NO_2$, F, Cl, Br and I; or $L^1$ is a bond; and $Y^2$ is selected from the group consisting of $C_{3-7}$ cycloalkyl, phenyl, and $C_{3-7}$ heterocyclyl; wherein the $C_{3-7}$ cycloalkyl, phenyl, and $C_{3-7}$ heterocyclyl represented by $Y^2$ are optionally fused to one benzene ring; wherein each $Y^2$ and each ring fused to $Y^2$ are optionally substituted with one substituent independently selected from the group consisting of $R^8$, C(O)$NHR^8$, F, Cl, Br and I.

In another embodiment of Formula (III), $L^1$ is $(CR^6R^7)_q$; and $Y^2$ is selected from the group consisting of $C_{3-7}$ cycloalkyl, $C_{4-7}$ cycloalkenyl, phenyl, and $C_{3-7}$ heterocyclyl; wherein $R^6$ and $R^7$, at each occurrence, are $R^{15}$ or hydrogen; and q is 1, 2, or 3.

In another embodiment of Formula (III), $L^1$ is selected from the group consisting of $(CR^6R^7)_q$, $(CR^6R^7)_s$—C(O)—$(CR^6R^7)_r$, and $(CR^6R^7)_s$—S(O)$_2$—$(CR^6R^7)_r$; q is 1, 2, or 3; s is 0; r is 0 or 1; $R^{6A}$ is independently selected from the group consisting of hydrogen, and $C_{1-6}$ alkyl; and $R^6$ and $R^7$, at each occurrence, are hydrogen.

In one embodiment of Formula (III), o is 0. In another embodiment of Formula (III), o is 2. In another embodiment of Formula (III), o is 0, 1, or 2. In another embodiment of Formula (III), o is 1 or 2; and $R^x$, at each occurrence, is independently selected from the group consisting of, $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, NHC(O)$R^5$, $NR^5$C(O)$R^5$, NHS(O)$_2R^5$, $NR^5$S(O)$_2R^5$, NHC(O)$OR^5$, $NR^5$C(O)$OR^5$, NHC(O)$NH_2$, NHC(O)$NHR^5$, NHC(O)$N(R^5)_2$, $NR^5$C(O)$NHR^5$, $NR^5$C(O)$N(R^5)_2$, C(O)$NH_2$, C(O)$NHR^5$, C(O)$N(R^5)_2$, C(O)NHOH, C(O)$NHOR^5$, C(O)$NHSO_2R^5$, C(O)$NR^5SO_2R^5$, $SO_2NH_2$, $SO_2NHR^5$, $SO_2N(R^5)_2$, C(O)H, C(O)OH, CN, $N_3$, $NO_2$, F, Cl, Br and I. In another embodiment of Formula (III), o is 1 or 2; and $R^x$, at each occurrence, is independently selected from the group consisting of $R^5$, CO(O)$R^5$, C(O)OH, CN, F, Cl, Br and I. In another embodiment of Formula (III), o is 1 or 2; $R^x$, at each occurrence, is independently selected from the group consisting of $R^5$, CO(O)$R^5$, C(O)OH, CN, F, Cl, Br and I; and $R^5$, at each occurrence, is independently selected from the group consisting of $C_{1-6}$ alkyl, $C_{2-6}$ alkenyl, $C_{1-6}$ haloalkyl, $C_{1-6}$ hydroxyalkyl, aryl, and cycloalkyl. In another embodiment of Formula (III), o is 1 or 2; $R^x$, at each occurrence, is independently selected from the group consisting of $R^5$, CN, F, Cl, Br and I; and $R^5$, at each occurrence, is independently selected from the group consisting of $C_{1-2}$ alkyl, and $C_1$ haloalkyl. In another embodiment of Formula (III), o is 1 or 2; $R^x$ is $R^5$ or CN; and $R^5$ is $CH_3$. In another embodiment of Formula (III), o is 1; and $R^x$ is CN.

In one embodiment of Formula (III), X is heteroaryl; wherein the heteroaryl represented by X is optionally substituted with one or two $R^4$;

$R^x$, at each occurrence, is independently selected from the group consisting of $R^5$, CO(O)$R^5$, C(O)OH, CN, F, Cl, Br and I;

$L^1$ is selected from the group consisting of $(CR^6R^7)_q$, $(CR^6R^7)_s$—C(O)—$(CR^6R^7)_r$, and $(CR^6R^7)_s$—S(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{3-7}$ cycloalkenyl, phenyl, and $C_{3-7}$ heterocyclyl are optionally fused to one benzene ring; wherein $Y^2$ is optionally substituted with one, two, or three substituents independently selected from the group consisting of $R^8$, $OR^8$, $SO_2R^8$, $CO(O)R^8$, $NHR^8$, $N(R^8)_2$, C(O)H, OH, CN, $NO_2$, F, Cl, Br and I; or $L^1$ is a bond; and $Y^2$ is selected from the group consisting of $C_{3-7}$ cycloalkyl, phenyl, and $C_{3-7}$ heterocyclyl; wherein the $C_{3-7}$ cycloalkyl, phenyl, and $C_{3-7}$ heterocyclyl represented by $Y^2$ are optionally fused to one benzene ring; wherein each $Y^2$ and each ring fused to $Y^2$ are optionally substituted with one substituent independently selected from the group consisting of $R^8$ and C(O)$NHR^8$;

$Z^1$ is selected from the group consisting of

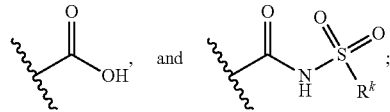

$R^2$, at each occurrence, is independently $C_{1-6}$ alkyl;

$R^4$, at each occurrence, is independently selected from the group consisting of $OR^{12}$ and halogen;

$R^5$, at each occurrence, is independently selected from the group consisting of $C_{1-6}$ alkyl, $C_{1-6}$ haloalkyl, $C_{1-6}$ hydroxyalkyl, aryl, and cycloalkyl;

$R^{6A}$ is independently selected from the group consisting of hydrogen and $C_{1-6}$ alkyl;

$R^6$ and $R^7$, at each occurrence, are each independently selected from the group consisting of hydrogen, $R^{13}$, and CO(O)$R^{15}$;

$R^8$, at each occurrence, is independently selected from the group consisting of $C_{1-6}$ alkyl, $C_{2-6}$ alkynyl, aryl, heterocyclyl, and cycloalkyl; wherein the $R^8 C_{1-6}$ alkyl, and $C_{2-6}$ alkynyl are optionally substituted with one, two, or three substituents independently selected from the group consisting of $R^{16}$, $OR^{16}$, $SO_2R^{16}$, $C(O)R^{16}$, $N(R^{16})_2$, OH, F, Cl, Br and I; wherein the $R^8$ aryl and heterocyclyl are optionally substituted with one substituent independently selected from the group consisting of $C_{1-6}$ alkyl, F, Cl, Br and I;

$R^k$, at each occurrence, is independently $C_{1-6}$ alkyl;

$R^{12}$ and $R^{13}$, at each occurrence, are each independently $C_{1-4}$ alkyl;

$R^{15}$, at each occurrence, is independently selected from the group consisting of $C_{1-4}$ alkyl, and aryl; wherein the $R^{15} C_{1-4}$ alkyl is optionally substituted with one substituent independently selected from the group consisting $C_{1-4}$ alkoxy, and heterocycloalkyl;

$R^{16}$, at each occurrence, is independently selected from the group consisting of $C_{1-4}$ alkyl, aryl, heterocycloalkyl, and heteroaryl;

q is 1, 2, or 3;

s is 0;

r is 0, or 1;

m is 0;

n is 0, or 1;

o is 0, 1, or 2; and p is 0.

Still another embodiment pertains to a compound having Formula (III) selected from the group consisting of 6-[8-(1,3-benzothiazol-2-ylcarbamoyl)-3,4-dihydroisoquinolin-2(1H)-yl]-3-(1-benzyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(pyridin-4-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(pyridin-3-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-hydroxybenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(1-phenylethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{4-[2-(dimethylamino)ethoxy]benzyl}-1H-pyrazol-4-yl)pyridine-2-carboxylic acid;

3-(1-benzyl-1H-pyrazol-4-yl)-6-{8-[(5,6-difluoro-1,3-benzothiazol-2-yl)carbamoyl]-3,4-dihydroisoquinolin-2(1H)-yl}pyridine-2-carboxylic acid;

6-[8-(1,3-benzothiazol-2-ylcarbamoyl)-3,4-dihydroisoquinolin-2(1H)-yl]-3-{1-[2-(4-fluorophenyl)ethyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(3-chlorobenzyl)-1H-pyrazol-4-yl]pyridine-2-carboxylic acid;

3-(1-benzyl-1H-pyrazol-4-yl)-6-{8-[(6-fluoro-1,3-benzothiazol-2-yl)carbamoyl]-3,4-dihydroisoquinolin-2(1H)-yl}pyridine-2-carboxylic acid;

3-(1-benzyl-1H-pyrazol-4-yl)-6-{8-[(6-methoxy-1,3-benzothiazol-2-yl)carbamoyl]-3,4-dihydroisoquinolin-2(1H)-yl}pyridine-2-carboxylic acid;

6-[8-(1,3-benzothiazol-2-ylcarbamoyl)-3,4-dihydroisoquinolin-2(1H)-yl]-3-(1-benzyl-3,5-dimethyl-1H-pyrazol-4-yl)pyridine-2-carboxylic acid;

6-[8-(1,3-benzothiazol-2-ylcarbamoyl)-3,4-dihydro)isoquinolin-2(1H)-yl]-3-[1-(3-methylbenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3-methoxybenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-chlorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[3-(benzyloxy)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(3-hydroxybenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{3-[2-(dimethylamino)ethoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-benzyl-3-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-benzyl-5-methyl-1H-pyrazol-4-yl)pyridine-2-carboxylic acid;

3-(1-benzyl-1H-pyrazol-4-yl)-6-{8-[(7-chloro-1,3-benzothiazol-2-yl)carbamoyl]-3,4-dihydroisoquinolin-2(1H)-yl}pyridine-2-carboxylic acid;

6-[8-(1,3-benzothiazol-2-ylcarbamoyl)-3,4-dihydroisoquinolin-2(1H)-yl]-3-(1-{[6-(pyrrolidin-1-yl)pyridin-2-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-phenyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(3-cyanobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2-chlorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(pyridin-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-benzyl-3-cyano-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(naphthalen-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[3-(3-methyl-1,2,4-oxadiazol-5-yl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-benzyl-3-(hydroxymethyl)-5-methyl-1H-pyrazol-4-yl]pyridine-2-carboxyl is acid;

6-[8-(1,3-benzothiazol-2-ylcarbamoyl)-3,4-dihydroisoquinolin-2(1H)-yl]-3-{1-[2-(benzyloxy)benzyl]-1H-pyrazol-1-yl}pyridine-2-carboxylic acid;

6-[8-(1,3-benzothiazol-2-ylcarbamoyl)-3,4-dihydroisoquinolin-2(1H)-yl]-3-(5-methyl-1-{[6-(pyrrolidin-1-yl)pyridin-2-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-benzyl-3-(ethoxycarbonyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[3-(dimethylamino)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-benzyl-3-carboxy-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(2-hydroxybenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2,3-dihydro-1H-inden-1-yl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2-phenylethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3,4-dihydro-2H-chromen-4-yl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{2-[2-(dimethylamino)ethoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(2-fluorobenzyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(cyclohexylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(cyclohexylmethyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-{[3-(dimethylamino)propyl]amino}-3-nitrobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-fluoro-3-nitrobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{2-[2-morpholin-4-yl)ethoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-([1-(4-{[3-(dimethylamino)propoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[2-(pyridin-4-ylmethoxy)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{2-[2-(dimethylamino)ethoxy]benzyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(tetrahydro-2H-pyran-4-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{2-[3-(dimethylamino)prop-1-yn-1-yl]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(2,3-difluorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3,5-difluorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2,5-difluorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2,6-difluorobenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(tetrahydro-2H-pyran-3-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2-nitrobenzol)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(biphenyl-3-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2,2-dimethylpropyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2-cyclohexylethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[3-(trifluoromethyl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(biphenyl-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(cyclopentylmethyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3-formylbenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-benzyl-5-phenyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[5-methyl-1-(tetrahydro-2H-pyran-3-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[(1-phenylcyclohexyl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{3-[(dimethylamino)methyl]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[3-(methylsulfonyl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(cyclohexylmethyl)-5-cyclopropyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(3,5-di-tert-butylbenzyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[2-morpholin-4-ylsulfonyl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(4,4-difluorcyclohexyl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[1-(trifluormethyl)cyclohexyl]methyl}-1-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(diphenylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[2-(morpholin-4-yl)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[3-morpholin-4-yl)-1-phenylpropyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[1-(tert-butoxycarbonyl)piperidin-4-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(5-methyl-1-{2-[2-(morpholin-4-yl)ethoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[2-(dimethylamino)benzyl]-1H-pyrazol-4-yl}pyridine-2-carboxylic acid;

6-[8-(1,3-benzothiaol-2-ylcarbamoyl)-3,4-dihydroisoquinolin-2(1H)-yl]-3-(5-methyl-1-{2-[3-(morpholin-4-yl)propoxy]benzyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{5-methyl-1-[(1-methylcyclohexyl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[2-(4-chlorophenyl)-4,4-dimethylcyclohex-1-en-1-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(cyclohexylmethyl)-5-ethyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[(1R,2R,5R)-6,6-dimethylbicyclo[3.1.1]hept-2-yl]methyl}-5-methyl-1H-pyrazol-4-yl) pyridine-2-carboxylic acid;

6-[8-(1,3-benzothiazol-2-ylcarbamoyl)-3,4-dihydroisoquinolin-2(1H)-yl]-3-(1-{[(1S,2R,5S)-6,6-dimethylbicyclo[3.1.1]hept-2-yl]methyl}-5-methyl-1H-pyrazol-4-yl) pyridine-2-carboxylic acid;

6-[8-(1,3-benzothiazol-2-ylcarbamoyl)-3,4-dihydroisoquinolin-2(1H)-yl]-3-(1-{[1-(2-methylpropyl)cyclohexyl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)cyclohexyl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[2-(2-methoxyethoxy)benzyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[(1R,2R,4R)-bicyclo[2.2.1]hept-5-en-2-ylmethyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,3-dimethylcyclohexyl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-[1-(3-methoxy-1-phenylpropyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(4-methoxy-1-phenylbutyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2-methoxy-2-oxo-1-phenylethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-(2-cyclohexyl-1-phenylethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[1-(3-methoxypropyl)cyclohexyl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{2-[3-hydroxy-2-(hydroxymethyl)-2-methylpropoxy]benzyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{5-methyl-1-[2-(tetrahydro-2H-pyran-4-ylmethoxy)benzyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[2-(1,4-dioxan-2-ylmethoxy)benzyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[1-(2-methoxyethoxy)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)cycloheptyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-[1-(piperidin-4-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[1-(methoxymethyl)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3,3-dimethyl-1-(morpholin-4-yl)cyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethyl)-3,3-dimethylcyclohexyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(3-methoxypropyl)cycloheptyl]methyl}-5-methyl-1H-pyrazol-4-yl)pyridine-2-carboxylic acid;

N-1,3-benzothiazol-2-yl)-2-{5-(1-{[1-(2-methoxyethyl)cycloheptyl]methyl}-5-methyl-1H-pyrazol-4-yl)-6-[(methylsulfonyl)carbamoyl]pyridin-2-yl}-1,2,3,4-tetrahydroisoquinoline-8-carboxamide;

6-[8-(1,3-benzothiazol-2-ylcarbamoyl)-3,4-dihydroisoquinolin-2(1H)-yl]-3-[1-(tetrahydro-2H-pyran-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[(1R,2R,3R,5S)-2-(2-methoxyethyl)-6,6-dimethylbicyclo[3.1.1]hept-3-yl]methyl}-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[1-(2-methoxyethoxy)cycloheptyl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[1-cyclohexyl-3-(morpholin-4-yl)propyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-[5-methyl-1-(tetrahydro-2H-pyran-2-ylmethyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-[5-methyl-1-({1-[3-(morpholin-4-yl)propoxy]cycloheptyl}methyl)-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[(1-methoxy-3,3-dimethylcyclohexyl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(5-methyl-1-{[1-(morpholin-4-yl)cyclohexyl]methyl}-1H-pyrazol-4-yl)pyridine-2-carboxylic acid, N-(1,3-benzothiazol-2-yl)-2-(5-{1-[(1-methoxy-3,3-dimethylcyclohexyl)methyl]-5-methyl-1H-pyrazol-4-yl}-6-[(methylsulfonyl)carbamoyl]pyridin-2-yl)-1,2,3,4-perhydroisoquinoline-8-carboxamide;

6-[8-(1,3-benzothiazol-2-ylcarbamoyl)-1-methyl-3,4-dihydroisoquinolin-2(1H)-yl]-3-{5-methyl-1-[(1-methylcyclohexyl)methyl]-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(1-methoxycyclohexyl)methyl]-5-methyl-1H-pyrazol-4-yl}pyridine-2-carboxylic acid;-

6-[8-(1,3-benzothiazol-2-ylcarbamoyl)-3,4-dihydroiso-quinolin-2(1H)-yl]-3-[1-({1-[2-(1,1-dioxidothiomorpholin-4-yl)ethoxy]cyclohexyl}methyl)-5-methyl-1H-pyrazol-4-yl]pyridine-2-carboxylic acid;

6-[8-(1,3-benzothiazol-2-ylcarbamoyl)-3,4-dihydroiso-quinolin-2(1H)-yl]-3-(1-{[1-(2-hydroxyethoxy)cyclohexyl]methyl}-5-methyl-1H-pyrazol-4-yl)pyridine-2-carboxylic acid;

6-[8-(1,3-benzothiazol-2-ylcarbamoyl)-3,4-dihydroiso-quinolin-2(1H)-yl]-3-(1-{[1-(2,3-dimethoxypropoxy)cycloheptyl]methyl}-5-methyl-1H-pyrazol-4-yl)pyridine-2-carboxylic acid;

6-[8-(1,3-benzothiazol-2-ylcarbamoyl)-3,4-dihydroiso-quinolin-2(1H)-yl]-3-(1-{[1-(1,4-dioxan-2-ylmethoxy)cycloheptyl]methyl}-5-methyl-1H-pyrazol-4-yl)pyridine-2-carboxylic acid;

6-[8-(1,3-benzothiazol-2-ylcarbamoyl)-3,4-dihydroiso-quinolin-2(1H)-yl]-3-[5-methyl-1-({1-[2-(morpholin-4-yl)-2-oxoethoxy]cyclohexyl}methyl)-1H-pyrazol-4-yl]pyridine-2-carboxylic acid;

6-[8-(1,3-benzothiazol-2-ylcarbamoyl)-3,4-dihydroiso-quinolin-2(1H)-yl]-3-(1-{[1-(2,3-dihydroxypropoxy)cycloheptyl]methyl}-5-methyl-1H-pyrazol-4-yl)pyridine-2-carboxylic acid;

6-[8-(1,3-benzothiazol-2-ylcarbamoyl)-3,4-dihydroiso-quinolin-2(1H)-yl]-3-[1-{3,3-dimethyl-1-[2-(methylsulfonyl)ethoxy]cyclohexyl}methyl)-5-methyl-1H-pyrazol-4-yl]pyridine-2-carboxylic acid;

6-[8-(1,3-benzothiazol-2-ylcarbamoyl)-3,4-dihydroiso-quinolin-2(1H)-yl]-3-(1-{[1-(2-methoxyethoxy)-3,3-dimethylcyclohexyl]methyl}-5-methyl-1H-pyrazol-4-yl)pyridine-2-carboxylic acid;

6-[8-(1,3-benzothiazol-2-ylcarbamoyl)-3,4-dihydroiso-quinolin-2(1H)-yl]-3-[1-(1-cyclohexyl-3-methoxypropyl)-5-methyl-1H-pyrazol-4-yl]pyridine-2-carboxylic acid;

6-[8-(1,3-benzothiazol-2-ylcarbamoyl)-3,4-dihydroiso-quinolin-2(1H)-yl]-3-[1({3,3-dimethyl-1-[2-(methylamino)ethoxy]cyclohexyl}methyl)-5-methyl-1H-pyrazol-4-yl]pyridine-2-carboxylic acid;

6-[8-(1,3-benzothiazol-2-ylcarbamoyl)-3,4-dihydroiso-quinolin-2(1H)-yl]-3-{5-methyl-1-[(2,6,6-trimethyltetrahydro-2H-pyran-2-yl)methyl]-1H-pyrazol-4-yl}pyridine-2-carboxylic acid; and therapeutically acceptable salts, metabolites, prodrugs, salts of metabolites, and salts of prodrugs thereof.

In another aspect, the present invention provides compounds of Formula (IV)

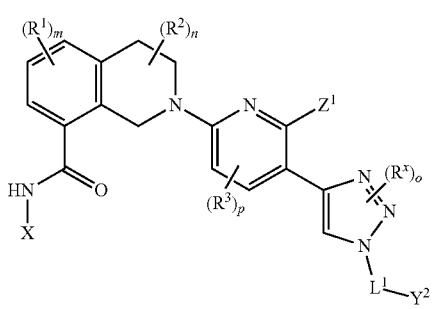

and therapeutically acceptable salts, metabolites, prodrugs, salts of metabolites, and salts of prodrugs thereof, wherein X, $L^1$, $Y^2$, $Z^1$, $R^1$, $R^2$, $R^3$, m, n, and p are as described herein for Formula (I); R' is as described herein for substituents on $Y^1$, and o is 0 or 1.

One embodiment of this invention pertains to compounds or therapeutically acceptable salts thereof, which are useful as inhibitors of anti-apoptotic Bcl-xL proteins, the compounds having Formula (IV)

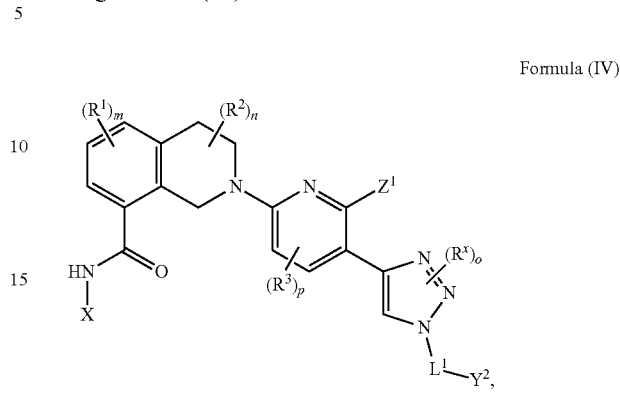

Formula (IV)

wherein

X is heteroaryl; wherein the heteroaryl represented by X is optionally substituted with one, two, three, or four $R^4$;

$R^x$ is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_1$, $NO_2$, F, Cl, Br and I;

$L^1$ is selected from the group consisting of $(CR^6R^7)_q$, $(CR^6R^7)_s$—O—$(CR^6R^7)_r$, $(CR^6R^7)_s$—C(O)_4$CR^6R^7)_r$, $(CR^6R^7)_s$—S—$(CR^6R^7)_r$, $(CR^6R^7)_s$—S(O)_2$—$(CR^6R^7)_r$, $(CR^6R^7)_s$—$NR^{6A}C(O)$—$(CR^6R^7)_r$, $(CR^6R^7)_s$—C(O)$NR^{6A}$—$(CR^6R^7)_r$, $(CR^6R^7)_s$—$NR^{6A}$—$(CR^6R^7)_r$, $(CR^6R^7)_s$—$S(O)_2NR^{6A}$—$(CR^6R^7)_r$, and $(CR^6R^7)_s$—$NR^{6A}S(O)_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I; or $L^1$ is a bond; and $Y^2$ is selected from the group consisting of $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl represented by $Y^2$ are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein each $Y^2$ and each ring fused to $Y^2$ are optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, $F$, $Cl$, $Br$ and $I$;

$Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and $CN$; or $Z^1$ is selected from the group consisting of

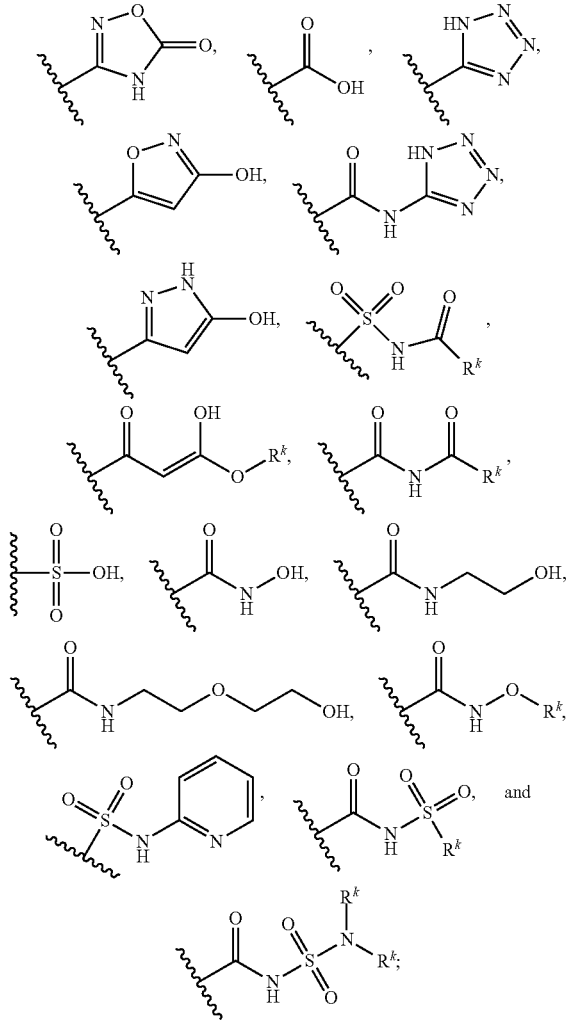

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^{12}R^{13}$, $OR^{12}$, $CN$, $NO_2$, halogen, $C(O)OR^{12}$, $C(O)NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^{14}$ and $R^{14}$;

$R^5$ is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

$R^6$ and $R^7$, at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $CO(O)H$, $C(O)H$, $OH$, $CN$, $N_3$, $NO_2$, $F$, $Cl$, $Br$ and $I$;

$R^8$, at each occurrence, is independently selected from the group consisting of $C_{1-6}$ alkyl, $C_{2-6}$ alkenyl, $C_{2-6}$ alkynyl, $C_{1-6}$ haloalkyl, aryl, heterocyclyl, cycloalkyl, and cycloalkenyl; wherein the $R^8$ $C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^{16}$, $NR^{16}S(O)_2R^6$, $NHC(O)OR^{16}$, $NR^{16}C(O)OR^{16}$, $NHC(O)NH_2$, $NHC(O)NHR^{16}$, $NHC(O)N(R^{16})_2$, $NR^{16}C(O)NHR^{16}$, $NR^{16}C(O)N(R^{16}$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH_2$, $SO_2NHR^{16}$, $SO_2N(R^{16})_2$, $CO(O)H$, $C(O)H$, $OH$, $CN$, $N_3$, $NO_2$, $F$, $Cl$, $Br$ and $I$; wherein the $R^8$ aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, $C(O)H$, $(O)$, $OH$, $CN$, $NO_2$, $OCF_3$, $OCF_2CF_3$, $F$, $Cl$, $Br$ and $I$;

$R^9$ is selected from the group consisting of $C_{1-6}$ alkyl, $C_{2-6}$ alkenyl, $C_{2-6}$ alkynyl, $C_{1-6}$ haloalkyl, cycloalkyl, phenyl and $(CH_2)_{1-4}$ phenyl; and $R^{10}$ and $R^{11}$, at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or $R^{10}$ and $R^{11}$, or $R^{10}$ and $R^9$, together with the atom to which each is attached are combined to form a heterocyclyl;

$R^k$, at each occurrence, is independently selected from the group consisting of $C_{1-6}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl; wherein the $R^k$ $C_{1-6}$ alkyl, $C_{2-6}$ alkenyl, and $C_{2-6}$ alkynyl are optionally substituted with aryl, heterocyclyl, cycloalkyl, or cycloalkenyl;

$R^{12}$ and $R^{11}$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^{14}$, at each occurrence, is independently selected from the group consisting of $C_{1-4}$ alkyl, $C_{2-4}$ alkenyl, $C_{2-4}$ alkynyl and $C_{1-4}$ haloalkyl;

$R^{12}$ and $R^{13}$, or $R^{12}$ and $R^{14}$, at each occurrence, together with the atom to which each is attached, are optionally combined to form a heterocyclyl;

$R^{15}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the $R^{15}C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ alkoxy, aryl, heterocycloalkyl, heterocycloalkenyl, heteroaryl, cycloalkyl, and cycloalkenyl, $NH_2$, $C(O)NH_2$, $SO_2NH_2$, $C(O)H$, $C(O)OH$, (O), OH, CN, $NO_2$, $OCF_3$, $OCF_2CF_3$, F, Cl, Br and I;

$R^{16}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocycloalkyl, heterocycloalkenyl, heteroaryl, cycloalkyl, and cycloalkenyl; wherein the $R^{16}C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one substituent independently selected from the group consisting of $OCH_3$, $OCH_2CH_2OCH_3$, and $OCH_2CH_2NHCH_3$;

q is 1, 2, or 3;
s is 0, 1, 2, or 3;
r is 0, 1, 2, or 3;
wherein the sum of s and r is 0, 1, or 2;
m is 0, 1, 2, or 3;
n is 0, 1, 2, 3, 4, 5, or 6;
o is 0 or 1; and
p is 0, 1, or 2.

In one embodiment of Formula (IV), in is 0, 1, 2, or 3; n is 0.1, 2, 3, 4, 5, or 6; and p is 0, 1, or 2. In another embodiment of Formula (IV), n is 0 or 1. In another embodiment of Formula (IV), n is 0 or 1; and each $R^2$ is independently deuterium or $C_{1-6}$ alkyl. In another embodiment of Formula (IV), m, n, and p are 0.

In one embodiment of Formula (IV), X is heteroaryl, which is optionally substituted with one, two, three or four $R^4$. In another embodiment of Formula (IV), X is heteroaryl, which is unsubstituted. In another embodiment of Formula (IV), X is heteroaryl, which is substituted with one $R^4$. In another embodiment of Formula (IV), X is heteroaryl, which is substituted with two $R^4$. In another embodiment of Formula (IV), X is heteroaryl, which is substituted with one $R^4$, and $R^4$ is $OR^{12}$ or halogen. In another embodiment of Formula (IV), X is heteroaryl, which is substituted with two $R^4$, and each $R^4$ is independently $OR^{12}$ or halogen. In another embodiment of Formula (IV), X is heteroaryl, which is substituted with one $R^4$, and $R^4$ is Cl, F, or methoxy. In another embodiment of Formula (IV), X is heteroaryl, which is substituted with two $R^4$, and each $R^4$ is independently F.

In one embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is $OR^{12}$ or halogen. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently $OR^{12}$ or halogen. In another embodiment of Formula (IV). X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is Cl, F, or methoxy. In another embodiment of Formula (IV), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently F.

In one embodiment of Formula (IV), X is benzo[d]thiazolyl, which is optionally substituted with one, two, three or four $R^4$. In another embodiment of Formula (IV), X is benzo[d]thiazolyl, which is unsubstituted. In another embodiment of Formula (IV), X is benzo[d]thiazolyl, which is substituted with one $R^4$. In another embodiment of Formula (IV), X is benzo[d]thiazolyl, which is substituted with two $R^4$. In another embodiment of Formula (IV), X is benzo[d]thiazolyl, which is substituted with one $R^4$, and $R^4$ is $OR^{12}$ or halogen. In another embodiment of Formula (IV), X is benzo[d]thiazolyl, which is substituted with two $R^4$, and each $R^4$ is independently $OR^{12}$ or halogen. In another embodiment of Formula (IV), X is benzo[d]thiazolyl, which is substituted with one $R^4$, and $R^4$ is Cl, F, or methoxy. In another embodiment of Formula (IV), X is benzo[d]thiazolyl, which is substituted with two $R^4$, and each $R^4$ is independently F.

In one embodiment of Formula (IV), $Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{10})NR^{10}R^{11}$, $C(=S)NR^{10}R^{11}$, $C(=NR^{10})NR^{10}R^{11}$, halogen, $NO_2$, and CN; or $Z^1$ is selected from the group consisting of

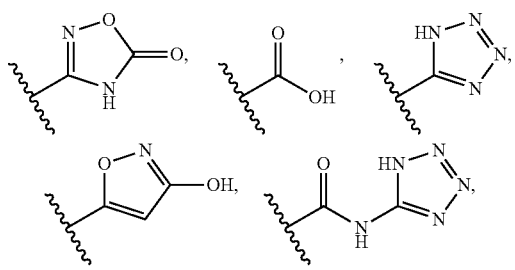

-continued

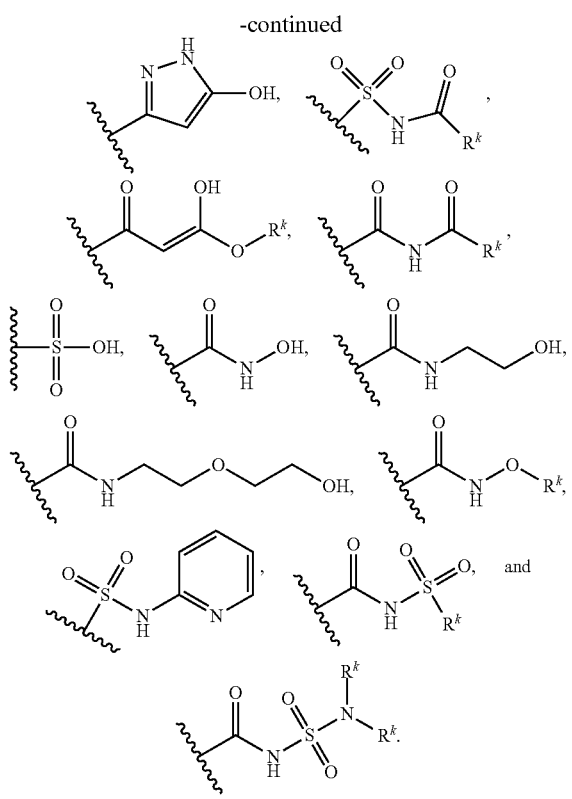

In another embodiment of Formula (IV), $Z^1$ is

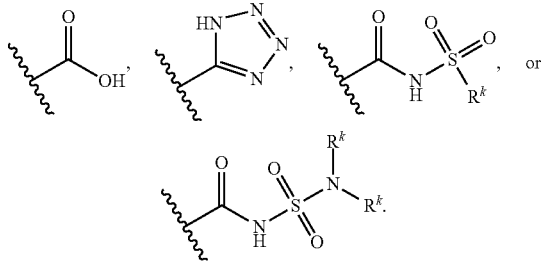

In another embodiment of Formula (IV), $Z^1$ is

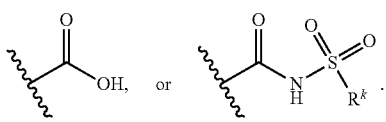

In another embodiment of Formula (IV), $Z^1$ is

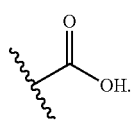

In one embodiment of Formula (IV), $L^1$ is selected from the group consisting of $(CR^6R^7)_q$, $(CR^6R^7)_s$—O—$(CR^6R^7)_r$, $(CR^6R^7)_s$—$(CR^6R^7)_r$, $(CR^6R^7)_s$—$(CR^6R^7)_r$, $(CR^6R^7)_s$—S(O)$_2$—$(CR^6R^7)_r$, $(CR^6R^7)_s$—NR$^{6A}$C(O)—$(CR^6R^7)_r$, $(CR^6R^7)_s$—C(O)NR$^{6A}$—$(CR^6R^7)_r$, $(CR^6R^7)_s$—NR$^{6A}$—$(CR^6R^7)_r$, $(CR^6R^7)_s$—$(CR^6R^7)_s$—S(O)$_2$NR$^{6A}$—$(CR^6R^7)_r$, and $(CR^6R^7)_s$—NR$^{6A}$S(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two rings selected from the group consisting of $C_{3-7}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I; or $L^1$ is a bond; and $Y^2$ is selected from the group consisting of $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl represented by $Y^2$ are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein each $Y^2$ and each ring fused to $Y^2$ are optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I.

In another embodiment of Formula (IV), $L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S(O)$_2$—$(CR^6R^7)_r$, $(CR^6R^7)_s$—NR$^{6A}$C(O)—$(CR^7R^7)_r$, $(CR^6R^7)_s$—NR$^{6A}$—$(CR^6R^7)_r$, and $(CR^6R^7)_s$—NR$^{6A}$S(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two benzene rings; wherein $Y^2$ is optionally substituted with one, two, or three substituents independently selected from the group consisting of $R^8$, $OR^8$, $SO_2R^8$, $CO(O)R^8$, $NHR^8$, $N(R^8)$, $C(O)H$, $OH$, $CN$, $NO_2$, F, Cl, Br and I; or $L^1$ is a bond; and $Y^2$ is selected from the group consisting of $C_{3-7}$ cycloalkyl, phenyl, and $C_{3-7}$ heterocyclyl; wherein the $C_{3-7}$ cycloalkyl, phenyl, and $C_{3-7}$ heterocyclyl represented by $Y^2$ are optionally fused to one benzene ring; wherein each $Y^2$ and each ring fused to $Y^2$ are optionally substituted with one substituent independently selected from the group consisting of $R^8$, $C(O)NHR^8$, F, Cl, Br and I.

In another embodiment of Formula (IV), $L^1$ is $(CR^6R^7)_q$; and $Y^2$ is selected from the group consisting of $C_{3-7}$ cycloalkyl, $C_{4-7}$ cycloalkenyl, phenyl, and $C_{3-7}$ heterocyclyl; wherein $R^6$ and $R^7$, at each occurrence, are $R^{15}$ or hydrogen; and q is 1, 2, or 3.

In another embodiment of Formula (IV), $L^1$ is selected from the group consisting of $(CR^6R^7)_q$, $(CR^6R^7)_s$—C(O)—$(CR^6R^7)_r$, and $(CR^6R^7)_s$—S(O)$_2$—$(CR^6R^7)_r$; q is 1, 2, or 3; s is 0; r is 0 or 1; $R^{6A}$ is independently selected from the group consisting of hydrogen, and $C_{1-6}$ alkyl; and $R^6$ and $R^7$, at each occurrence, are hydrogen.

In one embodiment of Formula (IV), o is 0. In another embodiment of Formula (IV), is I. In another embodiment of Formula (IV), o is 0 or 1. In another embodiment of Formula (IV), o is 1; and $R^x$ is independently selected from the group consisting of, $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, F, Cl, Br and I. In another embodiment of Formula (IV), o is 1; and $R^x$ is independently selected from the group consisting of $R^5$, $CO(O)R^5$, $CO(O)H$, $CN$, F, Cl, Br and I. In another embodiment of Formula (IV), o is 1; $R^5$, at each occurrence, is independently selected from the group consisting of $R^5$, $CO(O)R^5$, $CO(O)H$, CN, F, Cl, Br and I; and $R^5$ is independently selected from the group consisting of $C_{1-6}$ alkyl, $C_{2-6}$ alkenyl, $C_{1-6}$ haloalkyl, $C_{1-6}$ hydroxyalkyl, aryl, and cycloalkyl. In another embodiment of Formula (IV), o is 1; $R^x$ is independently selected from the group consisting of $R^5$, CN, F, Cl, Br and I; and $R^5$, at each occurrence, is independently selected from the group consisting of $C_{1-2}$ alkyl, and $C_1$ haloalkyl. In another embodiment of Formula (IV), o is 1; $R^x$ is $R^5$ or CN; and $R^5$ is $CH_3$. In another embodiment of Formula (IV), o is 1; and $R^x$ is CN. In another embodiment of Formula (IV), o is 1; $R^x$ is $R^5$; and $R^5$ is $CH_3$.

In one embodiment of Formula (IV), X is heteroaryl; wherein the heteroaryl represented by X is optionally substituted with one or two $R^4$;

$R^x$, at each occurrence, is independently selected from the group consisting of $R^5$, $CO(O)R^5$, $CO(O)H$, CN, F, Cl, Br and I;

$L^1$ is selected from the group consisting of $(CR^6R^7)_q$, $(CR^6R^7)_s$—$C(O)$—$(CR^6R^7)_r$, and $(CR^6R^7)_s$—$S(O)_2$—$(CR^6R^7)$ and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one benzene ring; wherein $Y^2$ is optionally substituted with one, two, or three substituents independently selected from the group consisting of $R^8$, $OR^8$, $SO_2R^8$, $CO(O)R^8$, $NHR^8$, $N(R^8)_2$, $C(O)H$, OH, CN, $NO_2$, F, Cl, Br and I; or $L^1$ is a bond; and $Y^2$ is selected from the group consisting of $C_{3-7}$ cycloalkyl, phenyl, and $C_{3-7}$ heterocyclyl; wherein the $C_{3-7}$ cycloalkyl, phenyl, and $C_{3-7}$ heterocyclyl represented by $Y^2$ are optionally fused to one benzene ring; wherein each $Y^2$ and each ring fused to $Y^2$ are optionally substituted with one substituent independently selected from the group consisting of $R^8$ and $C(O)NHR^8$;

$Z^1$ is selected from the group consisting of

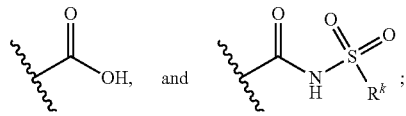

$R^2$, at each occurrence, is independently $C_{1-6}$ alkyl;
$R^4$, at each occurrence, is independently selected from the group consisting of $OR^{12}$ and halogen;

$R^5$, at each occurrence, is independently selected from the group consisting of $C_{1-6}$ alkyl, $C_{1-6}$ haloalkyl, $C_{1-6}$ hydroxyalkyl, aryl, and cycloalkyl;

$R^{6A}$ is independently selected from the group consisting of hydrogen and $C_{1-6}$ alkyl;

$R^6$ and $R^7$, at each occurrence, are each independently selected from the group consisting of hydrogen, $R^{15}$, and $CO(O)R^{15}$;

$R^8$, at each occurrence, is independently selected from the group consisting of $C_{1-6}$ alkyl, $C_{2-6}$ alkynyl, aryl, heterocyclyl, and cycloalkyl; wherein the $R^8$ $C_{1-6}$ alkyl, and $C_{2-6}$ alkynyl are optionally substituted with one, two, or three substituents independently selected from the group consisting of $R^{16}$, $OR^{16}$, $SO_2R^{16}$, $C(O)R^{16}$, $N(R^{16})_2$, OH, F, Cl, Br and I; wherein the $R^8$ aryl and heterocyclyl are optionally substituted with one substituent independently selected from the group consisting of $C_{1-6}$ alkyl, F, Cl, Br and I;

$R^k$, at each occurrence, is independently $C_{1-6}$ alkyl;

$R^{12}$ and $R^{13}$, at each occurrence, are each independently $C_{1-4}$ alkyl;

$R^{15}$, at each occurrence, is independently selected from the group consisting of $C_{1-4}$ alkyl, and aryl; wherein the $R^{15}$ $C_{1-4}$ alkyl is optionally substituted with one substituent independently selected from the group consisting $C_{1-4}$ alkoxy, and heterocycloalkyl;

$R^{16}$, at each occurrence, is independently selected from the group consisting of $C_{1-4}$ alkyl, aryl, heterocycloalkyl, and heteroaryl;

q is 1, 2, or 3;
s is 0;
r is 0, or 1;
m is 0;
n is 0, or 1;
o is 0 or 1; and
p is 0.

Still another embodiment pertains to a compound having Formula (IV) selected from the group consisting of
6-[8-(1,3-benzothiazol-2-ylcarbamoyl)-3,4-dihydroisoquinolin-2(1H)-yl]-3-(1-benzyl-1H-1,2,3-triazol-4-yl)pyridine-2-carboxylic acid;
6-[8-(1,3-benzothiazol-2-ylcarbamoyl)-3,4-dihydroisoquinolin-2(1H)-yl]-3-(1-{[(1S,2R,5S)-6,6-dimethylbicyclo[3.1.1]hept-2-yl]methyl}-5-methyl-1H-1,2,3-triazol-4-yl)pyridine-2-carboxylic acid;
6-[8-(1,3-benzothiazol-2-ylcarbamoyl)-3,4-dihydroisoquinolin-2(1H)-yl]-3-{1-[(1-methoxy-3,3-dimethylcyclohexyl)methyl]-5-methyl-1H-1,2,3-triazol-4-yl}pyridine-2-carboxylic acid, and therapeutically acceptable salts, metabolites, prodrugs, salts of metabolites, and salts of prodrugs thereof.

In another aspect, the present invention provides compounds of Formula (V)

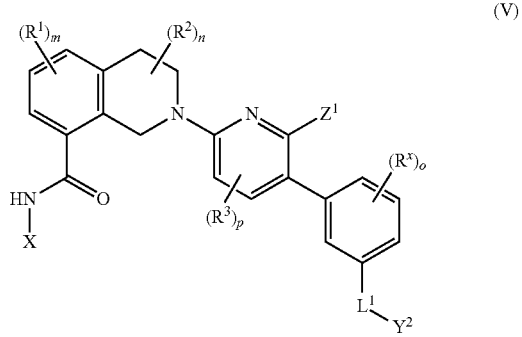

and therapeutically acceptable salts, metabolites, prodrugs, salts of metabolites, and salts of prodrugs thereof, wherein X, $L^1, Y^2, Z^1, R^1, R^2, R^3$, m, n, and p are as described herein for Formula (I); $R^x$ is as described herein for substituents on $Y^1$, and o is 0, 1, 2, 3, or 4.

One embodiment of this invention pertains to compounds or therapeutically acceptable salts thereof, which are useful as inhibitors of anti-apoptotic Bcl-xL proteins, the compounds having Formula (V)

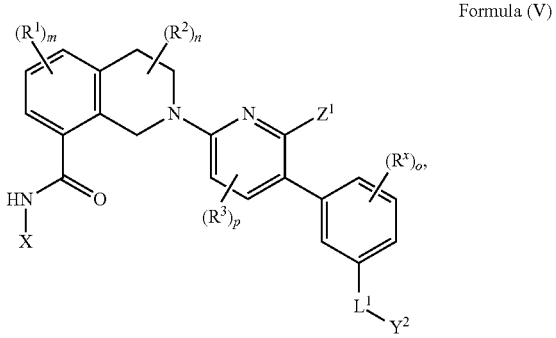

Formula (V)

wherein

X is heteroaryl; wherein the heteroaryl represented by X is optionally substituted with one, two, three, or four $R^4$;

$R^x$, at each occurrence, is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, F, Cl, Br and I;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S$(CR^6R^7)_r$, $(CR^6R^7)_s$—S(O)_2—$(CR^6R^7)_r$, $(CR^6R^7)_s$—NR$^{6A}$C(O)—$(CR^6R^7)_r$, $(CR^6R^7)_s$—C(O)NR$^{6A}$—$(CR^6R^7)_r$, $(CR^6R^7)_s$—NR$^{6A}$—$(CR^6R^7)_r$, $(CR^6R^7)_s$—S(O)_2NR$^{6A}$—$(CR^6R^7)_r$, and $(CR^6R^7)_s$—NR$^{6A}$S(O)_2—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I; or $L^1$ is a bond; and $Y^2$ is selected from the group consisting of $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl represented by $Y^2$ are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein each $Y^2$ and each ring fused to $Y^2$ are optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)$, $CO(O)H$, $C(O)H$, $OH$, $CN$, $N_3$, $NO_2$, F, Cl, Br and I;

$Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^{10}$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and CN; or $Z^1$ is selected from the group consisting of

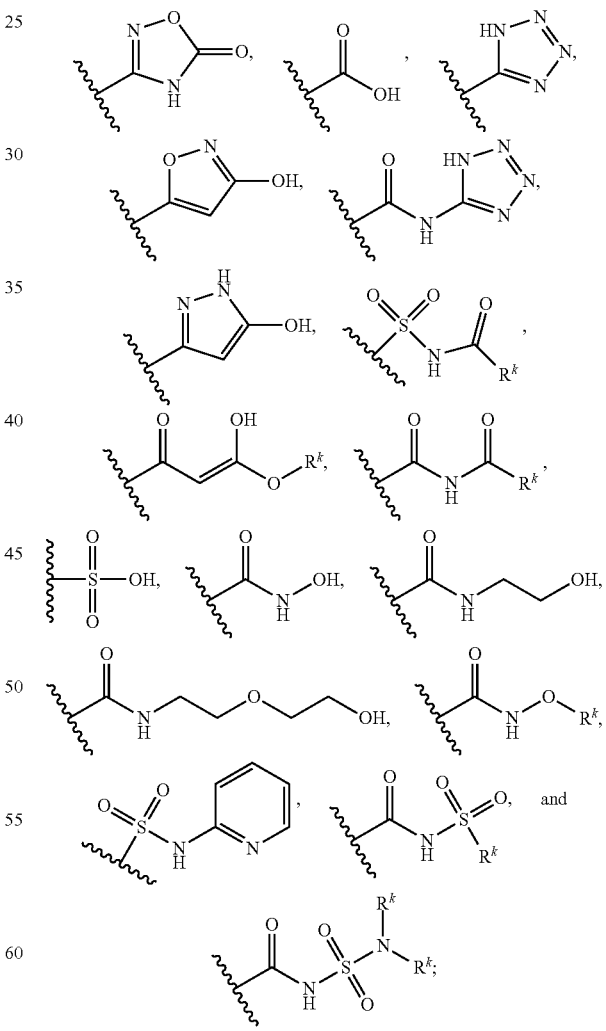

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^{12}R^{13}$, $OR^{12}$, CN, $NO_2$, halogen, $C(O)OR^{12}$, $C(O)NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^{14}$ and $R^{14}$;

$R^5$, at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

$R^6$ and $R^7$, at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{13}$, $SO_2N(R^{15})_2$, $CO(O)H$, $C(O)H$, OH, CN, $N_3$, $NO_2$, F, Cl, Br and I;

$R^8$, at each occurrence, is independently selected from the group consisting of $C_{1-6}$ alkyl, $C_{1-6}$ alkenyl, $C_{2-6}$ alkynyl, $C_{1-6}$ haloalkyl, aryl, heterocyclyl, cycloalkyl, and cycloalkenyl; wherein the $R^8 C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^{16}$, $NR^{16}S(O)_2R^{16}$, $NHC(O)OR^{16}$, $NR^{16}C(O)OR^{16}$, $NHC(O)NH_2$, $NHC(O)NHR^{16}$, $NHC(O)N(R^{16})_2$, $NR^{16}C(O)NHR^{16}$, $NR^{16}C(O)N(R^{16})_2$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH_2$, $SO_2NHR^{16}$, $SO_2N(R^{16})_2$, $CO(O)H$, $C(O)H$, OH, CN, $N_3$, $NO_2$, F, Cl, Br and I; wherein the $R^8$ aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, $C(O)H$, (O), OH, CN, $NO_2$, $OCF_3$, $OCF_2CF_3$, F, Cl, Br and I;

$R^9$ is selected from the group consisting of $C_{1-6}$ alkyl, $C_{2-6}$ alkenyl, $C_{2-6}$ alkynyl, $C_{1-6}$ haloalkyl, cycloalkyl, phenyl and $(CH_2)_{1-4}$ phenyl; and $R^{10}$ and $R^{11}$, at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or $R^{10}$ and $R^{11}$, or $R^{10}$ and $R^9$, together with the atom to which each is attached are combined to form a heterocyclyl;

$R^k$, at each occurrence, is independently selected from the group consisting of $C_{1-6}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl; wherein the $R^k C_{1-6}$ alkyl, $C_{2-6}$ alkenyl, and $C_{2-6}$ alkynyl are optionally substituted with aryl, heterocyclyl, cycloalkyl, or cycloalkenyl;

$R^{12}$ and $R^{13}$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^{14}$, at each occurrence, is independently selected from the group consisting of $C_{1-4}$ alkyl, $C_{2-4}$ alkenyl, $C_{2-4}$ alkynyl and $C_{1-4}$ haloalkyl;

$R^{12}$ and $R^{13}$, or $R^{12}$ and $R^{14}$, at each occurrence, together with the atom to which each is attached, are optionally combined to form a heterocyclyl;

$R^{15}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the $R^{15} C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ alkoxy, aryl, heterocycloalkyl, heterocycloalkenyl, heteroaryl, cycloalkyl, and cycloalkenyl, $NH_2$, $C(O)NH_2$, $SO_2NH_2$, $C(O)H$, $C(O)OH$, (O), OH, CN, $NO_2$, $OCF_3$, $OCF_2CF_3$, F, Cl, Br and I;

$R^{16}$, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocycloalkyl, heterocycloalkenyl, heteroaryl, cycloalkyl, and cycloalkenyl; wherein the $R^{16} C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one substituent independently selected from the group consisting of $OCH_3$, $OCH_2CH_2OCH_3$, and $OCH_2CH_2NHCH_3$;

q is 1, 2, or 3;
s is 0, 1, 2, or 3;
r is 0, 1, 2, or 3;
wherein the sum of s and r is 0, 1, or 2;
m is 0, 1, 2, or 3;
n is 0, 1, 2, 3, 4, 5, or 6;
o is 0, 1, 2, 3, or 4; and
p is 0, 1, or 2.

In one embodiment of Formula (V), m is 0, 1, 2, or 3; n is 0, 1, 2, 3, 4, 5, or 6; and p is 0, 1, or 2. In another embodiment of Formula (V), n is 0 or 1. In another embodiment of Formula (V), n is 0 or 1; and each $R^2$ is independently deuterium or $C_{1-6}$ alkyl. In another embodiment of Formula (V), m, n, and p are 0.

In one embodiment of Formula (V), X is heteroaryl, which is optionally substituted with one, two, three or four $R^4$. In another embodiment of Formula (V), X is heteroaryl, which is unsubstituted. In another embodiment of Formula (V), X is heteroaryl, which is substituted with one $R^4$. In another embodiment of Formula (V), X is heteroaryl, which is substituted with two $R^4$. In another embodiment of Formula (V), X is heteroaryl, which is substituted with one $R^4$, and $R^4$ is $OR^{12}$ or halogen. In another embodiment of Formula (V), X is heteroaryl, which is substituted with two $R^4$, and each $R^4$ is independently $OR^{12}$ or halogen. In another embodiment of Formula (V), X is heteroaryl, which is substituted with one $R^4$, and $R^4$ is Cl, F, or methoxy. In another embodiment of Formula (V), X is heteroaryl, which is substituted with two $R^4$, and each $R^4$ is independently F.

In one embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (V), X is benzo[d]thiazolyl, thiazolo[5,4-b]pyridinyl, thiazolo[4,5-c]

pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is $OR^{12}$ or halogen. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently $OR^{12}$ or halogen. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is Cl, F, or methoxy. In another embodiment of Formula (V), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$ and each $R^4$ is independently F.

In one embodiment of Formula (V), X is benzo[d]thiazolyl, which is optionally substituted with one, two, three or four $R^4$. In another embodiment of Formula (V), X is benzo[d]thiazolyl, which is unsubstituted. In another embodiment of Formula (V), X is benzo[d]thiazolyl, which is substituted with one $R^4$. In another embodiment of Formula (V), X is benzo[d]thiazolyl, which is substituted with two $R^4$. In another embodiment of Formula (V), X is benzo[d]thiazolyl, which is substituted with one $R^4$, and $R^4$ is $OR^{12}$ or halogen. In another embodiment of Formula (V), X is benzo[d]thiazolyl, which is substituted with two $R^4$, and each $R^4$ is independently $OR^{12}$ or halogen. In another embodiment of Formula (V), X is benzo[d]thiazolyl, which is substituted with one $R^4$, and $R^4$ is Cl, F, or methoxy. In another embodiment of Formula (V), X is benzo[d]thiazolyl, which is substituted with two $R^4$, and each $R^4$ is independently F.

In one embodiment of Formula (V), $Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and CN; or $Z^1$ is selected from the group consisting of

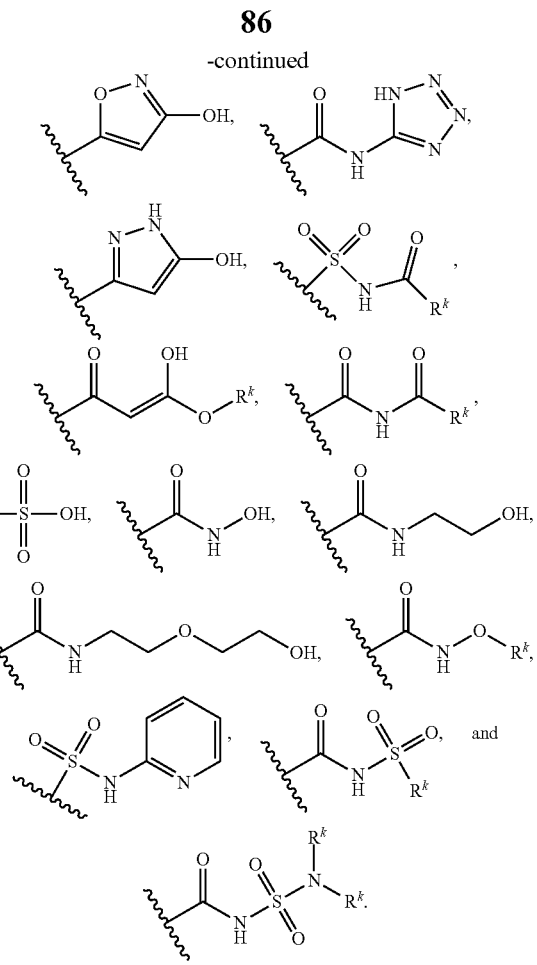

In another embodiment of Formula (V). $Z^1$ is

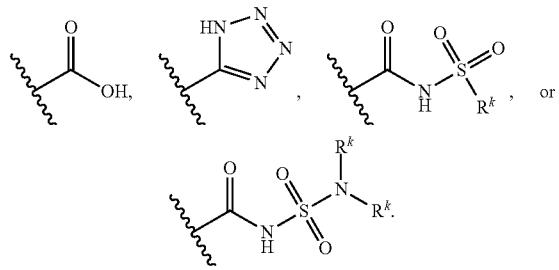

In another embodiment of Formula (V), $Z^1$ is

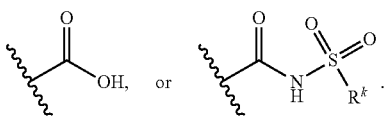

In another embodiment of Formula (V), $Z^1$ is

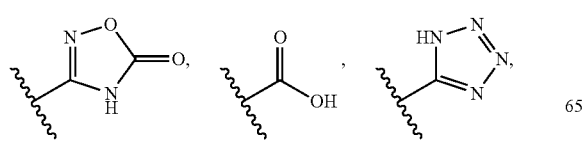

In one embodiment of Formula (V), $L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—$(CR^6R^7)_r$, $(CR^6R^7)_s$—S(O)$_2$—$(CR^6R^7)_r$, $(CR^6R^7)_s$—NR$^{64}$C(O)—$(CR^6R^7)_r$, $(CR^6R^7)_s$—C(O)NR$^{64}$—$(CR^6R^7)_r$, $(CR^6R^7)_s$—NR$^{64}$—$(CR^6R^7)_r$, $(CR^6R^7)_s$—S(O)$_2$NR$^{64}$—$(CR^6R^7)_r$, and $(CR^6R^7)_s$—NR$^{64}$S(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, $F$, $Cl$, $Br$ and $I$; or $L^1$ is a bond; and $Y^2$ is selected from the group consisting of $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl represented by $Y^2$ are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein each $Y^2$ and each ring fused to $Y^2$ are optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, $F$, $Cl$, $Br$ and $I$.

In another embodiment of Formula (V), $L^1$ is selected from the group consisting of $(CR^6R^7)_q$, $(CR^6R^7)_s$—O—$(CR^6R^7)_r$, $(CR^6R^7)C(O)$—$(CR^6R^7)_r$, $(CR^6R^7)_s$—S(O)$_2$—$(CR^6R^7)_r$, $(CR^6R^7)_s$—NR$^{64}$C(O)—$(CR^6R^7)_r$, $(CR^6R^7)_s$—NR$^{64}$—$(CR^6R^7)_r$, and $(CR^6R^7)_s$—NR$^{64}$S(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two benzene rings; wherein $Y^2$ is optionally substituted with one, two, or three substituents independently selected from the group consisting of $R^8$, $OR^8$, $SO_2R^8$, $CO(O)R^8$, $NHR^8$, $N(R^8)$, $C(O)H$, $OH$, $CN$, $NO_2$, $F$, $Cl$, $Br$ and $I$; or $L^1$ is a bond; and $Y^2$ is selected from the group consisting of $C_{3-7}$ cycloalkyl, phenyl, and $C_{3-7}$ heterocyclyl; wherein the $C_{3-7}$ cycloalkyl, phenyl, and $C_{3-7}$ heterocyclyl represented by $Y^2$ are optionally fused to one benzene ring; wherein each $Y^2$ and each ring fused to $Y^2$ are optionally substituted with one substituent independently selected from the group consisting of $R^8$, $C(O)NHR^8$, $F$, $Cl$, $Br$ and $I$.

In another embodiment of Formula (V), $L^1$ is $(CR^6R^7)_q$; and $Y^2$ is selected from the group consisting of $C_{3-7}$ cycloalkyl, $C_{4-7}$ cycloalkenyl, phenyl, and $C_{3-7}$ heterocyclyl; wherein $R^6$ and $R^7$, at each occurrence, are $R^{15}$ or hydrogen; and q is 1, 2, or 3.

In another embodiment of Formula (V), $L^1$ is selected from the group consisting of $(CR^6R^7)_q$, $(CR^6R^7)_s$—O—$(CR^6R^7)_q$, $(CR^6R^7)_s$—C(O)—$(CR^6R^7)_r$, $(CR^6R^7)_s$—S(O)—$(CR^6R^7)_r$, $(CR^6R^7)_s$—NR$^{64}$C(O)—$(CR^6R^7)_r$, $(CR^6R^7)_s$—NR$^{64}$—$(CR^6R^7)_r$, and $(CR^6R^7)_s$—NR$^{64}$S(O)$_2$—$(CR^6R^7)_r$; q is 1, 2, or 3; s is 0; r is 0 or 1; $R^{64}$ is independently selected from the group consisting of hydrogen, and $C_{1-6}$ alkyl; and $R^6$ and $R^{64}$ at each occurrence, are hydrogen.

In one embodiment of Formula (V), o is 0. In another embodiment of Formula (V), o is 1. In another embodiment of Formula (V), o is 0 or 1. In another embodiment of Formula (V), o is 0, 1, 2, 3, or 4. In another embodiment of Formula (V), o is 0, 1, 2, 3, or 4; and $R^x$, at each occurrence, is independently selected from the group consisting of, $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, $F$, $Cl$, $Br$ and $I$. In another embodiment of Formula (V), o is 1 or 2; and $R^x$, at each occurrence, is independently selected from the group consisting of $R^5CO(O)R^5$, $CO(O)H$, $CN$, $F$, $Cl$, $Br$ and $I$. In another embodiment of Formula (V), o is 1 or 2; $R^x$, at each occurrence, is independently selected from the group consisting of $R^5$, $CO(O)R^5$, $CO(O)H$. $CN$, $F$, $Cl$, $Br$ and $I$; and $R^5$, at each occurrence, is independently selected from the group consisting of $C_{1-6}$ alkyl, $C_{2-6}$ alkenyl, $C_{1-6}$ haloalkyl, $C_{1-6}$ hydroxyalkyl, aryl, and cycloalkyl. In another embodiment of Formula (V), o is 1; $R^x$, at each occurrence, is independently selected from the group consisting of $R^5$, $CN$, $F$, $Cl$, $Br$ and $I$; and $R^5$, at each occurrence, is independently selected from the group consisting of $C_{1-2}$ alkyl, and $C_1$ haloalkyl. In another embodiment of Formula (V), o is 1 or 2; $R^x$ is $R^5$ or $CN$; and $R^5$ is $CH_3$. In another embodiment of Formula (V), o is 1; and $R^x$ is $CN$. In another embodiment of Formula (V), o is 1; and $R^x$ is $CH_3$.

In one embodiment of Formula (V), X is heteroaryl; wherein the heteroaryl represented by X is optionally substituted with one or two $R^4$;

$R^x$, at each occurrence, is independently selected from the group consisting of $R^5$, $CO(O)R^5$, $CO(O)H$, $CN$, $F$, $Cl$, $Br$ and $I$;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S(O)$_2$—$(CR^6R^7)_r$, $(CR^6R^7)_s$—NR$^{64}$C(O)—$(CR^6R^7)_r$, $(CR^6R^7)_s$—NR$^{64}$—$(CR^6R^7)_r$, and $(CR^6R^7)_s$—NR$^{64}$S(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one benzene ring; wherein $Y^2$ is optionally substituted with one, two, or three substituents independently selected from the group consisting of $R^8$, $OR^8$, $SO_2R^8$, $CO(O)R^8$, $NHR^8$, $N(R^8)$, $C(O)H$, $OH$, $CN$, $NO_2$, $F$, $Cl$, $Br$ and $I$; or $L^1$ is a bond; and $Y^2$ is selected from the group consisting of $C_{3-7}$ cycloalkyl, phenyl, and $C_{3-7}$ heterocyclyl; wherein the $C_{3-7}$ cycloalkyl, phenyl, and $C_{3-7}$ heterocyclyl represented by $Y^2$ are optionally fused to one benzene ring; wherein each $Y^2$ and each ring fused to $Y^2$ are optionally substituted with one substituent independently selected from the group consisting of $R^8$ and $C(O)NHR^8$;

$Z^1$ is selected from the group consisting of

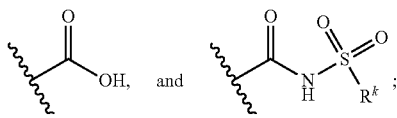

$R^2$, at each occurrence, is independently $C_{1-6}$ alkyl;
$R^4$, at each occurrence, is independently selected from the group consisting of $OR^{12}$ and halogen;
$R^5$, at each occurrence, is independently selected from the group consisting of $C_{1-6}$ alkyl, $C_{1-6}$ haloalkyl, $C_{1-6}$ hydroxyalkyl, aryl, and cycloalkyl;
$R^{6A}$ is independently selected from the group consisting of hydrogen and $C_{1-6}$ alkyl;
$R^6$ and $R^7$, at each occurrence, are each independently selected from the group consisting of hydrogen, $R^{15}$, and $CO(O)R^{15}$;
$R^8$, at each occurrence, is independently selected from the group consisting of $C_{1-4}$ alkyl, $C_{2-6}$ alkynyl, aryl, heterocyclyl, and cycloalkyl; wherein the $R^8 C_{1-6}$ alkyl, and $C_{2-6}$ alkynyl are optionally substituted with one, two, or three substituents independently selected from the group consisting of $R^{16}$, $OR^{16}$, $SO_2R^{16}$, $C(O)R^{16}$, $N(R^{16})_2$, OH, F, Cl, Br and I; wherein the $R^8$ aryl and heterocyclyl are optionally substituted with one substituent independently selected from the group consisting of $C_{1-6}$ alkyl, F, Cl, Br and I;
$R^k$, at each occurrence, is independently $C_{1-6}$ alkyl;
$R^{12}$ and $R^{13}$, at each occurrence, are each independently $C_{1-4}$ alkyl;
$R^{15}$, at each occurrence, is independently selected from the group consisting of $C_{1-4}$ alkyl, and aryl; wherein the $R^{15} C_{1-4}$ alkyl is optionally substituted with one substituent independently selected from the group consisting $C_{1-4}$ alkoxy, and heterocycloalkyl;
$R^{16}$, at each occurrence, is independently selected from the group consisting of $C_{1-4}$ alkyl, aryl, heterocycloalkyl, and heteroaryl;
q is 1, 2, or 3;
s is 0;
r is 0, or 1;
m is 0;
n is 0, or 1;
o is 0, 1, 2, 3, or 4; and
p is 0.

Still another embodiment pertains to a compound having Formula (V) selected from the group consisting of
6-[8-(1,3-benzothiazol-2-ylcarbamoyl)-3,4-dihydroisoquinolin-2(1H)-yl]-3-(4-phenoxyphenyl)pyridine-2-carboxylic acid;
6-[8-(1,3-benzothiazol-2-ylcarbamoyl)-3,4-dihydroisoquinolin-2(1H)-yl]-3-(3-phenoxyphenyl)pyridine-2-carboxylic acid;
6-[8-(1,3-benzothiazol-2-ylcarbamoyl)-3,4-dihydroisoquinolin-2(1H)-yl]-3-[3-(4-nitrophenoxy)phenyl]pyridine-2-carboxylic acid;
6-[8-(1,3-benzothiazol-2-ylcarbamoyl)-3,4-dihydroisoquinolin-2(1H)-yl]-3-[3-(4-chlorophenoxy)phenyl]pyridine-2-carboxylic acid;
6-[8-(1,3-benzothiazol-2-ylcarbamoyl)-3,4-dihydroisoquinolin-2(1H)-yl]-3-(3-benzylphenyl)pyridine-2-carboxylic acid;
6-[8-(1,3-benzothiazol-2-ylcarbamoyl)-3,4-dihydroisoquinolin-2(1H)-yl]-3-[3-(cyclohexylmethyl)-2-methylphenyl]pyridine-2-carboxylic acid;
6-[8-(1,3-benzothiazol-2-ylcarbamoyl)-3,4-dihydroisoquinolin-2(1H)-yl]-3-(4-methyl-3-phenoxyphenyl)pyridine-2-carboxylic acid;
6-[8-(1,3-benzothiazol-2-ylcarbamoyl)-3,4-dihydroisoquinolin-2(1H)-yl]-3-(2-methyl-5-phenoxyphenyl)pyridine-2-carboxylic acid;
6-[8-(1,3-benzothiazol-2-ylcarbamoyl)-3,4-dihydroisoquinolin-2(1H)-yl]-3-(2-methyl-3-phenoxyphenyl)pyridine-2-carboxylic acid;
6-[8-(1,3-benzothiazol-2-ylcarbamoyl)-3,4-dihydroisoquinolin-2(1H)-yl]-3-(2-methyl-4-phenoxyphenyl)pyridine-2-carboxylic acid;
6-[8-(1,3-benzothiazol-2-ylcarbamoyl)-3,4-dihydroisoquinolin-2(1H)-yl]-3-[3-(cyclohexylmethoxy)-2-methylphenyl]pyridine-2-carboxylic acid;
6-[8-(1,3-benzothiazol-2-ylcarbamoyl)-3,4-dihydroisoquinolin-2(1H)-yl]-3-[4-(cyclohexyloxy)-2-methylphenyl]pyridine-2-carboxylic acid;
6-[8-(1,3-benzothiazol-2-ylcarbamoyl)-3,4-dihydroisoquinolin-2(1H)-yl]-3-[3-(cyclohexyloxy)-2-methylphenyl]pyridine-2-carboxylic acid;
6-[8-(1,3-benzothiazol-2-ylcarbamoyl)-3,4-dihydroisoquinolin-2(1H)-yl]-3-[4-(cyclohexylmethoxy)-2-methylphenyl]pyridine-2-carboxylic acid;
6-[8-(1,3-benzothiazol-2-ylcarbamoyl)-3,4-dihydroisoquinolin-2(1H)-yl]-3-[2-cyano-3-(cyclohexyloxy)phenyl]pyridine-2-carboxylic acid;
6-[8-(1,3-benzothiazol-2-ylcarbamoyl)-3,4-dihydroisoquinolin-2(1H)-yl]-3-[2-chloro-3-(cyclohexyloxy)phenyl]pyridine-2-carboxylic acid;
6-[8-(1,3-benzothiazol-2-ylcarbamoyl)-3,4-dihydroisoquinolin-2(1H)-yl]-3-[3-(cyclohexylamino)-2-methylphenyl]pyridine-2-carboxylic acid;
6-[8-(1,3-benzothiazol-2-ylcarbamoyl)-3,4-dihydroisoquinolin-2(1H)-yl]-3-[3-(cyclohexyloxy)-2-fluorophenyl]pyridine-2-carboxylic acid;
6-[8-(1,3-benzothiazol-2-ylcarbamoyl)-3,4-dihydroisoquinolin-2(1H)-yl]-3-[3-(cyclohexyloxy)-2-(trifluoromethyl)phenyl]pyridine-2-carboxylic acid;
6-[8-(1,3-benzothiazol-2-ylcarbamoyl)-3,4-dihydroisoquinolin-2(1H)-yl]-3-{3-[(3,3-dimethylcyclohexyl)oxy]-2-methylphenyl}pyridine-2-carboxylic acid;
6-[8-(1,3-benzothiazol-2-ylcarbamoyl)-3,4-dihydroisoquinolin-2(1H)-yl]-3-{2-methyl-3-[methyl(phenyl)amino]phenyl}pyridine-2-carboxylic acid;
6-[8-(1,3-benzothiazol-2-ylcarbamoyl)-3,4-dihydroisoquinolin-2(1H)-yl]-3-{3-[(3,3-dimethylcyclohexyl)(methyl)amino]-2-methylphenyl}pyridine-2-carboxylic acid;
6-[8-(1,3-benzothiazol-2-ylcarbamoyl)-3,4-dihydroisoquinolin-2(1H)-yl]-3-{3-[(cyclohexylcarbonyl)(methyl)amino]-2-methylphenyl}pyridine-2-carboxylic acid;
6-[8-(1,3-benzothiazol-2-ylcarbamoyl)-3,4-dihydroisoquinolin-2(1H)-yl]-3-(2-methyl-3-{methyl[(1-methylcyclohexyl)carbonyl]amino}phenyl)pyridine-2-carboxylic acid;
6-[8-(1,3-benzothiazol-2-ylcarbamoyl)-3,4-dihydroisoquinolin-2(1H)-yl]-3-{2-cyano-3-[(cyclohexylsulfonyl)(methyl)amino]phenyl}pyridin-2-carboxylic acid;
6-[8-(1,3-benzothiazol-2-ylcarbamoyl)-3,4-dihydroisoquinolin-2(1H)-yl]-3-{2-cyano-3-[2-(tricyclo[3.3.1.1$^{3,7}$]dec-1-yl)pyrrolidin-1-yl]phenyl}pyridine-2-carboxylic acid; and therapeutically acceptable salts, metabolites, prodrugs, salts of metabolites, and salts of prodrugs thereof.-

In another aspect, the present invention provides compounds of Formula (VI)

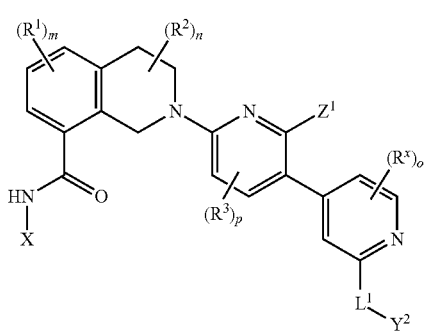

Formula (VI)

and therapeutically acceptable salts, metabolites, prodrugs, salts of metabolites, and salts of prodrugs thereof, wherein X, $L^1$, $Y^2$, $Z^1$, $R^1$, $R^2$, $R^3$, m, n, and p are as described herein for Formula (I); $R^x$ is as described herein for substituents on $Y^1$, and o is 0, 1, 2, or 3.

One embodiment of this invention pertains to compounds or therapeutically acceptable salts thereof, which are useful as inhibitors of anti-apoptotic Bcl-xL proteins, the compounds having Formula (VI)

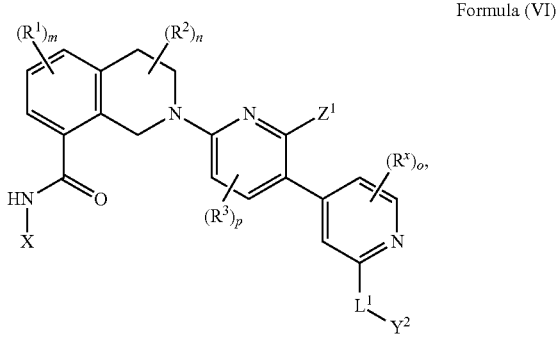

Formula (VI)

wherein

X is heteroaryl; wherein the heteroaryl represented by X is optionally substituted with one, two, three, or four $R^4$;

$R^x$, at each occurrence, is independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, F, Cl, Br and I;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—$NR^{6A}C(O)$—$(CR^6R^7)_r$, $(CR^6R^7)_s$—C(O) $NR^{6A}$—$(CR^6R^7)_r$, $(CR^6R^7)_s$—$NR^{6A}$—$(CR^6R^7)_r$, $(CR^6R^7)_s$—$S(O)_2NR^{6A}$—$(CR^6R^7)_r$, and $(CR^6R^7)_s$—$NR^{6A}S(O)_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I; or $L^1$ is a bond; and $Y^2$ is selected from the group consisting of $C_{3-7}$ cycloalkyl, $C_{4-7}$ cycloalkenyl, phenyl, and $C_{3-7}$ heterocyclyl; wherein the $C_{3-7}$ cycloalkyl, $C_4$, cycloalkenyl, phenyl, and $C_{3-7}$ heterocyclyl represented by $Y^2$ are optionally fused to one or two rings selected from the group consisting of $C_{3-8}$ cycloalkane, $C_{3-8}$ cycloalkene, benzene, $C_{5-6}$ heteroarene, $C_{3-8}$ heterocycloalkane, and $C_{3-8}$ heterocycloalkene; wherein each $Y^2$ and each ring fused to $Y^2$ are optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$. $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, F, Cl, Br and I;

$Z^1$ is selected from the group consisting of $C(O)OR^9$, $C(O)NR^{10}R^{11}$, $C(O)R^{11}$, $NR^{10}C(O)R^{11}$, $NR^{10}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{10}R^{11}$, $NR^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{10}$, $C(=NR^{10})NR^{10}R^{11}$, halogen, $NO_2$, and CN; or $Z^1$ is selected from the group consisting of

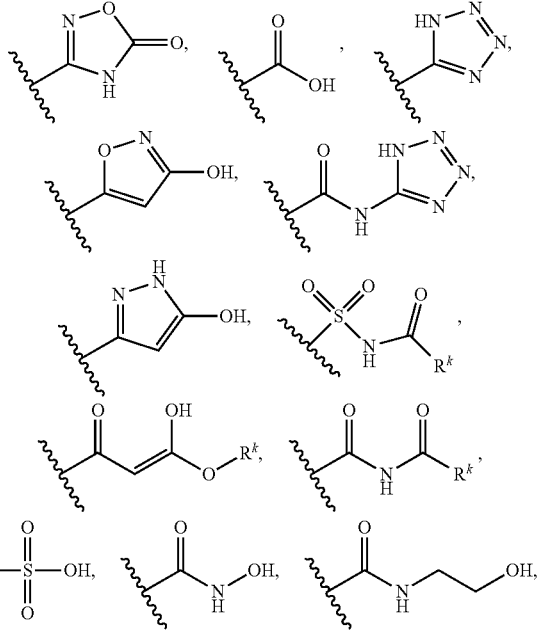

-continued

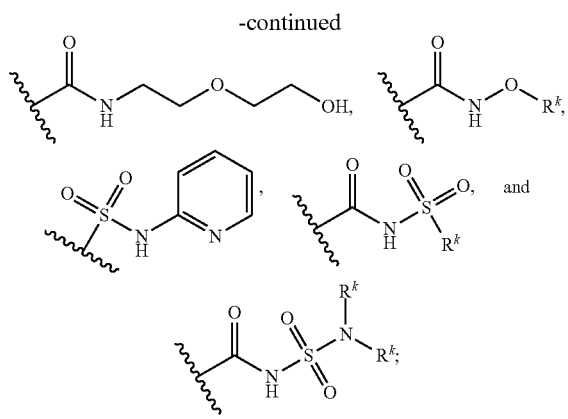

R¹, at each occurrence, is independently selected from the group consisting of halo, $C_{1-6}$ alkyl, $C_{2-6}$ alkenyl, $C_{2-6}$ alkynyl, and $C_{1-6}$ haloalkyl;

R², at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two R² that are attached to the same carbon atom, together with said carbon atom, optionally form a ring selected from the group consisting of heterocycloalkyl, heterocycloalkenyl, cycloalkyl, and cycloalkenyl;

R³, at each occurrence, is independently selected from the group consisting of halo, $C_{1-6}$ alkyl, $C_{2-6}$ alkenyl, $C_{2-6}$ alkynyl, and $C_{1-6}$ haloalkyl;

R⁴, at each occurrence, is independently selected from the group consisting of $NR^{12}R^{13}$, $OR^{12}$, CN, $NO_2$, halogen, $C(O)OR^{12}$, $C(O)NR^{12}R^{13}$, $NR^{12}C(O)R^{13}$, $NR^{12}S(O)_2R^{14}$, $NR^{12}S(O)R^{14}$, $S(O)_2R^{14}$, $S(O)R^{14}$ and $R^{14}$;

R⁵, at each occurrence, is independently selected from the group consisting of $C_{1-6}$ alkyl, $C_{2-6}$ alkenyl, $C_{2-6}$ alkynyl, $C_{1-6}$ haloalkyl, $C_{1-6}$ hydroxyalkyl, aryl, heterocyclyl, cycloalkyl, and cycloalkenyl;

$R^{6A}$ is independently selected from the group consisting of hydrogen, $C_{1-6}$ alkyl, $C_{2-6}$ alkenyl, $C_{2-6}$ alkynyl, and $C_{1-6}$ haloalkyl;

R⁶ and R⁷, at each occurrence, are each independently selected from the group consisting of hydrogen, $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $CO(O)H$, $C(O)H$, OH, CN, $N_3$, $NO_2$, F, Cl, Br and I;

R⁸, at each occurrence, is independently selected from the group consisting of $C_{1-6}$ alkyl, $C_{2-6}$ alkenyl, $C_{2-6}$ alkynyl, $C_{1-6}$ haloalkyl, aryl, heterocyclyl, cycloalkyl, and cycloalkenyl; wherein the $R^8C_{1-6}$ alkyl, $C_{2-6}$ alkenyl, $C_{2-6}$ alkynyl, and $C_{1-6}$ haloalkyl are optionally substituted with one, two, three, four, five, or six substituents independently selected from the group consisting of $R^{16}$, $OR^{16}$, $SR^{16}$, $S(O)R^{16}$, $SO_2R^{16}$, $C(O)R^{16}$, $CO(O)R^{16}$, $OC(O)R^{16}$, $OC(O)OR^{16}$, $NH_2$, $NHR^{16}$, $N(R^{16})_2$, $NHC(O)R^{16}$, $NR^{16}C(O)R^{16}$, $NHS(O)_2R^6$, $NR^{16}S(O)_2R^{16}$, $NHC(O)OR^{16}$, $NR^{16}C(O)OR^6$, $NHC(O)NH_2$, $NHC(O)NHR^{16}$, $NHC(O)N(R^{16})_2$, $NR^{16}C(O)NHR^{16}$, $NR^{16}C(O)N(R^6)_2$, $C(O)NH_2$, $C(O)NHR^{16}$, $C(O)N(R^{16})_2$, $C(O)NHOH$, $C(O)NHOR^{16}$, $C(O)NHSO_2R^{16}$, $C(O)NR^{16}SO_2R^{16}$, $SO_2NH_2$, $SO_2NHR^{16}$, $SO_2N(R^{16})_2$, $CO(O)H$, $C(O)H$, OH, CN, $N_3$, $NO_2$, F, Cl, Br and I; wherein the $R^8$ aryl, heterocyclyl, cycloalkyl, and cycloalkenyl are optionally substituted with one, two, or three substituents independently selected from the group consisting of $C_{1-6}$ alkyl, $C_{2-6}$ alkenyl, $C_{2-6}$ alkynyl, $C_{1-6}$ haloalkyl, $NH_2$, $C(O)NH_2$, $SO_2NH_2$, $C(O)H$, (O), OH, CN, $NO_2$, $OCF_3$, $OCF_2CF_3$, F, Cl, Br and I;

R⁹ is selected from the group consisting of $C_{1-6}$ alkyl, $C_{2-6}$ alkenyl, $C_{2-6}$ alkynyl, $C_{1-6}$ haloalkyl, cycloalkyl, phenyl and $(CH_2)_{1-4}$ phenyl; and R¹⁰ and R¹¹, at each occurrence, are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and $(CH_2)_{1-4}$-phenyl; or R¹⁰ and R¹¹, or R¹⁰ and R⁹, together with the atom to which each is attached are combined to form a heterocyclyl;

$R^k$, at each occurrence, is independently selected from the group consisting of $C_{1-4}$ alkyl, $C_{2-6}$ alkenyl, $C_{2-6}$ alkynyl, $C_{3-7}$ heterocycloalkyl, $C_{3-7}$ cycloalkyl and $C_{1-6}$ haloalkyl; wherein the $R^k C_{1-6}$ alkyl, $C_{2-6}$ alkenyl, and $C_{2-6}$ alkynyl are optionally substituted with aryl, heterocyclyl, cycloalkyl, or cycloalkenyl;

R¹² and R¹³, at each occurrence, are each independently selected from the group consisting of hydrogen, $C_{1-4}$ alkyl, $C_{2-4}$ alkenyl, $C_{2-4}$ alkynyl, $C_{2-4}$ haloalkyl and $(CH_2)_{1-4}$ phenyl;

R¹⁴, at each occurrence, is independently selected from the group consisting of $C_{1-4}$ alkyl, $C_{2-4}$ alkenyl, $C_{2-4}$ alkynyl and $C_{1-4}$ haloalkyl;

R¹² and R¹³, or R¹² and R¹⁴, at each occurrence, together with the atom to which each is attached, are optionally combined to form a heterocyclyl;

R¹⁵, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocyclyl, cycloalkyl, and cycloalkenyl; wherein the $R^{15}C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one, two, or three substituents independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ alkoxy, aryl, heterocycloalkyl, heterocycloalkenyl, heteroaryl, cycloalkyl, and cycloalkenyl, $NH_2$, $C(O)NH_2$, $SO_2NH_2$, $C(O)H$, $C(O)OH$, (O), OH, CN, $NO_2$, $OCF_3$, $OCF_2CF_3$, F, Cl, Br and I;

R¹⁶, at each occurrence, is independently selected from the group consisting of $C_{1-4}$ alkyl, $C_{2-4}$ alkenyl, $C_{2-4}$ alkynyl, $C_{1-4}$ haloalkyl, $C_{1-4}$ hydroxyalkyl, aryl, heterocycloalkyl, heterocycloalkenyl, heteroaryl, cycloalkyl, and cycloalkenyl; wherein the $R^{16}C_{1-4}$ alkyl, $C_{2-4}$ alkenyl, $C_{2-4}$ alkynyl, $C_{1-4}$ haloalkyl, and $C_{1-4}$ hydroxyalkyl are optionally substituted with one substituent independently selected from the group consisting of $OCH_3$, $OCH_2CH_2OCH_3$, and $OCH_2CH_2NHCH_3$;

q is 1, 2, or 3;
s is 0, 1, 2, or 3;
r is 0, 1, 2, or 3;
wherein the sum of s and r is 0, 1, or 2;
m is 0, 1, 2, or 3;
n is 0, 1, 2, 3, 4, 5, or 6;
o is 0, 1, 2, or 3; and
p is 0, 1, or 2.

In one embodiment of Formula (VI), m is 0, 1, 2, or 3; n is 0, 1, 2, 3, 4, 5, or 6; and p is 0, 1, or 2. In another embodiment of Formula (VI), n is 0 or 1. In another embodiment of Formula (VI), n is 0 or 1; and each R² is independently deuterium or $C_{1-6}$ alkyl. In another embodiment of Formula (VI), m, n, and p are 0.

In one embodiment of Formula (VI), X is heteroaryl, which is optionally substituted with one, two, three or four R⁴. In another embodiment of Formula (VI), X is heteroaryl, which is unsubstituted. In another embodiment of Formula (VI). X is heteroaryl, which is substituted with one $R^4$. In another embodiment of Formula (VI), X is heteroaryl, which is substituted with two $R^4$. In another embodiment of Formula (VI), X is heteroaryl, which is substituted with one $R^4$, and $R^4$ is $OR^2$ or halogen. In another embodiment of Formula (VI), X is heteroaryl, which is substituted with two $R^4$, and each $R^4$ is independently $OR^{12}$ or halogen. In another embodiment of Formula (VI), X is heteroaryl, which is substituted with one $R^4$, and $R^4$ is Cl, F, or methoxy. In another embodiment of Formula (VI), X is heteroaryl, which is substituted with two $R^4$, and each $R^4$ is independently F.

In one embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is $OR^{12}$ or halogen. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently $OR^{12}$ or halogen. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is Cl, F, or methoxy. In another embodiment of Formula (VI), X is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently F.

In one embodiment of Formula (VI), X is benzo[d]thiazolyl, which is optionally substituted with one, two, three or four $R^4$. In another embodiment of Formula (VI), X is benzo[d]thiazolyl, which is unsubstituted. In another embodiment of Formula (VI), X is benzo[d]thiazolyl, which is substituted with one $R^4$. In another embodiment of Formula (VI), X is benzo[d]thiazolyl, which is substituted with two $R^4$. In another embodiment of Formula (VI), X is benzo[d]thiazolyl, which is substituted with one $R^4$, and $R^4$ is $OR^{12}$ or halogen. In another embodiment of Formula (VI), X is benzo[d]thiazolyl, which is substituted with two $R^4$, and each $R^4$ is independently $OR^{12}$ or halogen. In another embodiment of Formula (VI), X is benzo[d]thiazolyl, which is substituted with one $R^4$, and $R^4$ is Cl, F, or methoxy. In another embodiment of Formula (VI), X is benzo[d]thiazolyl, which is substituted with two $R^4$, and each $R^4$ is independently F.

In one embodiment of Formula (VI), $Z^1$ is selected from the group consisting of $C(O)OR^9$, $C(O)NR^{10}R^{11}$, $C(O)R^{11}$, $NR^{10}C(O)NR^{11}$, $NR^{11}C(O)NR^{10}R^{11}$, $OC(O)NR^{10}R^{11}$, $NR^{10}C(O)OR^9$, $C(=NOR^{10})NR^{10}R^{11}$, $NR^{10}C(=NCN)NR^{11}R^{11}$, $R^{10}S(O)_2NR^{10}R^{11}$, $S(O)_2R^9$, $S(O)_2NR^{10}R^{11}$, $N(R^{10})S(O)_2R^{11}$, $NR^{10}C(=NR^{11})NR^{10}R^{11}$, $C(=S)NR^{10}R^{11}$, $C(=NR^{10})NR^{10}R^{11}$, halogen, $NO_2$, and CN; or $Z^1$ is selected from the group consisting of

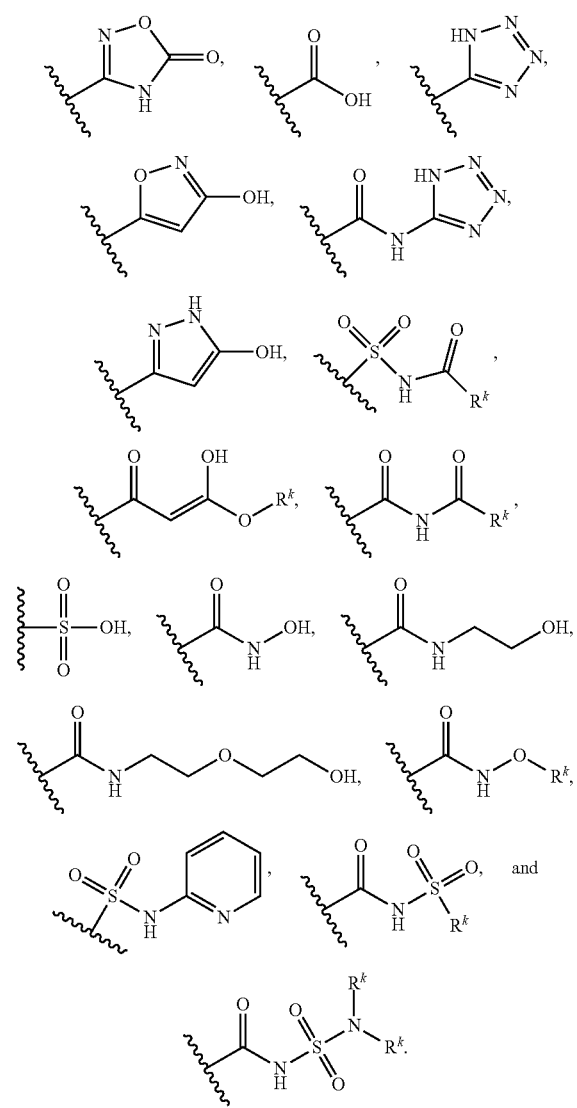

In another embodiment of Formula (VI), $Z^1$ is

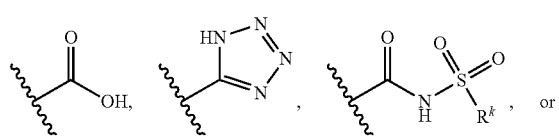

-continued

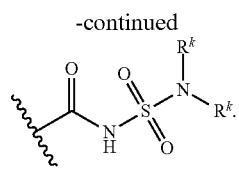

In another embodiment of Formula (VI), $Z^1$ is

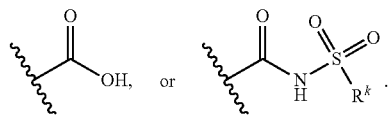

In another embodiment of Formula (VI), $Z^1$ is

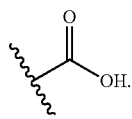

In one embodiment of Formula (VI), $L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S—$(CR^6R^7)_r$, $(CR^6R^7)_s$—S(O)$_2$—$(CR^6R^7)_r$, $(CR^6R^7)_s$—NR$^{6A}$C(O)—$(CR^6R^7)_r$, $(CR^6R^7)_s$—C(O)NR$^{6A}$—$(CR^6R^7)_r$, $(CR^6R^7)_s$—NR$^{6A}$—$(CR^6R^7)_r$, $(CR^6R^7)_s$—S(O)$_2$NR$^{6A}$—$(CR^6R^7)_r$, and $(CR^6R^7)_s$—NR$^{6A}$S(O—$(CR^6R^7)_r$,; and $Y^2$ is selected from the group consisting of $C_{3\text{-}11}$ branched chain alkyl, $C_{3\text{-}7}$ cycloalkyl, $C_{4\text{-}7}$ cycloalkenyl, phenyl, and $C_{3\text{-}7}$ heterocyclyl; wherein the $C_{3\text{-}7}$ cycloalkyl, $C_{4\text{-}7}$ cycloalkenyl, phenyl, and $C_{3\text{-}7}$ heterocyclyl are optionally fused to one or two rings selected from the group consisting of $C_{3\text{-}8}$ cycloalkane, $C_{3\text{-}8}$ cycloalkene, benzene, $C_{5\text{-}6}$ heteroarene, $C_{3\text{-}8}$ heterocycloalkane, and $C_{3\text{-}8}$ heterocycloalkene; wherein $Y^2$ is optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_2$, $NO$, $F$, $C$, $Br$ and $I$; or $L^1$ is a bond; and $Y^2$ is selected from the group consisting of $C_{3\text{-}7}$ cycloalkyl, $C_{4\text{-}7}$ cycloalkenyl, phenyl, and $C_{3\text{-}7}$ heterocyclyl; wherein the $C_{3\text{-}7}$ cycloalkyl, $C_{4\text{-}7}$ cycloalkenyl, phenyl, and $C_{3\text{-}7}$ heterocyclyl represented by $Y^2$ are optionally fused to one or two rings selected from the group consisting of $C_{3\text{-}8}$ cycloalkane, $C_{3\text{-}8}$ cycloalkene, benzene, $C_{1\text{-}6}$ heteroarene, $C_{3\text{-}8}$ heterocycloalkane, and $C_{3\text{-}8}$ heterocycloalkene; wherein each $Y^2$ and each ring fused to $Y^2$ are optionally substituted with one, two, three, four, or five substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $NHSO_2R^8$, $C(O)NR^8SO_2R^8$, $SO_2NH_2$, $SO_2NHR^8$, $SO_2N(R^8)_2$, $CO(O)H$, $C(O)H$, $OH$, $CN$, $N_3$, $NO_2$, $F$, $Cl$, $Br$ and $I$.

In another embodiment of Formula (VI), $L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S(O)$_2$—$(CR^6R^7)_r$, $(CR^6R^7)_s$—NR$^{6A}$C(O)—$(CR^6R^7)_r$, $(CR^6R^7)_s$—NR$^{6A}$—$(CR^6R^7)_r$, and $(CR^6R^7)_s$—NR$^{6A}$S(O)$_2$—$(CR^6R^7)_r$,; and $Y^2$ is selected from the group consisting of $C_{3\text{-}11}$ branched chain alkyl, $C_{3\text{-}7}$ cycloalkyl, $C_{4\text{-}7}$ cycloalkenyl, phenyl, and $C_{3\text{-}7}$ heterocyclyl; wherein the $C_{3\text{-}7}$ cycloalkyl, $C_{4\text{-}7}$ cycloalkenyl, phenyl, and $C_{3\text{-}7}$ heterocyclyl are optionally fused to one or two benzene rings; wherein $Y^2$ is optionally substituted with one, two, or three substituents independently selected from the group consisting of $R^8$, $OR^8$, $SO_2R^8$, $CO(O)R^8$, $NHR^8$, $N(R^8)_2$, $C(O)H$, $OH$, $CN$, $NO_2$, $F$, $Cl$, $Br$ and $I$; or $L^1$ is a bond; and $Y^2$ is selected from the group consisting of $C_{3\text{-}7}$ cycloalkyl, phenyl, and $C_{3\text{-}7}$ heterocyclyl; wherein the $C_{3\text{-}7}$ cycloalkyl, phenyl, and $C_{3\text{-}7}$ heterocyclyl represented by $Y^2$ are optionally fused to one benzene ring; wherein each $Y^2$ and each ring fused to $Y^2$ are optionally substituted with one substituent independently selected from the group consisting of $R^8$, $C(O)NHR^8$, $F$, $Cl$, $Br$ and $I$.

In another embodiment of Formula (VI), $L^1$ is $(CR^6R^7)_q$; and $Y^2$ is selected from the group consisting of $C_{3\text{-}7}$ cycloalkyl, $C_{4\text{-}7}$ cycloalkenyl, phenyl, and $C_{3\text{-}7}$ heterocyclyl; wherein $R^6$ and $R^7$, at each occurrence, are $R^{15}$ or hydrogen; and q is 1, 2, or 3.

In another embodiment of Formula (VI), $L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S(O)$_2$—$(CR^6R^7)_r$, $(CR^6R^7)_s$—NR$^{6A}$C(O)—$(CR^6R^7)_r$, $(CR^6R^7)_s$—NR$^{6A}$—$(CR^6R^7)_r$, and $(CR^6R^7)_s$—NR$^{6A}$S(O)$_2$—$(CR^6R^7)_r$,; q is 1, 2, or 3; s is 0; r is 0 or i; $R^{6A}$ is independently selected from the group consisting of hydrogen, and $C_{1\text{-}6}$ alkyl; and $R^6$ and $R^7$, at each occurrence, are hydrogen.

In one embodiment of Formula (VI), o is 0. In another embodiment of Formula (VI), o is 1. In another embodiment of Formula (VI), o is 0 or 1. In another embodiment of Formula (VI), o is 0, 1, 2, or 3. In another embodiment of Formula (VI), o is 0, 1, 2, or 3; and $R^x$, at each occurrence, is independently selected from the group consisting of, $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $CO(O)H$, $C(O)H$, $OH$, $CN$, $N_3$, $NO_2$, $F$, $Cl$, $Br$ and $I$. In another embodiment of Formula (VI), o is 1 or 2; and $R^5$, at each occurrence, is independently selected from the group consisting of $R^5$, $CO(O)R^5$, $CO(O)H$, $CN$, $F$, $Cl$, $Br$ and $I$. In another embodiment of Formula (VI), o is 1 or 2; $R^x$, at each occurrence, is independently selected from the group consisting of $R^5$, $CO(O)R^5$, $CO(O)H$, $CN$, $F$, $Cl$, $Br$ and $I$; and $R^5$, at each occurrence, is independently selected from the group consisting of $C_{1\text{-}6}$ alkyl, $C_{2\text{-}6}$ alkenyl, $C_{1\text{-}6}$ haloalkyl, $C_{1\text{-}6}$ hydroxyalkyl, aryl, and cycloalkyl. In another embodiment of Formula (VI), o is 1; $R^x$, at each occurrence, is independently selected from the group consisting of $R^5$, $CN$, $F$, $Cl$, $Br$ and $I$; and $R^5$, at each occurrence, is independently selected from the group consisting of $C_{1\text{-}2}$ alkyl, and $C_1$ haloalkyl. In another embodiment of Formula (VI), o is 1 or 2; $R^x$ is $R^5$ or CN; and $R^5$ is $CH_3$. In another embodiment of Formula (VI), o is 1; and $R^x$ is CN. In another embodiment of Formula (VI), o is 1; and $R^x$ is $CH_3$.

In one embodiment of Formula (VI), X is heteroaryl; wherein the heteroaryl represented by X is optionally substituted with one or two $R^4$;

$R^x$, at each occurrence, is independently selected from the group consisting of $R^5$, CO(O)$R^5$, CO(O)H, CN, F, Cl, Br and I;

$L^1$ is selected from the group consisting of $(CR^6R^7)_q$, $(CR^6R^7)_s$—O—$(CR^6R^7)_r$, $(CR^6R^7)_s$—C(O)—$(CR^6R^7)_r$, $(CR^6R^7)_s$—S(O)$_2$—$(CR^6R^7)_r$, $(CR^6R^7)_s$—NR$^{6A}$C(O)—$(CR^6R^7)_r$, $(CR^6R^7)_r$, —NR$^{6A}$—$(CR^6R^7)_r$, and $(CR^6R^7)_s$—NR$^{6A}$S(O)$_2$—$(CR^6R^7)_r$; and $Y^2$ is selected from the group consisting of $C_{3-11}$ branched chain alkyl, $C_{3-7}$ cycloalkyl, $C_{4-7}$ cycloalkenyl, phenyl, and $C_{3-7}$ heterocyclyl; wherein the $C_{3-7}$ cycloalkyl, $C_{4-7}$ cycloalkenyl, phenyl, and $C_{3-7}$ heterocyclyl are optionally fused to one benzene ring; wherein $Y^2$ is optionally substituted with one, two, or three substituents independently selected from the group consisting of $R^8$, $OR^8$, $SO_2R^8$, $CO(O)R^8$, $NHR^8$, $N(R^8)_2$, C(O)H, OH, CN, $NO_2$, F, Cl, Br and I; or $L^1$ is a bond; and $Y^2$ is selected from the group consisting of $C_{3-7}$ cycloalkyl, phenyl, and $C_{3-7}$ heterocyclyl; wherein the $C_{3-7}$ cycloalkyl, phenyl, and $C_{3-7}$ heterocyclyl represented by $Y^2$ are optionally fused to one benzene ring; wherein each $Y^2$ and each ring fused to $Y^2$ are optionally substituted with one substituent independently selected from the group consisting of $R^8$ and C(O)NHR$^8$;

$Z^1$ is selected from the group consisting of

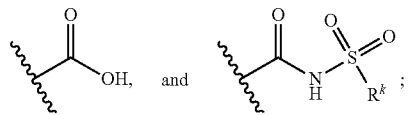

$R^2$, at each occurrence, is independently $C_{1-6}$ alkyl;

$R^4$, at each occurrence, is independently selected from the group consisting of $OR^{12}$ and halogen;

$R^5$, at each occurrence, is independently selected from the group consisting of $C_{1-6}$ alkyl, $C_{1-6}$ haloalkyl, $C_{1-6}$ hydroxyalkyl, aryl, and cycloalkyl;

$R^{6A}$ is independently selected from the group consisting of hydrogen and $C_{1-6}$ alkyl;

$R^6$ and $R^7$, at each occurrence, are each independently selected from the group consisting of hydrogen, $R^{15}$, and CO(O)$R^{15}$;

$R^8$, at each occurrence, is independently selected from the group consisting of $C_{1-6}$ alkyl, $C_{2-6}$ alkynyl, aryl, heterocyclyl, and cycloalkyl; wherein the $R^8C_{1-6}$ alkyl, and $C_{2-6}$ alkynyl are optionally substituted with one, two, or three substituents independently selected from the group consisting of $R^{16}$, $OR^{16}$, $SO_2R^{16}$, C(O)$R^{16}$, $N(R^{16})_2$, OH, F, Cl, Br and I; wherein the $R^8$ aryl and heterocyclyl are optionally substituted with one substituent independently selected from the group consisting of $C_{1-6}$ alkyl, F, Cl, Br and I;

$R^k$, at each occurrence, is independently $C_{1-6}$ alkyl;

$R^{12}$ and $R^{13}$, at each occurrence, are each independently $C_{1-4}$ alkyl;

$R^{15}$, at each occurrence, is independently selected from the group consisting of $C_{1-4}$ alkyl, and aryl; wherein the $R^{15}C_{1-4}$ alkyl is optionally substituted with one substituent independently selected from the group consisting $C_{1-4}$ alkoxy, and heterocycloalkyl;

$R^{16}$, at each occurrence, is independently selected from the group consisting of $C_{1-4}$ alkyl, aryl, heterocycloalkyl, and heteroaryl;

q is 1, 2, or 3;
s is 0;
r is 0, or 1;
m is 0;
n is 0, or 1;
o is 0, 1, 2, 3, or 4; and
p is 0.

Still another embodiment pertains to a compound having Formula (VI) selected from the group consisting of 6-[8-(1,3-benzothiazol-2-ylcarbamoyl)-3,4-dihydroisoquinolin-2(1H)-yl]-2'-(cyclohexyloxy)-3'-methyl-3,4'-bipyridine-2-carboxylic acid;

6-[8-(1,3-benzothiazol-2-ylcarbamoyl)-3,4-dihydroisoquinolin-2(1H)-yl]-2'-(cyclohexyloxy)-3,4'-bipyridine-2-carboxylic acid;

6-[8-(1,3-benzothiazol-2-ylcarbamoyl)-3,4-dihydroisoquinolin-2(1H)-yl]-2'-phenoxy-3,4'-bipyridine-2-carboxylic acid;

6-[8-(1,3-benzothiazol-2-ylcarbamoyl)-3,4-dihydroisoquinolin-2(1H)-yl]-3'-methyl-2'-phenoxy-3,4'-bipyridine-2-carboxylic acid;

6-[8-(1,3-benzothiazol-2-ylcarbamoyl)-3,4-dihydroisoquinolin-2(1H)-yl]-3'-methyl-2'-[methyl(phenyl)amino]-3,4'-bipyridine-2-carboxylic acid;

6-[8-(1,3-benzothiazol-2-ylcarbamoyl)-3,4-dihydroisoquinolin-2(1H)-yl]-2'-[cyclohexyl(methyl)amino]-3'-methyl-3,4'-bipyridine-2-carboxylic acid;

6-[8-(1,3-benzothiazol-2-ylcarbamoyl)-3,4-dihydroisoquinolin-2(1H)-yl]-3'-cyano-2'-[cyclohexyl(methyl)amino]-3,4'-bipyridine-2-carboxylic acid;

6-[8-(1,3-benzothiazol-2-ylcarbamoyl)-3,4-dihydroisoquinolin-2(1H)-yl]-3'-methyl-2'-(piperidin-1-yl)-3,4'-bipyridine-2-carboxylic acid; and therapeutically acceptable salts, metabolites, prodrugs, salts of metabolites, and salts of prodrugs thereof.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment comprises methods of treating autoimmune disease in a mammal comprising administering thereto a therapeutically acceptable amount of a compound having Formula (I).

Still another embodiment pertains to compositions for treating diseases during which anti-apoptotic Bcl-xL proteins are expressed, said compositions comprising an excipient and a therapeutically effective amount of the compound having Formula (I).

Still another embodiment pertains to methods of treating disease in a patient during which anti-apoptotic Bcl-xL proteins are expressed, said methods comprising administering to the patient a therapeutically effective amount of a compound having Formula (I).

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound having Formula (I).

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of a compound having Formula (I).

Still another embodiment pertains to compositions for treating diseases during which are expressed anti-apoptotic Bcl-xL proteins, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which are expressed anti-apoptotic Bcl-xL proteins, said methods comprising administering to the patient a therapeutically effective amount of a compound having Formula (I) and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said compositions comprising an excipient and a therapeutically effective amount of the compound having Formula (I) and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said methods comprising administering to the patient a therapeutically effective amount of the compound having Formula (I) and a therapeutically effective amount of one additional therapeutic agent or more than one additional therapeutic agent.

Metabolites of compounds having Formula (I), produced by in vitro or in vivo metabolic processes, may also have utility for treating diseases associated with anti-apoptotic Bcl-xL proteins.

Certain precursor compounds which may be metabolized in vitro or in vivo to form compounds having Formula (I) may also have utility for treating diseases associated with expression of anti-apoptotic Bcl-xL proteins.

Compounds having Formula (I) may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthalenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula (I) may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula (I) used to make a composition to be administered daily to a patient in a single dose or in divided doses is from about 0.03 to about 200 mg/kg body weight. Single dose compositions contain these amounts or a combination of submultiples thereof.

Compounds having Formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B.

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide) or ABT-737 (i.e., N-(4-(4-(4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, *Cancer Research* 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® ((G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199. MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies. IRESSA® (gefitinib). TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including P1-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMATA® (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD41 (zanolimumab). IGF1R-specific antibodies, lintuzumab, PANOREX® (edrecolomab), RENCAREX® (WX G250), RITUXAN® (rituximab), ticilimumab, trastuzumab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA® (fadrozole), FARESTON® (toremifene). FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol). MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TREL- STAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Data

Determination of the utility of compounds having Formula (I) as binders to and inhibitors of anti-apoptotic Bcl-xL proteins was performed using the Time Resolved-Fluorescence Resonance Energy Transfer (TR-FRET) Assay. Tb-anti-GST antibody was purchased from Invitrogen (Catalog No. PV4216).

Probe Synthesis

All reagents were used as obtained from the vendor unless otherwise specified. Peptide synthesis reagents including diisopropylethylamine (DIEA), dichloromethane (DCM), N-methylpyrrolidone (NMP), 2-(1H-benzotriazole-1-yl)-1,1,3,3-tetramethyluronium hexafluorophosphate (HBTU), N-hydroxybenzotriazole (HOBt) and piperidine were obtained from Applied Biosystems, Inc. (ABI), Foster City, Calif. or American Bioanalytical, Natick, Mass. Preloaded 9-Fluorenylmethyloxycarbonyl (Fmoc) amino acid cartridges (Fmoc-Ala-OH, Fmoc-Cys(Trt)-OH, Fmoc-Asp(tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmor-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) were obtained from ABI or Anaspec, San Jose, Calif. The peptide synthesis resin (Fmoc-Rink amide MBHA resin) and Finoc-Lys(Mtt)-OH were obtained from Novabiochem, San Diego, Calif. Single-isomer 6-carboxyfluorescein succinimidyl ester (6-FAM-NHS) was obtained from Anaspec. Trifluoroacetic acid (TFA) was obtained from Oakwood Products, West Columbia, S.C. Thioanisole, phenol, triisopropylsilane (TIS), 3,6-dioxa-1,8-octanedithiol (DODT) and isopropanol were obtained from Aldrich Chemical Co., Milwaukee, Wis. Matrix-assisted laser desorption ionization mass-spectra (MALDI-MS) were recorded on an Applied Biosystems Voyager DE-PRO MS). Electrospray mass-spectra (ESI-MS) were recorded on Finnigan SSQ7000 (Finnigan Corp., San Jose, Calif.) in both positive and negative ion mode.

General Procedure for Solid-Phase Peptide Synthesis (SPPS)

Peptides were synthesized with, at most, 250 μmol preloaded WANG resin/vessel on an ABI 433A peptide synthesizer using 250 μmol scale FASTMOC™ coupling cycles. Preloaded cartridges containing 1 mmol standard Fmoc-amino acids, except for the position of attachment of the fluorophore, where 1 mmol Fmoc-Lys(Mtt)—OH was placed in the cartridge, were used with conductivity feedback monitoring. N-terminal acetylation was accomplished by using 1 mmol acetic acid in a cartridge under standard coupling conditions.

Removal of 4-Methyltrityl (Mtt) from Lysine

The resin from the synthesizer was washed thrice with DCM and kept wet. 150 mL of 95:4:1 dichloromethane:triisopropylsilane:trifluoroacetic acid was flowed through the resin bed over 30 minutes. The mixture turned deep yellow then faded to pale yellow. 100 mL of DMF was flowed through the bed over 15 minutes. The resin was then washed thrice with DMF and filtered. Ninhydrin tests showed a strong signal for primary amine.

Resin Labeling with 6-Carboxyfluorescein-NHS (6-FAM-NHS)

The resin was treated with 2 equivalents 6-FAM-NHS in 1% DIEA/DMF and stirred or shaken at ambient temperature overnight. When complete, the resin was drained, washed thrice with DMF, thrice with (1×DCM and 1× methanol) and dried to provide an orange resin that was negative by ninhydrin test.

General Procedure for Cleavage and Deprotection of Resin-Bound Peptide

Peptides were cleaved from the resin by shaking for 3 hours at ambient temperature in a cleavage cocktail consisting of 80% TFA, 5% water. 5% thioanisole, 5% phenol, 2.5% TIS, and 2.5% EDT (1 mL/0.1 g resin). The resin was removed by filtration and rinsing twice with TFA. The TFA was evaporated from the filtrates, and product was precipitated with ether (10 mL/0.1 g resin), recovered by centrifugation, washed twice with ether (10 mL/0.1 g resin) and dried to give the crude peptide.

General Procedure for Purification of Peptides

The crude peptides were purified on a Gilson preparative HPLC system running Unipoint® analysis software (Gilson, Inc., Middleton, Wis.) on a radial compression column containing two 25×100 mm segments packed with Delta-Pak™ C18 15 μm particles with 100 Å pore size and eluted with one of the gradient methods listed below. One to two milliliters of crude peptide solution (10 mg/mL in 90% DMSO/water) was purified per injection. The peaks containing the product(s) from each run were pooled and lyophilized. All preparative runs were run at 20 mL/min with eluents as buffer A: 0.1% TFA-water and buffer B: acetonitrile.

General Procedure for Analytical HPLC

Analytical HPLC was performed on a Hewlett-Packard 1200 series system with a diode-array detector and a Hewlett-Packard 1046A fluorescence detector running HPLC 3D CHEMSTATION software version A.03.04 (Hewlett-Packard. Palo Alto, Calif.) on a 4.6×250 mm YMC column packed with ODS-AQ 5 μ particles with a 120 Å pore size and eluted with one of the gradient methods listed below after preequilibrating at the starting conditions for 7 minutes. Eluents were buffer A: 0.1% TFA-water and buffer B: acetonitrile. The flow rate for all gradients was 1 mL/min.

F-Bak: Peptide Probe Acetyl-GQVGRQLAIIGDK(6-FAM)INR—NH$_2$ (SEQ ID NO:1)

Fmoc-Rink amide MBHA resin was extended using the general peptide synthesis procedure to provide the protected resin-bound peptide (1.020 g). The Mtt group was removed, labeled with 6-FAM-NHS and cleaved and deprotected as described hereinabove to provide the crude product as an orange solid (0.37 g). This product was purified by RP-HPLC. Fractions across the main peak were tested by analytical RP-HPLC, and the pure fractions were isolated and lyophilized, with the major peak providing the title compound (0.0802 g) as a yellow solid; MALDI-MS m/z=2137.1 [(M+H)$^+$].

Alternative Synthesis of Peptide Probe F-Bak: Acetyl-GQVGRQLAIIGDK(6-FAM)INR-NH$_2$ (SEQ ID NO:1)

The protected peptide was assembeled on 0.25 mmol Fmoc-Rink amide MBHA resin (Novabiochem) on an Applied Biosystems 433A automated peptide synthesizer running FASTMOC™ coupling cycles using pre-loaded 1 mmol amino acid cartridges, except for the fluorescein(6-FAM)-labeled lysine, where 1 mmol Fmoc-Lys(4-methyltrityl) was weighed into the cartridge. The N-terminal acetyl group was incorporated by putting 1 mmol acetic acid in a cartridge and coupling as described hereinabove. Selective removal of the 4-methyltrityl group was accomplished with a solution of 95:4:1 DCM:TIS:TFA (v/v/v) flowed through the resin over 15 minutes, followed by quenching with a flow of dimethylformamide. Single-isomer 6 carboxyfluorescein-NHS was reacted with the lysine side-chain in 1% DIEA in N,N-dimethylformamide and confirmed complete by ninhydrin testing. The peptide was cleaved from the resin and side-chains deprotected by treating with 80:5:5:5:2.5:2.5 TFA/water/phenol/thioanisole/triisopropylsilane: 3,6-dioxa-1,8-octanedithiol (v/v/v/v/v/v), and the crude peptide was recovered by precipitation with diethyl ether. The crude peptide was purified by reverse-phase high-performance liquid chromatography, and its purity and identity were confirmed by analytical reverse-phase high-performance liquid chromatography and matrix-assisted laser-desorption mass-spectrometry (m/z=2137.1 ((M+H)+)).

Time Resolved-Fluorescence Resonance Energy Transfer (TR-FRET) Assay

The measurement of competition of compounds of Formula (I) with F-Bak for a Bcl-2 family protein (Bcl-xL) binding site using a Time Resolved Fluorescence Resonance Energy Transfer (TR-FRET) binding assay:

Test compounds were serially diluted in DMSO starting at 50 M (2× starting concentration; 10% DMSO) and 10 μL transferred into a 384-well plate. Then 10 μL of a protein/probe/antibody mix is added to each well at final concentrations listed in Table 1.

TABLE 1

| Protein | Probe | Protein (nM) | Probe (nM) | Antibody | Antibody (nM) |
|---------|-------|--------------|------------|----------|---------------|
| GST-Bcl-xL | F-Bak (GQVGRQLAIIGDK (6-FAM)INR-amide) SEQ ID NO: 1 | 1 | 100 | Tb-anti-GST | 1 |

The samples are then mixed on a shaker for 1 minute then incubated for an additional 2 hours at room temperature. For each assay plate, a probe/antibody and protein/antibody/probe mixture were included as a negative and a positive control, respectively. Fluorescence was measured on the ENVISION plate reader (Perkin Elmer) using a 340/35 nm excitation filter and 520/525 (F-Bak) and 495/510 nm (Tb-labeled anti-his antibody) emission filters. Dissociation constants ($K_i$) were determined using Wang's equation (Wang, Z.X. An 20 exact mathematical expression for describing competitive binding of two different ligands to protein molecule. FEBS Lett. 1995 360:111-114). The TR-FRET assay can be performed in the presence of varying concentrations of human serum (HS) or fetal bovine serum (FBS). TR-FRET assay results ($K_i$, in nanomolar) for representative compounds of Formula (I) are provided below in Table 2.

For comparison, the measurement of the competition of compounds of Formula (I) for other Bcl-2 family protein binding sites (e.g., Bcl-2) using the TR-FRET binding assay was accomplished by substituting GST-Bcl-xL in the TR-FRET assay with other GST-labeled protein, e.g., GST-Bcl-2, prepared in-house.

In one embodiment, compounds of Formula (I) selectively inhibit the Bcl-2 family protein, Bcl-$x_L$, over other Bcl-2 family proteins, such as Bcl-2. For comparison, data ($K_i$ in micromolar) from the measurement of the competition by certain compounds of Formula (I) (i.e., Examples 20, 43, 49, 82, 99, 107, 117, 130, 134, 148 159, 176 and 185 in Table 3) with F-Bak for the Bcl-2 binding site using the TR-FRET binding assay are 0.070, 0.023, 0.039, 0.033, 0.033, 0.056, 0.021, 0.076, 0.024, 0.075, 0.272, 0.177 and 0.014, respectively.

FL5.12 Cellular Assay

The efficacy of the compounds of Formula (I) can also be determined in cell-based killing assays using a variety of cell lines and mouse tumor models. For example, their activity on cell viability can be assessed on a panel of cultured tumorigenic and non-tumorigenic cell lines, as well as primary mouse or human cell populations. In one exemplary set of conditions, mouse FL5.12 cells transfected with Bcl-XL were cultured under standard conditions in RPMI with 2 mM glutamine, 1% 100 mM sodium pyruvate, 2% 1 M HEPES, 4 μL/L of β-mercaptoethanol, 1% penicillin-streptomycin, 10% FBS, and 10% WEHI-3B conditioned media (for IL-3). For assaying the compound activity, the cells were exchanged into an IL-3-depleted deprivation media, which was identical to the growth media except for the absence of FBS and WEHI-3B conditional media, for 2 days. Then the cells were exchanged to 3% FBS assay media (RPMI with 2 mM glutamine, 1% 100 mM sodium pyruvate, 2% 1 M HEPES, 4 μL/L of β-mercaptoethanol, 1% penicillin-streptomycin, 3% FBS). Compounds in series dilutions were added, and the cells were cultured for 24 hours. Compounds in series dilutions were added, and the cells were cultured for 24 hours. Cell viability was assayed using the CellTiter-Glo assay (Promega Corp., Madison, Wis.) according to the manufacturer instructions. Individual determinations were the result of duplicate values. Cell viability assay results ($EC_{50}$ in nanomolar) for representative compounds are provided below in Table 2.

TABLE 2

| | In Vitro Data | |
|---|---|---|
| EX | TR-FRET binding Bcl-xL Ki (nM) | FL5.12 Bcl-xL, IL3, EC 50 (nM) |
| 1 | 12 | 425 |
| 2 | 205 | n.d. |
| 3 | 258 | >1000 |
| 4 | 115 | n.d. |
| 5 | 19 | 408 |
| 6 | >1000 | n.d. |
| 7 | 312 | n.d. |
| 8 | 98 | n.d. |
| 9 | 6 | 378 |
| 10 | 68 | n.d. |
| 11 | 180 | >1000 |
| 12 | 8 | 51 |
| 13 | 12 | 498 |
| 14 | 12 | >1000 |
| 15 | 35 | >1000 |
| 16 | 159 | n.d. |
| 17 | 31 | >1000 |
| 18 | 38 | 621 |
| 19 | 28 | 398 |
| 20 | 2 | 13 |
| 21 | 183 | >1000 |
| 22 | 6 | 214 |
| 23 | 182 | >1000 |
| 24 | 64 | >1000 |
| 25 | 8 | 377 |
| 26 | 167 | >1000 |
| 27 | 315 | >1000 |
| 28 | 33 | >1000 |
| 29 | 18 | >1000 |
| 30 | 2 | 298 |
| 31 | 18 | >1000 |
| 32 | 5 | 216 |
| 33 | 169 | >1000 |
| 34 | 23 | 907 |
| 35 | 91 | n.d. |
| 36 | 8 | >1000 |
| 37 | 17 | 347 |
| 38 | 48 | >1000 |
| 39 | 56 | >1000 |
| 40 | 16 | 570 |
| 41 | 1 | 11 |
| 42 | 2 | 233 |

TABLE 2-continued

In Vitro Data

| EX | TR-FRET binding Bcl-xL Ki (nM) | FL5.12 Bcl-xL, IL3, EC 50 (nM) |
|---|---|---|
| 43 | 0.9 | 4 |
| 44 | 17 | >1000 |
| 45 | 19 | >1000 |
| 46 | 9 | >1000 |
| 47 | 16 | 881 |
| 48 | 7 | >1000 |
| 49 | 0.6 | 12 |
| 50 | 99 | >1000 |
| 51 | 122 | >1000 |
| 52 | 18 | 570 |
| 53 | 14 | 387 |
| 54 | 15 | 501 |
| 55 | 18 | 317 |
| 56 | 24 | 583 |
| 57 | 14 | 741 |
| 58 | 174 | >1000 |
| 59 | 424 | >1000 |
| 60 | 5 | 219 |
| 61 | 11 | 380 |
| 62 | 61 | >1000 |
| 63 | 2 | 27 |
| 64 | 61 | >1000 |
| 65 | 393 | >1000 |
| 66 | 3 | 60 |
| 67 | 7 | 106 |
| 68 | 279 | >1000 |
| 69 | 91 | >1000 |
| 70 | 5 | 58 |
| 71 | 18 | n.d. |
| 72 | 28 | >1000 |
| 73 | 0.9 | 8 |
| 74 | 6 | 335 |
| 75 | 28 | 919 |
| 76 | 29 | >1000 |
| 77 | 10 | 431 |
| 78 | 379 | >1000 |
| 79 | 0.5 | 19 |
| 80 | 4 | 253 |
| 81 | 0.6 | 37 |
| 82 | 0.5 | 8 |
| 83 | 0.5 | >1000 |
| 84 | 0.7 | 12 |
| 85 | 0.7 | 12 |
| 86 | 2 | 4 |
| 87 | 4 | 124 |
| 88 | 3 | 229 |
| 89 | 0.5 | 23 |
| 90 | 1 | n.d. |
| 91 | 0.9 | 30 |
| 92 | 2 | 56 |
| 93 | 16 | 295 |
| 94 | 5 | 253 |
| 95 | 11 | 542 |
| 96 | 12 | 620 |
| 97 | 2 | <1 |
| 98 | 2 | 421 |
| 99 | 0.9 | 60 |
| 100 | 3 | 66 |
| 101 | 0.4 | <1 |
| 102 | <0.1 | n.d. |
| 103 | 0.6 | >1000 |
| 104 | 14 | >1000 |
| 105 | 7 | >1000 |
| 106 | 0.1 | 234 |
| 107 | 0.2 | 10 |
| 108 | 9 | >1000 |
| 109 | 49 | >1000 |
| 110 | 0.3 | 90 |
| 111 | 21 | >1000 |
| 112 | 0.7 | 523 |
| 113 | 19 | >1000 |
| 114 | 0.2 | 220 |
| 115 | 5 | 916 |
| 116 | <0.1 | 667 |
| 117 | <0.1 | 131 |
| 118 | 0.2 | 361 |
| 119 | <0.1 | 762 |
| 120 | 0.4 | 859 |
| 121 | 0.1 | 87 |
| 122 | 117 | >1000 |
| 123 | <0.1 | 16 |
| 124 | <0.1 | 57 |
| 125 | 0.3 | 527 |
| 126 | 47 | >1000 |
| 127 | 2 | >1000 |
| 128 | 7 | >1000 |
| 129 | <0.1 | 18 |
| 130 | <0.1 | 30 |
| 131 | <0.1 | 9 |
| 132 | 3 | n.d. |
| 133 | 0.9 | n.d. |
| 134 | <0.1 | 0.9 |
| 135 | 78 | >1000 |
| 136 | 1.4 | >1000 |
| 137 | 1.5 | 363 |
| 138 | <0.1 | >1000 |
| 139 | 0.4 | >1000 |
| 140 | 2.3 | >1000 |
| 141 | 1 | 433 |
| 142 | 0.5 | >1000 |
| 143 | <0.1 | 19 |
| 144 | <0.1 | 213 |
| 145 | <0.1 | 0.2 |
| 146 | <0.1 | 11 |
| 147 | <0.1 | 1 |
| 148 | <0.1 | 13 |
| 149 | 0.3 | 986 |
| 150 | 0.2 | 339 |
| 151 | <0.1 | 0.6 |
| 152 | <0.1 | 1 |
| 153 | 0.3 | 587 |
| 154 | <0.1 | 15 |
| 155 | <0.1 | 7 |
| 156 | 0.2 | 15 |
| 157 | <0.1 | 0.3 |
| 158 | <0.1 | 364 |
| 159 | 0.2 | 31 |
| 160 | <0.1 | 14 |
| 161 | <0.1 | 7 |
| 162 | <0.1 | 5 |
| 163 | 0.4 | 211 |
| 164 | <0.1 | 308 |
| 165 | <0.1 | 9 |
| 166 | <0.1 | 30 |
| 167 | <0.1 | 81 |
| 168 | <0.1 | 14 |
| 169 | <0.1 | 10 |
| 170 | <0.1 | 0.5 |
| 171 | <0.1 | 97 |
| 172 | <0.1 | 1 |
| 173 | <0.1 | 0.1 |
| 174 | <0.1 | 210 |
| 175 | <0.1 | 33 |
| 176 | <0.1 | 10 |
| 177 | <0.1 | 24 |
| 178 | <0.1 | 0.2 |
| 179 | <0.1 | 6 |
| 181 | <0.1 | 241 |
| 182 | 0.2 | 6 |
| 183 | 0.7 | 507 |
| 184 | <0.1 | 2 |
| 185 | <0.1 | n.d. |
| 186 | <0.1 | n.d. |
| 187 | 0.4 | 318 |
| 188 | 0.5 | 546 |

EX = Example,
n.d. = no data available

Molt-4 Cellular Assay

Molt-4 (ATCC, Manassas, Va.) human acute lymphoblastic leukemia cells were plated 50,000 cells per well in 96-well tissue culture plates in a total volume of 100 μL tissue culture medium supplemented with 10% human serum (Invitrogen, Carlsbad, Calif.) and treated with a 3-fold serial dilution of the compounds of interest from 5 μM to 0.020 μL. Each concentration was tested in duplicate at least 3 separate times. The number of viable cells following 48 hours of compound treatment was determined using the CellTiter 96® Aqueous non-radioactive cell proliferation MTS assay according to manufacturer's recommendations (Promega Corp., Madison, Wis.). Molt-4 cell viability results (i.e. $EC_{50}$ in micromolar) for certain compounds of Formula (I), (i.e., Examples 81, 82, 84, 87, 124, 130, 134, 145, 151, 152, 166, 179, and 186 in Table 2), are 0.33, 0.135, 0.501, 1.2, 2.7, 0.532, 0.029, 0.081, 0.014, 0.006, 0.586, 0.493, and 0.006, respectively.

Single Dose Pharmacokinetics

The single dose pharmacokinetics of select compounds were evaluated in Sprague-Dawley rats (Charles River) after a 5 mg/kg oral dose (n=3) (10% DMSO in PEG-400) administered by gavage or by 5 mg/kg IV bolus dose (n=3) (10% DMSO in PEG-400). Compound and the internal standard were separated from each other and coextracted contaminants on a 50 mm×3 mm Keystone Betasil CN 5 μm column with an acetonitrile/0.1% trifluoroacetic acid mobile phase (50:50, by volume) at a flow rate of 0.7 mL/min. Analysis was performed on a Sciex API3000 biomolecular mass analyzer with a heated nebulizer interface. Compound and internal standard peak areas were determined using Sciex MacQuan software. The plasma drug concentration of each sample was calculated by least-squares linear regression analysis (nonweighted) of the peak area ratio (parent/internal standard) of the spiked plasma standards versus concentration. The plasma concentration data were submitted to multiexponential curve fitting using WinNonlin.3. The area under the plasma concentration-time curve was calculated using the linear trapezoidal rule for the plasma concentration-time profiles.

In pharmacology, bioavailability (BA) is a subcategory of absorption and is used to describe the fraction of an administered dose of unchanged drug that reaches the systemic circulation, one of the principal pharmacokinetic properties of drugs. By definition, when a medication is administered intravenously, its bioavailability is 100% (see Griffin. J. P. The Textbook of Pharmaceutical Medicine (6th Ed.). New Jersey: BMJ Books). However, when a medication is administered via other routes (such as orally), its bioavailability generally decreases (due to incomplete absorption and first-pass metabolism) and may vary from patient to patient. Bioavailability is one of the essential tools in pharmacokinetics, as bioavailability must be considered when calculating dosages for non-intravenous routes of administration. One way to calculate bioavailability of a drug or agent is by dividing the plasma concentration following an oral dose by the concentration following an intravenous dose. The oral bioavailability (as represented by % F) in Sprague-Dawley rats for representative compounds of the invention are provided below in Table 3.

In the drug discovery setting, it is generally accepted that Lipinski's "rule of 5" predicts that poor oral absorption or poor permeation is likely when two or more of the following metrics are satisfied: i) there are more than 5 hydrogen bond donors, ii) the molecular weight is greater than 500, iii) there are greater than 10 hydrogen bond acceptors (expressed as the sum of nitrogen and oxygen atoms), or iv) the calculated Log P (c Log P) is greater than 5 (Lipinski et al. Adv. Drug Del. Rev. 2001, 3-26). Indeed, the combination of high molecular weight (>500) and high c Log P (>5) is the best predictor of poor absorption or permeation. Compounds described herein generally exceed the recommended ranges pertaining to molecular weight (>500) and c Log P (>5), as shown in Table 3. It is notable, therefore, that Examples described herein have acceptable oral bioavailability in rats (as defined by % F>10, see Martin J. Med. Chem. 2005, 48, 3164), as illustrated in Table 3.

TABLE 3

PK Data, Rat p.o. dose

| EXAMPLE # | Molecular weight | cLogP | F (%), dose |
|---|---|---|---|
| 5 | 600.7 | 6.6 | 19, 5 mpk |
| 12 | 614.7 | 6.7 | 29, 5 mpk |
| 19 | 600.7 | 6.5 | 22, 5 mpk |
| 20 | 600.7 | 6.5 | 17, 5 mpk |
| 22 | 656.8 | 6.1 | 27, 5 mpk |
| 23 | 572.6 | 6.5 | 20, 5 mpk |
| 25 | 621.1 | 7.0 | 24, 5 mpk |
| 37 | 612.7 | 6.7 | 29, 5 mpk |
| 63 | 592.7 | 6.8 | 20, 5 mpk |
| 70 | 632.8 | 7.8 | 21, 5 mpk |
| 73 | 642.7 | 6.8 | 19, 5 mpk |
| 74 | 660.7 | 7.3 | 23, 5 mpk |
| 82 | 620.8 | 7.9 | 45, 5 mpk |
| 88 | 650.8 | 7.0 | 23, 5 mpk |
| 89 | 674.8 | 6.3 | 13, 5 mpk |
| 90 | 664.8 | 7.2 | 44, 5 mpk |
| 91 | 616.7 | 7.2 | 16, 5 mpk |
| 93 | 644.7 | 6.4 | 33, 5 mpk |
| 97 | 678.8 | 7.7 | 33, 5 mpk |
| 99 | 714.8 | 6.7 | 19, 5 mpk |
| 101 | 680.8 | 6.7 | 40, 5 mpk |
| 103 | 598.7 | 8.4 | 39, 5 mpk |
| 106 | 596.7 | 8.4 | 24, 5 mpk |
| 107 | 616.8 | 9.6 | 14, 5 mpk |
| 110 | 612.7 | 8.6 | 36, 5 mpk |
| 114 | 618.7 | 8.6 | 38, 5 mpk |
| 119 | 622.7 | 8.4 | 54, 5 mpk |
| 122 | 587.7 | 5.8 | 40, 5 mpk |
| 129 | 624.7 | 7.0 | 17, 5mpk |
| 130 | 630.6 | 7.8 | 32, 5 mpk |
| 131 | 713.9 | 6.0 | 11, 5 mpk |
| 134 | 678.9 | 8.0 | 50, 5 mpk |
| 146 | 692.9 | 8.4 | 16, 5 mpk |
| 147 | 692.9 | 8.5 | 37, 5 mpk |
| 148 | 756.0 | 7.0 | 18, 5 mpk |
| 151 | 694.9 | 7.5 | 30, 1 mpk |
| 154 | 608.72 | 5.7 | 22, 1 mpk |
| 156 | 625.8 | 8.8 | 39, 1 mpk |
| 157 | 664.8 | 8.1 | 30, 1 mpk |

Data in Table 2 and cited Molt-4 data show the utility of compounds of the invention to functionally inhibit anti-apoptotic Bcl-xL protein in a cellular context. The ability of compounds to kill FL5.12 cells over-expressing Bcl-xL or human tumor cell lines that are dependant upon Bcl-xL such as Molt-4 cells is a direct measure of the compound's ability to inhibit anti-apoptotic Bcl-xL protein function. Compounds of the invention are very effective in killing FL5.12 cells over-expressing Bcl-xL or human tumor cell lines that are dependant upon Bcl-xL such as Molt-4 cells as demonstrated by low $EC_{50}$ values. In addition, as demonstrated in Table 3, compounds of the invention have acceptable oral bioavailability in preclinical rodent studies, and therefore may find utility as orally-dosed therapeutics in a clinical setting.

Overexpression of Bcl-xL proteins correlates with resistance to chemotherapy, clinical outcome, disease progression, overall prognosis or a combination thereof in various cancers and disorders of the immune system. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordomna, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcomna, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

It is also expected that compounds having Formula (I) would inhibit growth of cells expressing Bcl-xL proteins derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, *mycobacterium avium intracellulare, mycobacterium tuberculosis,* myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherosclerotic disease, peripheral vascular disorders, peritonitis, pernicious anemia, phacogenic uveitis, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjögren's syndrome, skin allograft rejection, skin changes syndrome, small bowel transplant rejection, sperm autoimmunity, multiple sclerosis (all subtypes), spinal ataxia, spinocerebellar degenerations, spondyloarthopathy, sporadic, polyglandular deficiency type I, sporadic polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, *yersinia* and *salmonella*-associated arthropathy and the like.

Schemes and Experimentals

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene: DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; $MP-BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Schemes

Scheme 1

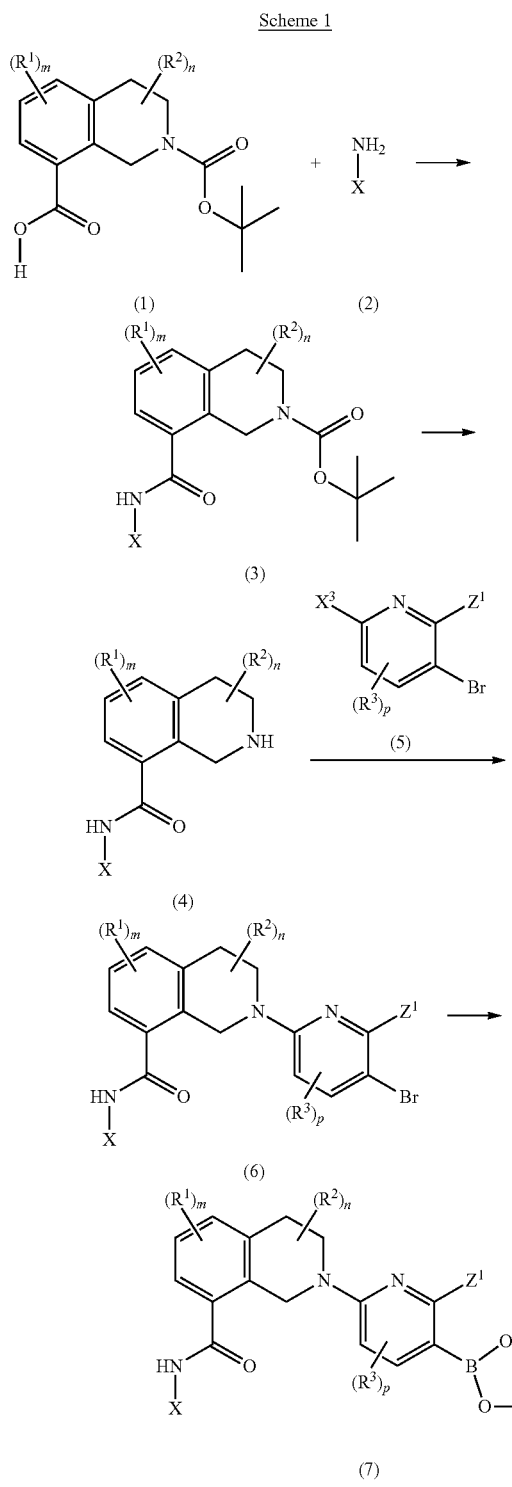

As shown in Scheme 1, compounds of formula (1), wherein $R^1$, $R^2$, n, and m are as described herein, can be reacted with compounds of formula (2) wherein X is as described herein, in the presence of a carboxyl activating agent such as but not limited to N-(3-dimethylaminopropyl)-N'-ethylcarbodiimide hydrochloride, and a catalyst such but not limited to 4-dimethylaminopyridine, to provide compounds of formula (3).

The reaction is typically performed at room temperature in a solvent such as but not limited to dichloromethane. Compounds of formula (4) can be prepared by reacting compounds of formula (3) with an acid such as but not limited to hydrochloric acid in a solvent such as but not limited to 1,4-dioxane. Compounds of formula (4) can be reacted with compounds of formula (5), wherein $Z^1$, $R^3$ and p are as described herein and $X^3$ is chloro or fluoro, in the presence of a base such as but not limited to cesium carbonate, to provide compounds of formula (6). The reaction is typically performed at an elevated temperature in a solvent such as but not limited to N,N-dimethylacetamide. Compounds of formula (7) can be prepared by reacting compounds of formula (6) with 4,4,5,5-tetramethyl-1,3,2-dioxaborolane in tetrahydrofuran, in the presence of a base such as but not limited to triethylamine, and a catalyst such as but not limited to [1,1'-bis(diphenylphosphino)ferrocene]dichloropalladium(II) dichloromethane. The reaction is typically performed at elevated temperature and with the addition of a solvent such as but not limited to acetonitrile. Additionally, the reaction may be performed in a microwave reactor.

Scheme 2

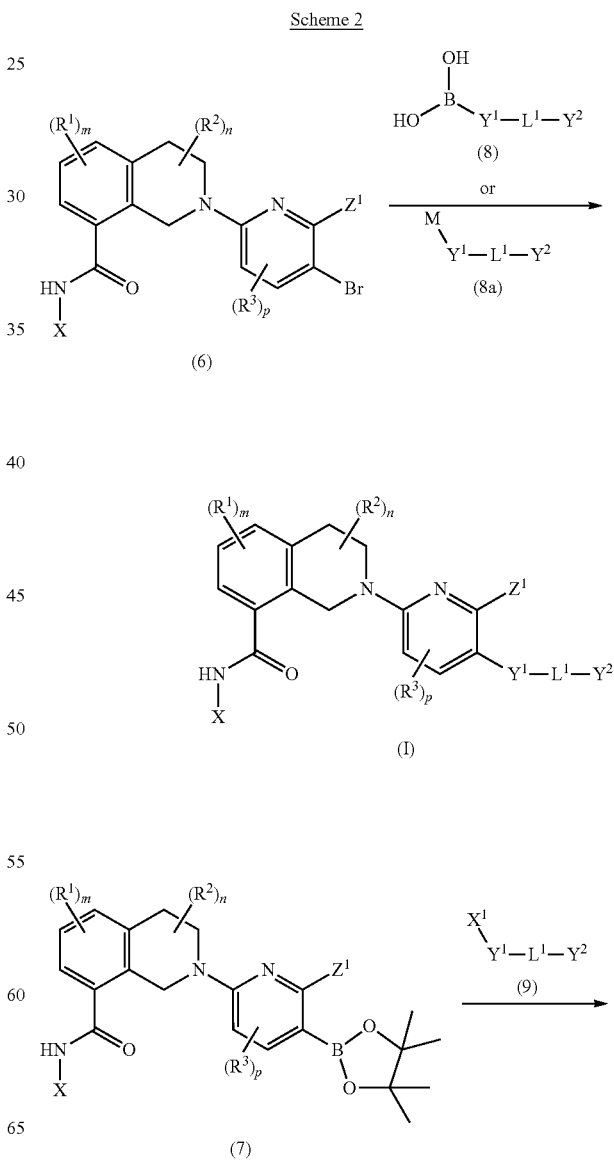

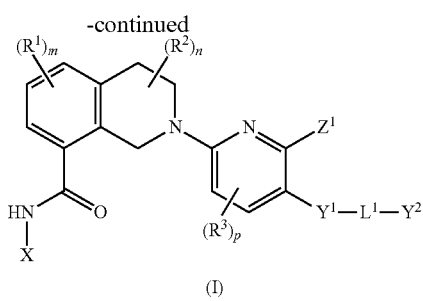

(I)

After preparation as described in Scheme 1, compounds of formula (6) can be reacted with a boronic acid (or the boronate equivalent) of formula (8) or an organotin or organozinc halide compound of formula (8a) wherein $Y^1$, $L^1$, and $Y^2$ are as described herein, and M is tributyltin or a zince halide, under Suzuki, Stille, or Negishi coupling conditions known to those skilled in the art and readily available in the literature to provide compounds of formula (I). Alternatively, compounds of formula (7), which can be prepared from compounds of formula (6) as described in Scheme 1, can be reacted with compounds of formula (9) wherein $X^1$ is a triflate or halide, and $Y^1$, $L^1$, and $Y^1$ are as described herein, under Suzuki coupling conditions known to those skilled in the art and readily available in the literature to provide compounds of formula (I).

can be reacted with alcohols of formula (11), wherein $L^1$ and $Y^2$ are as described herein, and cyanomethylenetributylphosphorane, to provide compounds of formula (12). The reaction is typically performed at ambient temperature in a solvent such as but not limited to toluene. Compounds of formula (14) can be prepared by adding compounds of formula (13) wherein $R^{12}$ is an appropriate substituent as described herein for substituents on $Y^1$, and $X^2$ is a halide, to a cold solution of compounds of formula (12) treated with n-butyllithium in hexanes. The reaction is typically performed in a solvent such as but not limited to tetrahydrofuran. Compounds of formula (14) can be treated with N-bromosuccinimide or N-iodosuccinimide to provide compounds of formula (15), wherein $X^4$ is bromo or iodo. The reaction is typically performed in a solvent such as N,N-dimethylformamide. Compounds of formula (15) can be reacted with compounds of formula (7) under Suzuki coupling conditions known to those skilled in the art and readily available in the literature to provide compounds of formula (17), which are representative of compounds of formula (I). Alternatively, compounds of formula (15) can be reacted with triisopropyl borate, in the presence of n-butyllithium in hexanes, followed by pinacol to provide compounds of formula (18). The additions are typically performed at low temperature in a solvent such as but not limited to tetrahydrofuran, toluene, or mixtures thereof. Alternatively, compounds of the formula (15) can be treated with 4,4,5,5-tetramethyl-1,3,2-dioxaborolane in the presence of a Scheme 3

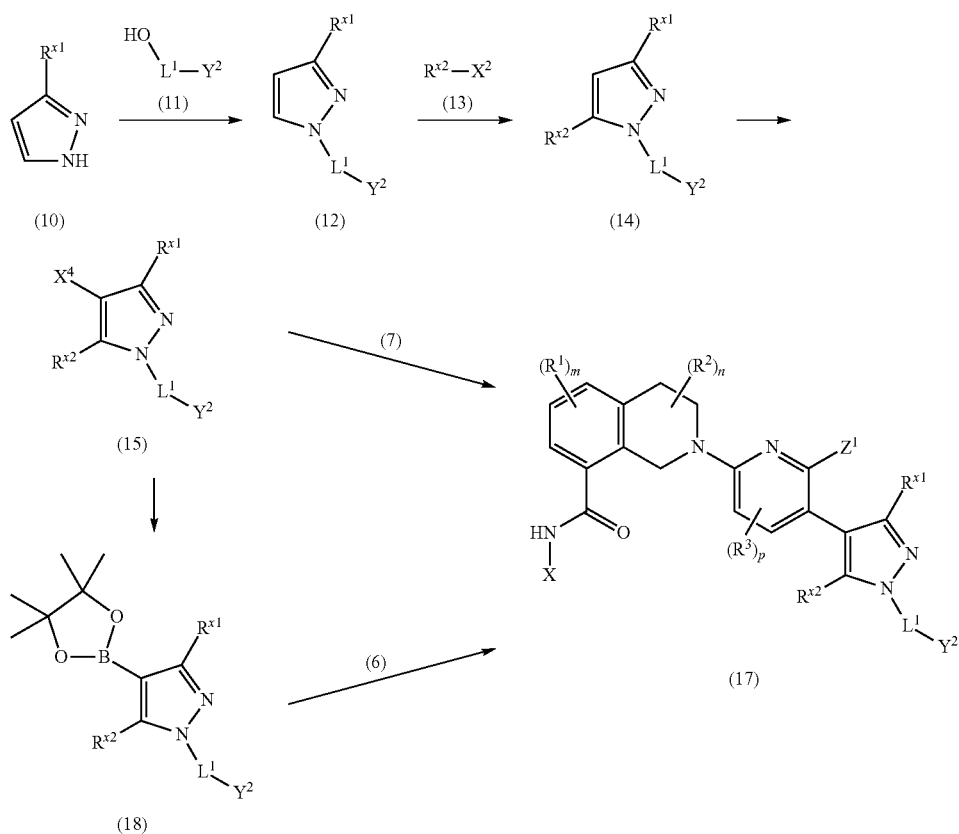

As shown in Scheme 3, pyrazoles of formula (10), wherein $Rx^1$ is hydrogen or a substituent on $Y^1$ as described herein, palladium catalyst system such as but not limited to bis(acetonitrile)palladium dichloride and SPhos in a solvent such as but not limited to 1,4-dioxane to provide compounds of the formula 18. The reaction is typically performed at elevated temperature. Compounds of formula (18) can be reacted with compounds of formula (6) under Suzuki coupling conditions known to those skilled in the art and readily available in the literature to provide compounds of formula (17), which are representative of compounds of formula (I).

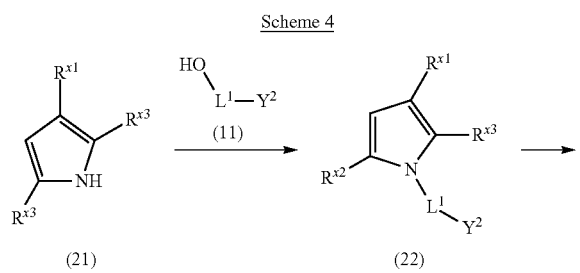

Scheme 4

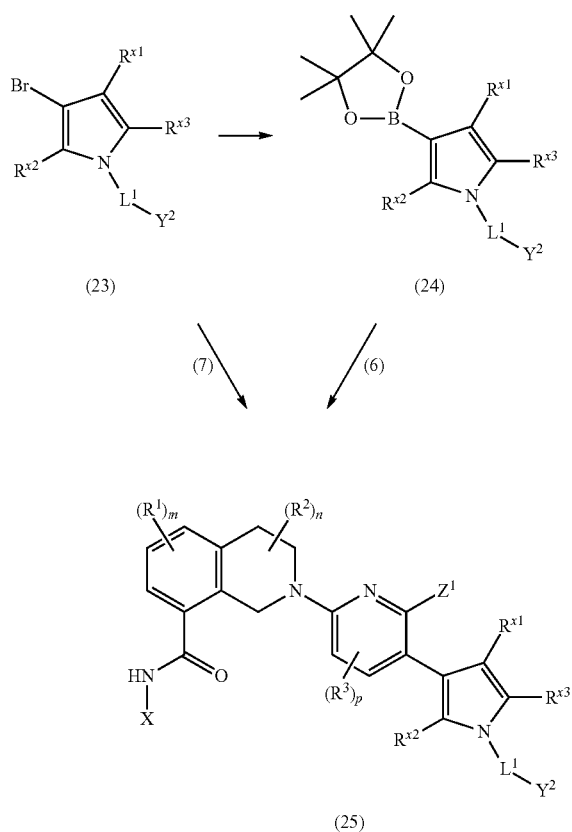

Pyrroles of formula (21) wherein $R^{x1}$, $R^{x2}$, and $R^{x3}$ are hydrogen or are as described herein for substituents on $Y^1$, can be reacted with alcohols of formula (11), wherein $Y^2$ and $L^1$ are as described herein, and cyanomethylenetributylphosphorane, to provide compounds of formula (22). The reaction is typically performed at ambient temperature in a solvent such as but not limited to toluene. Compounds of formula (22) can be treated with N-bromosuccinimide to provide compounds of formula (23). The reaction is typically performed in a solvent such as N,N-dimethylformamide. Compounds of formula (23) can be reacted with triisopropyl borate, in the presence of n-butyllithium in hexanes, followed by pinacol to provide compounds of formula (24). The additions are typically performed at low temperature in a solvent such as but not limited to tetrahydrofuran, toluene, or mixtures thereof. Alternatively, compounds of the formula (23) can be treated with 4,4,5,5-tetramethyl-1,3,2-dioxaborolane in the presence of a palladium catalyst system such as but not limited to bis(acetonitrile)palladium dichloride and SPhos in a solvent such as but not limited to 1,4-dioxane to provide compounds of the formula (24). The reaction is typically performed at an elevated temperature. Compounds of formula (24) can be reacted with compounds of formula (6) under Suzuki coupling conditions known to those skilled in the art and readily available in the literature to provide compounds of formula (25), which are representative of compounds of formula (I). Alternatively, compounds of formula (23) can be reacted with compounds of formula (7) under Suzuki coupling conditions known to those skilled in the art and readily available in the literature to provide compounds of formula (25), which are representative of compounds of formula (I).

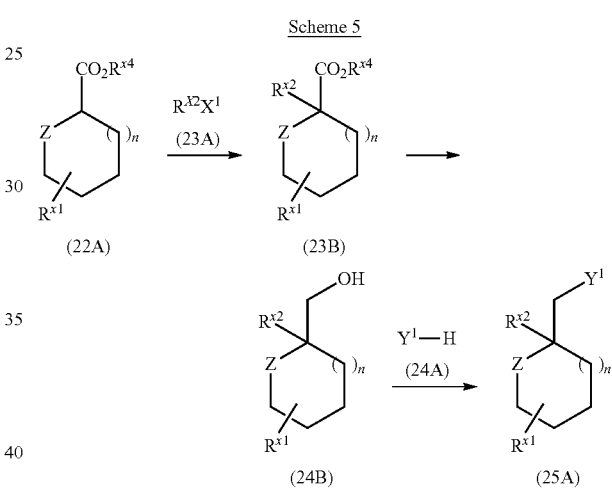

Scheme 5

Compounds of formula (22A), wherein Z is O, a substituted or unsubstituted N, or a substituted or unsubstituted C: $R^{x1}$ is hydrogen or is as described herein for substituents on $Y^2$; $R^{14}$ is alkyl; and n is 0, 1, or 2; can be added to a cooled solution of lithium diisopropylamide, followed by the addition of compounds of formula (23A); wherein $R^{x2}$ is an appropriate substituent as described herein for substituents on $Y^1$, and $X^1$ is a halide; to provide compounds of formula (23B). The reaction is typically performed at low temperature before warming to ambient temperature in a solvent such as but not limited to tetrahydrofuran. Compounds of formula (23B) can be reacted with $LiAlH_4$ to provide compounds of formula (24B). The reaction is typically performed at an elevated temperature in a solvent such as but not limited to diethyl ether. Compounds of formula (25A) can be prepared by reacting compounds of formula (24B) with compounds of formula (24A) wherein $Y^1$ is as described herein; and cyanomethylenetributylphosphorane. The reaction is typically performed at ambient temperature in a solvent such as but not limited to toluene. Compounds of formula (25A) can be processed in a manner similar to compounds of formula (12) in Scheme 3 and compounds of formula (22) in Scheme 4 to provide compounds of formula (I).

Scheme 6

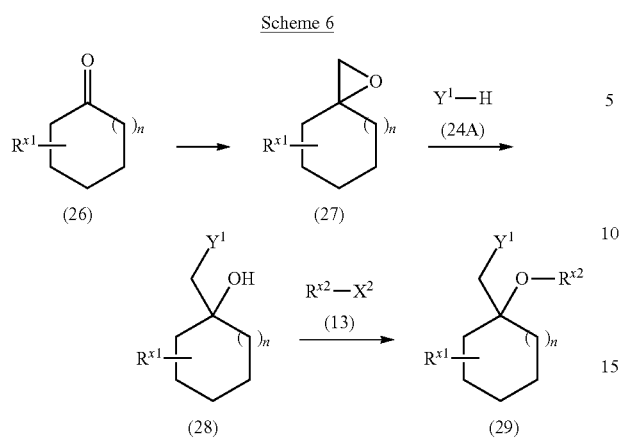

As shown in Scheme 6, compounds of formula (27), wherein $R^{x1}$ is hydrogen or a substituent on $Y^1$ as described herein, can be prepared by reacting compounds of formula (26) with trimethylsulfonium iodide, in the presence of potassium tert-butoxide. The reaction is typically performed at ambient temperature in an anhydrous solvent such as but not limited to dimethylsulfoxide. Compounds of formula (27) can be added to a mixture of compounds of formula (24A) and a base such as but not limited to cesium carbonate, to provide compounds of formula (28). The reaction is typically performed at elevated temperature in a solvent such as but not limited to N,N-dimethylformamide, and may be performed in a microwave reactor. Compounds of formula (28) can be treated with sodium hydride, followed by the addition of compounds of formula (13) to provide compounds of formula (29). The reaction is typically performed at ambient temperature in a solvent such as but not limited to tetrahydrofuran, and may involve the use of hexamethylphosphoramide. Compounds of formula (29) can be processed in a manner similar to compounds of formula (12) in Scheme 3 and compounds of formula (22) in Scheme 4 to provide compounds of formula (I).

Scheme 7

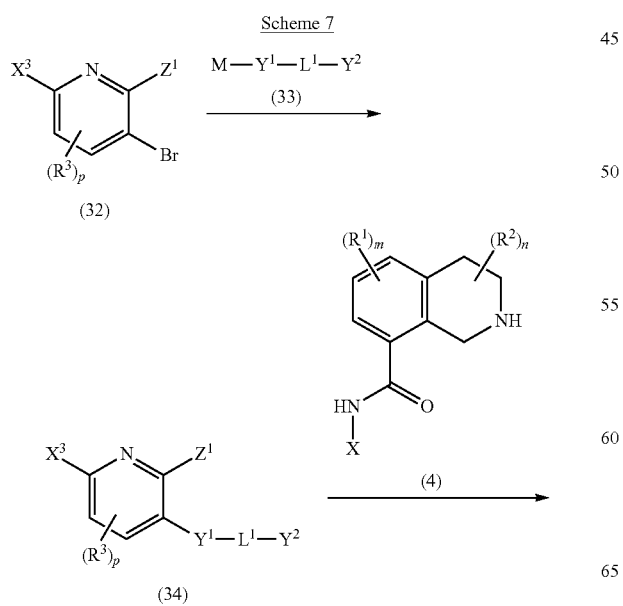

Compounds of formula (33) wherein M is a boronic acid, boronate, or tributyltin attached to $Y^1$ and $Y^1$, $L^1$, and $Y^2$ are as described herein, and $X^1$ is chloro or fluoro; can be reacted with compounds of formula (32) wherein $Z^1$, $R^3$, and p are as described herein, under Suzuki or Stille coupling conditions known to those skilled in the art and readily available in the literature to provide compounds of formula (34). Compounds of formula (34) can be reacted with compounds of formula (4), in the presence of a base such as but not limited to cesium carbonate, to provide compounds of formula (I). The reaction is typically performed at an elevated temperature in a solvent such as but not limited to N,N-dimethylacetamide.

Scheme 8

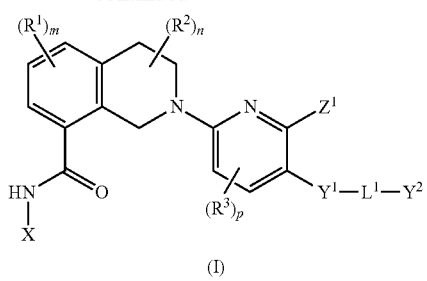

-continued

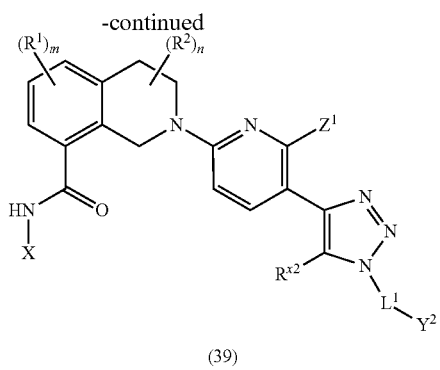

(39)

Triazoles of formula (36) can be prepared by reacting azides of formula (35), wherein $L^1$ and $Y^2$ are as described herein, with compounds of formula (36A) wherein $R^{x2}$ is alkyl, under conditions known to those skilled in the art and readily available in the literature. Compounds of formula (37), wherein $Z^1$ is as described herein, can be reacted with compounds of formula (36) under Stille coupling conditions known to those skilled in the art and readily available in the literature to provide compounds of formula (38). Compounds of formula (4), wherein $R^1$, $R^2$, X, m and n are as described herein, can be reacted with compounds of formula (38), in the presence of a base such as but not limited to cesium carbonate, to provide compounds of formula (39), which are representative of compounds of formula (I). The reaction is typically performed at an elevated temperature in a solvent such as but not limited to N,N-dimethylacetamide.

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), ACD/ChemSketch Version 12.01 (13 May 2009), Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

EXAMPLES

Example 1

6-[8-(1,3-benzothiazol-2-ylcarbamoyl)-3,4-dihydroisoquinolin-2(1H)-yl]-3-(1-benzyl-1H-pyrazol-4-yl)pyridine-2-carboxylic acid Example 1A tert-butyl 8-(benzo[d]thiazol-2-ylcarbamoyl)-3,4-dihydroisoquinoline-2(1H)-carboxylate To a solution of 2-(tert-butoxycarbonyl)-1,2,3,4-tetrahydroisoquinoline-8-carboxylic acid (6.8 g) and benzo[d]thiazol-2-amine (5.52 g) in dichloromethane (80 mL) was added 1-ethyl-3-[3-(dimethylamino)propyl]-carbodiimide hydrochloride (9.4 g) and 4-dimethylaminopyridine (6 g). The mixture was stirred at room temperature overnight. The reaction mixture was diluted with dichloromethane (400 mL), washed with 5% aqueous HCl, water, and brine, and dried over $Na_2SO_4$. The mixture was filtered and the filtrate was concentrated under reduced pressure to provide the title compound.

Example 1B

N-(benzo[d]thiazol-2-yl)-1,2,3,4-tetrahydroisoquinoline-8-carboxamide dihydrochloride To a solution of EXAMPLE 1A (8.5 g) in dichloromethane (80 mL) was added 2N HCl in ether (80 mL). The reaction mixture was stirred at room temperature overnight and concentrated under reduced pressure to provide the title compound.

Example 1C tert-butyl 3-bromo-6-chloropicolinate

Tosyl chloride (7.7 g) was added to a solution of 2-chloro-5-bromo picolinic acid (4 g) and pyridine (9.2 mL) in t-butanol (33 mL) at 0° C. The reaction was then stirred at room temperature for 12 hours. $NaHCO_3$ (aqueous, saturated) was then added and the mixture was extracted three times with ethyl acetate. The combined organic phases were washed with brine and dried over $Na_2SO_4$. Filtration and evaporation of the organic solvent provided the title compound which was used in the next step without further purification.

Example 1D tert-butyl 6-(8-(benzo[d]thiazol-2-ylcarbamoyl)-3,4-dihydroisoquinolin-2(1H)-yl)-3-bromopicolinate EXAMPLE 1C (0.736 g), EXAMPLE 1B (1.62 g), and $Cs_2CO_3$ (4.1 g) were stirred in 12 mL of anhydrous N,N-dimethylacetamide at 120° C. for 12 hours. The cooled reaction mixture was then diluted with ethyl acetate and 10% citric acid. The organic phase was washed three times with citric acid, once with water and brine, and dried over $Na_2SO_4$. Filtration and concentration afforded crude material, which was chromatographed on silica gel using 0-40% ethyl acetate in hexanes to provide the title compound.

Example 1E tert-butyl 6-(8-(benzo[d]thiazol-2-ylcarbamoyl)-3,4-dihydroisoquinolin-2(1H)-yl)-3-(1-benzyl-1H-pyrazol-4-yl)picolinate A mixture of EXAMPLE 1D (0.113 g), 1-benzyl-4-(4,4,5,5-tetramethyl-1,3,2-dioxaborolan-2-yl)-1H-pyrazole (0.063 g), tetrakis(triphenylphosphine)palladium(0) (0.023 g) and CsF (0.091 g) in 1,2-dimethoxyethane (2 mL) and methanol (1 mL) was heated at 120° C. for 30 minutes under microwave heating conditions. The reaction mixture was partitioned between water and ethyl acetate. The aqueous layer was extracted with additional ethyl acetate twice. The combined organic layers were washed with brine, dried over $MgSO_4$, filtered, and concentrated. The residue was purified by flash column chromatography on silica gel eluting with 35% ethyl acetate in hexanes to afford the title compound.

Example 1F

6-[8-(1,3-benzothiazol-2-ylcarbamoyl)-3,4-dihydroisoquinolin-2(1H)-yl]-3-(1-benzyl-1H-pyrazol-4-yl)pyridine-2-carboxylic acid EXAMPLE 1E (100 mg) in dichloromethane (3 mL) was treated with trifluoroacetic acid (3 mL). The reaction mixture was stirred at room temperature for 4 hours. The volatiles were removed under reduced pressure. The residue was purified by Prep HPLC using Gilson system eluting with 20-80% acetonitrile in water containing 0.1% v/v trifluoroacetic acid. The desired fractions were combined and freeze-dried to provide the title compound. $^1$H NMR (500 MHz, dimethylsulfoxide-$d_6$) δ ppm 12.86 (s, 1H), 8.04 (d, 1H), 7.92 (s, 1H), 7.80 (s, 1H), 7.79 (d, 1H), 7.71 (d, 1H), 7.61 (d, 1H), 7.67 (s, 1H), 7.42-7.50 (m, 2H), 7.23-7.38 (m, 7H), 6.94 (d, 1H), 5.33 (s, 2H), 4.94 (s, 2H), 3.86 (t, 2H), 3.00 (t, 2H).

Example 2

6-[8-(1,3-benzothiazol-2-ylcarbamoyl)-3,4-dihydroisoquinolin-2(1H)-yl]-3-[1-(pyridin-4-ylmethyl)-1H-pyrazol-4-yl]pyridine-2-carboxylic acid

Example 2A tert-butyl 6-(8-(benzo[d]thiazol-2-ylcarbamoyl)-3,4-dihydroisoquinolin-2(1H)-yl)-3-(1-(pyridin-4-ylmethyl)-1H-pyrazol-4-yl)picolinate The title compound was prepared by substituting 4-((4-(4,4,5,5-tetramethyl-1,3,2-dioxaborolan-2-yl)-1H-pyrazol-1-yl)methyl)pyridine for 1-benzyl-4-(4,4,5,5-tetramethyl-1,3,2-dioxaborolan-2-yl)-1H-pyrazole in EXAMPLE 1E.

Example 2B

6-[8-(1,3-benzothiazol-2-ylcarbamoyl)-3,4-dihydroisoquinolin-2(1H)-yl]-3-[1-(pyridin-4-ylmethyl)-1H-pyrazol-4-yl]pyridine-2-carboxylic acid The title compound was prepared by substituting EXAMPLE 2A for EXAMPLE 1E in EXAMPLE 1F. $^1$H NMR (500 MHz, dimethylsulfoxide-$d_6$) δ ppm 12.87 (s, 1H), 8.70 (d, 2H), 8.04 (d, 1H), 8.02 (s, 1H), 7.80 (d, 1H), 7.73 (d, 1H), 7.67 (s, 1H), 7.62 (d, 1H), 7.34-7.50 (m, 6H), 6.97 (d, 1H), 5.59 (s, 2H), 4.96 (s, 2H), 3.87 (t, 2H), 3.01 (t, 2H).

Example 3

6-[8-(1,3-benzothiazol-2-ylcarbamoyl)-3,4-dihydroisoquinolin-2(1H)-yl]-3-[1-(pyridin-3-ylmethyl)-1H-pyrazol-4-yl]pyridine-2-carboxylic acid

Example 3A tert-butyl 6-(8-(benzo[d]thiazol-2-ylcarbamoyl)-3,4-dihydroisoquinolin-2(1H)-yl)-3-(1-(pyridin-3-ylmethyl)-1H-pyrazol-4-yl)picolinate The title compound was prepared by substituting 3-((4-(4,4,5,5-tetramethyl-1,3,2-dioxaborolan-2-yl)-1H-pyrazol-1-yl)methyl)pyridine for 1-benzyl-4-(4,4,5,5-tetramethyl-1,3,2-dioxaborolan-2-yl)-1H-pyrazole in EXAMPLE 1E.

Example 3B

6-[8-(1,3-benzothiazol-2-ylcarbamoyl)-3,4-dihydroisoquinolin-2(1H)-yl]-3-[1-(pyridin-3-ylmethyl)-1H-pyrazol-4-yl]pyridine-2-carboxylic acid The title compound was prepared by substituting EXAMPLE 3A for EXAMPLE 1E in EXAMPLE 1F. $^1$H NMR (500 MHz, dimethylsulfoxide-$d_6$) δ ppm 12.85 (s, 1H), 8.70 (d, 2H), 8.62-8.63 (m, 2H), 8.04 (d, 1H), 8.00 (s, 1H), 7.90 (d, 1H), 7.80 (d, 1H), 7.71 (d, 1H), 7.85-7.62 (m, 3H), 7.34-7.50 (m, 5H), 6.95 (d, 1H), 5.46 (s, 2H), 4.95 (s, 2H), 3.87 (t, 2H), 3.00 (t, 2H).

Example 4

6-[8-(1,3-benzothiazol-2-ylcarbamoyl)-3,4-dihydroisoquinolin-2(1H)-yl]-3-[1-(4-hydroxybenzyl)-1H-pyrazol-4-yl]pyridine-2-carboxylic acid

Example 4A 1-(benzyloxy)-4-(bromomethyl)benzene

A mixture of (4-(benzyloxy)phenyl)methanol (2.14 g) and lithium bromide (1.0 g) in N,N-dimethylformamide (20 mL) was cooled to 0° C. To this solution was added $PBr_3$ (1.0 mL). The solution was stirred at room temperature for 2 hours. The reaction mixture was partitioned between water and ethyl acetate. The aqueous layer was extracted with additional ethyl acetate, twice. The combined organic layers were washed with brine, dried over $MgSO_4$, filtered, and concentrated. The residue was purified by flash column chromatography on silica gel eluting with 5% ethyl acetate in hexanes to provide the title compound.

Example 4B 1-(4-(benzyloxy)benzyl)-4-(4,4,5,5-tetramethyl-1,3,2-dioxaborolan-2-yl)-1H-pyrazole A mixture of EXAMPLE 4A (0.54 g) and 4-(4,4,5,5-tetramethyl-1,3,2-dioxaborolan-2-yl)-1H-pyrazole (0.377 g) in N,N-dimethylformamide (5 mL) was cooled to 0° C. To this solution was added 60% sodium hydride (0.096 g). The solution was stirred at room temperature overnight. The reaction mixture was partitioned between water and ethyl acetate. The aqueous layer was extracted with additional ethyl acetate twice. The combined organic layers were washed with brine, dried over $MgSO_4$, filtered, and concentrated. The residue was purified by flash column chromatography on silica gel eluting with 25% ethyl acetate in hexanes to provide the title compound.

Example 4C tert-butyl 6-(8-(benzo[d]thiazol-2-ylcarbamoyl)-3,4-dihydroisoquinolin-2(1H)-yl)-3-(1-(4-(benzyloxy)benzyl)-1H-pyrazol-4-yl)picolinate The title compound was prepared by substituting EXAMPLE of 4B for 3-((4-(4,4,5,5-tetramethyl-1,3,2-dioxaborolan-2-yl)-1H-pyrazol-1-yl)methyl)pyridine in EXAMPLE 1E.

Example 4D tert-butyl 6-(8-(benzo[d]thiazol-2-ylcarbamoyl)-3,4-dihydroisoquinolin-2(1H)-yl)-3-(1-(4-hydroxybenzyl)-1H-pyrazol-4-yl)picolinate A mixture of EXAMPLE 4C (0.05 g) and 5% palladium on carbon (0.1 g) in ethanol (5 mL) was treated with a balloon of hydrogen. The reaction mixture was stirred overnight. The solid was removed by filtration, and filtrate was concentrated to provide the title compound.

Example 4E

6-[8-(1,3-benzothiazol-2-ylcarbamoyl)-3,4-dihydroisoquinolin-2(1H)-yl]-3-[1-(4-hydroxybenzyl)-1H-pyrazol-4-yl]pyridine-2-carboxylic acid The title compound was prepared by substituting EXAMPLE 4D for EXAMPLE 1E in EXAMPLE 1F. $^1$H NMR (500 MHz, dimethylsulfoxide-$d_6$) δ ppm 12.84 (s, 1H), 8.04 (d, 1H), 7.83 (s, 1H), 7.79 (d, 1H), 7.69 (d, 1H), 7.61 (d, 1H), 7.54 (s, 1H), 7.46-7.50 (m, 1H), 7.42-7.46 (m, 1H), 7.34-7.38 (m, 2H), 7.08-7.12 (m, 2H), 6.93 (d, 1H), 6.69-6.73 (m, 2H), 5.17 (s, 2H), 4.94 (s, 2H), 3.86 (t, 2H), 2.99 (t, 2H).

Example 5

6-[8-(1,3-benzothiazol-2-ylcarbamoyl)-3,4-dihydroisoquinolin-2(1H)-yl]-3-[1-(1-phenylethyl)-1H-pyrazol-4-yl]pyridine-2-carboxylic acid

Example 5A

The title compound was prepared by substituting (1-bromoethyl)benzene for EXAMPLE 4A in EXAMPLE 4B.

Example 5B tert-butyl 6-(8-(benzo[d]thiazol-2-ylcarbamoyl)-3,4-dihydroisoquinolin-2(1H)-yl)-3-(1-(1-phenylethyl)-1H-pyrazol-4-yl)picolinate The title compound was prepared by substituting EXAMPLE 5A for 3-((4-(4,4,5,5-tetramethyl-1,3,2-dioxaborolan-2-yl)-1H-pyrazol-1-yl)methyl)pyridine in EXAMPLE 1E.

Example 5C

6-[8-(1,3-benzothiazol-2-ylcarbamoyl)-3,4-dihydroisoquinolin-2(1H)-yl]-3-[1-(1-phenylethyl)-1H-pyrazol-4-yl]pyridine-2-carboxylic acid The title compound was prepared by substituting EXAMPLE 5B for EXAMPLE 1E in EXAMPLE 1F. $^1$H NMR (500 MHz, dimethylsulfoxide-$d_6$) δ ppm 12.79 (s, 1H), 7.97 (d, 1H), 7.88 (s, 1H), 7.73 (d, 1H), 7.65 (d, 1H), 7.54 (d, 1H), 7.50 (s, 1H), 7.55-7.56 (m, 1H), 7.24-7.30 (m, 4H), 7.17-7.20 (m, 3H), 6.97 (d, 1H), 5.54 (q, 1H), 4.87 (s, 2H), 3.79 (t, 2H), 2.93 (t, 2H).

Example 6

6-[8-(1,3-benzothiazol-2-ylcarbamoyl)-3,4-dihydroisoquinolin-2(1H)-yl]-3-(1-{4-[2-(dimethylamino)ethoxy]benzyl}-1H-pyrazol-4-yl)pyridine-2-carboxylic acid

Example 6A tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(4-(benzyloxy)benzyl)-1H-pyrazol-4-yl)picolinate A mixture of EXAMPLE 4C (0.30 g) and (2-(chloromethoxy)ethyl)trimethylsilane (0.094 g) in tetrahydrofuran (4 mL) was treated with triethylamine (0.122 g) at room temperature. The reaction was stirred for 1 hour. The reaction mixture was partitioned between water and ethyl acetate. The aqueous layer was extracted with additional ethyl acetate twice. The combined organic layers were washed with brine, dried over $MgSO_4$, filtered, and concentrated. The residue was purified by flash column chromatography on silica gel eluting with 5% ethyl acetate in hexanes to provide the title compound.

Example 6B tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(4-hydroxybenzyl)-1H-pyrazol-4-yl)picolinate The title compound was prepared by substituting EXAMPLE 6A for EXAMPLE 4C in EXAMPLE 4D.

Example 6C tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(4-(2-(dimethylamino)ethoxy)benzyl)-1H-pyrazol-4-yl)picolinate A mixture of EXAMPLE 6B (0.18 g), 2-(dimethylamino)ethanol (0.102 g), and triphenylphosphine (0.299 g) in tetrahydrofuran (3 mL) was stirred for 5 minutes at 0° C. To this solution was added (E)-di-tert-butyl diazene-1,2-dicarboxylate (0.263 g). The reaction mixture was stirred at room temperature for 16 hours. The solvent was removed, and the residue was purified by flash column chromatography on silica gel using 5-50% ethyl acetate in hexanes to provide the title compound.

Example 6D

6-[8-(1,3-benzothiazol-2-ylcarbamoyl)-3,4-dihydroisoquinolin-2(1H)-yl]-3-(1-{4-[2-(dimethylamino)ethoxy]benzyl}-1H-pyrazol-4-yl)pyridine-2-carboxylic acid EXAMPLE 6C (0.08 g) in dichloromethane (3 mL) was treated with trifluoroacetic acid (3 mL). The reaction mixture was stirred at room temperature for 16 hours. The volatiles were removed under reduced pressure. The residue was purified by Prep HPLC using a Gilson system eluting with 20-80% acetonitrile in 0.1% water. The desired fractions were combined and freeze-dried to provide the title compound. $^1$H NMR (500 MHz, dimethylsulfoxide-d$_6$) δ ppm 9.55 (s, 1H), 8.03 (d, 1H), 7.88 (s, 1H), 7.78 (d, 1H), 7.68 (d, 1H), 7.60 (d, 1H), 7.54 (s, 1H), 7.41-7.48 (m, 2H), 7.33-7.36 (m, 2H), 7.25 (d, 2H), 6.96 (d, 2H), 6.93 (d, Hz, 1H), 5.24 (s, 2H), 4.94 (s, 2H), 4.93 (s, 2H), 4.26-4.28 (m, 2H), 3.85 (t, 2H), 2.97-2.99 (m, 2H), 2.83 (s, 6H).

Example 7

3-(1-benzyl-1H-pyrazol-4-yl)-6-{8-[(5,6-difluoro-1, 3-benzothiazol-2-yl)carbamoyl]-3,4-dihydroiso-quinolin-2(1H)-yl}pyridine-2-carboxylic acid Example 7A methyl 2-(5-bromo-6-(tert-butoxycarbonyl)pyridin-2-yl)-1,2,3,4-tetrahydroisoquinoline-8-carboxylate A solution of methyl 1,2,3,4-tetrahydroisoquinoline-8-carboxylate (1.00 g), EXAMPLE 1C (1.68 g) and cesium carbonate (2.56 g) was stirred together in N,N-dimethylacetamide (10 mL) at 110° C. overnight. The reaction was cooled, diluted with ethyl acetate (50 mL) and washed with water (2×25 mL) and brine (25 mL), dried over magnesium sulfate, filtered, and concentrated. Silica gel chromatography using 1-30% ethyl acetate in hexanes provided the title compound.

Example 7B methyl 2-(5-(1-benzyl-1H-pyrazol-4-yl)-6-(tert-butoxycarbonyl)pyridin-2-yl)-1,2,3,4-tetrahydroisoquinoline-8-carboxylate The title compound was prepared by substituting EXAMPLE 7A for EXAMPLE 1D in EXAMPLE 1E.

Example 7C 2-(5-(1-benzyl-1H-pyrazol-4-yl)-6-(tert-butoxycarbonyl)pyridin-2-yl)-1,2,3,4-tetrahydroisoquinoline-8-carboxylic To a solution of EXAMPLE 7B (0.565 g) in tetrahydrofuran (4 mL) and methanol (2 mL) was added NaOH (1.292 ml, 1 M) and the reaction was stirred at room temperature overnight. The reaction was diluted with ethyl acetate (50 mL) and quenched with 1N aqueous HCl (1.3 mL) and diluted with water (20 mL). The organic layer was separated, dried over magnesium sulfate, filtered, and concentrated. Silica gel chromatography eluting with a gradient of 0.5% to 3% methanol/dichloromethane provided the title compound.

Example 7D tert-butyl 3-(1-benzyl-1H-pyrazol-4-yl)-6-(8-(5,6-difluorobenzo[d]thiazol-2-ylcarbamoyl)-3,4-dihydroisoquinolin-2(1H)-yl)picolinate EXAMPLE 7C (0.086 g), 5,6-difluorobenzo[d]thiazol-2-amine (0.034 g), 1-ethyl-3-[3-(dimethylamino)propyl]-carbodiimide hydrochloride (0.048 g) and 4-dimethylaminopyridine (0.041 g) were combined together in dichloromethane (1 mL) and stirred overnight. The reaction was loaded onto silica gel and eluted using a gradient of 0.25% to 2.0% methanol/dichloromethane to provide the title compound.

Example 7E 3-(1-benzyl-1H-pyrazol-4-yl)-6-{8-[(5,6-difluoro-1, 3-benzothiazol-2-yl)carbamoyl]-3,4-dihydroiso-quinolin-2(1H)-yl}pyridine-2-carboxylic acid To a solution of EXAMPLE 7D (0.085 g) in dichloromethane (0.5 mL) was added TFA (0.5 mL) and the reaction was stirred overnight. The reaction mixture was concentrated and dried to provide the title compound. $^1$H NMR (300 MHz, dimethylsulfoxide-d$_6$) δ ppm 12.98 (s, 1H), 8.20 (dd, 1H), 7.93-7.83 (m, 2H), 7.70 (d, 1H), 7.58 (dd, 2H), 7.47-7.19 (m, 7H), 6.94 (d, 1H), 5.32 (s, 2H), 4.93 (s, 2H), 3.86 (t, 2H), 2.99 (t, 2H).

Example 8

6-[8-(1,3-benzothiazol-2-ylcarbamoyl)-3,4-dihydroisoquinolin-2(1H)-yl]-3-{1-[2-(4-fluorophenyl) ethyl]-1H-pyrazol-4-yl}pyridine-2-carboxylic acid Example 8A 1-(4-fluorophenethyl)-4-(4,4,5,5-tetramethyl-1,3,2-dioxaborolan-2-yl)-1H-pyrazole The title compound was prepared by substituting 1-(2-bromoethyl)-4-fluorobenzene for EXAMPLE 4A in EXAMPLE 4B.

Example 8B tert-butyl 6-(8-(benzo[d]thiazol-2-ylcarbamoyl)-3,4-dihydroisoquinolin-2(1H)-yl)-3-(1-(4-fluorophenethyl)-1H-pyrazol-4-yl)picolinate The title compound was prepared by substituting EXAMPLE 8A for 1-benzyl-4-(4,4,5,5-tetramethyl-1,3,2-dioxaborolan-2-yl)-1H-pyrazole in EXAMPLE 1E.

Example 8C

6-[8-(1,3-benzothiazol-2-ylcarbamoyl)-3,4-dihydroisoquinolin-2(1H)-yl]-3-{1-[2-(4-fluorophenyl) ethyl]-1H-pyrazol-4-yl}pyridine-2-carboxylic acid To EXAMPLE 8B (0.040 g) in dichloromethane (1 mL) was added TFA (1 mL) and the reaction stirred overnight. The reaction was concentrated, dissolved in dichloromethane and loaded onto silica gel and eluted using a gradient of 0.5% to 5% methanol/dichloromethane to provide the title compound. $^1$H NMR (300 MHz, dimethylsulfoxide-d$_6$) δ 13.04 (s, 1H), 12.84 (s, 1H), 8.04 (dd, 1H), 7.79 (d, 1H), 7.71 (d, 1H), 7.62 (t, 2H), 7.54-7.32 (m, 5H), 7.22-7.14 (m, 2H), 7.11-7.01 (m, 2H), 6.93 (d, 1H), 4.94 (s, 2H), 4.30 (t, 2H), 3.08 (t, 2H), 3.08 (t, 2H), 3.00 (t, 2H).

Example 9

6-[8-(1,3-benzothiazol-2-ylcarbamoyl)-3,4-dihydroisoquinolin-2(1H)-yl]-3-[1-(3-chlorobenzyl)-1H-pyrazol-4-yl]pyridine-2-carboxylic acid

Example 9A tert-butyl 6-(8-(benzo[d]thiazol-2-yl((2-(trimethylsilyl)ethoxy)methyl)carbamoyl)-3,4-dihydroisoquinolin-2(1H)-yl)-3-bromopicolinate The title compound was prepared by substituting EXAMPLE 1D for EXAMPLE 4C in EXAMPLE 6A.

Example 9B tert-butyl 6-(8-(benzo[d]thiazol-2-yl((2-(trimethylsilyl)ethoxy)methyl)carbamoyl)-3,4-dihydroisoquinolin-2(1H)-yl)-3-(1H-pyrazol-4-yl)picolinate The title compound was prepared by substituting 4-(4,4,5,5-tetramethyl-1,3,2-dioxaborolan-2-yl)-1H-pyrazole for 1-benzyl-4-(4,4,5,5-tetramethyl-1,3,2-dioxaborolan-2-yl)-1H-pyrazole and EXAMPLE 9A for EXAMPLE 1D in EXAMPLE 1E.

Example 9C

6-[8-(1,3-benzothiazol-2-ylcarbamoyl)-3,4-dihydroisoquinolin-2(1H)-yl]-3-[1-(3-chlorobenzyl)-1H-pyrazol-4-yl]pyridine-2-carboxylic acid A solution of EXAMPLE 9B (0.178 g), 1-(bromomethyl)-3-chlorobenzene (0.080 g) and cesium carbonate (0.170 g) was stirred together in N,N-dimethylformamide (2 mL) at room temperature. After 3 hours, the reaction was diluted with ethyl acetate (25 mL) and washed with water (20 mL), brine (20 mL), dried over magnesium sulfate, filtered, and concentrated. The residue was dissolved in dichloromethane (1 mL) and treated with TFA (1 mL) and stirred overnight. The mixture was concentrated, dissolved in dichloromethane and loaded onto silica gel and eluted using a gradient of 0.5% to 4% methanol/dichloromethane to provide the title compound. $^1$H NMR (300 MHz, dimethylsulfoxide-$d_6$) δ ppm 12.84 (s, 1H), 8.04 (dd, 1H), 7.95 (d, 1H), 7.79 (d, 1H), 7.71 (d, 1H), 7.60 (dd, 2H), 7.53-7.28 (m, 7H), 7.22-7.16 (m, 1H), 6.95 (d, 1H), 5.35 (s, 2H), 4.95 (s, 2H), 3.87 (t, 2H), 3.00 (t, 2H).

Example 10

3-(1-benzyl-1H-pyrazol-4-yl)-6-{8-[(6-fluoro-1,3-benzothiazol-2-yl)carbamoyl]-3,4-dihydroisoquinolin-2(1H)-yl}pyridine-2-carboxylic acid

Example 10A tert-butyl 3-(1-benzyl-1H-pyrazol-4-yl)-6-(8-(6-fluorobenzo[d]thiazol-2-ylcarbamoyl)-3,4-dihydroisoquinolin-2(1H)-yl)picolinate The title compound was prepared according to the procedure in EXAMPLE 7D by substituting 5,6-difluorobenzo[d]thiazol-2-amine with 6-fluorobenzo[d]thiazol-2-amine.

Example 10B 3-(1-benzyl-1H-pyrazol-4-yl)-6-{8-[(6-fluoro-1,3-benzothiazol-2-yl)carbamoyl]-3,4-dihydroisoquinolin-2(1H)-yl}pyridine-2-carboxylic acid The title compound was prepared according to the procedure in EXAMPLE 7E by substituting EXAMPLE 7D with EXAMPLE 10A. $^1$H NMR (300 MHz, dimethylsulfoxide-$d_6$) δ ppm 12.87 (s, 1H), 7.95 (dd, 1H), 7.91 (s, 1H), 7.80 (dd, 1H), 7.70 (d, 1H), 7.59 (m, 2H), 7.32 (m, 9H), 6.94 (d, 1H), 5.32 (s, 2H), 4.93 (s, 2H), 3.86 (t, 2H), 3.00 (t, 2H).

Example 11

3-(1-benzyl-1H-pyrazol-4-yl)-6-{8-[(6-methoxy-1,3-benzothiazol-2-yl)carbamoyl]-3,4-dihydroisoquinolin-2(1H)-yl}pyridine-2-carboxylic acid

Example 11A tert-butyl 3-(1-benzyl-1H-pyrazol-4-yl)-6-(8-(6-methoxybenzo[d]thiazol-2-ylcarbamoyl)-3,4-dihydroisoquinolin-2(1H)-yl)picolinate The title compound was prepared according to the procedure in EXAMPLE 7D by substituting 5,6-difluorobenzo[d]thiazol-2-amine with 6-methoxybenzo[d]thiazol-2-amine.

Example 11B 3-(1-benzyl-1H-pyrazol-4-yl)-6-{8-[(6-methoxy-1,3-benzothiazol-2-yl)carbamoyl]-3,4-dihydroisoquinolin-2(1H)-yl}pyridine-2-carboxylic acid The title compound was prepared according to the procedure in EXAMPLE 7E by substituting EXAMPLE 7D with EXAMPLE 1A. $^1$H NMR (300 MHz, dimethylsulfoxide-$d_6$) δ ppm 12.72 (s, 1H), 7.92 (s, 1H), 7.70 (dd, 2H), 7.62 (d, 1H), 7.58 (m, 2H), 7.32 (m, 8H), 7.07 (dd, 1H), 6.94 (d, 1H), 5.32 (s, 2H), 4.93 (s, 2H), 3.85 (m, 5H), 2.99 (t, 2H).

Example 12

6-[8-(1,3-benzothiazol-2-ylcarbamoyl)-3,4-dihydroisoquinolin-2(1H)-yl]-3-(1-benzyl-3,5-dimethyl-1H-pyrazol-4-yl)pyridine-2-carboxylic acid

Example 12A 1-benzyl-3,5-dimethyl-4-(4,4,5,5-tetramethyl-1,3,2-dioxaborolan-2-yl)-1H-pyrazole The title compound was prepared by substituting 3,5-dimethyl-4-(4,4,5,5-tetramethyl-1,3,2-dioxaborolan-2-yl)-1H-pyrazole for 4-(4,4,5,5-tetramethyl-1,3,2-dioxaborolan-2-yl)-1H-pyrazole and benzyl bromide for EXAMPLE 4A in EXAMPLE 4B.

Example 12B tert-butyl 6-(8-(benzo[d]thiazol-2-ylcarbamoyl)-3,4-dihydroisoquinolin-2(1H)-yl)-3-(1-benzyl-3,5-dimethyl-1H-pyrazol-4-yl)picolinate The title compound was prepared by substituting EXAMPLE 12A for 1-benzyl-4-(4,4,5,5-tetramethyl-1,3,2-dioxaborolan-2-yl)-1H-pyrazole in EXAMPLE 1E.

Example 12C

6-[8-(1,3-benzothiazol-2-ylcarbamoyl)-3,4-dihydroisoquinolin-2(1H)-yl]-3-(1-benzyl-3,5-dimethyl-1H-pyrazol-4-yl)pyridine-2-carboxylic acid The title compound was prepared by substituting EXAMPLE 12B for EXAMPLE 1E in EXAMPLE 1F. $^1$H NMR (500 MHz, dimethylsulfoxide-$d_6$) δ ppm 12.86 (s, 1H), 8.04 (d, 1H), 7.79 (d, 1H), 7.62 (d, 1H), 7.44-7.49 (m, 3H), 7.31-7.39 (m, 4H), 7.27 (d, 1H), 7.10 (d, 2H), 6.96 (d, 1H), 5.23 (s, 1H), 4.97 (s, 2H), 3.90 (t, 2H), 3.02 (t, 2H), 1.97 (s, 3H), 1.95 (s, 3H).

Example 13

6-[8-(1,3-benzothiazol-2-ylcarbamoyl)-3,4-dihydroisoquinolin-2(1H)-yl]-3-[1-(3-methylbenzyl)-1H-pyrazol-4-yl]pyridine-2-carboxylic acid

Example 13A 1-(3-methylbenzyl)-4-(4,4,5,5-tetramethyl-1,3,2-dioxaborolan-2-yl)-1H-pyrazole The title compound was prepared by substituting 3-methylbenzyl bromide for EXAMPLE 4A in EXAMPLE 4B.

Example 13B tert-butyl 6-(8-(benzo[d]thiazol-2-ylcarbamoyl)-3,4-dihydroisoquinolin-2(1H)-yl)-3-(1-(3-methylbenzyl)-1H-pyrazol-4-yl)picolinate The title compound was prepared by substituting EXAMPLE 13A for 1-benzyl-4-(4,4,5,5-tetramethyl-1,3,2-dioxaborolan-2-yl)-1H-pyrazole in EXAMPLE 1E.

Example 13C

6-[8-(1,3-benzothiazol-2-ylcarbamoyl)-3,4-dihydroisoquinolin-2(1H)-yl]-3-[1-(3-methylbenzyl)-1H-pyrazol-4-yl]pyridine-2-carboxylic acid The title compound was prepared by substituting EXAMPLE 13B for EXAMPLE 1E in EXAMPLE 1F. $^1$H NMR (500 MHz, dimethylsulfoxide-$d_6$) δ ppm 12.86 (s, 1H), 8.04 (d, 1H), 7.90 (s, 1H), 7.79 (d, 1H), 7.71 (d, 1H), 760-7.83 (m, 3H), 7.56 (s, 1H), 7.34-7.50 (m, 5H), 7.22 (t, 1H), 7.02-7.10 (m, 3H), 6.94 (d, 1H), 5.27 (s, 1H), 4.94 (s, 2H), 3.86 (t, 2H), 3.00 (t, 2H), 2.27 (s, 3H).

Example 14

6-[8-(1,3-benzothiazol-2-ylcarbamoyl)-3,4-dihydroisoquinolin-2(1H)-yl]-3-[1-(3-methoxybenzyl)-1H-pyrazol-4-yl]pyridine-2-carboxylic acid

Example 14A 1-(3-methoxybenzyl)-4-(4,4,5,5-tetramethyl-1,3,2-dioxaborolan-2-yl)-1H-pyrazole The title compound was prepared by substituting 3-methoxylbenzyl bromide for EXAMPLE 4A in EXAMPLE 4B.

Example 14B tert-butyl 6-(8-(benzo[d]thiazol-2-ylcarbamoyl)-3,4-dihydroisoquinolin-2(1H)-yl)-3-(1-(3-methoxybenzyl)-1H-pyrazol-4-yl)picolinate The title compound was prepared by substituting EXAMPLE 14A for 1-benzyl-4-(4,4,5,5-tetramethyl-1,3,2-dioxaborolan-2-yl)-1H-pyrazole in EXAMPLE 1E.

Example 14C

6-[8-(1,3-benzothiazol-2-ylcarbamoyl)-3,4-dihydroisoquinolin-2(1H)-yl]-3-[1-(3-methoxybenzyl)-1H-pyrazol-4-yl]pyridine-2-carboxylic acid The title compound was prepared by substituting EXAMPLE 14B for EXAMPLE 1E in EXAMPLE 1F. $^1$H NMR (500 MHz, dimethylsulfoxide-$d_6$) δ ppm 12.85 (s, 1H), 8.04 (d, 1H), 7.91 (s, 1H), 7.79 (d, 1H), 7.71 (d, 1H), 761 (d, 1H), 7.57 (s, 1H), 7.52-7.50 (m, 2H), 7.34-7.38 (m, 2H), 7.32-7.27 (m, 1H), 6.94 (d, 1H), 6.84-6.86 (m, 1H), 6.79-6.80 (m, 2H), 5.29 (s, 2H), 4.94 (s, 2H), 3.88 (t, 2H), 3.71 (s, 3H), 3.00 (t, 2H).

Example 15

6-[8-(1,3-benzothiazol-2-ylcarbamoyl)-3,4-dihydroisoquinolin-2(1H)-yl]-3-[1-(4-chlorobenzyl)-1H-pyrazol-4-yl]pyridine-2-carboxylic acid

Example 15A 1-(4-chlorobenzyl)-4-(4,4,5,5-tetramethyl-1,3,2-dioxaborolan-2-yl)-1H-pyrazole The title compound was prepared by substituting 1-(bromomethyl)-4-chlorobenzene for EXAMPLE 4A in EXAMPLE 4B.

Example 15B

6-[8-(1,3-benzothiazol-2-ylcarbamoyl)-3,4-dihydroisoquinolin-2(1H)-yl]-3-[1-(4-chlorobenzyl)-1H-pyrazol-4-yl]pyridine-2-carboxylic acid A solution of EXAMPLE 1D (0.205 g), EXAMPLE 15A (0.165 g), cesium fluoride (0.197 g) and tetrakis(triphenylphosphine)palladium(0) (0.030 g) were stirred together in 1,2-dimethoxyethane (1 mL) and methanol (0.5 mL) and heated in a Biotage Initiator microwave reactor at 120° C. for 30 minutes. The reaction was concentrated, loaded onto silica gel and eluted using a gradient of 0.5% to 2.5% methanol/dichloromethane to give the corresponding ester which was dissolved in dichloromethane (1 mL) and treated with TFA (1 mL). After stirring overnight the reaction was concentrated, loaded onto silica gel and eluted using a gradient of 0.5% to 2.5% methanol/dichloromethane to provide the title compound. $^1$H NMR (300 MHz, dimethylsulfoxide-$d_6$) δ ppm 12.85 (s, 2H), 8.04 (dd, 1H), 7.92 (d, 1H), 7.79 (d, 1H), 7.70 (d, 1H), 7.61 (d, 1H), 7.58 (d, 1H), 7.52-7.31 (m, 6H), 7.29-7.22 (m, 2H), 6.94 (d, 1H), 5.33 (s, 2H), 4.94 (s, 2H), 3.87 (t, 2H), 3.00 (t, 2H).

Example 16

6-[8-(1,3-benzothiazol-2-ylcarbamoyl)-3,4-dihydroisoquinolin-2(1H)-yl]-3-{1-[3-(benzyloxy)benzyl]-1H-pyrazol-4-yl}pyridine-2-carboxylic acid

Example 16A 1-(benzyloxy)-3-(bromomethyl)benzene

The title compound was prepared by substituting (3-(benzyloxy)phenyl)methanol for (4-(benzyloxy)phenyl)methanol in EXAMPLE 4A.

Example 16B 1-(3-(benzyloxy)benzyl)-4-(4,4,5,5-tetramethyl-1,3,2-dioxaborolan-2-yl)-1H-pyrazole The title compound was prepared by substituting EXAMPLE 16A for EXAMPLE 4A in EXAMPLE 4B.

Example 16C tert-butyl 6-(8-(benzo[d]thiazol-2-ylcarbamoyl)-3,4-dihydroisoquinolin-2(1H)-yl)-3-(1-(3-(benzyloxy)benzyl)-1H-pyrazol-4-yl)picolinate The title compound was prepared by substituting EXAMPLE 16B for 1-benzyl-4-(4,4,5,5-tetramethyl-1,3,2-dioxaborolan-2-yl)-1H-pyrazole in EXAMPLE 1E.

Example 16D

6-[8-(1,3-benzothiazol-2-ylcarbamoyl)-3,4-dihydroisoquinolin-2(1H)-yl]-3-{1-[3-(benzyloxy)benzyl]-1H-pyrazol-4-yl}pyridine-2-carboxylic acid The title compound was prepared by substituting EXAMPLE 16C for EXAMPLE 1E in EXAMPLE 1F. $^1$H NMR (500 MHz, dimethylsulfoxide-$d_6$) δ ppm 12.86 (s, 1H), 8.04 (d, 1H), 7.91 (s, 1H), 7.79 (d, 1H), 7.71 (d, 1H), 761 (d, 1H), 7.57 (s, 1H), 7.32-7.51 (m, 9H), 7.06 (d, 2H), 6.92-6.96 (m, 2H), 6.80 (d, 1H), 6.84-6.86 (m, 1H), 6.79-6.80 (m, 2H), 5.29 (s, 2H), 5.07 (s, 2H), 4.95 (s, 2H), 3.87 (t, 2H), 3.00 (t, 2H).

Example 17

6-[8-(1,3-benzothiazol-2-ylcarbamoyl)-3,4-dihydroisoquinolin-2(1H)-yl]-3-[1-(3-hydroxybenzyl)-1H-pyrazol-4-yl]pyridine-2-carboxylic acid The title compound was prepared by substituting EXAMPLE 16D for EXAMPLE 4C in EXAMPLE 4D. $^1$H NMR (500 MHz, dimethylsulfoxide-$d_6$) δ ppm 12.85 (s, 1H), 9.41 (s, 1H), 8.04 (d, 1H), 7.89 (s, 1H), 7.71 (d, 1H), 761 (d, 1H), 7.57 (s, 1H), 7.42-7.50 (m, 2H), 7.34-7.38 (m, 2H), 7.11 (t, 1H), 6.94 (d, 1H), 6.62-6.67 (m, 3H), 5.23 (s, 2H), 4.94 (s, 2H), 3.86 (t, 2H), 3.00 (t, 2H).

Example 18

6-[8-(1,3-benzothiazol-2-ylcarbamoyl)-3,4-dihydroisoquinolin-2(1H)-yl]-3-(1-{3-[2-(dimethylamino)ethoxy]benzyl}-1H-pyrazol-4-yl)pyridine-2-carboxylic acid

Example 18A tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(3-(benzyloxy)benzyl)-1H-pyrazol-4-yl)picolinate The title compound was prepared by substituting EXAMPLE 16C for EXAMPLE 4C in EXAMPLE 6A.

Example 18B tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(3-hydroxybenzyl)-1H-pyrazol-4-yl)picolinate The title compound was prepared by substituting EXAMPLE 18A for EXAMPLE 4C in EXAMPLE 4D.

Example 18C tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(3-(2-(dimethylamino)ethoxy)benzyl)-1H-pyrazol-4-yl)picolinate The title compound was prepared by substituting EXAMPLE 18B for EXAMPLE 6B in EXAMPLE 6C.

Example 18D

6-[8-(1,3-benzothiazol-2-ylcarbamoyl)-3,4-dihydroisoquinolin-2(1H)-yl]-3-(1-{3-[2-(dimethylamino)ethoxy]benzyl}-1H-pyrazol-4-yl)pyridine-2-carboxylic acid The title compound was prepared by substituting EXAMPLE 18(C for EXAMPLE 6C in EXAMPLE 6D. $^1$H NMR (500 MHz, dimethylsulfoxide-$d_6$) δ ppm 12.86 (s, 1H), 9.55 (s, 1H), 8.04 (d, 1H), 7.92 (s, 1H), 7.80 (d, 1H), 7.71 (d, 1H), 762 (d, 1H), 7.59 (s, 1H), 7.42-7.50 (m, 2H), 7.28-7.38 (m, 3H), 6.89-6.96 (m, 3H), 6.85 (s, 3H), 5.31 (s, 2H), 4.95 (s, 2H), 4.25-4.28 (m, 2H), 3.87 (t, 2H), 3.00 (t, 2H), 2.84 (s, 6H).

Example 19

6-[8-(1,3-benzothiazol-2-ylcarbamoyl)-3,4-dihydroisoquinolin-2(1H)-yl]-3-(1-benzyl-3-methyl-1H-pyrazol-4-yl)pyridine-2-carboxylic acid

Example 19A 1-benzyl-3-methyl-4-(4,4,5,5-tetramethyl-1,3,2-dioxaborolan-2-yl)-1H-pyrazole The title compound was prepared by substituting 3-methyl-4-(4,4,5,5-tetramethyl-1,3,2-dioxaborolan-2-yl)-1H-pyrazole for 4-(4,4,5,5-tetramethyl-1,3,2-dioxaborolan-2-yl)-1H-pyrazole and benzyl bromide for EXAMPLE 4A in EXAMPLE 4B.

Example 19B

The title compound was prepared by substituting EXAMPLE 19A for 1-benzyl-4-(4,4,5,5-tetramethyl-1,3,2-dioxaborolan-2-yl)-1H-pyrazole in EXAMPLE 1E.

Example 19C

6-[8-(1,3-benzothiazol-2-ylcarbamoyl)-3,4-dihydroisoquinolin-2(1H)-yl]-3-(1-benzyl-3-methyl-1H-pyrazol-4-yl)pyridine-2-carboxylic acid The title compound was prepared by substituting EXAMPLE 19B for EXAMPLE 1E in EXAMPLE 1F. $^1$H NMR (500 MHz, dimethylsulfoxide-$d_6$) δ ppm 12.85 (s, 1H), 8.04 (d, 1H), 7.79 (d, 1H), 7.66 (s, 1H), 762 (d, 1H), 7.54 (d, 1H), 7.43-7.50 (m, 2H), 7.21-7.38 (m, 7H), 6.94 (d, 1H), 5.32 (s, 2H), 4.95 (s, 2H), 3.89 (t, 2H), 3.01 (t, 2H), 2.03 (s, 3H).

Example 20

6-[8-(1,3-benzothiazol-2-ylcarbamoyl)-3,4-dihydroisoquinolin-2(1H)-yl]-3-(1-benzyl-5-methyl-1H-pyrazol-4-yl)pyridine-2-carboxylic acid

Example 20A 1-benzyl-5-methyl-4-(4,4,5,5-tetramethyl-1,3,2-dioxaborolan-2-yl)-1H-pyrazole The title compound was prepared as a minor regioisomer using the procedure described in EXAMPLE 19A.

Example 20B tert-butyl 6-(8-(benzo[d]thiazol-2-ylcarbamoyl)-3,4-dihydroisoquinolin-2(1H)-yl)-3-(1-benzyl-5-methyl-1H-pyrazol-4-yl)picolinate The title compound was prepared by substituting EXAMPLE 20A for 1-benzyl-4-(4,4,5,5-tetramethyl-1,3,2-dioxaborolan-2-yl)-1H-pyrazole in EXAMPLE 1E.

Example 20C

6-[8-(1,3-benzothiazol-2-ylcarbamoyl)-3,4-dihydroisoquinolin-2(1H)-yl]-3-(1-benzyl-5-methyl-1H-pyrazol-4-yl)pyridine-2-carboxylic acid The title compound was prepared by substituting EXAMPLE 20B for EXAMPLE 1E in EXAMPLE 1F. $^1$H NMR (500 MHz, dimethylsulfoxide-$d_6$) δ ppm 12.86 (s, 1H), 8.04 (d, 1H), 7.79 (d, 1H), 7.62 (d, 1H), 7.52 (d, 1H), 7.43-7.49 (m, 2H), 7.31-7.38 (m, 5H), 7.25-7.28 (m, 1H), 7.11 (d, 2H), 6.95 (d, 1H), 5.32 (s, 2H), 4.96 (s, 2H), 3.88 (t, 2H), 3.01 (t, 2H), 2.08 (s, 3H).

Example 21

3-(1-benzyl-1H-pyrazol-4-yl)-6-{8-[(7-chloro-1,3-benzothiazol-2-yl)carbamoyl]-3,4-dihydroisoquinolin-2(1H)-yl}pyridine-2-carboxylic acid

Example 21A tert-butyl 3-(1-benzyl-1H-pyrazol-4-yl)-6-(8-(7-chlorobenzo[d]thiazol-2-ylcarbamoyl)-3,4-dihydroisoquinolin-2(1H)-yl)picolinate The title compound was prepared according to the procedure in EXAMPLE 7D by substituting 5,6-difluorobenzo[d]thiazol-2-amine with 4-chlorobenzo[d]thiazol-2-amine.

Example 21B 3-(1-benzyl-1H-pyrazol-4-yl)-6-{8-[(7-chloro-1,3-benzothiazol-2-yl)carbamoyl]-3,4-dihydroisoquinolin-2(1H)-yl}pyridine-2-carboxylic acid The title compound was prepared according to the procedure in EXAMPLE 7E by substituting EXAMPLE 7D with EXAMPLE 21A. $^1$H NMR (300 MHz, dimethylsulfoxide-$d_6$) δ ppm 13.07 (s, 1H), 7.91 (s, 1H), 7.79 (d, 1H), 7.71 (d, 2H), 7.63 (d, 1H), 7.57 (s, 1H), 7.37 (m, 8H), 6.96 (d, 2H), 5.32 (s, 2H), 4.94 (s, 2H), 3.87 (t, 2H), 3.00 (t, 2H).

Example 22

6-[8-(1,3-benzothiazol-2-ylcarbamoyl)-3,4-dihydroisoquinolin-2(1H)-yl]-3-(1-{[6-(pyrrolidin-1-yl)pyridin-2-yl]methyl}-1H-pyrazol-4-yl)pyridine-2-carboxylic acid

Example 22A 2-(pyrrolidin-1-yl)-6-((4-(4,4,5,5-tetramethyl-1,3,2-dioxaborolan-2-yl)-1H-pyrazol-1-yl)methyl)pyridine The title compound was prepared by substituting 2-(bromomethyl)-6-(pyrrolidin-1-yl)pyridine for EXAMPLE 4A in EXAMPLE 4B.

Example 22B tert-butyl 6-(8-(benzo[d]thiazol-2-ylcarbamoyl)-3,4-dihydroisoquinolin-2(1H)-yl)-3-(1-((6-(pyrrolidin-1-yl)pyridin-2-yl)methyl)-1H-pyrazol-4-yl)picolinate EXAMPLE 1D (0.100 g), EXAMPLE 22A (0.094 g), tetrakis(triphenylphosphine)palladium(0) (10.22 mg) and cesium carbonate (0.173 g) were stirred together in N,N-dimethylformamide (0.6 mL), dioxane (0.4 mL), and water (0.2 mL) and the reaction degassed with nitrogen and heated at 100° C. for 1 hour. The reaction was diluted with ethyl acetate (25 mL) and washed with water (25 mL) and brine (25 mL), dried over magnesium sulfate, filtered, and concentrated. Silica gel chromatography eluting with methanol/dichloromethane provided the title compound.

Example 22C

6-[8-(1,3-benzothiazol-2-ylcarbamoyl)-3,4-dihydroisoquinolin-2(1H)-yl]-3-(1-{[6-(pyrrolidin-1-yl)pyridin-2-yl]methyl}-1H-pyrazol-4-yl)pyridine-2-carboxylic acid The title compound was prepared by substituting EXAMPLE 22B for EXAMPLE 8B in EXAMPLE 8C. $^1$H NMR (300 MHz, dimethylsulfoxide-$d_6$) δ ppm 12.86 (s, 1H), 8.04 (d, 1H), 7.96 (d, 1H), 7.79 (d, 1H), 7.72 (d, 1H), 7.65-7.32 (m, 7H), 6.95 (1H), 6.52 (d, 1H), 6.21 (d, 1H), 5.30 (s, 2H), 4.95 (s, 2H), 3.87 (t, 2H), 3.40 (tt, 4H), 3.00 (t, 2H), 1.94 (t, 4H).

Example 23

6-[8-(1,3-benzothiazol-2-ylcarbamoyl)-3,4-dihydroisoquinolin-2(1H)-yl]-3-(1-phenyl-1H-pyrazol-4-yl)pyridine-2-carboxylic acid

Example 23A tert-butyl 6-(8-(benzo[d]thiazol-2-ylcarbamoyl)-3,4-dihydroisoquinolin-2(1H)-yl)-3-(1-phenyl-1H-pyrazol-4-yl)picolinate The title compound was prepared by substituting 1-phenyl-4-(4,4,5,5-tetramethyl-1,3,2-dioxaborolan-2-yl)-1H-pyrazole for 1-benzyl-4-(4,4,5,5-tetramethyl-1,3,2-dioxaborolan-2-yl)-1H-pyrazole in EXAMPLE 1E.

Example 23B

6-[8-(1,3-benzothiazol-2-ylcarbamoyl)-3,4-dihydroisoquinolin-2(1H)-yl]-3-(1-phenyl-1H-pyrazol-4-yl)pyridine-2-carboxylic acid The title compound was prepared by substituting EXAMPLE 23B for EXAMPLE 1E in EXAMPLE 1F. $^1$H NMR (500 MHz, dimethylsulfoxide-$d_6$) δ ppm 12.87 (s, 1H), 8.57 (s, 1H), 8.05 (d, 1H), 7.79-7.83 (m, 5H), 7.62 (d, 1H), 7.43-7.53 (m, 5H), 7.30-7.39 (m, 3H), 7.01 (d, 1H), 4.98 (s, 2H), 3.90 (t, 2H), 3.02 (t, 2H).

Example 24

6-[8-(1,3-benzothiazol-2-ylcarbamoyl)-3,4-dihydroisoquinolin-2(1H)-yl]-3-[1-(3-cyanobenzyl)-1H-pyrazol-4-yl]pyridine-2-carboxylic acid

Example 24A 3-((4-(4,4,5,5-tetramethyl-1,3,2-dioxaborolan-2-yl)-1H-pyrazol-1-yl)methyl)benzonitrile The title compound was prepared by substituting 3-(bromomethyl)benzonitrile for EXAMPLE 4A in EXAMPLE 4B.

Example 24B tert-butyl 6-(8-(benzo[d]thiazol-2-ylcarbamoyl)-3,4-dihydroisoquinolin-2(1H)-yl)-3-(1-(3-cyanobenzyl)-1H-pyrazol-4-yl)picolinate The title compound was prepared by substituting EXAMPLE 24A for EXAMPLE 22A in EXAMPLE 22B.

Example 24C

6-[8-(1,3-benzothiazol-2-ylcarbamoyl)-3,4-dihydroisoquinolin-2(1H)-yl]-3-[1-(3-cyanobenzyl)-1H-pyrazol-4-yl]pyridine-2-carboxylic acid The title compound was prepared by substituting EXAMPLE 24B for EXAMPLE 8B in EXAMPLE 8C. $^1$H NMR (300 MHz, dimethylsulfoxide-$d_6$) δ ppm 12.98 (d, 2H), 8.07-8.01 (m, 1H), 7.97 (s, 1H), 7.82-7.68 (m, 4H), 7.65-7.53 (m, 4H), 7.51-7.31 (m, 4H), 6.95 (d, 1H), 5.41 (s, 2H), 4.95 (s, 2H), 3.87 (t, 2H), 3.00 (t, 2H).

Example 25

6-[8-(1,3-benzothiazol-2-ylcarbamoyl)-3,4-dihydroisoquinolin-2(1H)-yl]-3-[1-(2-chlorobenzyl)-1H-pyrazol-4-yl]pyridine-2-carboxylic acid

Example 25A 1-(2-chlorobenzyl)-4-(4,4,5,5-tetramethyl-1,3,2-dioxaborolan-2-yl)-1H-pyrazole The title compound was prepared by substituting 1-(bromomethyl)-2-chlorobenzene for EXAMPLE 4A in EXAMPLE 4B.

Example 25B tert-butyl 6-(8-(benzo[d]thiazol-2-ylcarbamoyl)-3,4-dihydroisoquinolin-2(1H)-yl)-3-(1-(2-chlorobenzyl)-1H-pyrazol-4-yl)picolinate The title compound was prepared by substituting EXAMPLE 25A for EXAMPLE 22A in EXAMPLE 22B.

Example 25C

6-[8-(1,3-benzothiazol-2-ylcarbamoyl)-3,4-dihydroisoquinolin-2(1H)-yl]-3-[1-(2-chlorobenzyl)-1H-pyrazol-4-yl]pyridine-2-carboxylic acid The title compound was prepared by substituting EXAMPLE 25B for EXAMPLE 8B in EXAMPLE 8C. $^1$H NMR (300 MHz, dimethylsulfoxide-$d_6$) δ ppm 12.85 (s, 2H), 8.04 (d, 1H), 7.93 (s, 1H), 7.79 (d, 1H), 7.72 (d, 1H), 7.61 (d, 2H), 7.52-7.27 (m, 7H), 7.01 (dd, 1H), 6.95 (d, 1H), 5.43 (s, 2H), 4.95 (s, 2H), 3.87 (t, 2H), 3.00 (t, 2H).

Example 26

6-[8-(1,3-benzothiazol-2-ylcarbamoyl)-3,4-dihydroisoquinolin-2(1H)-yl]-3-[1-(pyridin-2-ylmethyl)-1H-pyrazol-4-yl]pyridine-2-carboxylic acid

Example 26A tert-butyl 6-(8-(benzo[d]thiazol-2-ylcarbamoyl)-3,4-dihydroisoquinolin-2(1H)-yl)-3-(1-(pyridin-2-ylmethyl)-1H-pyrazol-4-yl)picolinate The title compound was prepared by substituting 2-((4-(4,4,5,5-tetramethyl-1,3,2-dioxaborolan-2-yl)-1H-pyrazol-1-yl)methyl)pyridine for 1-benzyl-4-(4,4,5,5-tetramethyl-1,3,2-dioxaborolan-2-yl)-1H-pyrazole in EXAMPLE 1E.

Example 26B

6-[8-(1,3-benzothiazol-2-ylcarbamoyl)-3,4-dihydroisoquinolin-2(1H)-yl]-3-[1-(pyridin-2-ylmethyl)-1H-pyrazol-4-yl]pyridine-2-carboxylic acid The title compound was prepared by substituting EXAMPLE 26A for EXAMPLE 1E in EXAMPLE 1F. $^1$H NMR (500 MHz, dimethylsulfoxide-$d_6$) δ ppm 12.87 (s, 1H), 8.57 (d, 1H), 8.04 (d, 1H), 7.97 (s, 1H), 7.82-7.86 (m, 1H), 7.79 (d, 1H), 7.73 (d, 1H), 7.61-7.62 (m, 2H), 7.42-7.50 (m, 2H), 7.34-7.39 (m, 3H), 7.11 (d, 1H), 6.95 (d, 1H), 5.45 (s, 2H), 4.95 (s, 2H), 3.87 (t, 2H), 3.00 (t, 2H).

Example 27

6-[8-(1,3-benzothiazol-2-ylcarbamoyl)-3,4-dihydroisoquinolin-2(1H)-yl]-3-(1-benzyl-3-cyano-1H-pyrazol-4-yl)pyridine-2-carboxylic acid

Example 27A 1-benzyl-4-(4,4,5,5-tetramethyl-1,3,2-dioxaborolan-2-yl)-1H-pyrazole-3-carbonitrile The title compound was prepared by substituting benzyl bromide for EXAMPLE 4A and 4-(4,4,5,5-tetramethyl-1,3,2-dioxaborolan-2-yl)-1H-pyrazole-3-carbonitrile for 4-(4,4,5,5-tetramethyl-1,3,2-dioxaborolan-2-yl)-1H-pyrazole in EXAMPLE 4B.

Example 27B tert-butyl 6-(8-(benzo[d]thiazol-2-ylcarbamoyl)-3,4-dihydroisoquinolin-2(1H)-yl)-3-(1-benzyl-3-cyano-1H-pyrazol-4-yl)picolinate The title compound was prepared by substituting EXAMPLE 27A for 1-benzyl-4-(4,4,5,5-tetramethyl-1,3,2-dioxaborolan-2-yl)-1H-pyrazole in EXAMPLE 1E.

Example 27C

6-[8-(1,3-benzothiazol-2-ylcarbamoyl)-3,4-dihydroisoquinolin-2(1H)-yl]-3-(1-benzyl-3-cyano-1H-pyrazol-4-yl)pyridine-2-carboxylic acid The title compound was prepared by substituting EXAMPLE 27B for EXAMPLE 1E in EXAMPLE 1F. $^1$H NMR (500 MHz, dimethylsulfoxide-$d_6$) δ ppm 12.86 (s, 1H), 8.15 (s, 1H), 8.04 (d, 1H), 7.80 (d, 1H), 7.66 (d, 1H), 7.62 (d, 1H), 7.43-7.49 (m, 2H), 7.29-7.39 (m, 7H), 7.05 (d, 1H), 5.45 (s, 2H), 5.01 (s, 2H), 3.92 (t, 2H), 3.02 (t, 2H).

Example 28

6-[8-(1,3-benzothiazol-2-ylcarbamoyl)-3,4-dihydroisoquinolin-2(1H)-yl]-3-[1-(naphthalen-2-ylmethyl)-1H-pyrazol-4-yl]pyridine-2-carboxylic acid

Example 28A 1-(naphthalen-2-ylmethyl)-4-(4,4,5,5-tetramethyl-1,3,2-dioxaborolan-2-yl)-1H-pyrazole The title compound was prepared by substituting 2-(bromomethyl)naphthalene for EXAMPLE 4A in EXAMPLE 4B.

Example 28B tert-butyl 6-[8-(1,3-benzothiazol-2-ylcarbamoyl)-3,4-dihydroisoquinolin-2(1H)-yl]-3-[1-(naphthalen-2-ylmethyl)-1H-pyrazol-4-yl]pyridine-2-carboxylate The title compound was prepared by substituting EXAMPLE 28A for EXAMPLE 22A in EXAMPLE 22B.

Example 28C

6-[8-(1,3-benzothiazol-2-ylcarbamoyl)-3,4-dihydroisoquinolin-2(1H)-yl]-3-[1-(naphthalen-2-ylmethyl)-1H-pyrazol-4-yl]pyridine-2-carboxylic acid The title compound was prepared by substituting EXAMPLE 28B for EXAMPLE E in EXAMPLE 1F. $^1$H NMR (400 MHz, dimethylsulfoxide-$d_6$) δ ppm 12.83 (br s, 1H), 8.04 (d, 1H), 7.98 (s, 1H), 7.88 (m, 3H), 7.78 (m, 2H), 7.72 (d, 1H), 7.60 (m, 2H), 7.50 (m, 3H), 7.36 (m, 4H), 6.94 (d, 1H), 5.50 (s, 2H), 4.95 (s, 2H), 3.87 (t, 2H), 3.00 (t, 2H).

Example 29

6-[8-(1,3-benzothiazol-2-ylcarbamoyl)-3,4-dihydroisoquinolin-2(1H)-yl]-3-{1-[3-(3-methyl-1,2,4-oxadiazol-5-yl)benzyl]-1H-pyrazol-4-yl}pyridine-2-carboxylic acid

Example 29A 3-methyl-5-(3-((4-(4,4,5,5-tetramethyl-1,3,2-dioxaborolan-2-yl)-1H-pyrazol-1-yl)methyl)phenyl)-1,2,4-oxadiazole The title compound was prepared by substituting 5-(3-(bromomethyl)phenyl)-3-methyl-1,2,4-oxadiazole for EXAMPLE 4A in EXAMPLE 4B.

Example 29B tert-butyl 6-(8-(benzo[d]thiazol-2-ylcarbamoyl)-3,4-dihydroisoquinolin-2(1H)-yl)-3-(1-(3-(3-methyl-1,2,4-oxadiazol-5-yl)benzyl)-1H-pyrazol-4-yl)picolinate The title compound was prepared by substituting EXAMPLE 29A for EXAMPLE 22A in EXAMPLE 22B.

Example 29C

6-[8-(1,3-benzothiazol-2-ylcarbamoyl)-3,4-dihydroisoquinolin-2(1H)-yl]-3-{1-[3-(3-methyl-1,2,4-oxadiazol-5-yl)benzyl]-1H-pyrazol-4-yl}pyridine-2-carboxylic acid The title compound was prepared by substituting EXAMPLE 29B for EXAMPLE 8B in EXAMPLE 8C. $^1$H NMR (300 MHz, dimethylsulfoxide-$d_6$) δ ppm 12.85 (m, 2H), 8.08-7.97 (m, 4H), 7.79 (d, 1H), 7.72 (d, 1H), 7.65-7.52 (m, 4H), 7.51-7.31 (m, 4H), 6.95 (d, 1H), 5.47 (s, 2H), 4.95 (s, 2H), 3.87 (t, 2H), 3.00 (t, 2H), 2.40 (s, 3H).

Example 30

6-[8-(1,3-benzothiazol-2-ylcarbamoyl)-3,4-dihydroisoquinolin-2(1H)-yl]-3-[1-benzyl-3-(hydroxymethyl)-5-methyl-1H-pyrazol-4-yl]pyridine-2-carboxylic acid

Example 30A tert-butyl 6-(8-(benzo[d]thiazol-2-ylcarbamoyl)-3,4-dihydroisoquinolin-2(1H)-yl)-3-(4,4,5,5-tetramethyl-1,3,2-dioxaborolan-2-yl)picolinate A mixture of EXAMPLE 1D (1.2 g), 1.0 M 4,4,5,5-tetramethyl-1,3,2-dioxaborolane in tetrahydrofuran (4.24 mL), triethylamine (0.92 mL), and [1,1'-bis(diphenylphosphino)ferrocene]dichloropalladium(II) dichloromethane (0.087 g) in $CH_3CN$ (15 mL) was heated at 100° C. in a Biotage Initiator microwave reactor for 30 minutes. After cooling, the reaction mixture was partitioned between water and ethyl acetate. The organic layer was extracted with additional ethyl acetate twice. The combined organic layers were washed with brine, dried over $MgSO_4$, filtered, and concentrated. The residue was purified by flash column chromatography on silica gel to provide the title compound.

Example 30B ethyl 1-benzyl-4-bromo-5-methyl-1H-pyrazole-3-carboxylate

The title compound was prepared by substituting (1-bromomethyl)benzene for EXAMPLE 4A and methyl 4-bromo-5-methyl-1H-pyrazole-3-carboxylate for 4-(4,4,5,5-tetramethyl-1,3,2-dioxaborolan-2-yl)-1H-pyrazole in EXAMPLE 4B.

Example 30C

(1-benzyl-4-bromo-5-methyl-1H-pyrazol-3-yl)methanol

EXAMPLE 30B (0.281 g) in tetrahydrofuran (10 mL) was treated with 1.0 M $LiAlH_4$ in tetrahydrofuran (1.0 mL) at 0° C. After the reaction was complete, the reaction mixture was quenched by 1.0 N aqueous HCl. It was then partitioned between water and ethyl acetate. The organic layer was extracted with additional ethyl acetate twice. The combined organic layers were washed with brine, dried over $MgSO_4$, filtered, and concentrated. The residue was purified by flash column chromatography on silica gel to provide the title compound.

Example 30D tert-butyl 6-(8-(benzo[d]thiazol-2-ylcarbamoyl)-3,4-dihydroisoquinolin-2(1H)-yl)-3-(1-benzyl-3-(hydroxymethyl)-5-methyl-1H-pyrazol-4-yl)picolinate The title compound was prepared by substituting EXAMPLE 30A for 1-benzyl-4-(4,4,5,5-tetramethyl-1,3,2-dioxaborolan-2-yl)-1H-pyrazole and EXAMPLE 30C for EXAMPLE 1D in EXAMPLE 1E.

Example 30E

6-[8-(1,3-benzothiazol-2-ylcarbamoyl)-3,4-dihydroisoquinolin-2(1H)-yl]-3-[1-benzyl-3-(hydroxymethyl)-5-methyl-1H-pyrazol-4-yl]pyridine-2-carboxylic acid The title compound was prepared by substituting EXAMPLE 30D for EXAMPLE 1E in EXAMPLE 1F. $^1$H NMR (500 MHz, dimethylsulfoxide-$d_6$) δ ppm 12.87 (s, 1H), 8.03 (d, 1H), 7.79 (d, 1H), 7.62 (d, 1H), 7.56 (d, 1H), 7.43-7.49 (m, 2H), 7.31-7.39 (m, 7H), 7.24-7.28 (m, 1H), 7.11 (d, 2H), 6.98 (d, 1H), 5.28 (s, 2H), 4.97 (s, 2H), 4.20 (s, 2H), 3.91 (t, 2H), 3.02 (t, 2H), 1.97 (s, 3H).

Example 31

6-[8-(1,3-benzothiazol-2-ylcarbamoyl)-3,4-dihydroisoquinolin-2(1H)-yl]-3-{1-[2-(benzyloxy)benzyl]-1H-pyrazol-4-yl}pyridine-2-carboxylic acid

Example 31A

1-(benzyloxy)-2-(bromomethyl)benzene

The title compound was prepared by substituting (2-(benzyloxy)phenyl)methanol for (4-(benzyloxy)phenyl)methanol in EXAMPLE 4A.

Example 31B

1-(2-(benzyloxy)benzyl)-4-(4,4,5,5-tetramethyl-1,3,2-dioxaborolan-2-yl)-1H-pyrazole The title compound was prepared by substituting EXAMPLE 31A for EXAMPLE 4A in EXAMPLE 4B.

Example 31C tert-butyl 6-(8-(benzo[d]thiazol-2-ylcarbamoyl)-3,4-dihydroisoquinolin-2(1H)-yl)-3-(1-(2-(benzyloxy)benzyl)-1H-pyrazol-4-yl)picolinate The title compound was prepared by substituting EXAMPLE 31B for 1-benzyl-4-(4,4,5,5-tetramethyl-1,3,2-dioxaborolan-2-yl)-1H-pyrazole in EXAMPLE 1E.

Example 31D

6-[8-(1,3-benzothiazol-2-ylcarbamoyl)-3,4-dihydroisoquinolin-2(1H)-yl]-3-{1-[2-(benzyloxy)benzyl]-1H-pyrazol-4-yl}pyridine-2-carboxylic acid The title compound was prepared by substituting EXAMPLE 31C for EXAMPLE 1E in EXAMPLE 1F. $^1$H NMR (500 MHz, dimethylsulfoxide-$d_6$) δ ppm 12.85 (s, 1H), 8.04 (d, 1H), 7.79-7.80 (m, 2H), 7.61-7.63 (m, 2H), 7.56 (s, 1H), 7.40-7.50 (m, 4H), 7.25-7.38 (m, 6H), 7.09 (d, 2H), 6.98-7.00 (m, 1H), 6.89-9.94 (m, 2H), 5.32 (s, 2H), 5.17 (s, 2H), 4.95 (s, 2H), 3.87 (t, 2H), 2.98 (t, 2H).

Example 32

6-[8-(1,3-benzothiazol-2-ylcarbamoyl)-3,4-dihydroisoquinolin-2(1H)-yl]-3-(5-methyl-1-{[6-(pyrrolidin-1-yl)pyridin-2-yl]methyl}-1H-pyrazol-4-yl)pyridine-2-carboxylic acid and 6-(8-(1,3-benzothiazol-2-ylcarbamoyl)-3,4-dihydroisoquinolin-2(1H)-yl)-3-(3-methyl-1-((6-(pyrrolidin-1-yl)pyridin-2-yl)methyl)-1H-pyrazol-4-yl)pyridine-2-carboxylic acid Example 32A 2-((5-methyl-4-(4,4,5,5-tetramethyl-1,3,2-dioxaborolan-2-yl)-1H-pyrazol-1-yl)methyl)-6-(pyrrolidin-1-yl)pyridine and 2-((3-methyl-4-(4,4,5,5-tetramethyl-1,3,2-dioxaborolan-2-yl)-1H-pyrazol-1-yl)methyl)-6-(pyrrolidin-1-yl)pyridine The title compounds were prepared by substituting 2-(bromomethyl)-6-(pyrrolidin-1-yl)pyridine for EXAMPLE 4A and 3-methyl-4-(4,4,5,5-tetramethyl-1,3,2-dioxaborolan-2-yl)-1H-pyrazole for 4-(4,4,5,5-tetramethyl-1,3,2-dioxaborolan-2-yl)-1H-pyrazole in EXAMPLE 4B. The title compounds were isolated as a 2:1 mixture of the regioisomeric pyrazole isomers, and were used in the next step without further purification.

Example 32B tert-butyl 6-(8-(1,3-benzothiazol-2-ylcarbamoyl)-3,4-dihydroisoquinolin-2(1H)-yl)-3-(5-methyl-1-((6-(pyrrolidin-1-yl)pyridin-2-yl)methyl)-1H-pyrazol-4-yl)pyridine-2-carboxylate and tert-butyl 6-(8-(1,3-benzothiazol-2-ylcarbamoyl)-3,4-dihydroisoquinolin-2(1H)-yl)-3-(3-methyl-1-((6-(pyrrolidin-1-yl)pyridin-2-yl)methyl)-1H-pyrazol-4-yl)pyridine-2-carboxylate The titles compound were prepared by substituting EXAMPLE 32A for EXAMPLE 22A in EXAMPLE 22B. The title compounds were isolated as a 2:1 mixture of the regioisomeric pyrazole isomers.

Example 32C

6-[8-(1,3-benzothiazol-2-ylcarbamoyl)-3,4-dihydroisoquinolin-2(1H)-yl]-3-(5-methyl-1-{[6-(pyrrolidin-1-yl)pyridin-2-yl]methyl}-1H-pyrazol-4-yl)pyridine-2-carboxylic acid and 6-(8-(1,3-benzothiazol-2-ylcarbamoyl)-3,4-dihydroisoquinolin-2(1H)-yl)-3-(3-methyl-1-((6-(pyrrolidin-1-yl)pyridin-2-yl)methyl)-1H-pyrazol-4-yl)pyridine-2-carboxylic acid The title compounds were prepared by substituting EXAMPLE 32B for EXAMPLE 8B in EXAMPLE 8C. The title compounds were isolated as a 2:1 mixture of the regioisomeric pyrazole isomers. $^1$H NMR (300 MHz, dimethylsulfoxide-$d_6$) δ ppm 12.86 (s, 2H), 8.04 (d, 1H), 7.79 (d, 1H), 7.62 (d, 1H), 7.57-7.29 (m, 7H), 6.97 (d, 1H), 6.42 (m, 1H), 6.02 (d, 1H), 4.96 (s, 2H), 3.89 (m, 2H), 3.39 (d, 4H), 3.17 (s, 2H), 2.99 (m, 2H), 2.17 (s, 3H), 1.93 (m, 4H).
Isomeric Pyrazole: $^1$H NMR (300 MHz, DMSO) δ 12.86 (s, 2H), 8.04 (d, 1H), 7.79 (d, 1H), 7.69 (s, 1H), 7.62 (d, 1H), 7.57-7.29 (m, 6H), 6.97 (d, 1H), 6.42 (m, 1H), 6.02 (d, 1H), 4.96 (s, 2H), 3.89 (m, 2H), 3.39 (d, 4H), 3.17 (s, 2H), 2.99 (m, 2H), 2.04 (s, 3H), 1.93 (m, 4H).

Example 33

6-[8-(1,3-benzothiazol-2-ylcarbamoyl)-3,4-dihydroisoquinolin-2(1H)-yl]-3-[1-benzyl-3-(ethoxycarbonyl)-5-methyl-1H-pyrazol-4-yl]pyridine-2-carboxylic acid Example 33A tert-butyl 6-(8-(benzo[d]thiazol-2-ylcarbamoyl)-3,4-dihydroisoquinolin-2(1H)-yl)-3-(1-benzyl-3-(ethoxycarbonyl)-5-methyl-1H-pyrazol-4-yl)picolinate The title compound was prepared by substituting EXAMPLE 30A for 4-(4,4,5,5-tetramethyl-1,3,2-dioxaborolan-2-yl)-1H-pyrazole and EXAMPLE 30B for EXAMPLE 1D in EXAMPLE 1E.

Example 33B

6-[8-(1,3-benzothiazol-2-ylcarbamoyl)-3,4-dihydroisoquinolin-2(1H)-yl]-3-[1-benzyl-3-(ethoxycarbonyl)-5-methyl-1H-pyrazol-4-yl]pyridine-2-carboxylic acid The title compound was prepared by substituting EXAMPLE 33A for EXAMPLE 1E in EXAMPLE 1F. $^1$H NMR (500 MHz, dimethylsulfoxide-$d_6$) δ ppm 12.87 (s, 1H), 8.35 (d, 1H), 7.79 (d, 1H), 7.62 (d, 1H), 7.43-7.49 (m, 3H), 7.34-7.38 (m, 4H), 7.30 (d, 1H), 7.12 (d, 2H), 6.99 (d, 1H), 5.44 (s, 2H), 4.99 (s, 2H), 4.01-4.06 (m, 2H), 3.93-3.96 (m, 2H), 3.02 (t, 2H), 2.00 (s, 3H), 1.05 (t, 3H).

Example 34

6-[8-(1,3-benzothiazol-2-ylcarbamoyl)-3,4-dihydroisoquinolin-2(1H)-yl]-3-{1-[3-(dimethylamino)benzyl]-1H-pyrazol-4-yl}pyridine-2-carboxylic acid Example 34A N,N-dimethyl-3-((4-(4,4,5,5-tetramethyl-1,3,2-dioxaborolan-2-yl)-1H-pyrazol-1-yl)methyl)aniline To a solution of (3-(dimethylamino)phenyl)methanol (0.100 g), 4-(4,4,5,5-tetramethyl-1,3,2-dioxaborolan-2-yl)-1H-pyrazole (0.167 g) and cyanomethylenetributylphosphorane (0.208 g) were added and stirred together in toluene (1 mL) at room temperature. After stirring overnight the reaction was loaded directly onto silica gel and eluted using a gradient of 5% to 35% ethyl acetate/hexanes to provide the title compound.

Example 34B tert-butyl 6-(8-(benzo[d]thiazol-2-ylcarbamoyl)-3,4-dihydroisoquinolin-2(1H)-yl)-3-(1-(3-(dimethylamino)benzyl)-1H-pyrazol-4-yl)picolinate The title compound was prepared by substituting EXAMPLE 34A for EXAMPLE 22A in EXAMPLE 22B.

Example 34C

6-[8-(1,3-benzothiazol-2-ylcarbamoyl)-3,4-dihydroisoquinolin-2(1H)-yl]-3-{1-[3-(dimethylamino)benzyl]-1H-pyrazol-4-yl}pyridine-2-carboxylic acid The title compound was prepared by substituting EXAMPLE 34B for EXAMPLE 8B in EXAMPLE 8C. $^1$H NMR (300 MHz, dimethylsulfoxide-d$_6$) δ ppm 12.85 (s, 1H), 8.04 (dd, 1H), 7.88 (d, 1H), 7.79 (d, 1H), 7.70 (d, 1H), 7.61 (d, 1H), 7.56 (d, 1H), 7.53-7.44 (m, 1H), 7.44-7.31 (m, 3H), 7.20-7.10 (m, 1H), 6.94 (d, 1H), 6.67 (d, 2H), 6.53 (t, 1H), 5.24 (s, 2H), 4.94 (s, 2H), 3.87 (t, 2H), 3.00 (t, 2H), 2.87 (s, 6H).

Example 35

6-[8-(1,3-benzothiazol-2-ylcarbamoyl)-3,4-dihydroisoquinolin-2(1H)-yl]-3-(1-benzyl-3-carboxy-5-methyl-1H-pyrazol-4-yl)pyridine-2-carboxylic acid EXAMPLE 33B (0.05 g) in dioxane (2 mL) and methanol (0.5 mL) was treated with 2.0N aqueous NaOH (1 mL). The reaction mixture was heated at 90° C. for 1 hours. The solvents were removed under reduced pressure, and the residue was purified by reverse phase Prep HPLC using Gilson system. The desired fractions were combined and freeze-dried to provide the title compound. $^1$H NMR (500 MHz, dimethylsulfoxide-d$_6$) δ ppm 12.86 (s, 1H), 8.03 (d, 1H), 7.79 (d, 1H), 7.62 (d, 1H), 7.44-7.49 (m, 3H), 7.34-7.39 (m, 4H), 7.29 (d, 1H), 7.13 (d, 2H), 7.00 (d, 1H), 5.41 (s, 2H), 4.98 (s, 2H), 3.87 (t, 2H) 3.03 (t, 2H), 1.98 (s, 3H).

Example 36

6-[8-(1,3-benzothiazol-2-ylcarbamoyl)-3,4-dihydroisoquinolin-2(1H)-yl]-3-[1-(2-hydroxybenzyl)-1H-pyrazol-4-yl]pyridine-2-carboxylic acid The title compound was prepared by substituting EXAMPLE 31D for EXAMPLE 4C in EXAMPLE 4D. $^1$H NMR (500 MHz, dimethylsulfoxide-d$_6$) δ ppm 12.86 (s, 1H), 9.75 (s, 1H), 8.04 (d, 1H), 7.83 (s, 1H), 7.80 (d, 1H), 7.70 (d, 1H), 761 (d, 1H), 7.55 (s, 1H), 7.46-7.50 (m, 1H), 7.42-7.43 (m, 1H), 7.34-7.37 (m, 2H), 7.09-7.13 (m, 1H), 6.90-6.94 (m, 2H), 6.82-6.64 (m, 1H), 6.72-6.76 (m, 1H), 5.23 (s, 2H), 4.94 (s, 2H), 3.86 (t, 2H), 2.99 (t, 2H).

Example 37

6-[8-(1,3-benzothiazol-2-ylcarbamoyl)-3,4-dihydroisoquinolin-2(1H)-yl]-3-[1-(2,3-dihydro-1H-inden-1-yl)-1H-pyrazol-4-yl]pyridine-2-carboxylic acid

Example 37A 1-(2,3-dihydro-1H-inden-1-yl)-4-(4,4,5,5-tetramethyl-1,3,2-dioxaborolan-2-yl)-1H-pyrazole The title compound was prepared by substituting 2,3-dihydro-1H-inden-1-ol for (3-(dimethylamino)phenyl)methanol in EXAMPLE 34A.

Example 37B tert-butyl 6-(8-(benzo[d]thiazol-2-ylcarbamoyl)-3,4-dihydroisoquinolin-2(1H)-yl)-3-(1-(2,3-dihydro-1H-inden-1-yl)-1H-pyrazol-4-yl)picolinate The title compound was prepared by substituting EXAMPLE 37A for EXAMPLE 22A in EXAMPLE 22B.

Example 37C

6-[8-(1,3-benzothiazol-2-ylcarbamoyl)-3,4-dihydroisoquinolin-2(1H)-yl]-3-[1-(2,3-dihydro-1H-inden-1-yl)-1H-pyrazol-4-yl]pyridine-2-carboxylic acid The title compound was prepared by substituting EXAMPLE 37B for EXAMPLE 8B in EXAMPLE 8C. $^1$H NMR (300 MHz, dimethylsulfoxide-d$_6$) δ ppm 12.84 (s, 2H), 8.04 (d, 1H), 7.83 (d, 1H), 7.79 (d, 1H), 7.72 (d, 1H), 7.61 (d, 1H), 7.56 (d, 1H), 7.53-7.44 (m, 1H), 7.44-7.31 (m, 4H), 7.30-7.23 (m, 1H), 7.17 (t, 1H), 7.05 (d, 1H), 6.93 (d, 1H), 5.95-5.82 (m, 1H), 4.94 (s, 2H), 3.86 (t, 2H), 3.21-3.06 (m, 1H), 3.06-2.84 (m, 3H), 2.68-2.54 (m, 1H), 2.40 (m, 1H).

Example 38

6-[8-(1,3-benzothiazol-2-ylcarbamoyl)-3,4-dihydroisoquinolin-2(1H)-yl]-3-[1-(2-phenylethyl)-1H-pyrazol-4-yl]pyridine-2-carboxylic acid

Example 38A 1-phenethyl-4-(4,4,5,5-tetramethyl-1,3,2-dioxaborolan-2-yl)-1H-pyrazole The title compound was prepared by substituting 2-phenylethanol for (3-(dimethylamino)phenyl)methanol in EXAMPLE 34A.

Example 38B tert-butyl6-[8-(1,3-benzothiazol-2-ylcarbamoyl)-3,4-dihydroisoquinolin-2(1H)-yl]-3-[1-(2-phenylethyl)-1H-pyrazol-4-yl]pyridine-2-carboxylate The title compound was prepared by substituting EXAMPLE 38A for EXAMPLE 22A in EXAMPLE 22B.

Example 38C

6-[8-(1,3-benzothiazol-2-ylcarbamoyl)-3,4-dihydroisoquinolin-2(1H)-yl]-3-[1-(2-phenylethyl)-1H-pyrazol-4-yl]pyridine-2-carboxylic acid The title compound was prepared by substituting EXAMPLE 38B for EXAMPLE 8B in EXAMPLE 8C. $^1$H NMR (500 MHz, dimethylsulfoxide-d$_6$) δ ppm 12.87 (br s, 1H), 8.04 (d, 1H), 7.80 (d, 1H), 7.73 (s, 1H), 7.64 (d, 1H), 7.61 (d, 1H), 7.54 (s, 1H), 7.48 (m, 1H), 7.42 (d, 1H), 7.36 (t, 2H), 7.26 (m, 2H), 7.18 (m, 2H), 6.94 (d, 1H), 4.94 (s, 2H), 4.32 (t, 2H), 3.86 (t, 2H), 3.09 (t, 2H), 3.00 (t, 2H).

Example 39

6-[8-(1,3-benzothiazol-2-ylcarbamoyl)-3,4-dihydroisoquinolin-2(1H)-yl]-3-[1-(3,4-dihydro-2H-chromen-4-yl)-1H-pyrazol-4-yl]pyridine-2-carboxylic acid

Example 39A 1-(chroman-4-yl)-4-(4,4,5,5-tetramethyl-1,3,2-dioxaborolan-2-yl)-1H-pyrazole The title compound was prepared by substituting chroman-4-ol for (3-(dimethylamino)phenyl)methanol in EXAMPLE 34A.

Example 39B tert-butyl 6-(8-(benzo[d]thiazol-2-ylcarbamoyl)-3,4-dihydroisoquinolin-2(1H)-yl)-3-(1-(chroman-4-yl)-1H-pyrazol-4-yl)picolinate The title compound was prepared by substituting EXAMPLE 39A for EXAMPLE 22A in EXAMPLE 22B.

Example 39C

6-[8-(1,3-benzothiazol-2-ylcarbamoyl)-3,4-dihydroisoquinolin-2(1H)-yl]-3-[1-(3,4-dihydro-2H-chromen-4-yl)-1H-pyrazol-4-yl]pyridine-2-carboxylic acid The title compound was prepared by substituting EXAMPLE 39B for EXAMPLE 8B in EXAMPLE 8C. $^1$H NMR (300 MHz, dimethylsulfoxide-d$_6$) δ ppm 12.84 (s, 2H), 8.08-7.99 (m, 1H), 7.80 (t, 2H), 7.72 (d, 1H), 7.66-7.57 (m, 2H), 7.52-7.44 (m, 1H), 7.44-7.31 (m, 3H), 7.19 (m, 1H), 6.93 (d, 1H), 6.90-6.78 (m, 3H), 5.65 (t, 1H), 4.94 (s, 2H), 4.38-4.15 (m, 2H), 3.86 (t, 2H), 3.00 (t, 2H), 2.41-2.18 (m, 2H).

Example 40

6-[8-(1,3-benzothiazol-2-ylcarbamoyl)-3,4-dihydroisoquinolin-2(1H)-yl]-3-(1-{2-[2-(dimethylamino)ethoxy]benzyl}-1H-pyrazol-4-yl)pyridine-2-carboxylic acid

Example 40A tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(2-(benzyloxy)benzyl)-1H-pyrazol-4-yl)picolinate The title compound was prepared by substituting EXAMPLE 31C. for EXAMPLE 4C in EXAMPLE 6A.

Example 40B tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(2-hydroxybenzyl)-1H-pyrazol-4-yl)picolinate The title compound was prepared by substituting EXAMPLE 40A for EXAMPLE 4C in EXAMPLE 4D.

Example 40C tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(2-(2-(dimethylamino)ethoxy)benzyl)-1H-pyrazol-4-yl)picolinate The title compound was prepared by substituting EXAMPLE 40B for EXAMPLE 6B in EXAMPLE 6C.

Example 40D

66-[8-(1,3-benzothiazol-2-ylcarbamoyl)-3,4-dihydroisoquinolin-2(1H)-yl]-3-(1-{2-[2-(dimethylamino)ethoxy]benzyl}-1H-pyrazol-4-yl)pyridine-2-carboxylic acid The title compound was prepared by substituting EXAMPLE 40C for EXAMPLE 6C in EXAMPLE 6D. $^1$H NMR (500 MHz, dimethylsulfoxide-d$_6$) δ ppm 12.87 (s, 1H), 9.64 (s, 1H), 8.04 (d, 1H), 7.86 (s, 1H), 7.80 (d, 1H), 7.71 (d, 1H), 761-7.63 (m, 2H), 7.46-7.50 (m, 2H), 7.42-7.44 (m, 1H), 7.31-7.38 (m, 3H), 7.10 (dd, 1H), 7.07 (d, 1H), 6.94-6.99 (m, 2H), 5.37 (s, 2H), 4.35-4.36 (m, 2H), 3.86 (t, 2H), 3.57 (m, 1H), 3.00 (t, 2H), 2.90 (s, 6H).

Example 41

6-[8-(1,3-benzothiazol-2-ylcarbamoyl)-3,4-dihydroisoquinolin-2(1H)-yl]-3-[1-(2-fluorobenzyl)-5-methyl-1H-pyrazol-4-yl]pyridine-2-carboxylic acid

Example 41A 1-(2-fluorobenzyl)-5-methyl-4-(4,4,5,5-tetramethyl-1,3,2-dioxaborolan-2-yl)-1H-pyrazole The title compound was prepared by substituting 3-methyl-4-(4,4,5,5-tetramethyl-1,3,2-dioxaborolan-2-yl)-1H-pyrazole for 4-(4,4,5,5-tetramethyl-1,3,2-dioxaborolan-2-yl)-1H-pyrazole and 2-fluorobenzyl bromide for EXAMPLE 4A in EXAMPLE 4B.

Example 41B tert-butyl 6-(8-(benzo[d]thiazol-2-ylcarbamoyl)-3,4-dihydroisoquinolin-2(1H)-yl)-3-(1-(2-fluorobenzyl)-5-methyl-1H-pyrazol-4-yl)picolinate The title compound was prepared by substituting EXAMPLE 41A for 1-benzyl-4-(4,4,5,5-tetramethyl-1,3,2-dioxaborolan-2-yl)-1H-pyrazole in EXAMPLE 1E.

Example 41C

6-[8-(1,3-benzothiazol-2-ylcarbamoyl)-3,4-dihydroisoquinolin-2(1H)-yl]-3-[1-(2-fluorobenzyl)-5-methyl-1H-pyrazol-4-yl]pyridine-2-carboxylic acid The title compound was prepared by substituting EXAMPLE 41B for EXAMPLE 1E in EXAMPLE 1F. $^1$H NMR (500 MHz, dimethylsulfoxide-$d_6$) δ ppm 12.85 (s, 1H), 8.04 (d, 1H), 7.79 (d, 1H), 7.62 (d, 1H), 7.52 (d, 1H), 7.43-7.49 (m, 2H), 7.32-7.38 (m, 4H), 7.20-7.25 (m, 1H), 7.13-7.17 (m, 1H), 6.96 (d, 1H), 6.88-6.93 (m, 1H), 5.35 (s, 2H), 4.96 (s, 2H), 3.88-3.91 (m, 2H), 3.01 (t, 2H), 2.12 (s, 3H).

Example 42

6-[8-(1,3-benzothiazol-2-ylcarbamoyl)-3,4-dihydroisoquinolin-2(1H)-yl]-3-[1-(cyclohexylmethyl)-1H-pyrazol-4-yl]pyridine-2-carboxylic acid

Example 42A 1-(cyclohexylmethyl)-4-(4,4,5,5-tetramethyl-1,3,2-dioxaborolan-2-yl)-1H-pyrazole The title compound was prepared by substituting (bromomethyl)cyclohexane for EXAMPLE 4A in EXAMPLE 4B.

Example 42B tert-butyl 6-(8-(benzo[d]thiazol-2-ylcarbamoyl)-3,4-dihydroisoquinolin-2(1H)-yl)-3-(1-(cyclohexylmethyl)-1H-pyrazol-4-yl)picolinate The title compound was prepared by substituting EXAMPLE 42A for EXAMPLE 22A in EXAMPLE 22B.

Example 42C

6-[8-(1,3-benzothiazol-2-ylcarbamoyl)-3,4-dihydroisoquinolin-2(1H)-yl]-3-[1-(cyclohexylmethyl)-1H-pyrazol-4-yl]pyridine-2-carboxylic acid The title compound was prepared by substituting EXAMPLE 42B for EXAMPLE 8B in EXAMPLE 8C. $^1$H NMR (300 MHz, dimethylsulfoxide-$d_6$) δ ppm 12.85 (s, 2H), 8.04 (d, 1H), 7.79 (d, 1H), 7.74 (d, 1H), 7.68 (s, 1H), 7.61 (d, 1H), 7.52 (s, 1H), 7.51-7.44 (m, 1H), 7.42 (d, 1H), 7.36 (s, 2H), 6.94 (d, 1H), 4.94 (s, 2H), 3.91 (d, 2H), 3.86 (t, 2H), 3.00 (t, 2H), 1.76 (m, 1H), 1.70-1.56 (m, 3H), 1.51 (d, 2H), 1.26-1.02 (m, 3H), 0.92 (m, 2H).

Example 43

6-[8-(1,3-benzothiazol-2-ylcarbamoyl)-3,4-dihydroisoquinolin-2(1H)-yl]-3-[1-(cyclohexylmethyl)-5-methyl-1H-pyrazol-4-yl]pyridine-2-carboxylic acid

Example 43A 1-(cyclohexylmethyl)-5-methyl-4-(4,4,5,5-tetramethyl-1,3,2-dioxaborolan-2-yl)-1H-pyrazole The title compound was prepared by substituting 5-methyl-4-(4,4,5,5-tetramethyl-1,3,2-dioxaborolan-2-yl)-1H-pyrazole for 4-(4,4,5,5-tetramethyl-1,3,2-dioxaborolan-2-yl)-1H-pyrazole and (bromomethyl)cyclohexane for EXAMPLE 4A in EXAMPLE 4B.

Example 43B tert-butyl 6-(8-(benzo[d]thiazol-2-ylcarbamoyl)-3,4-dihydroisoquinolin-2(1H)-yl)-3-(1-(cyclohexylmethyl)-5-methyl-1H-pyrazol-4-yl)picolinate The title compound was prepared by substituting EXAMPLE 43A for EXAMPLE 22A in EXAMPLE 22B.

Example 43C

6-[8-(1,3-benzothiazol-2-ylcarbamoyl)-3,4-dihydroisoquinolin-2(1H)-yl]-3-[1-(cyclohexylmethyl)-5-methyl-1H-pyrazol-4-yl]pyridine-2-carboxylic acid The title compound was prepared by substituting EXAMPLE 43B for EXAMPLE 8B in EXAMPLE 8C. $^1$H NMR (300 MHz, dimethylsulfoxide-$d_6$) δ ppm 12.84 (s, 1H), 8.03 (d, 1H), 7.79 (d, 1H), 7.61 (d, 1H), 7.48 (s, 3H), 7.39-7.31 (m, 2H), 7.26 (s, 1H), 6.94 (d, 1H), 4.95 (s, 2H), 3.86 (s, 4H), 3.01 (t, 2H), 2.10 (s, 3H), 1.88-1.71 (m, 1H), 1.65 (s, 3H), 1.53 (d, 2H), 1.26-1.05 (m, 3H), 0.98 (t, 2H).

Example 44

6-[8-(1,3-benzothiazol-2-ylcarbamoyl)-3,4-dihydroisoquinolin-2(1H)-yl]-3-[1-(4-{[3-(dimethylamino)propyl]amino}-3-nitrobenzyl)-1H-pyrazol-4-yl]pyridine-2-carboxylic acid N,N-Dimethylpropane-1,3-diamine (50 mg) and EXAMPLE 45B (90 mg) in tetrahydrofuran (10 mL) were treated with triethylamine (0.1 mL) at 70° C. for 2 days. The reaction mixture was concentrated and the crude residue was dissolved in a mixture of dichloromethane (5 mL) and TFA (5 mL). The resulting mixture was stirred for 12 hours and concentrated. The residue was purified by reverse phase chromatography, eluting with a gradient of 40%-80% acetonitrile in 0.1% TFA water over 40 minutes to provide the title compound as a TFA salt. $^1$H NMR (400 MHz, dimethylsulfoxide-$d_6$) δ ppm 13.08 (s, 1H), 12.85 (s, 1H), 9.28 (s, 1H), 8.23 (t, 1H), 8.11 (d, 1H), 8.04 (d, 1H), 7.94 (s, 1H), 7.79 (d, 1H), 7.69 (d, 1H), 7.61 (d, 1H), 7.57 (s, 1H), 7.45-7.52 (m, 2H), 7.40-7.44 (m, 1H), 7.36 (t, 2H), 7.07 (d, 1H), 6.94 (d, 1H), 5.25 (s, 2H), 4.94 (s, 2H), 3.86 (t, 2H), 3.05-3.15 (m, 2H), 3.00 (t, 2H), 2.76 (d, 6H), 1.86-1.98 (m, 2H).

Example 45

6-[8-(1,3-benzothiazol-2-ylcarbamoyl)-3,4-dihydroisoquinolin-2(1H)-yl]-3-[1-(4-fluoro-3-nitrobenzyl)-1H-pyrazol-4-yl]pyridine-2-carboxylic acid

Example 45A 1-(4-fluoro-3-nitrobenzyl)-4-(4,4,5,5-tetramethyl-1,3,2-dioxaborolan-2-yl)-1H-pyrazole The title compound was prepared by substituting 4-(bromomethyl)-1-fluoro-2-nitrobenzene for EXAMPLE 4A in EXAMPLE 4B.

Example 45B tert-butyl 6-(8-(benzo[d]thiazol-2-ylcarbamoyl)-3,4-dihydroisoquinolin-2(1H)-yl)-3-(1-(4-fluoro-3-nitrobenzyl)-1H-pyrazol-4-yl)picolinate The title compound was prepared by substituting EXAMPLE 45A for 1-benzyl-4-(4,4,5,5-tetramethyl-1,3,2-dioxaborolan-2-yl)-1H-pyrazole in EXAMPLE 1E.

Example 45C

6-[8-(1,3-benzothiazol-2-ylcarbamoyl)-3,4-dihydroisoquinolin-2(1H)-yl]-3-[1-(4-fluoro-3-nitrobenzyl)-1H-pyrazol-4-yl]pyridine-2-carboxylic acid The title compound was prepared by substituting EXAMPLE 45B for EXAMPLE 8B in EXAMPLE 8C. $^1$H NMR (400 MHz, dimethylsulfoxide-$d_6$) δ ppm 12.84 (s, 1H), 8.10 (dd, 1H), 8.04 (d, 1H), 7.99 (s, 1H), 7.79 (d, 1H), 7.65-7.73 (m, 2H), 7.54-7.64 (m, 3H), 7.45-7.51 (m, 1H), 7.40-7.45 (m, 1H), 7.36 (t, 2H), 6.95 (d, 1H), 5.45 (s, 2H), 4.95 (s, 2H), 3.87 (t, 2H), 3.00 (t, 2H).

Example 46

6-[8-(1,3-benzothiazol-2-ylcarbamoyl)-3,4-dihydroisoquinolin-2(1H)-yl]-3-(1-{2-[2-(morpholin-4-yl)ethoxy]benzyl}-1H-pyrazol-4-yl)pyridine-2-carboxylic acid

Example 46A tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(2-(2-morpholinoethoxy)benzyl)-1H-pyrazol-4-yl)picolinate The title compound was prepared by substituting EXAMPLE 40B for EXAMPLE 6B and 2-morpholinoethanol for 2-(dimethylamino)ethanol in EXAMPLE 6C.

Example 46B

6-[8-(1,3-benzothiazol-2-ylcarbamoyl)-3,4-dihydroisoquinolin-2(1H)-yl]-3-(1-{2-[2-(morpholin-4-yl)ethoxy]benzyl}-1H-pyrazol-4-yl)pyridine-2-carboxylic acid The title compound was prepared by substituting EXAMPLE 46A for EXAMPLE 1E in EXAMPLE 1F. $^1$H NMR (500 MHz, dimethylsulfoxide-$d_6$) δ ppm 12.87 (s, 1H), 8.04 (d, 1H), 7.83 (s, 1H), 7.80 (d, 1H), 7.72 (d, 1H), 7.62 (d, 1H), 7.59 (s, 1H), 7.46-7.50 (m, 1H), 7.42-7.44 (m, 1H), 7.31-7.38 (m, 3H), 7.07-7.09 (m, 2H), 6.93-6.99 (m, 2H), 5.35 (s, 2H), 4.95 (s, 2H), 4.38-4.40 (m, 2H), 3.86 (t, 2H), 3.60-3.63 (m, 2H), 3.00 (t, 2H).

Example 47

6-[8-(1,3-benzothiazol-2-ylcarbamoyl)-3,4-dihydroisoquinolin-2(1H)-yl]-3-(1-{2-[3-(dimethylamino)propoxy]benzyl}-1H-pyrazol-4-yl)pyridine-2-carboxylic acid

Example 47A tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(2-(3-(dimethylamino)propoxy)benzyl)-1H-pyrazol-4-yl)picolinate The title compound was prepared by substituting EXAMPLE 40B for EXAMPLE 6B and 3-(dimethylamino)propan-1-ol for 2-(dimethylamino)ethanol in EXAMPLE 6C.

Example 47B

6-[8-(1,3-benzothiazol-2-ylcarbamoyl)-3,4-dihydroisoquinolin-2(1H)-yl]-3-(1-{2-[3-(dimethylamino)propoxy]benzyl}-1H-pyrazol-4-yl)pyridine-2-carboxylic acid The title compound was prepared by substituting EXAMPLE 47A for EXAMPLE 1E in EXAMPLE 1F. $^1$H NMR (500 MHz, dimethylsulfoxide-$d_6$) δ ppm 12.86 (s, 1H), 9.38 (s, 1H), 8.04 (d, 1H), 7.82 (s, 1H), 7.80 (d, 1H), 7.71 (d, 1H), 7.62 (d, 1H), 7.59 (s, 1H), 7.46-7.50 (m, 1H), 7.42-7.44 (m, 1H), 7.35-7.38 (m, 2H), 7.29-7.32 (m, 1H), 7.06 (dd, 1H), 7.01 (d, 1H), 6.92-6.95 (m, 2H), 5.30 (s, 2H), 4.94 (s, 2H), 4.08 (t, 2H), 3.86 (t, 2H), 3.21-3.25 (m, 2H), 3.00 (t, 2H), 2.80 (s, 6H), 2.09-2.14 (m, 2H).

Example 48

6-[8-(1,3-benzothiazol-2-ylcarbamoyl)-3,4-dihydroisoquinolin-2(1H)-yl]-3-{1-[2-(pyridin-4-ylmethoxy)benzyl]-1H-pyrazol-4-yl}pyridine-2-carboxylic acid

Example 48A tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(2-(pyridin-4-ylmethoxy)benzyl)-1H-pyrazol-4-yl)picolinate The title compound was prepared by substituting EXAMPLE 40B for EXAMPLE 6B and pyridin-4-ylmethanol for 2-(dimethylamino)ethanol in EXAMPLE 6C.

Example 48B

6-[8-(1,3-benzothiazol-2-ylcarbamoyl)-3,4-dihydroisoquinolin-2(1H)-yl]-3-{1-[2-(pyridin-4-ylmethoxy)benzyl]-1H-pyrazol-4-yl}pyridine-2-carboxylic acid The title compound was prepared by substituting EXAMPLE 48A for EXAMPLE 1E in EXAMPLE 1F. $^1$H NMR (500 MHz, dimethylsulfoxide-$d_6$) δ ppm 12.84 (s, 1H), 9.38 (s, 1H), 8.71 (d, 2H), 8.04 (d, 1H), 7.84 (s, 1H), 7.79 (d, 1H), 7.72 (d, 2H), 7.67 (d, 1H), 7.61 (d, 1H), 7.59 (s, 1H), 7.46-7.50 (m, 1H), 7.42-7.43 (m, 1H), 7.34-7.38 (m, 2H), 7.27-7.32 (m, 1H), 7.04-7.09 (m, 2H), 6.96-6.98 (m, 1H), 6.93 (d, 1H), 5.41 (s, 2H), 5.38 (s, 2H), 4.94 (s, 2H), 3.86 (t, 2H), 2.99 (t, 2H).

Example 49

6-[8-(1,3-benzothiazol-2-ylcarbamoyl)-3,4-dihydroisoquinolin-2(1H)-yl]-3-(1-{2-[2-(dimethylamino)ethoxy]benzyl}-5-methyl-1H-pyrazol-4-yl)pyridine-2-carboxylic acid

Example 49A 1-(2-(benzyloxy)benzyl)-5-methyl-4-(4,4,5,5-tetramethyl-1,3,2-dioxaborolan-2-yl)-1H-pyrazole The title compound was prepared by substituting 5-methyl-4-(4,4,5,5-tetramethyl-1,3,2-dioxaborolan-2-yl)-1H-pyrazole for 4-(4,4,5,5-tetramethyl-1,3,2-dioxaborolan-2-yl)-1H-pyrazole and EXAMPLE 31A for EXAMPLE 4A in EXAMPLE 4B. The desired product was isolated via Prep HPLC using a Gilson system.

Example 49B tert-butyl 6-(8-(benzo[d]thiazol-2-ylcarbamoyl)-3,4-dihydroisoquinolin-2(1H)-yl)-3-(1-(2-(benzyloxy)benzyl)-5-methyl-1H-pyrazol-4-yl)picolinate The title compound was prepared by substituting EXAMPLE 49A for 1-benzyl-4-(4,4,5,5-tetramethyl-1,3,2-dioxaborolan-2-yl)-1H-pyrazole in EXAMPLE 1E.

Example 49C tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(2-(benzyloxy)benzyl)-5-methyl-1H-pyrazol-4-yl)picolinate The title compound was prepared by substituting EXAMPLE 49B for EXAMPLE 4C in EXAMPLE 6A.

Example 49D tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(2-hydroxybenzyl)-5-methyl-1H-pyrazol-4-yl)picolinate The title compound was prepared by substituting EXAMPLE 49C for EXAMPLE 4C in EXAMPLE 4D.

Example 49E tert-butyl 6-(8-(benzo[d]thiazol-2-yl((2-(trimethylsilyl)ethoxy)methyl)carbamoyl)-3,4-dihydroisoquinolin-2(1H)-yl)-3-(1-(2-(2-(dimethylamino)ethoxy)benzyl)-5-methyl-1H-pyrazol-4-yl)picolinate The title compound was prepared by substituting EXAMPLE 49D for EXAMPLE 6B in EXAMPLE 6C.

Example 49F

6-[8-(1,3-benzothiazol-2-ylcarbamoyl)-3,4-dihydroisoquinolin-2(1H)-yl]-3-(1-{2-[2-(dimethylamino)ethoxy]benzyl}-5-methyl-1H-pyrazol-4-yl)pyridine-2-carboxylic acid The title compound was prepared by substituting EXAMPLE 49E for EXAMPLE 1E in EXAMPLE 1F. $^1$H NMR (500 MHz, dimethylsulfoxide-$d_6$) δ ppm 12.86 (s, 1H), 9.67 (s, 1H), 8.04 (d, 1H), 7.79 (d, 1H), 7.55-7.64 (m, 2H), 7.52 (d, 1H), 7.43-7.50 (m, 3H), 7.29-7.39 (m, 3H), 7.07 (d, 1H), 6.93-6.98 (m, 2H), 6.77 (dd, 1H), 5.34 (s, 2H), 4.96 (s, 2H), 4.36-4.39 (m, 2H), 3.89 (t, 2H), 3.58 (d, 2H), 3.01 (t, 2H), 2.93 (d, 6H), 2.09 (s, 3H).

Example 50

6-[8-(1,3-benzothiazol-2-ylcarbamoyl)-3,4-dihydroisoquinolin-2(1H)-yl]-3-[1-(tetrahydro-2H-pyran-4-ylmethyl)-1H-pyrazol-4-yl]pyridine-2-carboxylic acid Example 50A 1-((tetrahydro-2H-pyran-4-yl)methyl)-4-(4,4,5,5-tetramethyl-1,3,2-dioxaborolan-2-yl)-1H-pyrazole The title compound was prepared by substituting (tetrahydro-2H-pyran-4-yl)methanol for (3-(dimethylamino)phenyl)methanol in EXAMPLE 34A.

Example 50B tert-butyl 6-(8-(benzo[d]thiazol-2-ylcarbamoyl)-3,4-dihydroisoquinolin-2(1H)-yl)-3-(1-((tetrahydro-2H-pyran-4-yl)methyl)-1H-pyrazol-4-yl)picolinate The title compound was prepared by substituting EXAMPLE 50A for EXAMPLE 22A in EXAMPLE 22B.

Example 50C

6-[8-(1,3-benzothiazol-2-ylcarbamoyl)-3,4-dihydroisoquinolin-2(1H)-yl]-3-[1-(tetrahydro-2H-pyran-4-ylmethyl)-1H-pyrazol-4-yl]pyridine-2-carboxylic acid The title compound was prepared by substituting EXAMPLE 50B for EXAMPLE 8B in EXAMPLE 8C. $^1$H NMR (300 MHz, dimethylsulfoxide-$d_6$) δ ppm 12.85 (s, 2H), 8.06-8.01 (m, 1H), 7.79 (d, 1H), 7.76 (d, 1H), 7.69 (d, 1H), 7.61 (d, 1H), 7.53 (d, 1H), 7.51-7.44 (m, 1H), 7.42 (d, 1H), 7.39-7.32 (m, 2H), 6.94 (d, 1H), 4.94 (s, 2H), 3.99 (d, 2H), 3.83 (dt, 4H), 3.24 (td, 2H), 3.00 (t, 2H), 2.01 (ddd, 1H), 1.46-1.31 (m, 2H), 1.22 (dd, 2H).

Example 51

6-[8-(1,3-benzothiazol-2-ylcarbamoyl)-3,4-dihydroisoquinolin-2(1H)-yl]-3-(1-{2-[3-(dimethylamino)prop-1-yn-1-yl]benzyl}-1H-pyrazol-4-yl)pyridine-2-carboxylic acid

Example 51A 1-(2-bromobenzyl)-4-(4,4,5,5-tetramethyl-1,3,2-dioxaborolan-2-yl)-1H-pyrazole The title compound was prepared by substituting 1-bromo-2-(bromomethyl)benzene for EXAMPLE 4A in EXAMPLE 4B.

Example 51B

N,N-dimethyl-3-(2-((4-(4,4,5,5-tetramethyl-1,3,2-dioxaborolan-2-yl)-1H-pyrazol-1-yl)methyl)phenyl)prop-2-yn-1-amine EXAMPLE 51A (0.11 g), N,N-dimethylprop-2-yn-1-amine (0.1 g), tetrakis(triphenylphosphine)palladium(0) (0.05 g), copper(I) iodide (0.01 g) and triethylamine (0.3 mL) were suspended in N,N-dimethylformamide (2 mL) in a 5 mL microwave tube. The mixture was heated at 110° C. in a microwave reactor (Biotage, Iniator) for 30 minutes. Additional tetrakis(triphenylphosphine)palladium(0) (0.05 g) was added, and the mixture was heated in a microwave reactor (Biotage, Iniator) at 120° C. for 1 hour. The crude product was filtered and purified by PrepHPLC (Gilson, C18, Phenomenex®, 250×21.2 mm column) and was eluted with 30-100% CH$_3$CN/water with 0.1% TFA to provide the title compound.

Example 51C tert-butyl 6-(8-(benzo[d]thiazol-2-ylcarbamoyl)-3,4-dihydroisoquinolin-2(1H)-yl)-3-(1-(2-(3-(dimethylamino)prop-1-ynyl)benzyl)-1H-pyrazol-4-yl)picolinate The title compound was prepared by substituting EXAMPLE 51B for 1-benzyl-4-(4,4,5,5-tetramethyl-1,3,2-dioxaborolan-2-yl)-1H-pyrazole in EXAMPLE 1E.

Example 51D

6-[8-(1,3-benzothiazol-2-ylcarbamoyl)-3,4-dihydroisoquinolin-2(1H)-yl]-3-(1-{2-[3-(dimethylamino)prop-1-yn-1-yl]benzyl}-1H-pyrazol-4-yl)pyridine-2-carboxylic acid The title compound was prepared by substituting EXAMPLE 51C for EXAMPLE 1E in EXAMPLE 1F. $^1$H NMR (500 MHz, dimethylsulfoxide-d$_6$) δ ppm 12.86 (m, 1H), 8.04 (d, 1H), 7.92 (m, 1H), 7.80 (d, 1H), 7.71 (d, 1H), 7.59 (m, 3H), 7.41 (m, 7H), 7.12 (d, 1H), 6.94 (d, 1H), 5.50 (s, 2H), 4.95 (s, 2H), 4.38 (s, 2H), 3.87 (t, 2H), 3.00 (t, 2H), 2.89 (s, 6H).

Example 52

6-[8-(1,3-benzothiazol-2-ylcarbamoyl)-3,4-dihydroisoquinolin-2(1H)-yl]-3-[1-(2,3-difluorobenzyl)-1H-pyrazol-4-yl]pyridine-2-carboxylic acid

Example 52A 1-(2,3-difluorobenzyl)-4-(4,4,5,5-tetramethyl-1,3,2-dioxaborolan-2-yl)-1H-pyrazole The title compound was prepared by substituting 1-(bromomethyl)-2,3-difluorobenzene for EXAMPLE 4A in EXAMPLE 4B.

Example 52B tert-butyl 6-[8-(1,3-benzothiazol-2-ylcarbamoyl)-3,4-dihydroisoquinolin-2(1H)-yl]-3-[1-(2,3-difluorobenzyl)-1H-pyrazol-4-yl]pyridine-2-carboxylate The title compound was prepared by substituting EXAMPLE 52A for EXAMPLE 22A in EXAMPLE 22B.

Example 52C

6-[8-(1,3-benzothiazol-2-ylcarbamoyl)-3,4-dihydroisoquinolin-2(1H)-yl]-3-[1-(2,3-difluorobenzyl)-1H-pyrazol-4-yl]pyridine-2-carboxylic acid The title compound was prepared by substituting EXAMPLE 52B for EXAMPLE 7D in EXAMPLE 7E. $^1$H NMR (500 MHz, dimethylsulfoxide-d$_6$) δ ppm 12.87 (br s, 1H), 8.04 (d, 1H), 7.94 (s, 1H), 7.79 (d, 1H), 7.71 (d, 1H), 7.61 (d, 1H), 7.59 (s, 1H), 7.48 (t, 1H), 7.42 (d, 1H), 7.36 (m, 3H), 7.19 (m, 1H), 7.01 (m, 1H), 6.94 (d, 1H), 5.44 (s, 2H), 4.95 (s, 2H), 3.87 (t, 2H), 3.00 (t, 2H).

Example 53

6-[8-(1,3-benzothiazol-2-ylcarbamoyl)-3,4-dihydroisoquinolin-2(1H)-yl]-3-[1-(3,5-difluorobenzyl)-1H-pyrazol-4-yl]pyridine-2-carboxylic acid

Example 53A 1-(3,5-difluorobenzyl)-4-(4,4,5,5-tetramethyl-1,3,2-dioxaborolan-2-yl)-1H-pyrazole The title compound was prepared by substituting 1-(bromomethyl)-3,5-difluorobenzene for EXAMPLE 4A in EXAMPLE 4B.

Example 53B tert-butyl 6-[8-(1,3-benzothiazol-2-ylcarbamoyl)-3,4-dihydroisoquinolin-2(1H)-yl]-3-[1-(3,5-difluorobenzyl)-1H-pyrazol-4-yl]pyridine-2-carboxylate The title compound was prepared by substituting EXAMPLE 53A for EXAMPLE 22A in EXAMPLE 22B.

Example 53C

6-[8-(1,3-benzothiazol-2-ylcarbamoyl)-3,4-dihydroisoquinolin-2(1H)-yl]-3-[1-(3,5-difluorobenzyl)-1H-pyrazol-4-yl]pyridine-2-carboxylic acid The title compound was prepared by substituting EXAMPLE 53B for EXAMPLE 7D in EXAMPLE 7E. $^1$H NMR (500 MHz, dimethylsulfoxide-$d_6$) δ ppm 12.85 (br s, 1H), 8.04 (d, 1H), 7.96 (s, 1H), 7.79 (d, 1H), 7.72 (d, 1H), 7.62 (d, 1H), 7.61 (s, 1H), 7.48 (t, 1H), 7.43 (d, 1H), 7.36 (t, 2H), 7.17 (m, 1H), 6.94 (d, 1H), 6.92 (m, 2H), 5.38 (s, 2H), 4.95 (s, 2H), 3.87 (t, 2H), 3.00 (t, 2H).

Example 54

6-[8-(1,3-benzothiazol-2-ylcarbamoyl)-3,4-dihydroisoquinolin-2(1H)-yl]-3-[1-(2,5-difluorobenzyl)-1H-pyrazol-4-yl]pyridine-2-carboxylic acid Example 54A 1-(2,5-difluorobenzyl)-4-(4,4,5,5-tetramethyl-1,3,2-dioxaborolan-2-yl)-1H-pyrazole The title compound was prepared by substituting 1-(bromomethyl)-2,5-difluorobenzene for EXAMPLE 4A in EXAMPLE 4B.

Example 54B tert-butyl 6-[8-(1,3-benzothiazol-2-ylcarbamoyl)-3,4-dihydroisoquinolin-2(1H)-yl]-3-[1-(2,5-difluorobenzyl)-1H-pyrazol-4-yl]pyridine-2-carboxylate The title compound was prepared by substituting EXAMPLE 54A for EXAMPLE 22A in EXAMPLE 22B.

Example 54C

6-[8-(1,3-benzothiazol-2-ylcarbamoyl)-3,4-dihydroisoquinolin-2(1H)-yl]-3-[1-(2,5-difluorobenzyl)-1H-pyrazol-4-yl]pyridine-2-carboxylic acid The title compound was prepared by substituting EXAMPLE 54B for EXAMPLE 7D in EXAMPLE 7E. $^1$H NMR (500 MHz, dimethylsulfoxide-$d_6$) δ ppm 12.87 (br s, 1H), 8.04 (d, 1H), 7.94 (s, 1H), 7.79 (d, 1H), 7.71 (d, 1H), 7.62 (d, 1H), 7.60 (s, 1H), 7.48 (t, 1H), 7.43 (d, 1H), 7.36 (t, 2H), 7.29 (m, 1H), 7.22 (m, 1H), 7.00 (m, 1H), 6.95 (d, 1H), 5.39 (s, 2H), 4.95 (s, 2H), 3.87 (t, 2H), 3.00 (t, 2H).

Example 55

6-[8-(1,3-benzothiazol-2-ylcarbamoyl)-3,4-dihydroisoquinolin-2(1H)-yl]-3-[1-(2,6-difluorobenzyl)-1H-pyrazol-4-yl]pyridine-2-carboxylic acid Example 55A 1-(2,6-difluorobenzyl)-4-(4,4,5,5-tetramethyl-1,3,2-dioxaborolan-2-yl)-1H-pyrazole The title compound was prepared by substituting 1-(bromomethyl)-2,6-difluorobenzene for EXAMPLE 4A in EXAMPLE 4B.

Example 55B tert-butyl 6-[8-(1,3-benzothiazol-2-ylcarbamoyl)-3,4-dihydroisoquinolin-2(1H)-yl]-3-[1-(2,6-difluorobenzyl)-1H-pyrazol-4-yl]pyridine-2-carboxylate The title compound was prepared by substituting EXAMPLE 55A for EXAMPLE 22A in EXAMPLE 22B.

Example 55C

6-[8-(1,3-benzothiazol-2-ylcarbamoyl)-3,4-dihydroisoquinolin-2(1H)-yl]-3-[1-(2,6-difluorobenzyl)-1H-pyrazol-4-yl]pyridine-2-carboxylic acid The title compound was prepared by substituting EXAMPLE 55B for EXAMPLE 7D in EXAMPLE 7E. $^1$H NMR (500 MHz, dimethylsulfoxide-$d_6$) δ ppm 12.85 (br s, 1H), 8.04 (d, 1H), 7.87 (s, 1H), 7.79 (d, 1H), 7.70 (d, 1H), 7.61 (d, 1H), 7.53 (s, 1H), 7.48 (m, 2H), 7.42 (d, 1H), 7.36 (t, 2H), 7.14 (t, 2H), 6.93 (d, 1H), 5.37 (s, 2H), 4.94 (s, 2H), 3.87 (t, 2H), 3.00 (t, 2H).

Example 56

6-[8-(1,3-benzothiazol-2-ylcarbamoyl)-3,4-dihydroisoquinolin-2(1H)-yl]-3-[1-(tetrahydro-2H-pyran-3-ylmethyl)-1H-pyrazol-4-yl]pyridine-2-carboxylic acid Example 56A 1-((tetrahydro-2H-pyran-3-yl)methyl)-4-(4,4,5,5-tetramethyl-1,3,2-dioxaborolan-2-yl)-1H-pyrazole The title compound was prepared by substituting (tetrahydro-2H-pyran-3-yl)methanol for (3-(dimethylamino)phenyl)methanol in EXAMPLE 34A.

Example 56B tert-butyl 6-(8-(benzo[d]thiazol-2-ylcarbamoyl)-3,4-dihydroisoquinolin-2(1H)-yl)-3-(1-((tetrahydro-2H-pyran-3-yl)methyl)-1H-pyrazol-4-yl)picolinate The title compound was prepared by substituting EXAMPLE 56A for EXAMPLE 22A in EXAMPLE 22B.

Example 56C

6-[8-(1,3-benzothiazol-2-ylcarbamoyl)-3,4-dihydroisoquinolin-2(1H)-yl]-3-[1-(tetrahydro-2H-pyran-3-ylmethyl)-1H-pyrazol-4-yl]pyridine-2-carboxylic acid The title compound was prepared by substituting EXAMPLE 56B for EXAMPLE 8B in EXAMPLE 8C. $^1$H NMR (300 MHz, dimethylsulfoxide-$d_6$) δ ppm 12.85 (s, 2H), 8.07-8.01 (m, 1H), 7.76 (d, 1H), 7.69 (d, 1H), 7.61 (d, 1H), 7.53 (d, 1H), 7.51-7.44 (m, 1H), 7.43 (d, 1H), 7.35 (dd, 3H), 6.94 (d, 1H), 4.94 (s, 2H), 4.00 (dd, 2H), 3.87 (t, 2H), 3.75-3.64 (m, 1H), 3.60 (dd, 1H), 3.38-3.26 (m, 1H), 3.14 (dd, 1H), 3.00 (t, 2H), 2.02 (s, 1H), 1.61 (dd, 2H), 1.52-1.34 (m, 1H), 1.21 (d, 1H).

Example 57

6-[8-(1,3-benzothiazol-2-ylcarbamoyl)-3,4-dihydroisoquinolin-2(1H)-yl]-3-[1-(2-nitrobenzyl)-1H-pyrazol-4-yl]pyridine-2-carboxylic acid

Example 57A 1-(2-nitrobenzyl)-4-(4,4,5,5-tetramethyl-1,3,2-dioxaborolan-2-yl)-1H-pyrazole The title compound was prepared by substituting 1-(bromomethyl)-2-nitrobenzene for EXAMPLE 4A in EXAMPLE 4B.

Example 57B tert-butyl 6-(8-(benzo[d]thiazol-2-ylcarbamoyl)-3,4-dihydroisoquinolin-2(1H)-yl)-3-(1-(2-nitrobenzyl)-1H-pyrazol-4-yl)picolinate The title compound was prepared by substituting EXAMPLE 57A for 1-benzyl-4-(4,4,5,5-tetramethyl-1,3,2-dioxaborolan-2-yl)-1H-pyrazole in EXAMPLE 1E.

Example 57C

6-[8-(1,3-benzothiazol-2-ylcarbamoyl)-3,4-dihydroisoquinolin-2(1H)-yl]-3-[1-(2-nitrobenzyl)-1H-pyrazol-4-yl]pyridine-2-carboxylic acid The title compound was prepared by substituting EXAMPLE 57B for EXAMPLE 1E in EXAMPLE 1F. $^1$H NMR (300 MHz, dimethylsulfoxide-$d_6$) δ ppm 12.85 (s, 1H), 8.09 (dd, 1H), 8.03 (d, 1H), 7.95 (s, 1H), 7.75 (m, 3H), 7.47 (m, 8H), 6.96 (d, 1H), 6.87 (dd, 1H), 5.72 (s, 2H), 4.95 (s, 2H), 3.87 (t, 2H), 3.00 (t, 2H).

Example 58

6-[8-(1,3-benzothiazol-2-ylcarbamoyl)-3,4-dihydroisoquinolin-2(1H)-yl]-3-[1-(biphenyl-3-ylmethyl)-1H-pyrazol-4-yl]pyridine-2-carboxylic acid

Example 58A

1-Biphenyl-3-ylmethyl-4-(4,4,5,5-tetramethyl-[1,3,2]dioxaborolan-2-yl)-1H-pyrazole The title compound was prepared by substituting 3-(bromomethyl)biphenyl for EXAMPLE 4A in EXAMPLE 4B.

Example 58B

6-[8-(1,3-benzothiazol-2-ylcarbamoyl)-3,4-dihydroisoquinolin-2(1H)-yl]-3-[1-(biphenyl-3-ylmethyl)-1H-pyrazol-4-yl]pyridine-2-carboxylic acid tert-butyl ester EXAMPLE 58A (76 mg) and EXAMPLE 1D (100 mg) were added to 1,4-dioxane (1.5 mL). 2M aqueous sodium carbonate (0.265 mL) was added. The solution was degassed and flushed with nitrogen three times. Dichloro[1,1'-bis(diphenylphosphino)ferrocene]palladium (II) dichloromethane adduct (14 mg) was added. The solution was degassed and flushed with nitrogen and then heated at 70° C. for 16 hours. The solution was cooled, added to water, extracted with 50% ethyl acetate in hexanes, washed with brine, dried on anhydrous sodium sulfate, and concentrated under vacuum. The crude material was purified on silica gel using 30-50% ethyl acetate in hexanes.

Example 58C

6-[8-(1,3-benzothiazol-2-ylcarbamoyl)-3,4-dihydroisoquinolin-2(1H)-yl]-3-[1-(biphenyl-3-ylmethyl)-1H-pyrazol-4-yl]pyridine-2-carboxylic acid The title compound was prepared by substituting EXAMPLE 58B for EXAMPLE 7D in EXAMPLE 7E. $^1$H NMR (400 MHz, dimethylsulfoxide-$d_6$) δ ppm 12.84 (bs, 1H), 8.04 (d, 1H), 7.98 (d, 1H), 7.80 (d, 1H), 7.72 (d, 1H), 7.66-7.53 (m, 6H), 7.51-7.32 (m, 8H), 7.23 (d, 1H), 6.95 (d, 1H), 5.40 (s, 2H), 4.94 (s, 2H), 3.87 (t, 2H), 3.00 (t, 2H).

Example 59

6-[8-(1,3-benzothiazol-2-ylcarbamoyl)-3,4-dihydroisoquinolin-2(1H)-yl]-3-[1-(2,2-dimethylpropyl)-1H-pyrazol-4-yl]pyridine-2-carboxylic acid

Example 59A 1-neopentyl-4-(4,4,5,5-tetramethyl-1,3,2-dioxaborolan-2-yl)-1H-pyrazole The title compound was prepared by substituting 2,2-dimethylpropan-1-ol for (3-(dimethylamino)phenyl)methanol in EXAMPLE 34A.

Example 59B tert-butyl 6-(8-(benzo[d]thiazol-2-ylcarbamoyl)-3,4-dihydroisoquinolin-2(1H)-yl)-3-(1-neopentyl-1H-pyrazol-4-yl)picolinate The title compound was prepared by substituting EXAMPLE 59A for EXAMPLE 22A in EXAMPLE 22B.

Example 59C

6-[8-(1,3-benzothiazol-2-ylcarbamoyl)-3,4-dihydroisoquinolin-2(1H)-yl]-3-[1-(2,2-dimethylpropyl)-1H-pyrazol-4-yl]pyridine-2-carboxylic acid The title compound was prepared by substituting EXAMPLE 59B for EXAMPLE 8B in EXAMPLE 8C. $^1$H NMR (300 MHz, dimethylsulfoxide-$d_6$) δ ppm 13.08-12.70 (m, 1H), 8.04 (dd, 1H), 7.79 (d, 1H), 7.71 (dd, 2H), 7.66-7.58 (m, 1H), 7.53 (d, 1H), 7.52-7.45 (m, 1H), 7.45-7.31 (m, 3H), 6.94 (d, 1H), 4.94 (s, 2H), 3.94-3.79 (m, 4H), 3.00 (t, 2H), 0.89 (s, 9H).

Example 60

6-[8-(1,3-benzothiazol-2-ylcarbamoyl)-3,4-dihydroisoquinolin-2(1H)-yl]-3-[1-(2-cyclohexylethyl)-1H-pyrazol-4-yl]pyridine-2-carboxylic acid

Example 60A 1-(2-cyclohexylethyl)-4-(4,4,5,5-tetramethyl-1,3,2-dioxaborolan-2-yl)-1H-pyrazole The title compound was prepared by substituting (2-bromoethyl)cyclohexane for EXAMPLE 4A in EXAMPLE 4B.

Example 60B tert-butyl 6-[8-(1,3-benzothiazol-2-ylcarbamoyl)-3,
4-dihydroisoquinolin-2(1H)-yl]-3-[1-(2-cyclohexyl-
ethyl)-1H-pyrazol-4-yl]pyridine-2-carboxylate The title compound was prepared by substituting EXAMPLE 60A for EXAMPLE 22A in EXAMPLE 22B.

Example 60C

6-[8-(1,3-benzothiazol-2-ylcarbamoyl)-3,4-dihy-
droisoquinolin-2(1H)-yl]-3-[1-(2-cyclohexylethyl)-
1H-pyrazol-4-yl]pyridine-2-carboxylic acid The title compound was prepared by substituting EXAMPLE 60B for EXAMPLE 7D in EXAMPLE 7E. $^1$H NMR (400 MHz, dimethylsulfoxide-$d_6$) δ 12.87 (br s, 1H), 8.04 (d, 1H), 7.80 (s, 1H), 7.79 (d, 1H), 7.70 (d, 1H), 7.61 (d, 1H), 7.51 (s, 1H), 7.48 (m, 1H), 7.42 (d, 1H), 7.36 (t, 2H), 6.94 (d, 1H), 4.95 (s, 2H), 4.10 (t, 2H), 3.87 (t, 2H), 3.00 (t, 2H), 1.66 (m, 7H), 1.15 (m, 4H), 0.90 (m, 2H).

Example 61

6-[8-(1,3-benzothiazol-2-ylcarbamoyl)-3,4-dihy-
droisoquinolin-2(1H)-yl]-3-{1-[3-(trifluoromethyl)
benzyl]-1H-pyrazol-4-yl}pyridine-2-carboxylic acid

Example 61A

1-[3-(trifluoromethyl)benzyl]-4-(4,4,5,5-tetramethyl-
1,3,2-dioxaborolan-2-yl)-1H-pyrazole The title compound was prepared by substituting 1-(bromomethyl)-3-(trifluormethyl)benzene for EXAMPLE 4A in EXAMPLE 4B.

Example 61B tert-butyl 6-[8-(1,3-benzothiazol-2-ylcarbamoyl)-3,
4-dihydroisoquinolin-2(1H)-yl]-3-{1-[3-(trifluorom-
ethyl)benzyl]-1H-pyrazol-4-yl}pyridine-2-carboxy-
late The title compound was prepared by substituting EXAMPLE 61A for EXAMPLE 22A in EXAMPLE 22B.

Example 61C

6-[8-(1,3-benzothiazol-2-ylcarbamoyl)-3,4-dihy-
droisoquinolin-2(1H)-yl]-3-{1-[3-(trifluoromethyl)
benzyl]-1H-pyrazol-4-yl}pyridine-2-carboxylic acid The title compound was prepared by substituting EXAMPLE 61B for EXAMPLE 7D in EXAMPLE 7E. $^1$H NMR (400 MHz, dimethylsulfoxide-$d_6$) δ 12.85 (br s, 1H), 8.04 (d, 1H), 8.00 (s, 1H), 7.79 (d, 1H), 7.71 (d, 1H), 7.62 (d, 1H), 7.61 (m, 4H), 7.48 (m, 3H), 7.36 (t, 2H), 6.94 (d, 1H), 5.45 (s, 2H), 4.95 (s, 2H), 3.87 (t, 2H), 3.00 (t, 2H).

Example 62

6-[8-(1,3-benzothiazol-2-ylcarbamoyl)-3,4-dihy-
droisoquinolin-2(1H)-yl]-3-[1-(biphenyl-2-ylm-
ethyl)-1H-pyrazol-4-yl]pyridine-2-carboxylic acid

Example 62A

1-Biphenyl-2-ylmethyl-4-(4,4,5,5-tetramethyl-[1,3,2]
dioxaborolan-2-yl)-1H-pyrazole The title compound was prepared by substituting 2-(bromomethyl)biphenyl for EXAMPLE 4A in EXAMPLE 4B.

Example 62B

6-[8-(1,3-benzothiazol-2-ylcarbamoyl)-3,4-dihy-
droisoquinolin-2(1H)-yl]-3-[1-(biphenyl-2-ylm-
ethyl)-1H-pyrazol-4-yl]pyridine-2-carboxylic acid
tert-butyl ester The title compound was prepared by substituting EXAMPLE 62A for EXAMPLE 58A in EXAMPLE 58B.

Example 62C

6-[8-(1,3-benzothiazol-2-ylcarbamoyl)-3,4-dihy-
droisoquinolin-2(1H)-yl]-3-[1-(biphenyl-2-ylm-
ethyl)-1H-pyrazol-4-yl]pyridine-2-carboxylic acid The title compound was prepared by substituting EXAMPLE 62B for EXAMPLE 7D in EXAMPLE 7E. $^1$H NMR (400 MHz, dimethylsulfoxide-$d_6$) δ ppm 12.86 (bs, 1H), 8.04 (d, 1H), 7.80 (d, 1H), 7.68-7.65 (m, 2H), 7.72 (d, 1H), 7.61 (d, 1H), 7.50-7.31 (m, 1H), 7.26 (dd, 1H), 7.07 (dd, 1H), 6.94 (d, 1H), 5.26 (s, 2H), 4.94 (s, 2H), 3.87 (t, 2H), 3.00 (t, 2H).

Example 63

6-[8-(1,3-benzothiazol-2-ylcarbamoyl)-3,4-dihy-
droisoquinolin-2(1H)-yl]-3-[1-(cyclopentylmethyl)-
5-methyl-1H-pyrazol-4-yl]pyridine-2-carboxylic
acid

Example 63A 1-(cyclopentylmethyl)-1H-pyrazole

A flask was charged with pyrazole (380 mg), (bromomethyl)cyclopentane (968 mg), tetrabutylammonium bromide (18 mg), 50% aqueous NaOH (0.6 mL) and toluene (1.5 mL) and the mixture was heated to 110° C. for 4.5 hours. The reaction mixture was cooled to room temperature and partitioned between toluene (3×10 mL) and H$_2$O (10 mL). The extracts were dried (MgSO$_4$), filtered, and concentrated to give the title compound.

Example 63B 1-(cyclopentylmethyl)-5-methyl-1H-pyrazole

A solution of EXAMPLE 63A (727 mg) in tetrahydrofuran (10 mL) was chilled to −45° C. n-Butyllithium (2.3 M solution in hexanes, 2.52 mL) was added dropwise over 5 minutes. The reaction was stirred for 1.5 hours, during which time the temperature increased to −20° C. Iodomethane (0.368 mL) was added dropwise over 3 minutes. The reaction was stirred for 30 minutes between −20 and −15° C. Water (25 mL) was added and the mixture was extracted with ethyl acetate (3×25 mL). The extracts were dried ($Na_2SO_4$), filtered, and concentrated to provide the title compound.

Example 63C 4-bromo-1-(cyclopentylmethyl)-5-methyl-1H-pyrazole

EXAMPLE 63B (570 mg) was dissolved in N,N-dimethylformamide (5 mL) and N-bromosuccinimide (649 mg) was added. The reaction was stirred at room temperature for 2.5 hours. 10% Aqueous $Na_2S_2O_3$ (10 mL) and water (20 mL) were added and the reaction was extracted with ethyl acetate (3×25 mL). The combined extracts were dried ($Na_2SO_4$), filtered, and concentrated. Silica gel chromatography (gradient from 0 to 10% ethyl acetate-hexanes over 25 minutes) provided the title compound.

Example 63D 1-(cyclopentylmethyl)-5-methyl-4-(4,4,5,5-tetramethyl-1,3,2-dioxaborolan-2-yl)-1H-pyrazole EXAMPLE 63C (220 mg), bis(pinacolato)diboron (276 mg) and potassium acetate (240 mg) were combined in N,N-dimethylformamide (3 mL) and the mixture was degassed with $N_2$. [1,1'-Bis(diphenylphosphino)ferrocene]dichloropalladium(II) (44 mg) was added, the reaction vessel was sealed, and the mixture was heated to 90° C. for 18 hours. The reaction mixture was partitioned between $H_2O$ (15 mL) and ethyl acetate, and the aqueous layer was extracted with ethyl acetate (3×10 mL). The extracts were dried ($Na_2SO_4$), filtered, and concentrated, and the residue was purified by flash chromatography (gradient from 0 to 10% ethyl acetate/hexanes) to provide the title compound.

Example 63E tert-butyl 6-(8-(benzo[d]thiazol-2-ylcarbamoyl)-3,4-dihydroisoquinolin-2(1H)-yl)-3-(1-(cyclopentylmethyl)-5-methyl-1H-pyrazol-4-yl)picolinate The title compound was prepared by substituting EXAMPLE 63D for EXAMPLE 22A in EXAMPLE 22B.

Example 63F

6-[8-(1,3-benzothiazol-2-ylcarbamoyl)-3,4-dihydroisoquinolin-2(1H)-yl]-3-[1-(cyclopentylmethyl)-5-methyl-1H-pyrazol-4-yl]pyridine-2-carboxylic acid The title compound was prepared by substituting EXAMPLE 63E for EXAMPLE 8B in EXAMPLE 8C. $^1$H NMR (300 MHz, dimethylsulfoxide-$d_6$) δ ppm 12.70-12.88 (m, 2H), 8.04 (d, 1H), 7.79 (d, 1H), 7.61 (d, 1H), 7.41-7.52 (m, 3H), 7.32-7.39 (m, 2H), 7.25 (s, 1H), 6.94 (d, 1H), 4.95 (s, 2H), 3.94 (d, 2H), 3.89 (t, 2H), 3.01 (t, 2H), 2.28-2.38 (m, 1H), 2.12 (s, 3H), 1.42-1.66 (m, 6H), 1.20-1.32 (m, 2H).

Example 64

6-[8-(1,3-benzothiazol-2-ylcarbamoyl)-3,4-dihydroisoquinolin-2(1H)-yl]-3-[1-(3-formylbenzyl)-1H-pyrazol-4-yl]pyridine-2-carboxylic acid Example 64A 3-[4-(4,4,5,5-Tetramethyl-[1,3,2]dioxaborolan-2-yl)-pyrazol-1-ylmethyl]-benzaldehyde The title compound was prepared by substituting 3-(bromomethyl)benzaldehyde for EXAMPLE 4A in EXAMPLE 4B.

Example 64B

6-[8-(1,3-benzothiazol-2-ylcarbamoyl)-3,4-dihydroisoquinolin-2(1H)-yl]-3-[1-(3-formylbenzyl)-1H-pyrazol-4-yl]pyridine-2-carboxylic acid tert-butyl ester The title compound was prepared by substituting EXAMPLE 64A for EXAMPLE 58A in EXAMPLE 58B.

Example 64C

6-[8-(1,3-benzothiazol-2-ylcarbamoyl)-3,4-dihydroisoquinolin-2(1H)-yl]-3-[1-(3-formylbenzyl)-1H-pyrazol-4-yl]pyridine-2-carboxylic acid The title compound was prepared by substituting EXAMPLE 64B for EXAMPLE 7D in EXAMPLE 7E. $^1$H NMR (400 MHz, dimethylsulfoxide-$d_6$) δ ppm 12.85 (bs, 1H), 9.98 (s, 1H), 8.04 (d, 1H), 7.98 (s, 1H), 7.87-7.78 (m, 3H), 7.72 (d, 1H), 7.63-7.54 (m, 3H), 7.51-7.32 (m, 5H), 6.95 (d, 1H), 5.45 (s, 2H), 4.95 (s, 2H), 3.87 (t, 2H), 3.00 (t, 2H).

Example 65

6-[8-(1,3-benzothiazol-2-ylcarbamoyl)-3,4-dihydroisoquinolin-2(1H)-yl]-3-(1-benzyl-5-phenyl-1H-pyrazol-4-yl)pyridine-2-carboxylic acid Example 65A ethyl 2-(2-phenyl-1,3-dioxolan-2-yl)acetate A solution of ethyl 3-oxo-3-phenylpropanoate (23.74 g) in toluene, ethyleneglycol (23.04 g), and p-toluenesulfonic acid (200 mg) in toluene (300 mL) was stirred under reflux with a Dean-Stark trap for 15 hours. The cooled mixture was poured onto saturated aqueous sodium bicarbonate (100 mL) and the organic layer was washed with water, brine and dried over $Na_2SO_4$. Filtration and evaporation of solvent provided the title compound which was used in the next reaction without further purification.

Example 65B 2-(2-phenyl-1,3-dioxolan-2-yl)acetaldehyde

To a solution of EXAMPLE 65A (2.36 g) in toluene (30 mL) was added diisobutylaluminum hydride (1.5M in toluene, 8 mL) at −78° C. After stirring for 10 minutes the reaction mixture was quenched by addition of water. The precipitate was removed by filtration through diatomaceous earth. The filtrate was washed with water and brine and dried over $Na_2SO_4$. Filtration and evaporation of solvent provided the title compound.

Example 65C tert-butyl 1-benzyl-2-(2-(2-phenyl-1,3-dioxolan-2-yl)ethyl)hydrazinecarboxylate To a solution of tert-butyl 1-benzylhydrazinecarboxylate (2.3 g, prepared according to Eur. J. Org. Chem. 2010, 3815-3822) and EXAMPLE 65B (2 g) in dichloromethane (30 mL) was added sodium triacetoxyborohydride (3.3 g). The mixture was stirred at room temperature, overnight. The mixture was diluted with ethyl acetate (300 mL) and washed with aqueous NaOH, water, and brine and dried over $Na_2SO_4$. Filtration and evaporation of solvent gave the expected product.

Example 65D tert-butyl 1-benzyl-2-(3-oxo-3-phenylpropyl)hydrazinecarboxylate

To a solution of EXAMPLE 65C (3.86 g) in acetone (5 mL) and water (5 mL) was added pyridinium p-toluenesulfonate (120 mg). The mixture was stirred at 100° C. in a Biotage Initiator microwave reactor for 10 minutes. The mixture was diluted with ethyl acetate (200 mL) and washed with water and brine and dried over $Na_2SO_4$. Filtration and evaporation of the solvent gave the crude product which was used without further purification in the next reaction.

Example 65E 1-benzyl-5-phenyl-1H-pyrazole

To a solution of EXAMPLE 65D (3.1 g) in dichloromethane (10 mL) was added TFA (10 mL) and the mixture was stirred overnight. The mixture was concentrated under vacuum and the residue was dissolved in ethyl acetate (300 mL) and washed with 2N aqueous NaOH, water and brine. The combined organic layers were concentrated, and the residue was dissolved in dichloroethane (30 mL) and $MnO_2$ (2.5 g) was added. The mixture was stirred overnight. Filtration and evaporation of the solvent provided the title compound.

Example 65F 1-benzyl-4-iodo-5-phenyl-1H-pyrazole

To a solution of EXAMPLE 65E (270 mg) in N,N-dimethylformamide (5 mL) was added N-iodosuccinimide (259 mg). The mixture was stirred overnight. The mixture was diluted with ethyl acetate (200 mL) and washed with aqueous sodium bisulfite, water, and brine. The organic layers were combined, and evaporation of the solvent provided the title compound.

Example 65G

6-[8-(1,3-benzothiazol-2-ylcarbamoyl)-3,4-dihydroisoquinolin-2(1H)-yl]-3-(1-benzyl-5-phenyl-1H-pyrazol-4-yl)pyridine-2-carboxylic acid To a mixture of EXAMPLE 30A (200 mg) and EXAMPLE 65F (118 mg) in dioxane (9 mL) was added tetrakis(triphenylphosphine)palladium(0) (19 mg) and saturated aqueous $NaHCO_3$ (3 mL). The mixture was purged with argon and stirred at 120° C. in a Biotage initiator microwave reactor for 30 minutes. The mixture was diluted with ethyl acetate (200 mL) and washed with water and brine and dried over $Na_2SO_4$. Filtration and evaporation of the solvent gave crude product which was loaded on a silica gel cartridge and eluted with 20% ethyl acetate in dichloromethane to give the crude product which was dissolved in dichloromethane (3 mL) and TFA (3 mL) and stirred overnight. After evaporation of the solvent, the residue was loaded on a silica gel cartridge and eluted with 5% methanol in dichloromethane to provide the title compound. $^1$H NMR (300 MHz, $CDCl_3$) δ ppm 7.91 (dd, 3H), 7.75 (s, 1H), 7.64 (t, 1H), 7.54 (t, 1H), 7.48 (m, 2H), 7.35 (d, 1H), 7.29 (m, 8H), 7.14 (m, 2H), 7.07 (m, 2H), 6.81 (d, 1H), 5.36 (s, 2H), 5.20 (s, 1H), 3.78 (t, 2H), 3.11 (t, 2H)

Example 66

6-[8-(1,3-benzothiazol-2-ylcarbamoyl)-3,4-dihydroisoquinolin-2(1H)-yl]-3-[5-methyl-1-(tetrahydro-2H-pyran-3-ylmethyl)-1H-pyrazol-4-yl]pyridine-2-carboxylic acid Example 66A 1-((tetrahydro-2H-pyran-3-yl)methyl)-1H-pyrazole The title compound was prepared by substituting (tetrahydro-2H-pyran-3-yl)methanol for (3-(dimethylamino)phenyl)methanol and 1H-pyrazole for 4-(4,4,5,5-tetramethyl-1,3,2-dioxaborolan-2-yl)-1H-pyrazole in EXAMPLE 34A.

Example 66B 5-methyl-1-((tetrahydro-2H-pyran-3-yl)methyl)-1H-pyrazole

The title compound was prepared by substituting EXAMPLE 66A for EXAMPLE 63A in EXAMPLE 63B.

Example 66C 4-iodo-5-methyl-1-((tetrahydro-2H-pyran-3-yl)methyl)-1H-pyrazole

The title compound was prepared by substituting EXAMPLE 66B for EXAMPLE 65E in EXAMPLE 65F.

Example 66D tert-butyl 6-(8-(benzo[d]thiazol-2-ylcarbamoyl)-3,4-dihydroisoquinolin-2(1H)-yl)-3-(5-methyl-1-((tetrahydro-2H-pyran-3-yl)methyl)-1H-pyrazol-4-yl)picolinate A mixture of EXAMPLE 30A (0.220 g), EXAMPLE 66C (0.100 g) and tetrakis(triphenylphosphine)palladium(0) (0.019 g) was added dioxane (3 mL) and saturated aqueous $NaHCO_3$ solution (2 mL). The reaction was degassed with nitrogen then heated to 120° C. for 30 minutes. The mixture was partioned between ethyl acetate (75 mL) and water (75 mL) and filtered to remove solids. The organic layer was dried over magnesium sulfate, filtered, and concentrated. Silica gel chromatography, eluting with a gradient of 0.5% to 3.0% methanol/dichloromethane, provided the title compound.

Example 66E

6-[8-(1,3-benzothiazol-2-ylcarbamoyl)-3,4-dihydroisoquinolin-2(1H)-yl]-3-[5-methyl-1-(tetrahydro-2H-pyran-3-ylmethyl)-1H-pyrazol-4-yl]pyridine-2-carboxylic acid The title compound was prepared by substituting EXAMPLE 66D for EXAMPLE 8B in EXAMPLE 8C. $^1$H NMR (300 MHz, dimethylsulfoxide-$d_6$) δ ppm 12.84 (s, 1H), 8.03 (d, 1H), 7.79 (d, 1H), 7.61 (d, 1H), 7.52-7.40 (m, 3H), 7.40-7.31 (m, 2H), 7.27 (s, 1H), 6.95 (d, 1H), 4.96 (d, 2H), 3.93 (ddd, 3H), 3.75-3.64 (m, 1H), 3.59 (dd, 1H), 3.46-3.29 (m, 1H), 3.16 (s, 1H), 3.01 (s, 2H), 2.11 (s, 3H), 2.02 (s, 1H), 1.81-1.52 (m, 2H), 1.45 (ddd, 1H), 1.37-1.17 (m, 2H).

Example 67

6-[8-(1,3-benzothiazol-2-ylcarbamoyl)-3,4-dihydroisoquinolin-2(1H)-yl]-3-{1-[(1-phenylcyclohexyl)methyl]-1H-pyrazol-4-yl}pyridine-2-carboxylic acid

Example 67A (1-phenylcyclohexyl)methanol

To a solution of 1-phenylcyclohexanecarboxylic acid (1.32 g) in tetrahydrofuran (30 mL) at 0° C. was slowly added 2 M LiAlH$_4$ in tetrahydrofuran (6.46 mL). The resulting mixture was stirred at room temperature overnight and cooled to 0° C. Ice water was added to quench the reaction. The resulting mixture was diluted with ethyl acetate and washed with 1 N aqueous NaOH and water. The organic layer was dried over Na$_2$SO$_4$, filtered, and concentrated to provide the title compound.

Example 67B 1-((1-phenylcyclohexyl)methyl)-4-(4,4,5,5-tetramethyl-1,3,2-dioxaborolan-2-yl)-1H-pyrazole The title compound was prepared by substituting EXAMPLE 67A for (3-(dimethylamino)phenyl)methanol in EXAMPLE 34A.

Example 67C tert-butyl 6-(8-(benzo[d]thiazol-2-ylcarbamoyl)-3,4-dihydroisoquinolin-2(1H)-yl)-3-(1-((1-phenylcyclohexyl)methyl)-1H-pyrazol-4-yl)picolinate The title compound was prepared by substituting EXAMPLE 67B for 1-benzyl-4-(4,4,5,5-tetramethyl-1,3,2-dioxaborolan-2-yl)-1H-pyrazole in EXAMPLE 1E.

Example 67D

6-[8-(1,3-benzothiazol-2-ylcarbamoyl)-3,4-dihydroisoquinolin-2(1H)-yl]-3-{1-[(1-phenylcyclohexyl)methyl]-1H-pyrazol-4-yl}pyridine-2-carboxylic acid The title compound was prepared by substituting EXAMPLE 67C for EXAMPLE 8B in EXAMPLE 8C. $^1$H NMR (400 MHz, dimethylsulfoxide-$d_6$) δ ppm 12.85 (s, 2H), 8.04 (d, 1H), 7.80 (d, 1H), 7.61 (d, 1H), 7.39-7.51 (m, 4H), 7.32-7.39 (m, 2H), 7.25-7.32 (m, 2H), 7.14-7.24 (m, 3H), 6.87-6.94 (m, 2H), 4.92 (s, 2H), 4.11 (s, 2H), 3.85 (t, 2H), 2.98 (t, 2H), 2.13 (s, 2H), 1.51-1.65 (m, 4H), 1.42 (s, 1H), 1.16-1.33 (m, 3H).

Example 68

6-[8-(1,3-benzothiazol-2-ylcarbamoyl)-3,4-dihydroisoquinolin-2(1H)-yl]-3-(1-{3-[(dimethylamino)methyl]benzyl}-1H-pyrazol-4-yl)pyridine-2-carboxylic acid

Example 68A

6-[8-(1,3-benzothiazol-2-ylcarbamoyl)-3,4-dihydroisoquinolin-2(1H)-yl]-3-(1-{3-[(dimethylamino)methyl]benzyl}-1H-pyrazol-4-yl)pyridine-2-carboxylic acid tert butyl ester 64B (100 mg) was dissolved in dichloromethane (1 mL). Dimethylamine (2M, 0.373 mL) was added, and the solution was stirred at room temperature for 15 minutes. Sodium triacetoxyborohydride (38 mg) was then added, and the solution was stirred at room temperature for 16 hours. After this time more dimethylamine (2M, 0.373 mL) and sodium triacetoxyborohydride (38 mg) was added, and the solution was stirred for another 16 hours. The crude material was then purified on silica gel using 20% methanol (dichloromethane).

Example 68B

6-[8-(1,3-benzothiazol-2-ylcarbamoyl)-3,4-dihydroisoquinolin-2(1H)-yl]-3-(1-{3-[(dimethylamino)methyl]benzyl}-1H-pyrazol-4-yl)pyridine-2-carboxylic acid The title compound was prepared by substituting EXAMPLE 68A for EXAMPLE 7D in EXAMPLE 7E to isolate the title compound as the mono trifluoroacetic acid salt. $^1$H NMR (400 MHz, dimethylsulfoxide-$d_6$) δ ppm 12.84 (bs, 1H), 9.57 (bs, 1H), 8.04 (d, 1H), 7.92 (s, 1H), 7.80 (d, 1H), 7.71 (d, 1H), 7.64-7.57 (m, 2H), 7.51-7.32 (m, 8H), 6.95 (d, 1H), 5.37 (s, 2H), 4.95 (s, 2H), 4.25 (d, 2H), 3.87 (t, 2H), 3.00 (t, 2H), 2.71 (s, 3H), 2.70 (s, 3H).

Example 69

6-[8-(1,3-benzothiazol-2-ylcarbamoyl)-3,4-dihydroisoquinolin-2(1H)-yl]-3-{1-[3-(methylsulfonyl)benzyl]-1H-pyrazol-4-yl}pyridine-2-carboxylic acid

Example 69A 1-(3-methanesulfonyl-benzyl)-4-(4,4,5,5-tetramethyl-[1,3,2]dioxaborolan-2-yl)-1H-pyrazole The title compound was prepared by substituting 1-(bromomethyl)-3-(methylsulfonyl)benzene for EXAMPLE 4A in EXAMPLE 4B.

Example 69B

6-[8-(1,3-benzothiazol-2-ylcarbamoyl)-3,4-dihydroisoquinolin-2(H)-yl]-3-{1-[3-(methylsulfonyl)benzyl]-1H-pyrazol-4-yl}pyridine-2-carboxylic acid tert-butyl ester The title compound was prepared by substituting EXAMPLE 69A for EXAMPLE 58A in EXAMPLE 58B.

Example 69C

6-[8-(1,3-benzothiazol-2-ylcarbamoyl)-3,4-dihydroisoquinolin-2(1H)-yl]-3-{1-[3-(methylsulfonyl)benzyl]-1H-pyrazol-4-yl}pyridine-2-carboxylic acid The title compound was prepared by substituting EXAMPLE 69B for EXAMPLE 7D in EXAMPLE 7E. $^1$H NMR (400 MHz, dimethylsulfoxide-$d_6$) δ ppm 12.85 (bs, 1H), 8.04 (d, 1H), 7.99 (s, 1H), 7.89-7.84 (m, 3H), 7.78 (s, 1H), 7.72 (d, 1H), 7.65-7.61 (m, 3H), 7.56-7.37 (m, 4H), 6.96 (d, 1H), 5.47 (s, 2H), 4.95 (s, 2H), 3.87 (t, 2H), 3.20 (s, 3H), 3.00 (t, 2H).

Example 70

6-[8-(1,3-benzothiazol-2-ylcarbamoyl)-3,4-dihydroisoquinolin-2(1H)-yl]-3-[1-(cyclohexylmethyl)-5-cyclopropyl-1H-pyrazol-4-yl]pyridine-2-carboxylic acid

Example 70A 2-(5-cyclopropyl-1H-pyrazol-3-yl)isoindoline-1,3-dione

5-Cyclopropyl-1H-pyrazol-3-amine (5 g) was slurried in dioxane (80 mL) and N,N-dimethylformamide (80 mL), then phthalic anhydride (6 g) was added and the reaction was heated at 120° C. for 4 days. The reaction was cooled and concentrated. The crude material was triturated with isopropyl ether/ethanol 1/1 (30 mL) to provide the title compound.

Example 70B 2-(1-(cyclohexylmethyl)-5-cyclopropyl-1H-pyrazol-3-yl)isoindoline-1,3-dione EXAMPLE 70A (4.5 g) was dissolved in N,N-dimethylformamide (77 mL), then (bromomethyl)cyclohexane (4.0 g) was added, followed by 95% sodium hydride (0.6 g). The reaction was heated at 70° C. for 2 hours. The reaction mixture was then cooled, diluted with water and extracted with ethyl acetate. The organic layer was washed with brine and the combined aqueous layers were back-extracted with ethyl acetate. The combined organic layers were dried over $Na_2SO_4$. The crude material was purified by column chromatography on silica gel using 0-4% ethyl acetate in dichloromethane to give a mixture of the title compound and the 3-cyclopropyl isomer.

Example 70C 1-(cyclohexylmethyl)-5-cyclopropyl-1H-pyrazol-3-amine

EXAMPLE 70B (1.4 g) was dissolved in ethanol (70 mL) then hydrazine hydrate (1.1 mL) was added and the reaction heated under reflux for 40 minutes. The reaction was then cooled and filtered, and the filtrate was concentrated to give the crude product. The title compound was isolated by column chromatography on silica gel using 0.5-2.0% methanol in dichloromethane.

Example 70D 1-(cyclohexylmethyl)-5-cyclopropyl-1H-pyrazole

EXAMPLE 70C (415 mg) was dissolved in tetrahydrofuran (12 mL), then isoamyl nitrite (774 mg) was added and the reaction was heated at 60° C. overnight. The reaction was then cooled, concentrated, and purified by column chromatography on silica gel using 85/15 hexanes/ethyl acetate.

Example 70E 4-bromo-1-(cyclohexylmethyl)-5-cyclopropyl-1H-pyrazole

The title compound was prepared by substituting EXAMPLE 70D for EXAMPLE 63B in EXAMPLE 63C.

Example 70F 1-(cyclohexylmethyl)-5-cyclopropyl-4-(4,4,5,5-tetramethyl-1,3,2-dioxaborolan-2-yl)-1H-pyrazole The title compound was prepared by substituting EXAMPLE 70E for EXAMPLE 84C in EXAMPLE 84D, except the crude product was purified by column chromatography on silica gel using 5-12% ethyl acetate in hexanes.

Example 70G tert-butyl 6-[8-(1,3-benzothiazol-2-ylcarbamoyl)-3,4-dihydroisoquinolin-2(1H)-yl]-3-[1-(cyclohexylmethyl)-5-cyclopropyl-1H-pyrazol-4-yl]pyridine-2-carboxylate The title compound was prepared by substituting EXAMPLE 70F for EXAMPLE 22A in EXAMPLE 22B.

Example 70H

6-[8-(1,3-benzothiazol-2-ylcarbamoyl)-3,4-dihydroisoquinolin-2(1H)-yl]-3-[1-(cyclohexylmethyl)-5-cyclopropyl-1H-pyrazol-4-yl]pyridine-2-carboxylic acid The title compound was prepared by substituting EXAMPLE 70G for EXAMPLE 8B in EXAMPLE 8C. $^1$H NMR (400 MHz, dimethylsulfoxide-$d_6$) δ ppm 12.85 (br s, 1H), 8.03 (d, 1H), 7.79 (d, 1H), 7.61 (d, 1H), 7.54 (d, 1H), 7.45 (m, 2H), 7.36 (m, 2H), 7.22 (s, 1H), 6.93 (d, 1H), 4.96 (s, 2H), 3.97 (d, 2H), 3.89 (t, 2H), 3.01 (t, 2H), 1.60-1.69 (m, 7H), 1.16 (m, 3H), 0.98 (m, 2H), 0.79 (m, 2H), 0.25 (m, 2H).

Example 71

6-[8-(1,3-benzothiazol-2-ylcarbamoyl)-3,4-dihydroisoquinolin-2(1H)-yl]-3-[1-(3,5-di-tert-butylbenzyl)-1H-pyrazol-4-yl]pyridine-2-carboxylic acid

Example 71A 1-(3,5-di-tert-butylbenzyl)-4-(4,4,5,5-tetramethyl-1,3,2-dioxaborolan-2-yl)-1H-pyrazole The title compound was prepared by substituting 1-(bromomethyl)-3,5-di-tert-butylbenzene for EXAMPLE 4A in EXAMPLE 4B.

Example 71B tert-butyl 6-[8-(1,3-benzothiazol-2-ylcarbamoyl)-3,
4-dihydroisoquinolin-2(1H)-yl]-3-[1-(3,5-di-tert-
butylbenzyl)-1H-pyrazol-4-yl]pyridine-2-carboxy-
late The title compound was prepared by substituting EXAMPLE 71A for EXAMPLE 22A in EXAMPLE 22B.

Example 71C

6-[8-(1,3-benzothiazol-2-ylcarbamoyl)-3,4-dihy-
droisoquinolin-2(1H)-yl]-3-[1-(3,5-di-tert-butylben-
zyl)-1H-pyrazol-4-yl]pyridine-2-carboxylic acid The title compound was prepared by substituting EXAMPLE 718 for EXAMPLE 7D in EXAMPLE 7E. $^1$H NMR (400 MHz, dimethylsulfoxide-$d_6$) δ ppm 12.86 (br s, 1H), 8.04 (d, 1H), 7.93 (s, 1H), 7.79 (d, 1H), 7.69 (d, 1H), 7.61 (d, 1H), 7.58 (s, 1H), 7.48 (m, 1H), 7.43 (d, 1H), 7.36 (t, 2H), 7.29 (m, 1H), 7.05 (d, 2H), 6.94 (d, 1H), 5.29 (s, 2H), 4.95 (s, 2H), 3.87 (t, 2H), 3.00 (t, 2H), 1.24 (s, 18H).

Example 72

6-[8-(1,3-benzothiazol-2-ylcarbamoyl)-3,4-dihy-
droisoquinolin-2(1H)-yl]-3-{1-[2-(morpholin-4-yl-
sulfonyl)benzyl]-1H-pyrazol-4-yl}pyridine-2-car-
boxylic acid

Example 72A

4-{2-[4-(4,4,5,5-Tetramethyl-[1,3,2]dioxaborolan-2-
yl)-pyrazol-1-ylmethyl]-benzenesulfonyl}-morpho-
line The title compound was prepared by substituting 1-(bromomethyl)-2-(phenylsulfonylmethyl)benzene for EXAMPLE 4A in EXAMPLE 4B.

Example 72B

6-[8-(1,3-benzothiazol-2-ylcarbamoyl)-3,4-dihy-
droisoquinolin-2(1H)-yl]-3-{1-[2-(morpholin-4-yl-
sulfonyl)benzyl]-1H-pyrazol-4-yl}pyridine-2-car-
boxylic acid tert-butyl ester The title compound was prepared by substituting EXAMPLE 72A for EXAMPLE 58A in EXAMPLE 58B.

Example 72C

6-[8-(1,3-benzothiazol-2-ylcarbamoyl)-3,4-dihy-
droisoquinolin-2(1H)-yl]-3-{1-[2-(morpholin-4-yl-
sulfonyl)benzyl]-1H-pyrazol-4-yl}pyridine-2-car-
boxylic acid The title compound was prepared by substituting EXAMPLE 72B for EXAMPLE 7D in EXAMPLE 7E. $^1$H NMR (400 MHz, dimethylsulfoxide-$d_6$) δ ppm 12.84 (bs, 1H), 8.04 (d, 1H), 7.87 (d, 1H), 7.80 (d, 1H), 7.74 (d, 1H), 7.65-7.52 (m, 5H), 7.51-7.32 (m, 5H), 6.97 (d, 1H), 5.74 (s, 2H), 4.96 (s, 2H), 3.88 (t, 2H), 3.64 (m, 4H), 3.26 (m, 4H), 3.00 (t, 2H).

Example 73

6-[8-(1,3-benzothiazol-2-ylcarbamoyl)-3,4-dihy-
droisoquinolin-2(1H)-yl]-3-{1-[(4,4-difluorocyclo-
hexyl)methyl]-5-methyl-1H-pyrazol-4-yl}pyridine-
2-carboxylic acid

Example 73A (4,4-difluorocyclohexyl)methanol

To a solution of ethyl 4,4-difluorocyclohexanecarboxylate (1.000 g) in diethyl ether (5 mL) was added lithium aluminum hydride (1.0M in tetrahydrofuran) (6.24 mL) at 0° C. The reaction was allowed to warm to room temperature and was stirred for 2 hours. The reaction was cooled to 0° C. and quenched with water (0.24 mL). 15% Aqueous NaOH (0.24 mL) was added followed by more water (0.72 mL). The reaction was stirred for 1 hour, and magnesium sulfate was added. The mixture was filtered and concentrated to provide the title compound.

Example 73B 1-((4,4-difluorocyclohexyl)methyl)-1H-pyrazole

The title compound was prepared by substituting EXAMPLE 73A for (3-(dimethylamino)phenyl)methanol and 1H-pyrazole for 4-(4,4,5,5-tetramethyl-1,3,2-dioxaborolan-2-yl)-1H-pyrazole in EXAMPLE 34A.

Example 73C 4-bromo-1-((4,4-difluorocyclohexyl)methyl)-5-me-
thyl-1H-pyrazole A solution of EXAMPLE 73B (0.795 g) in tetrahydrofuran (15 mL) was cooled to −40° C. n-BuLi (1.6 M in hexanes, 2.98 mL) was added and the reaction was stirred for 1 hour, then CH$_3$I (0.298 mL) was added and the reaction warmed to 0° C. The reaction was diluted with ethyl acetate (25 mL) and washed with water (25 mL) and brine (25 mL). The combined organic layers were dried over magnesium sulfate, filtered and concentrated. The residue was dissolved in N,N-dimethylformamide (10 mL) and N-bromosuccinimide (0.777 g) was added. After 1 hour, the reaction was diluted with ethyl acetate (75 mL), washed with water (50 mL) and brine (50 mL), dried over magnesium sulfate, filtered and concentrated. Silica gel chromatography eluting with a gradient of hexanes/ethyl acetate provided the title compound.

Example 73D 1-((4,4-difluorocyclohexyl)methyl)-5-methyl-4-(4,4,
5,5-tetramethyl-1,3,2-dioxaborolan-2-yl)-1H-pyra-
zole The title compound was prepared by substituting EXAMPLE 73C for EXAMPLE 84C in EXAMPLE 84D.

Example 73E tert-butyl 6-(8-(benzo[d]thiazol-2-ylcarbamoyl)-3,4-
dihydroisoquinolin-2(1H)-yl)-3-(1-((4,4-difluorocy-
clohexyl)methyl)-5-methyl-1H-pyrazol-4-yl)picoli-
nate The title compound was prepared by substituting EXAMPLE 73D for EXAMPLE 22A in EXAMPLE 22B.

Example 73F

6-[8-(1,3-benzothiazol-2-ylcarbamoyl)-3,4-dihydroisoquinolin-2(1H)-yl]-3-{1-[(4,4-difluorocyclohexyl)methyl]-5-methyl-1H-pyrazol-4-yl}pyridine-2-carboxylic acid The title compound was prepared by substituting EXAMPLE 73E for EXAMPLE 8B in EXAMPLE 8C. $^1$H NMR (300 MHz, dimethylsulfoxide-$d_6$) δ ppm 12.86 (s, 2H), 8.04 (d, 1H), 7.79 (d, 1H), 7.61 (d, 1H), 7.56-7.40 (m, 3H), 7.36 (ddd, 2H), 7.28 (s, 1H), 6.95 (d, 1H), 4.95 (s, 2H), 4.09-3.81 (m, 4H), 3.02 (d, 2H), 2.11 (s, 3H), 1.79 (m, 7H), 1.25 (d, 2H).

Example 74

6-[8-(1,3-benzothiazol-2-ylcarbamoyl)-3,4-dihydroisoquinolin-2(1H)-yl]-3-(1-{[1-(trifluoromethyl)cyclohexyl]methyl}-1H-pyrazol-4-yl)pyridine-2-carboxylic acid

Example 74A (1-(trifluoromethyl)cyclohexyl)methanol

The title compound was prepared by substituting 1-trifluoromethylcyclohexanecarboxylic acid for 1-phenylcyclohexanecarboxylic acid in EXAMPLE 67A.

Example 74B 4-(4,4,5,5-tetramethyl-1,3,2-dioxaborolan-2-yl)-1((1-(trifluoromethyl)cyclohexyl)methyl)-1H-pyrazole The title compound was prepared by substituting EXAMPLE 74A for (3-(dimethylamino)phenyl)methanol in EXAMPLE 34A.

Example 74C tert-butyl 6-(8-(benzo[d]thiazol-2-ylcarbamoyl)-3,4-dihydroisoquinolin-2(1H)-yl)-3-(14(1-(trifluoromethyl)cyclohexyl)methyl)-1H-pyrazol-4-yl)picolinate The title compound was prepared by substituting EXAMPLE 74B for 1-benzyl-4-(4,4,5,5-tetramethyl-1,3,2-dioxaborolan-2-yl)-1H-pyrazole in EXAMPLE 1E.

Example 74D

6-[8-(1,3-benzothiazol-2-ylcarbamoyl)-3,4-dihydroisoquinolin-2(1H)-yl]-3-(1-{[1-(trifluoromethyl)cyclohexyl]methyl}-1H-pyrazol-4-yl)pyridine-2-carboxylic acid The title compound was prepared by substituting EXAMPLE 74C for EXAMPLE 8B in EXAMPLE 8C. $^1$H NMR (400 MHz, dimethylsulfoxide-$d_6$) δ ppm 12.87 (s, 2H), 8.04 (d, 1H), 7.80 (d, 1H), 7.69-7.73 (m, 2H), 7.57-7.63 (m, 2H), 7.45-7.51 (m, 1H), 7.41-7.44 (m, 1H), 7.36 (t, 2H), 6.94 (d, 1H), 4.95 (s, 2H), 4.42 (s, 2H), 3.87 (t, 2H), 3.00 (t, 2H), 1.46-1.73 (m, 9H), 1.17-1.32 (m, 1H).

Example 75

6-[8-(1,3-benzothiazol-2-ylcarbamoyl)-3,4-dihydroisoquinolin-2(1H)-yl]-3-[1-(diphenylmethyl)-1H-pyrazol-4-yl]pyridine-2-carboxylic acid

Example 75A 1-benzhydryl-4-bromo-1H-pyrazole

A solution of 4-bromo-1H-pyrazole (0.294 g), (bromomethylene)dibenzene (0.494 g) and triethylamine (0.418 mL) in tetrahydrofuran (5 mL) was stirred at 60° C. for 24 hours. The reaction mixture was concentrated and purified by chromatography on silica gel using 0-20% ethyl acetate/hexanes as eluent to provide the title compound.

Example 75B tert-butyl 3-(1-benzhydryl-1H-pyrazol-4-yl)-6-(8-(benzo[d]thiazol-2-ylcarbamoyl)-3,4-dihydroisoquinolin-2(1H)-yl)picolinate A suspension of EXAMPLE 30A (100 mg), EXAMPLE 75A (77 mg), tris(dibenzylideneacetone)dipalladium(0) (7.47 mg), 1,3,5,7-tetramethyl-6-phenyl-2,4,8-trioxa-6-phosphaadamantane (7.16 mg) and potassium phosphate (104 mg) in tetrahydrofuran (1.5 mL) and water (0.500 mL) was heated under microwave conditions (Biotage) at 80° C. for 30 minutes. The reaction mixture was diluted with ethyl acetate, and the organic layer was separated, dried and purified by chromatography on silica gel using 10-60% ethyl acetate/hexanes as eluent to provide the title compound.

Example 75C

6-[8-(1,3-benzothiazol-2-ylcarbamoyl)-3,4-dihydroisoquinolin-2(1H)-yl]-3-[1-(diphenylmethyl)-1H-pyrazol-4-yl]pyridine-2-carboxylic acid A suspension of EXAMPLE 75B (30 mg) and lithium hydroxide (2 mg) in tetrahydrofuran and methanol (2:1, 1 mL) was heated at 60° C. for 16 hours. The reaction mixture was quenched with HCl (0.2 mL, 1M), concentrated and purified by chromatography on silica gel using 0-5% methanol/dichloromethane as eluent to provide the title compound. $^1$H NMR (300 MHz, dimethylsulfoxide-$d_6$) δ ppm 13.14 (s, 1H), 12.87 (s, 1H), 8.04 (d, 1H), 7.82 (s, 1H), 7.79 (d, 1H), 7.73 (d, 1H), 7.66 (s, 1H), 7.61 (d, 1H), 7.44-7.51 (m, 1H), 7.40-7.44 (m, 1H), 7.29-7.40 (m, 5H), 7.19 (d, 4H), 6.93 (t, 2H), 4.94 (s, 2H), 3.94 (s, 1H), 3.86 (t, 2H), 2.99 (t, 1H).

Example 76

6-[8-(1,3-benzothiazol-2-ylcarbamoyl)-3,4-dihydroisoquinolin-2(1H)-yl]-3-{1-[2-(morpholin-4-yl)benzyl]-1H-pyrazol-4-yl}pyridine-2-carboxylic acid

Example 76A 4-(2-((4-bromo-1H-pyrazol-1-yl)methyl)phenyl)morpholine

The title compound was prepared by substituting 4-bromo-1H-pyrazole for 4-(4,4,5,5-tetramethyl-1,3,2-dioxaborolan- 2-yl)-1H-pyrazole and (2-morpholinophenyl)methanol for (3-(dimethylamino)phenyl)methanol in EXAMPLE 34A.

Example 76B tert-butyl 6-(8-(benzo[d]thiazol-2-ylcarbamoyl)-3,4-dihydroisoquinolin-2(1H)-yl)-3-(1-(2-morpholinobenzyl)-1H-pyrazol-4-yl)picolinate The title compound was prepared by substituting EXAMPLE 76A for EXAMPLE 77D in EXAMPLE 77E.

Example 76C

6-[8-(1,3-benzothiazol-2-ylcarbamoyl)-3,4-dihydroisoquinolin-2(1H)-yl]-3-{1-[2-(morpholin-4-yl)benzyl]-1H-pyrazol-4-yl}pyridine-2-carboxylic acid The title compound was prepared by substituting EXAMPLE 76B for EXAMPLE 8B in EXAMPLE 8C. $^1$H NMR (300 MHz, dimethylsulfoxide-$d_6$) δ ppm 12.84 (s, 1H), 8.04 (d, 1H), 7.89 (s, 1H), 7.79 (d, 1H), 7.72 (d, 1H), 7.61 (d, 1H), 7.57 (s, 1H), 7.40-7.51 (m, 2H), 7.36 (t, 2H), 7.24-7.32 (m, 1H), 7.18-7.23 (m, 1H), 7.02-7.10 (m, 1H), 6.94 (d, 1H), 6.86-6.92 (m, 1H), 5.41 (s, 2H), 4.94 (s, 2H), 3.87 (t, 2H), 3.72-3.78 (m, 4H), 3.00 (t, 2H), 2.78-2.86 (m, 4H).

Example 77

6-[8-(1,3-benzothiazol-2-ylcarbamoyl)-3,4-dihydroisoquinolin-2(1H)-yl]-3-{1-[3-(morpholin-4-yl)-1-phenylpropyl]-1H-pyrazol-4-yl}pyridine-2-carboxylic acid

Example 77A 1-(3,3-dimethoxy-1-phenylpropyl)-1H-pyrazole

To a solution of 1-benzyl-1H-pyrazole (0.653 g) in tetrahydrofuran (5 mL) cooled to −78° C. was dropwise added 1.6M n-butyllithium (2.84 mL). The reaction mixture was stirred for 60 minutes, and 2-chloro-1,1-dimethoxyethane (0.517 mL) was added, and stirring continued for 3 hours. The reaction mixture was allowed to slowly warm up to room temperature, and was quenched with water, extracted with ether, dried over $Na_2SO_4$, filtered, and concentrated. The product was purified by chromatography on silica gel using 0-20% ethyl acetate/hexanes as the eluent to provide the title compound.

Example 77B 4-bromo-1-(3,3-dimethoxy-1-phenylpropyl)-1H-pyrazole

The title compound was prepared by substituting EXAMPLE 77A for EXAMPLE 63B in EXAMPLE 63C.

Example 77C 3-(4-bromo-1H-pyrazol-1-yl)-3-phenylpropanal

A solution of EXAMPLE 77B (0.34 g) and hydrochloric acid (2 mL) in tetrahydrofuran (3.5 mL) was stirred at room temperature for 16 hours. The reaction mixture was concentrated, redissolved in dichloromethane, dried over magnesium sulfate, filtered, and used in the next step without purification.

Example 77D 4-(3-(4-bromo-1H-pyrazol-1-yl)-3-phenylpropyl)morpholine

A suspension of EXAMPLE 77C (150 mg), morpholine (0.117 mL), acetic acid (0.062 mL) and solid-supported MP-$CNBH_3$ (Argonaut Technologies, 885 mg, 2.63 mmol/g) in dichloromethane (4 mL) and methanol (2 mL) was shaken at room temperature for 18 hours. The reaction mixture was filtered, concentrated and purified by RP HPLC (30-100% $CH_3CN$/water/0.1% TFA) to provide the title compound.

Example 77E tert-butyl 6-(8-(benzo[d]thiazol-2-ylcarbamoyl)-3,4-dihydroisoquinolin-2(1H)-yl)-3-(1-(3-morpholino-1-phenylpropyl)-1H-pyrazol-4-yl)picolinate A suspension of EXAMPLE 30A (100 mg), EXAMPLE 77D (50 mg), tris(dibenzylideneacetone)dipalladium(0) (14 mg), 1,3,5,7-tetramethyl-6-phenyl-2,4,8-trioxa-6-phosphaadamantane (24 mg) and potassium phosphate (104 mg) in tetrahydrofuran (3 mL) and water (1.5 mL) was heated under microwave conditions (Biotage) at 140° C. for 5 minutes. The reaction mixture was diluted with ethyl acetate, separated, and purified by chromatography on silica gel using 10-60% ethyl acetate/hexanes as eluent to provide the title compound.

Example 77F

6-[8-(1,3-benzothiazol-2-ylcarbamoyl)-3,4-dihydroisoquinolin-2(1H)-yl]-3-{1-[3-(morpholin-4-yl)-1-phenylpropyl]-1H-pyrazol-4-yl}pyridine-2-carboxylic acid The title compound was prepared by substituting EXAMPLE 77E for EXAMPLE 8B in EXAMPLE 8C. $^1$H NMR (300 MHz, dimethylsulfoxide-$d_6$) δ ppm 12.85 (s, 1H), 9.65 (s, 1H), 8.04 (d, 1H), 7.97 (s, 1H), 7.79 (d, 1H), 7.72 (d, 1H), 7.67 (s, 1H), 7.61 (d, 1H), 7.45-7.52 (m, 1H), 7.42 (t, 1H), 7.29-7.39 (m, 7H) 6.95 (d, 1H), 5.57 (dd, 1H), 4.95 (s, 2H), 3.96 (d, 4H), 3.82-3.90 (m, 2H), 3.60 (t, 2H), 3.46 (d, 2H), 3.04-3.17 (m, 4H), 3.00 (t, 2H), 2.76-2.93 (m, 2H).

Example 78

6-[8-(1,3-benzothiazol-2-ylcarbamoyl)-3,4-dihydroisoquinolin-2(1H)-yl]-3-(1-{[1-(tert-butoxycarbonyl)piperidin-4-yl]methyl}-1H-pyrazol-4-yl)pyridine-2-carboxylic acid

Example 78A tert-butyl 4-((4-bromo-1H-pyrazol-1-yl)methyl)piperidine-1-carboxylate The title compound was prepared by substituting 4-bromo-1H-pyrazole for 4-(4,4,5,5-tetramethyl-1,3,2-dioxaborolan-2-yl)-1H-pyrazole and tert-butyl 4-(hydroxymethyl)piperidine-1-carboxylate for (3-(dimethylamino)phenyl)methanol in EXAMPLE 34A.

Example 78B tert-butyl 6-(8-(benzo[d]thiazol-2-ylcarbamoyl)-3,4-dihydroisoquinolin-2(1H)-yl)-3-(1-((1-(tert-butoxycarbonyl)piperidin-4-yl)methyl)-1H-pyrazol-4-yl)picolinate The title compound was prepared by substituting EXAMPLE 78A for EXAMPLE 77D in EXAMPLE 77E.

Example 78C

6-[8-(1,3-benzothiazol-2-ylcarbamoyl)-3,4-dihydroisoquinolin-2(1H)-yl]-3-(1-{[1-(tert-butoxycarbonyl)piperidin-4-yl]methyl}-1H-pyrazol-4-yl)pyridine-2-carboxylic acid The title compound was prepared by substituting EXAMPLE 78B for EXAMPLE 75B in EXAMPLE 75C. $^1$H NMR (300 MHz, dimethylsulfoxide-$d_6$) δ ppm 12.58-13.32 (m, 1H), 8.04 (d, 1H), 7.79 (d, 1H), 7.76 (s, 1H), 7.69 (d, 1H), 7.61 (d, 1H), 7.54 (s, 1H), 7.45-7.51 (m, 1H), 7.39-7.44 (m, 1H), 7.36 (t, 2H), 6.93 (d, 1H), 4.94 (s, 2H), 3.80-4.04 (m, 4H), 3.00 (t, 2H), 2.69 (d, 2H), 1.86-2.02 (m, 1H), 1.45 (d, 2H), 1.37 (s, 9H), 0.93-1.14 (m, 2H).

Example 79

6-[8-(1,3-benzothiazol-2-ylcarbamoyl)-3,4-dihydroisoquinolin-2(1H)-yl]-3-(5-methyl-1-{2-[2-(morpholin-4-yl)ethoxy]benzyl}-1H-pyrazol-4-yl)pyridine-2-carboxylic acid

Example 79A 1-(2-(benzyloxy)benzyl)-4-iodo-5-methyl-1H-pyrazole

The title compound was prepared by substituting 3-methyl-4-iodopyrazole for 4-(4,4,5,5-tetramethyl-1,3,2-dioxaborolan-2-yl)-1H-pyrazole and 1-(benzyloxy)-2-(bromomethyl)benzene for EXAMPLE 4A in EXAMPLE 4B.

Example 79B 2-((4-iodo-5-methyl-1H-pyrazol-1-yl)methyl)phenol

In a 20 mL round-bottomed flask, EXAMPLE 79A (0.65 g) was added to dichloromethane (5 mL) to give a solution. The solution was cooled to 0° C., and tribromoborane (1.7 mL, 1M in hexane) was added slowly. After stirring at room temperature for 4 hours, methanol (10 mL) was added slowly. The solvent was removed, and the residue taken up into dichloromethane and purified by flash chromatography (Varian, Superflash SF25-40 g column), eluting with 0-30% ethyl acetate/hexane to provide the title compound.

Example 79C

EXAMPLE 79B (0.05 g), 2-(morpholino)ethanol (0.03 g), di-tert-butyl azodicarboxylate (0.06 g) and triphenylphosphine (0.1 g) were stirred at room temperature overnight. The crude product was purified by flash chromatography (Varian, Superflash SF25-40 g column), eluting with 0-10% methanol in dichloromethane to provide the title compound.

Example 79D

Tert-butyl 6-(8-(benzo[d]thiazol-2-ylcarbamoyl)-3,4-dihydroisoquinolin-2(1H)-yl)-3-(5-methyl-1-(2-(2-morpholinoethoxy)benzyl)-1H-pyrazol-4-yl)picolinate The title compound was prepared by substituting EXAMPLE 79C for EXAMPLE 77D in EXAMPLE 77E.

Example 79E

6-[8-(1,3-benzothiazol-2-ylcarbamoyl)-3,4-dihydroisoquinolin-2(1H)-yl]-3-(5-methyl-1-{2-[2-(morpholin-4-yl)ethoxy]benzyl}-1H-pyrazol-4-yl)pyridine-2-carboxylic acid The title compound was prepared by substituting EXAMPLE 79D for EXAMPLE 1E in EXAMPLE 1F. $^1$H NMR (300 MHz, dimethylsulfoxide-$d_6$) δ ppm 12.84 (s, 1H), 9.84 (s, 1H), 8.03 (d, 1H), 7.79 (d, 1H), 7.57 (m, 2H), 7.36 (m, 6H), 7.08 (d, 1H), 6.94 (m, 2H), 6.66 (d, 1H), 5.32 (s, 2H), 4.96 (s, 2H), 4.39 (m, 2H), 4.01 (m, 2H), 3.89 (t, 2H), 3.25 (m, 2H), 3.01 (t, 2H), 2.07 (d, 3H).

Example 80

6-[8-(1,3-benzothiazol-2-ylcarbamoyl)-3,4-dihydroisoquinolin-2(1H)-yl]-3-{1-[2-(dimethylamino)benzyl]-1H-pyrazol-4-yl}pyridine-2-carboxylic acid

Example 80A (2-(dimethylamino)phenyl)methanol

In a 250 mL round-bottomed flask, (3-(dimethylamino)phenyl)methanol (1 g) and paraformaldehyde (2.5 g) were added to acetic acid (150 mL) to give a suspension. Sodium cyanoborohydride (2.6 g) was added slowly. The mixture was stirred at room temperature overnight. After concentration of the solvent, water and ethyl acetate (1:1, 100 mL) were added. After separation, the aqueous layer was extracted by ethyl acetate (2×20 mL). The combined organic layers were washed with water (3×50 mL), saturated aqueous $NaHCO_3$ (2×30 mL), and dried over $Na_2SO_4$. After filtration and concentration, the residue was taken up into $CH_2Cl_2$ and the product was purified by flash chromatography (Varian, Superflash SF40-80 g column), eluting with 0-20% methanol/dichloromethane, to provide the title compound.

Example 80B 2-((4-iodo-1H-pyrazol-1-yl)methyl)-N,N-dimethylaniline

The title compound was prepared by substituting 4-iodopyrazole for 4-(4,4,5,5-tetramethyl-1,3,2-dioxaborolan-2-yl)-1H-pyrazole and EXAMPLE 80A for EXAMPLE 4A in EXAMPLE 4B.

Example 80C

Tert-butyl 6-(8-(benzo[d]thiazol-2-ylcarbamoyl)-3,4-dihydroisoquinolin-2(1H)-yl)-3-(1-(2-(dimethylamino)benzyl)-1H-pyrazol-4-yl)picolinate The title compound was prepared by substituting EXAMPLE 80B for EXAMPLE 77D in EXAMPLE 77E.

Example 80D

6-[8-(1,3-benzothiazol-2-ylcarbamoyl)-3,4-dihydroisoquinolin-2(1H)-yl]-3-{1-[2-(dimethylamino)benzyl]-1H-pyrazol-4-yl}pyridine-2-carboxylic acid The title compound was prepared by substituting EXAMPLE 80C for EXAMPLE 1E in EXAMPLE 1F. $^1$H NMR (300 MHz, dimethylsulfoxide-$d_6$) δ ppm 12.84 (s, 1H), 8.04 (d, 1H), 7.89 (s, 1H), 7.79 (d, 1H), 7.72 (d, 1H), 7.61 (m, 2H), 7.37 (m, 6H), 7.03 (m, 1H), 6.94 (d, 1H), 6.85 (d, 1H), 5.42 (s, 2H), 4.95 (s, 2H), 3.87 (t, 2H), 3.00 (t, 2H), 2.71 (s, 6H).

Example 81

6-[8-(1,3-benzothiazol-2-ylcarbamoyl)-3,4-dihydroisoquinolin-2(1H)-yl]-3-(5-methyl-1-{2-[3-(morpholin-4-yl)propoxy]benzyl}-1H-pyrazol-4-yl)pyridine-2-carboxylic acid

Example 81A 4-(3-(2-((4-iodo-5-methyl-1H-pyrazol-1-yl)methyl)phenoxy)propyl)morpholine The title compound was prepared by substituting 3-morpholinopropan-1-ol for 2-morpholinoethanol in EXAMPLE 79C.

Example 81B

Tert-butyl 6-(8-(benzo[d]thiazol-2-ylcarbamoyl)-3,4-dihydroisoquinolin-2(1H)-yl)-3-(5-methyl-1-(2-(3-morpholinopropoxy)benzyl)-1H-pyrazol-4-yl)picolinate The title compound was prepared by substituting EXAMPLE 81A for EXAMPLE 77D in EXAMPLE 77E.

Example 81C

6-[8-(1,3-benzothiazol-2-ylcarbamoyl)-3,4-dihydroisoquinolin-2(1H)-yl]-3-(5-methyl-1-{2-[3-(morpholin-4-yl)propoxy]benzyl}-1H-pyrazol-4-yl)pyridine-2-carboxylic acid The title compound was prepared by substituting EXAMPLE 811B for EXAMPLE 1E in EXAMPLE 1F. $^1$H NMR (300 MHz, dimethylsulfoxide-$d_6$) δ ppm 12.84 (s, 1H), 8.04 (d, 1H), 7.79 (d, 1H), 7.44 (m, 9H), 6.95 (m, 3H), 6.60 (d, 1H), 5.29 (s, 2H), 4.96 (s, 2H), 4.12 (t, 2H), 3.95 (m, 4H), 3.57 (m, 4H), 3.36 (m, 2H), 3.07 (m, 4H), 2.17 (m, 2H), 2.07 (s, 3H).

Example 82

6-[8-(1,3-benzothiazol-2-ylcarbamoyl)-3,4-dihydroisoquinolin-2(1H)-yl]-3-{5-methyl-1-[(1-methylcyclohexyl)methyl]-1H-pyrazol-4-yl}pyridine-2-carboxylic acid

Example 82A (1-methylcyclohexyl)methanol

The title compound was prepared by substituting 1-methylcyclohexanecarboxylic acid for ethyl 4,4-difluorocyclohexanecarboxylate in EXAMPLE 73A.

Example 82B 1-((1-methylcyclohexyl)methyl)-1H-pyrazole

The title compound was prepared by substituting EXAMPLE 82A for (3-(dimethylamino)phenyl)methanol and 1H-pyrazole for 4-(4,4,5,5-tetramethyl-1,3,2-dioxaborolan-2-yl)-1H-pyrazole in EXAMPLE 34A.

Example 82C 4-bromo-5-methyl-1-((1-methylcyclohexyl)methyl)-1H-pyrazole

The title compound was prepared by substituting EXAMPLE 82B for EXAMPLE 63A in EXAMPLE 63B and then substituting that product for EXAMPLE 63B in EXAMPLE 63C.

Example 82D 5-methyl-1-((1-methylcyclohexyl)methyl)-4-(4,4,5,5-tetramethyl-1,3,2-dioxaborolan-2-yl)-1H-pyrazole The title compound was prepared by substituting EXAMPLE 82C for EXAMPLE 63C in EXAMPLE 63D.

Example 82E tert-butyl 6-(8-(benzo[d]thiazol-2-ylcarbamoyl)-3,4-dihydroisoquinolin-2(1H)-yl)-3-(5-methyl-1-((1-methylcyclohexyl)methyl)-1H-pyrazol-4-yl)picolinate A mixture of EXAMPLE 1D (0.240 g), EXAMPLE 82D (0.135 g), 1,3,5,7-tetramethyl-6-phenyl-2,4,8-trioxa-6-phosphaadamantane (0.012 g), potassium phosphate (0.315 g) and tris(dibenzylideneacetone)dipalladium(0) (0.022 g) were added to N,N-dimethylformamide (0.6 mL), dioxane (0.4 mL) and water (0.2 mL). The reaction was degassed with nitrogen, sealed and heated to 110° C. After 3 hours the reaction was cooled, diluted with ethyl acetate (50 mL) and washed with water (30 mL) and brine (30 mL). The reaction was dried over magnesium sulfate, filtered, and concentrated. Silica gel chromatography eluting with a gradient of 5% to 45% ethyl acetate/hexanes over 30 minutes provided the title compound.

Example 82F

6-[8-(1,3-benzothiazol-2-ylcarbamoyl)-3,4-dihydroisoquinolin-2(1H)-yl]-3-{5-methyl-1-[(1-methylcyclohexyl)methyl]-1H-pyrazol-4-yl}pyridine-2-carboxylic acid The title compound was prepared by substituting EXAMPLE 82E for EXAMPLE 8B in EXAMPLE 8C. $^1$H NMR (300 MHz, CDCl$_3$) δ ppm 7.85 (dt, 1H), 7.68-7.62 (m, 1H), 7.59 (dd, 1H), 7.53 (d, 1H), 7.45-7.30 (m, 5H), 7.01 (d, 1H), 5.17 (s, 2H), 3.89 (m, 4H), 3.12 (s, 2H), 2.09 (s, 3H), 1.49 (m, 10H), 0.96 (s, 3H).

Example 83

6-[8-(1,3-benzothiazol-2-ylcarbamoyl)-3,4-dihydroisoquinolin-2(1H)-yl]-3-(1-{[2-(4-chlorophenyl)-4,4-dimethylcyclohex-1-en-1-yl]methyl}-1H-pyrazol-4-yl)pyridine-2-carboxylic acid

Example 83A methyl 4,4-dimethyl-2-(trifluoromethylsulfonyloxy)cyclohex-1-enecarboxylate To a suspension of hexane washed NaH (17 g) in dichloromethane (700 mL) was added 5,5-dimethyl-2-methoxycarbonylcyclohexanone (38.5 g) dropwise at 0° C. After stirring for 30 minutes, the mixture was cooled to −78° C. and trifluoroacetic anhydride (40 mL) was added. The reaction mixture was warmed to room temperature and stirred for 24 hours. The organic layer was washed with brine, dried ($Na_2SO_4$), filtered, and concentrated to provide the title compound.

Example 83B methyl 2-(4-chlorophenyl)-4,4-dimethylcyclohex-1-enecarboxylate

EXAMPLE 83A (62.15 g), 4-chlorophenylboronic acid (32.24 g), CsF (64 g) and tetrakis(triphenylphosphine)palladium(0) (2 g) in 2:1 dimethoxyethane/methanol (600 mL) were heated to 70° C. for 24 hours. The mixture was concentrated. Diethyl ether (4×200 mL) was added and the mixture was filtered. The combined ether solution was concentrated to provide the title compound.

Example 83C (2-(4-chlorophenyl)-4,4-dimethylcyclohex-1-enyl)methanol

To a mixture of $LiBH_4$ (13 g), EXAMPLE 83B (53.8 g) and ether (400 mL), was added methanol (25 mL) slowly by syringe. The mixture was stirred at room temperature for 24 hours. The reaction was quenched with 1N HCl with ice-cooling. The mixture was diluted with water and extracted with ether (3×100 mL). The combined extracts were dried ($Na_2SO_4$), filtered, and concentrated. The crude product was purified on silica gel with 0-30% ethyl acetate/hexanes.

Example 83D

1-[2-(4-Chloro-phenyl)-4,4-dimethyl-cyclohex-1-enylmethyl]-4-(4,4,5,5-tetramethyl-[1,3,2]dioxaborolan-2-yl)-1H-pyrazole 4-(4,4,5,5-tetramethyl-1,3,2-dioxaborolan-2-yl)-1H-pyrazole (340 mg) and EXAMPLE 83C (400 mg) were dissolved in toluene (12 mL). Cyanomethylenetributylphosphorane (462 mg) was added, and the solution was mixed at room temperature for 16 hours. The solution was concentrated and purified on silica gel using 10% ethyl acetate in hexanes.

Example 83E

6-[8-(1,3-benzothiazol-2-ylcarbamoyl)-3,4-dihydroisoquinolin-2(1H)-yl]-3-(1-{[2-(4-chlorophenyl)-4,4-dimethylcyclohex-1-en-1-yl]methyl}-1H-pyrazol-4-yl)pyridine-2-carboxylic acid tert-butyl ester The title compound was prepared by substituting EXAMPLE 83D for EXAMPLE 58A in EXAMPLE 58B.

Example 83F

6-[8-(1,3-benzothiazol-2-ylcarbamoyl)-3,4-dihydroisoquinolin-2(1H)-yl]-3-(1-{[2-(4-chlorophenyl)-4,4-dimethylcyclohex-1-en-1-yl]methyl}-1H-pyrazol-4-yl)pyridine-2-carboxylic acid The title compound was prepared by substituting EXAMPLE 83E for EXAMPLE 7D in EXAMPLE 7E. $^1$H NMR (400 MHz, dimethylsulfoxide-$d_6$) δ ppm 12.85 (bs, 1H), 8.05 (d, 1H), 7.80 (d, 1H), 7.71 (d, 1H), 7.61 (d, 1H), 7.51-7.31 (m, 10H), 6.95 (d, 1H), 4.95 (s, 2H), 4.53 (s, 2H), 3.87 (t, 2H), 3.00 (t, 2H), 2.05 (bs, 2H), 1.88 (t, 2H), 1.36 (t, 2H), 0.92 (s, 6H).

Example 84

6-[8-(1,3-benzothiazol-2-ylcarbamoyl)-3,4-dihydroisoquinolin-2(1H)-yl]-3-[1-(cyclohexylmethyl)-5-ethyl-1H-pyrazol-4-yl]pyridine-2-carboxylic acid

Example 84A 1-(cyclohexylmethyl)-1H-pyrazole

The title compound was prepared by substituting (bromomethyl)cyclohexane for (bromomethyl)cyclopentane in EXAMPLE 63A.

Example 84B 1-(cyclohexylmethyl)-5-ethyl-1H-pyrazole

The title compound was prepared by substituting EXAMPLE 84A for EXAMPLE 63A and ethyl iodide for iodomethane in EXAMPLE 63B.

Example 84C 4-bromo-1-(cyclohexylmethyl)-5-ethyl-1H-pyrazole

The title compound was prepared by substituting EXAMPLE 84B for EXAMPLE 63B in EXAMPLE 63C.

Example 84D 1-(cyclohexylmethyl)-5-ethyl-4-(4,4,5,5-tetramethyl-1,3,2-dioxaborolan-2-yl)-1H-pyrazole EXAMPLE 84C (225 mg) was placed into a flask and degassed with $N_2$. Tetrahydrofuran (3 mL) and toluene (2 mL) were added and the solution was cooled to −78° C. Triisopropyl borate (0.23 mL) was added, followed by dropwise addition of n-butyllithium (2.3 M in hexanes, 0.6 mL) over 5 minutes. The mixture was stirred for 10 minutes at −78° C. and then a degassed solution of pinacol (135 mg) in tetrahydrofuran (1 mL) was added over 2 minutes. After stirring for 10 minutes at −78° C., the reaction was warmed to room temperature and stirred for 1 hour. Water (0.07 mL) was then added and the mixture was stirred for 2 hours. The crude reaction mixture was concentrated to dryness to provide the title compound.

Example 84E tert-butyl 6-(8-(benzo[d]thiazol-2-ylcarbamoyl)-3,4-dihydroisoquinolin-2(1H)-yl)-3-(1-(cyclohexylmethyl)-5-ethyl-1H-pyrazol-4-yl)picolinate The title compound was prepared by substituting EXAMPLE 84D for EXAMPLE 22A in EXAMPLE 22B.

Example 84F

6-[8-(1,3-benzothiazol-2-ylcarbamoyl)-3,4-dihydroisoquinolin-2(1H)-yl]-3-[1-(cyclohexylmethyl)-5-ethyl-1H-pyrazol-4-yl]pyridine-2-carboxylic acid The title compound was prepared by substituting EXAMPLE 84E for EXAMPLE 8B in EXAMPLE 8C. $^1$H NMR (300 MHz, dimethylsulfoxide-$d_6$) δ ppm 12.87 (s, 1H), 12.61-12.90 (br s, 1H), 8.04 (d, 1H), 7.79 (d, 1H), 7.79 (d, 1H), 7.62 (d, 1H), 7.41-7.51 (m, 3H), 7.32-7.40 (m, 2H), 7.21 (s, 1H), 6.93 (d, 1H), 4.95 (s, 2H), 3.88 (t, 2H), 3.83 (d, 2H), 3.01 (t, 2H), 2.54 (q, 2H), 1.76-1.93 (m, 1H), 1.58-1.72 (m, 3H), 1.52 (d, 2H), 1.08-1.25 (m, 3H), 0.96 (t, 3H), 0.89-1.05 (m, 2H).

Example 85

6-[8-(1,3-benzothiazol-2-ylcarbamoyl)-3,4-dihydroisoquinolin-2(1H)-yl]-3-(1-{[(1R,2R,5R)-6,6-dimethylbicyclo[3.1.1]hept-2-yl]methyl}-5-methyl-1H-pyrazol-4-yl)pyridine-2-carboxylic acid Example 85A 1-(((1R,2R,5R)-6,6-dimethylbicyclo[3.1.1]heptan-2-yl)methyl)-1H-pyrazole The title compound was prepared by substituting ((1R,2R,5R)-6,6-dimethylbicyclo[3.1.1]heptan-2-yl)methanol for (3-(dimethylamino)phenyl)methanol and pyrazole for 4-(4,4,5,5-tetramethyl-1,3,2-dioxaborolan-2-yl)-1H-pyrazole in EXAMPLE 34A.

Example 85B 1-(((1R,2R,5R)-6,6-dimethylbicyclo[3.1.1]heptan-2-yl)methyl)-5-methyl-1H-pyrazole The title compound was prepared by substituting EXAMPLE 85A for EXAMPLE 63A in EXAMPLE 63B.

Example 85C 4-bromo-1-(((1R,2R,5R)-6,6-dimethylbicyclo[3.1.1]heptan-2-yl)methyl)-5-methyl-1H-pyrazole The title compound was prepared by substituting EXAMPLE 85B for EXAMPLE 63B in EXAMPLE 63C.

Example 85D 1-(((1R,2R,5R)-6,6-dimethylbicyclo[3.1.1]heptan-2-yl)methyl)-5-methyl-4-(4,4,5,5-tetramethyl-1,3,2-dioxaborolan-2-yl)-1H-pyrazole The title compound was prepared by substituting EXAMPLE 85C for EXAMPLE 84C in EXAMPLE 84D.

Example 85E tert-butyl 6-(8-(benzo[d]thiazol-2-ylcarbamoyl)-3,4-dihydroisoquinolin-2(1H)-yl)-3-(1-(((1R,2R,5R)-6,6-dimethylbicyclo[3.1.1]heptan-2-yl)methyl)-5-methyl-1H-pyrazol-4-yl)picolinate The title compound was prepared by substituting EXAMPLE 85D for EXAMPLE 82D in EXAMPLE 82E.

Example 85F

6-[8-(1,3-benzothiazol-2-ylcarbamoyl)-3,4-dihydroisoquinolin-2(1H)-yl]-3-(1-{[(1R,2R,5R)-6,6-dimethylbicyclo[3.1.1]hept-2-yl]methyl}-5-methyl-1H-pyrazol-4-yl)pyridine-2-carboxylic acid The title compound was prepared by substituting EXAMPLE 85E for EXAMPLE 88 in EXAMPLE 8C. $^1$H NMR (300 MHz, dimethylsulfoxide-$d_6$) δ ppm 12.86 (s, 1H), 12.77 (br s, 1H), 8.04 (d, 1H), 7.79 (d, 1H), 7.61 (d, 1H), 7.47 (m, 3H), 7.35 (m, 2H), 7.25 (s, 1H), 6.94 (d, 1H), 4.95 (s, 2H), 3.89 (d, 2H), 3.84 (d, 2H), 3.01 (t, 2H), 2.49 (m, 1H), 2.08 (s, 3H), 2.04 (m, 1H), 1.84 (m, 1H), 1.73 (m, 2H), 1.60 (t, 1H), 1.51 (m, 1H), 1.41 (d, 1H), 1.35 (m, 1H), 1.15 (s, 3H), 0.78 (s, 3H).

Example 86

6-[8-(1,3-benzothiazol-2-ylcarbamoyl)-3,4-dihydroisoquinolin-2(1H)-yl]-3-(1-{[(1S,2R,5S)-6,6-dimethylbicyclo[3.1.1]hept-2-yl]methyl}-5-methyl-1H-pyrazol-4-yl)pyridine-2-carboxylic acid Example 86A 1-(((1S,2R,5S)-6,6-dimethylbicyclo[3.1.1]heptan-2-yl)methyl)-1H-pyrazole The title compound was prepared by substituting ((1S,2R,5S)-6,6-dimethylbicyclo[3.1.1]heptan-2-yl)methanol for (3-(dimethylamino)phenyl)methanol and pyrazole for 4-(4,4,5,5-tetramethyl-1,3,2-dioxaborolan-2-yl)-1H-pyrazole in EXAMPLE 34A.

Example 86B 1-(((1S,2R,5S)-6,6-dimethylbicyclo[3.1.1]heptan-2-yl)methyl)-5-methyl-1H-pyrazole The title compound was prepared by substituting EXAMPLE 86A for EXAMPLE 63A in EXAMPLE 63B.

Example 86C 4-bromo-1-(((1S,2R,5S)-6,6-dimethylbicyclo[3.1.1]heptan-2-yl)methyl)-5-methyl-1H-pyrazole The title compound was prepared by substituting EXAMPLE 86B for EXAMPLE 63B in EXAMPLE 63C.

Example 86D 1-(((1S,2R, S)-6,6-dimethylbicyclo[3.1.1]heptan-2-yl)methyl)-5-methyl-4-(4,4,5,5-tetramethyl-1,3,2-dioxaborolan-2-yl)-1H-pyrazole The title compound was prepared by substituting EXAMPLE 86C for EXAMPLE 84C in EXAMPLE 84D.

Example 86E tert-butyl 6-(8-(benzo[d]thiazol-2-ylcarbamoyl)-3,4-dihydroisoquinolin-2(1H)-yl)-3-(1-(((1S,2R,5S)-6,6-dimethylbicyclo[3.1.1]heptan-2-yl)methyl)-5-methyl-1H-pyrazol-4-yl)picolinate A reaction vessel was charged with EXAMPLE 1D (200 mg), EXAMPLE 86D (183 mg), tris(dibenzylideneacetone)dipalladium(0) (18.30 mg), 1,3,5,7-tetramethyl-6-phenyl-2,4,8-trioxa-6-phosphaadamantane (10.34 mg) and $K_3PO_4$ (263 mg) and the vessel was sealed with a septum and purged with $N_2$. A sparged mixture of dioxane (1 mL) and water (1.000 mL) was added to the degassed reagents and the mixture was heated to 110° C. for 5 hours. The reaction mixture was partitioned between water (15 mL) and ethyl acetate (3×20 mL). The combined organics were washed with brine, dried ($Na_2SO_4$), filtered, and concentrated. The title compound was purified by flash chromatography (gradient from 0 to 50% ethyl acetate/hexanes).

Example 86F

6-[8-(1,3-benzothiazol-2-ylcarbamoyl)-3,4-dihydroisoquinolin-2(1H)-yl]-3-(1-{[(1S,2R,5S)-6,6-dimethylbicyclo[3.1.1]hept-2-yl]methyl}-5-methyl-1H-pyrazol-4-yl)pyridine-2-carboxylic acid The title compound was prepared by substituting EXAMPLE 85E for EXAMPLE 8B in EXAMPLE 8C. 1H NMR (300 MHz, dimethylsulfoxide-$d_6$) δ ppm 12.86 (s, 1H), 12.56-13.01 (br s, 1H), 8.04 (d, 1H), 7.79 (d, 1H), 7.61 (d, 1H), 7.40-7.52 (m, 3H), 7.30-7.40 (m, 2H), 7.26 (s, 1H), 6.95 (d, 1H), 4.95 (s, 2H), 3.91-4.09 (m, 2H), 3.89 (t, 2H), 3.01 (t, 2H), 2.51-2.60 (m, 1H), 2.21-2.36 (m, 1H), 2.11 (s, 3H), 1.68-1.98 (m, 5H), 1.54 (s, 1H), 1.17 (s, 3H), 1.11 (s, 3H), 0.85 (d, 1H).

Example 87

6-[8-(1,3-benzothiazol-2-ylcarbamoyl)-3,4-dihydroisoquinolin-2(1H)-yl]-3-(1-{[1-(2-methylpropyl)cyclohexyl]methyl}-1H-pyrazol-4-yl)pyridine-2-carboxylic acid

Example 87A (1-isobutylcyclohexyl)methanol

To a solution of lithium diisopropylamide (2.0 M, 7.74 mL) at −78° C. was added methyl cyclohexanecarboxylate (2.0 g) dropwise as a solution in tetrahydrofuran (20 mL). After stirring for 30 minutes. 1-iodo-2-methylpropane (1.956 mL) was added dropwise as a solution in tetrahydrofuran (1 mL). The reaction was allowed to warm to room temperature and stirred overnight. The reaction was quenched with 1N HCl (25 mL) and diluted with water (25 mL) and extracted into diethyl ether (50 mL). The ether layer was washed with brine (30 mL), dried over magnesium sulfate, filtered and concentrated. The residue was dissolved in diethyl ether (25 mL) and lithium aluminum hydride (1.0M in tetrahydrofuran, 16.88 mL) was added dropwise. After stirring overnight, the reaction was quenched with water (0.65 mL), 15% aqueous NaOH (0.65 mL), more water (1.95 mL), then magnesium sulfate was added and the reaction filtered and concentrated. The residue was loaded onto silica gel and eluted using a gradient of 3% to 20% ethyl acetate/hexanes to provide the title compound.

Example 87B 1-((1-isobutylcyclohexyl)methyl)-4-(4,4,5,5-tetramethyl-1,3,2-dioxaborolan-2-yl)-1H-pyrazole The title compound was prepared by substituting EXAMPLE 87A for (3-(dimethylamino)phenyl)methanol in EXAMPLE 34A.

Example 87C

6-[8-(1,3-benzothiazol-2-ylcarbamoyl)-3,4-dihydroisoquinolin-2(1H)-yl]-3-(1-{[1-(2-methylpropyl)cyclohexyl]methyl}-1H-pyrazol-4-yl)pyridine-2-carboxylic acid EXAMPLE 1D (0.150 g), EXAMPLE 87B (0.119 g), bis(triphenylphosphine)palladium(II) dichloride (0.019 g) and cesium carbonate (0.259 g) were stirred together in N,N-dimethylformamide (0.45 mL), dioxane (0.3 mL) and water (0.15 mL) in a microwave reactor at 120° C. for 15 minutes. The reaction was loaded onto silica gel and eluted using a gradient of 5% to 50%. The corresponding ester was collected, treated with dichloromethane (0.5 mL) and TFA (0.5 mL) and stirred overnight. The reaction was concentrated, loaded onto silica gel and eluted using a gradient of 0.25% to 2.5% methanol/dichloromethane to provide the title compound. $^1$H NMR (300 MHz, dimethylsulfoxide-$d_6$) δ ppm 13.19-12.64 (m, 2H), 8.08-8.00 (m, 1H), 7.82-7.76 (m, 1H), 7.74-7.67 (m, 2H), 7.66-7.57 (m, 1H), 7.54 (s, 1H), 7.51-7.45 (m, 1H), 7.37 (d, 3H), 6.94 (d, 1H), 4.94 (s, 2H), 4.03 (s, 2H), 3.87 (s, 2H), 3.00 (s, 2H), 1.90-1.68 (m, 1H), 1.28 (m, 10H), 1.19-1.09 (m, 2H), 0.91 (d, 6H).

Example 88

6-[8-(1,3-benzothiazol-2-ylcarbamoyl)-3,4-dihydroisoquinolin-2(1H)-yl]-3-(1-{[1-(2-methoxyethyl)cyclohexyl]methyl}-1H-pyrazol-4-yl)pyridine-2-carboxylic acid

Example 88A methyl 1-(2-methoxyethyl)cyclohexanecarboxylate

To a cooled (−78° C.) solution of lithium diisopropylamide (2.0 M, 20 mL) in tetrahydrofuran (20 mL) was added methyl cyclohexanecarboxylate (5.0 g) in tetrahydrofuran (30 mL). The mixture was stirred at −78° C. for 30 minutes and a solution of 1-bromo-2-methoxyethane (5.86 g) in tetrahydrofuran (10 mL) was added. The mixture was stirred overnight and the temperature was allowed to warm up to room temperature. The mixture was quenched with aqueous NH$_4$Cl and extracted with ethyl acetate (200 mL) and washed with water (3×), brine and dried over Na$_2$SO$_4$. Filtration and evaporation of solvent gave crude product which was used in the next reaction without further purification.

Example 88B (1-(2-methoxyethyl)cyclohexyl)methanol

A solution of EXAMPLE 88A (7.0 g) in diethyl ether (30 mL) was added dropwise to a suspension of LiAlH$_4$ (1.32 g) in diethyl ether (50 mL). Once the addition was finished, the mixture was refluxed for 90 minutes. Then cooled to 0° C. and 2N NaOH (50 mL) was added slowly. Once a semi-solid appeared at the bottom of the flask, ethyl acetate (300 mL) was added and the mixture was stirred vigorously for 30 minutes. The top clear layer was decanted and more ethyl acetate (200 mL) was added to the mixture and stirred for another 15 minutes. The top organic layer was decanted and combined with the previous one. The combined organic layers were washed with 2N aqueous NaOH, water, brine and dried over Na$_2$SO$_4$. Filtration and evaporation of solvent gave the title compound.

Example 88C 1-((1-(2-methoxyethyl)cyclohexyl)methyl)-4-(4,4,5,5-tetramethyl-1,3,2-dioxaborolan-2-yl)-1H-pyrazole The title compound was prepared by substituting EXAMPLE 88B for (3-(dimethylamino)phenyl)methanol in EXAMPLE 34A.

Example 88D

6-[8-(1,3-benzothiazol-2-ylcarbamoyl)-3,4-dihydroisoquinolin-2(1H)-yl]-3-(1-{[1-(2-methoxyethyl)cyclohexyl]methyl}-1H-pyrazol-4-yl)pyridine-2-carboxylic acid To a mixture of EXAMPLE 1D (162 mg) and EXAMPLE 88C (100 mg) in dioxane (9 mL) was added tetrakis(triphenylphosphine)palladium(0) (17 mg) and saturated aqueous NaHCO$_3$ (3 mL). The mixture was purged with argon and stirred at 120° C. in a Biotage initiator microwave reactor for 30 minutes. The mixture was diluted with ethyl acetate (200 mL) and washed with water, brine and dried over Na$_2$SO$_4$. Filtration and evaporation of solvent gave crude product which was loaded on a silica gel cartridge and eluted with 20% ethyl acetate in dichloromethane to give product which was dissolved in dichloromethane (3 mL) and TFA (3 mL) and stirred overnight. After evaporation of solvent, the residue was loaded on a silica gel cartridge and eluted with 5% methanol in dichloromethane to give the pure acid. $^1$H NMR (300 MHz, dimethylsulfoxide-d$_6$) δ ppm 12.84 (s, 1H), 8.04 (d, 1H), 7.79 (d, 1H), 7.72 (s, 2H), 7.68 (s, 1H), 7.61 (d, 1H), 7.54 (m, 2H), 7.43 (m, 6H), 6.94 (d, 2H), 4.94 (s, 2H), 4.01 (s, 2H), 3.87 (t, 2H), 3.39 (t, 2H), 3.21 (m, 2H), 3.00 (t, 2H), 1.38 (m, 12H).

Example 89

6-[8-(1,3-benzothiazol-2-ylcarbamoyl)-3,4-dihydroisoquinolin-2(1H)-yl]-3-{1-[2-(2-methoxyethoxy)benzyl]-5-methyl-1H-pyrazol-4-yl}pyridine-2-carboxylic acid Example 89A 4-iodo-1-(2-(2-methoxyethoxy)benzyl)-5-methyl-1H-pyrazole The title compound was prepared by substituting 2-methoxyethanol for 2-morpholinoethanol in EXAMPLE 79C.

Example 89B

Tert-butyl 6-(8-(benzo[d]thiazol-2-ylcarbamoyl)-3,4-dihydroisoquinolin-2(1H)-yl)-3-(1-(2-(2-methoxyethoxy)benzyl)-5-methyl-1H-pyrazol-4-yl)picolinate The title compound was prepared by substituting EXAMPLE 89A for EXAMPLE 77D in EXAMPLE 77E.

Example 89C

6-[8-(1,3-benzothiazol-2-ylcarbamoyl)-3,4-dihydroisoquinolin-2(1H)-yl]-3-{1-[2-(2-methoxyethoxy)benzyl]-5-methyl-1H-pyrazol-4-yl}pyridine-2-carboxylic acid The title compound was prepared by substituting EXAMPLE 89B for EXAMPLE 1E in EXAMPLE 1F. $^1$H NMR (300 MHz, dimethylsulfoxide-d$_6$) δ ppm 12.85 (s, 1H), 8.04 (d, 1H), 7.79 (d, 1H), 7.61 (d, 1H), 7.48 (m, 3H), 7.35 (m, 3H), 7.24 (m, 1H), 7.03 (d, 1H), 6.96 (d, 1H), 6.87 (t, 1H), 6.69 (t, 1H), 5.22 (s, 2H), 4.96 (s, 2H), 4.15 (m, 2H), 3.89 (t, 2H), 3.69 (m, 2H), 3.32 (s, 3H), 3.02 (t, 2H), 2.10 (s, 3H).

Example 90

6-[8-(1,3-benzothiazol-2-ylcarbamoyl)-3,4-dihydroisoquinolin-2(1H)-yl]-3-(1-{[1-(2-methoxyethyl)cyclohexyl]methyl}-5-methyl-1H-pyrazol-4-yl)pyridine-2-carboxylic acid Example 90A 1-((1-(2-methoxyethyl)cyclohexyl)methyl)-1H-pyrazole The title compound was prepared by substituting EXAMPLE 88B for (3-(dimethylamino)phenyl)methanol and pyrazole for 4-(4,4,5,5-tetramethyl-1,3,2-dioxaborolan-2-yl)-1H-pyrazole in EXAMPLE 34A.

Example 90B 1-((1-(2-methoxyethyl)cyclohexyl)methyl)-5-methyl-1H-pyrazole

The title compound was prepared by substituting EXAMPLE 90A for EXAMPLE 63A in EXAMPLE 63B.

Example 90C 4-iodo-1-((1-(2-methoxyethyl)cyclohexyl)methyl)-5-methyl-1H-pyrazole The title compound was prepared by substituting EXAMPLE 90B for EXAMPLE 65E in EXAMPLE 65F.

Example 90D

6-[8-(1,3-benzothiazol-2-ylcarbamoyl)-3,4-dihydroisoquinolin-2(1H)-yl]-3-(1-{[1-(2-methoxyethyl)cyclohexyl]methyl}-5-methyl-1H-pyrazol-4-yl)pyridine-2-carboxylic acid The title compound was prepared by first substituting EXAMPLE 90C for EXAMPLE 77D in EXAMPLE 77E, and then substituting the product from that reaction for EXAMPLE 8B in EXAMPLE 8C. $^1$H NMR (300 MHz, dimethylsulfoxide-$d_6$) δ ppm 12.85 (s, 1H), 8.04 (d, 1H), 7.80 (d, 1H), 7.40 (m, 8H), 7.29 (s, 1H), 6.96 (d, 2H), 4.95 (s, 2H), 3.88 (m, 4H), 3.37 (t, 2H), 3.21 (s, 3H), 3.00 (t, 2H), 2.11 (s, 3H), 1.59 (t, 2H), 1.34 (m, 10H).

Example 91

6-[8-(1,3-benzothiazol-2-ylcarbamoyl)-3,4-dihydroisoquinolin-2(1H)-yl]-3-{1-[(1R,2R,4R)-bicyclo[2.2.1]hept-5-en-2-ylmethyl]-5-methyl-1H-pyrazol-4-yl}pyridine-2-carboxylic acid

Example 91A 1-((1R,2R,4R)-bicyclo[2.2.1]hept-5-en-2-ylmethyl)-1H-pyrazole

The title compound was prepared by substituting (1R,2R,4R)-bicyclo[2.2.1]hept-5-en-2-ylmethanol for (3-(dimethylamino)phenyl)methanol and pyrazole for 4-(4,4,5,5-tetramethyl-1,3,2-dioxaborolan-2-yl)-1H-pyrazole in EXAMPLE 34A.

Example 91B 1-((1R,2R,4R)-bicyclo[2.2.1]hept-5-en-2-ylmethyl)-5-methyl-1H-pyrazole The title compound was prepared by substituting EXAMPLE 91A for EXAMPLE 63A in EXAMPLE 63B.

Example 91C 1-((1R,2R,4R)-bicyclo[2.2.1]hept-5-en-2-ylmethyl)-4-bromo-5-methyl-1H-pyrazole The title compound was prepared by substituting EXAMPLE 91B for EXAMPLE 63B in EXAMPLE 63C.

Example 91D 1-((1R,2R,4R)-bicyclo[2.2.1]hept-5-en-2-ylmethyl)-5-methyl-4-(4,4,5,5-tetramethyl-1,3,2-dioxaborolan-2-yl)-1H-pyrazole The title compound was prepared by substituting EXAMPLE 91C for EXAMPLE 84C in EXAMPLE 84D.

Example 91E tert-butyl 6-(8-(benzo[d]thiazol-2-ylcarbamoyl)-3,4-dihydroisoquinolin-2(1H)-yl)-3-(1-((1R,2R,4R)-bicyclo[2.2.1]hept-5-en-2-ylmethyl)-5-methyl-1H-pyrazol-4-yl)picolinate The title compound was prepared by substituting EXAMPLE 91D for EXAMPLE 86D in EXAMPLE 86E.

Example 91F

6-[8-(1,3-benzothiazol-2-ylcarbamoyl)-3,4-dihydroisoquinolin-2(1H)-yl]-3-{1-[(1R,2R,4R)-bicyclo[2.2.1]hept-5-en-2-ylmethyl]-5-methyl-1H-pyrazol-4-yl}pyridine-2-carboxylic acid The title compound was prepared by substituting EXAMPLE 91E for EXAMPLE 8B in EXAMPLE 8C. $^1$H NMR (300 MHz, dimethylsulfoxide-$d_6$) δ ppm 12.84 (s, 1H), 12.56-13.05 (br s, 1H), 7.79 (d, 1H) 8.04 (d, 1H), 7.61 (d, 1H), 7.50 (d, 1H), 7.40-7.50 (m, 2H), 7.32-7.40 (m, 2H), 7.27 (s, 1H), 6.95 (d, 1H), 6.25 (dd, 1H), 6.08 (dd, 1H), 4.95 (s, 2H), 3.89 (t, 2H), 3.76 (dd, 1H), 3.64 (dd, 1H), 3.01 (t, 2H), 2.79 (m, 1H), 2.63 (m, 1H), 2.54-2.59 (m, 1H), 2.11 (s, 3H), 1.75-1.85 (m, 1H), 1.33 (dd, 1H), 1.20-1.26 (m, 1H), 0.59-0.67 (m, 1H).

Example 92

6-[8-(1,3-benzothiazol-2-ylcarbamoyl)-3,4-dihydroisoquinolin-2(1H)-yl]-3-{1-[(3,3-dimethylcyclohexyl)methyl]-1H-pyrazol-4-yl}pyridine-2-carboxylic acid

Example 92A (3,3-dimethylcyclohexyl)methanol

To a suspension of (methoxymethyl)triphenylphosphonium chloride (3.26 g) in tetrahydrofuran (20 mL) at 0° C. was added n-butyllithium (2.5 M, 5.94 mL) dropwise. The reaction was stirred for 15 minutes, then 3,3-dimethylcyclohexanone (1.000 g) as a solution in tetrahydrofuran (3 mL) was added dropwise. After the addition, the reaction was allowed to warm to room temperature and stir for 2 hours. The reaction was diluted with diethyl ether (50 mL) and washed with 1N aqueous HCl (50 mL), brine (50 mL), dried over magnesium sulfate, filtered and concentrated. Silica gel chromatography eluting with a gradient of 1% to 5% ethyl acetate/hexanes gave the vinyl ether. The material was dissolved in tetrahydrofuran (25 mL) and added HCl (27.7 mL) and stirred overnight. The reaction was diluted with diethyl ether (50 mL) and washed with brine (50 mL), dried over magnesium sulfate and concentrated. The residue was dissolved in methanol (10 mL) and sodium borohydride (0.090 g) was added and the mixture was stirred for 1 hours. The reaction was diluted with diethyl ether (50 mL) and washed with 1M aqueous HCl (50 mL) and brine (50 mL). The combined organic layers dried over magnesium sulfate, filtered, and concentrated.

Silica gel chromatography eluting with a gradient of 5% to 30% ethyl acetate/hexanes provided the title compound.

Example 92B 1-((3,3-dimethylcyclohexyl)methyl)-4-(4,4,5,5-tetramethyl-1,3,2-dioxaborolan-2-yl)-1H-pyrazole The title compound was prepared by substituting EXAMPLE 92A for (3-(dimethylamino)phenyl)methanol in EXAMPLE 34A.

Example 92C tert-butyl 6-(8-(benzo[d]thiazol-2-ylcarbamoyl)-3,4-dihydroisoquinolin-2(1H)-yl)-3-(1-((3,3-dimethylcyclohexyl)methyl)-1H-pyrazol-4-yl)picolinate The title compound was prepared by substituting EXAMPLE 92B for EXAMPLE 22A in EXAMPLE 22B.

Example 92D

6-[8-(1,3-benzothiazol-2-ylcarbamoyl)-3,4-dihydroisoquinolin-2(1H)-yl]-3-{1-[(3,3-dimethylcyclohexyl)methyl]-1H-pyrazol-4-yl}pyridine-2-carboxylic acid The title compound was prepared by substituting EXAMPLE 92C for EXAMPLE 8B in EXAMPLE 8C. $^1$H NMR (300 MHz, dimethylsulfoxide-$d_6$) δ ppm 12.85 (s, 1H), 8.04 (d, 1H), 7.79 (d, 1H), 7.74 (d, 1H), 7.70 (d, 1H), 7.61 (d, 1H), 7.52 (d, 1H), 7.51-7.45 (m, 1H), 7.44-7.32 (m, 3H), 6.94 (d, 1H), 4.94 (s, 2H), 3.92-3.81 (m, 4H), 3.00 (t, 2H), 1.95 (s, 1H), 1.58-0.91 (m, 6H), 0.85 (m, 6H), 0.79 (d, 2H).

Example 93

6-[8-(1,3-benzothiazol-2-ylcarbamoyl)-3,4-dihydroisoquinolin-2(1H)-yl]-3-[1-(3-methoxy-1-phenylpropyl)-1H-pyrazol-4-yl]pyridine-2-carboxylic acid

Example 93A 1-(3-methoxy-1-phenylpropyl)-1H-pyrazole

The title compound was prepared by substituting 1-bromo-2-methoxyethane for 2-chloro-1,1-dimethoxyethane in EXAMPLE 77A.

Example 93B 4-iodo-1-(3-methoxy-1-phenylpropyl)-1H-pyrazole

The title compound was prepared by substituting EXAMPLE 93A for EXAMPLE 66B in EXAMPLE 66C.

Example 93C tert-butyl 6-(8-(benzo[d]thiazol-2-ylcarbamoyl)-3,4-dihydroisoquinolin-2(1H)-yl)-3-(1-(3-methoxy-1-phenylpropyl)-1H-pyrazol-4-yl)picolinate The title compound was prepared by substituting EXAMPLE 93B for EXAMPLE 77D in EXAMPLE 77E.

Example 93D

6-[8-(1,3-benzothiazol-2-ylcarbamoyl)-3,4-dihydroisoquinolin-2(1H)-yl]-3-[1-(3-methoxy-1-phenylpropyl)-1H-pyrazol-4-yl]pyridine-2-carboxylic acid The title compound was prepared by substituting EXAMPLE 93C for EXAMPLE 1E in EXAMPLE 1F. $^1$H NMR (300 MHz, dimethylsulfoxide-$d_6$) δ ppm 12.84 (s, 1H), 8.04 (d, 1H), 7.98 (s, 1H), 7.79 (d, 1H), 7.71 (d, 1H), 7.61 (d, 1H), 7.58 (s, 1H), 7.47 (t, 1H), 7.39-7.44 (m, 1H), 7.25-7.39 (m, 7H), 6.94 (d, 1H), 5.51 (dd, 1H), 4.94 (s, 2H), 3.86 (t, 2H), 3.09-3.24 (m, 5H), 2.99 (t, 2H), 2.53-2.62 (m, 1H), 2.24-2.38 (m, 1H).

Example 94

6-[8-(1,3-benzothiazol-2-ylcarbamoyl)-3,4-dihydroisoquinolin-2(1H)-yl]-3-[1-(4-methoxy-1-phenylbutyl)-1H-pyrazol-4-yl]pyridine-2-carboxylic acid

Example 94A 1-(4-methoxy-1-phenylbutyl)-1H-pyrazole

The title compound was prepared by substituting 1-bromo-3-methoxypropane for 2-chloro-1,1-dimethoxyethane in EXAMPLE 77A.

Example 94B 4-iodo-1-(4-methoxy-1-phenylbutyl)-1H-pyrazole

The title compound was prepared by substituting EXAMPLE 94A for EXAMPLE 65E in EXAMPLE 65F.

Example 94C tert-butyl 6-(8-(benzo[d]thiazol-2-ylcarbamoyl)-3,4-dihydroisoquinolin-2(1H)-yl)-3-(1-(4-methoxy-1-phenylbutyl)-1H-pyrazol-4-yl)picolinate The title compound was prepared by substituting EXAMPLE 94B for EXAMPLE 77D in EXAMPLE 77E.

Example 94D

6-[8-(1,3-benzothiazol-2-ylcarbamoyl)-3,4-dihydroisoquinolin-2(1H)-yl]-3-[1-(4-methoxy-1-phenylbutyl)-1H-pyrazol-4-yl]pyridine-2-carboxylic acid The title compound was prepared by substituting EXAMPLE 94C for EXAMPLE 1E in EXAMPLE 1F. $^1$H NMR (300 MHz, dimethylsulfoxide-$d_6$) δ ppm 12.84 (s, 1H), 8.04 (d, 1H), 7.96 (s, 1H), 7.79 (d, 1H), 7.71 (d, 1H), 7.61 (d, 1H), 7.57 (s, 1H), 7.44-7.52 (m, 1H), 7.40-7.44 (m, 1H), 7.21-7.39 (m, 7H), 6.93 (d, 1H), 5.41 (dd, 1H), 4.94 (s, 2H), 3.86 (t, 2H), 3.31 (t, 2H), 3.18 (s, 3H), 2.24-2.40 (m, 1H), 2.03-2.19 (m, 1H), 1.27-1.47 (m, 2H).

Example 95

6-[8-(1,3-benzothiazol-2-ylcarbamoyl)-3,4-dihydroisoquinolin-2(1H)-yl]-3-[1-(2-methoxy-2-oxo-1-phenylethyl)-1H-pyrazol-4-yl]pyridine-2-carboxylic acid

Example 95A methyl 2-phenyl-2-(1H-pyrazol-1-yl)acetate

The title compound was prepared by substituting dimethyl carbonate for 2-chloro-1,1-dimethoxyethane in EXAMPLE 77A.

Example 95B methyl 3-bromo-2-phenyl-2-(1H-pyrazol-1-yl)acetate

The title compound was prepared by substituting EXAMPLE 95A for EXAMPLE 63B in EXAMPLE 63C.

Example 95C tert-butyl 6-(8-(benzo[d]thiazol-2-ylcarbamoyl)-3,4-dihydroisoquinolin-2(1H)-yl)-3-(1-(2-methoxy-2-oxo-1-phenylethyl)-1H-pyrazol-4-yl)picolinate The title compound was prepared by substituting EXAMPLE 95B for EXAMPLE 77D in EXAMPLE 77E.

Example 95D

6-[8-(1,3-benzothiazol-2-ylcarbamoyl)-3,4-dihydroisoquinolin-2(1H)-yl]-3-[1-(2-methoxy-2-oxo-1-phenylethyl)-1H-pyrazol-4-yl]pyridine-2-carboxylic acid The title compound was prepared by substituting EXAMPLE 95C for EXAMPLE 1E in EXAMPLE 1F. $^1$H NMR (300 MHz, dimethylsulfoxide-$d_6$) δ ppm 12.84 (s, 1H), 8.04 (d, 1H), 7.83 (s, 1H), 7.79 (d, 1H), 7.72 (d, 1H), 7.64 (s, 1H), 7.61 (d, 1H), 7.31-7.51 (m, 9H), 6.93 (d, 1H), 6.52 (s, 1H), 4.94 (s, 2H), 3.86 (t, 2H), 3.71 (s, 3H), 2.99 (t, 2H).

Example 96

6-[8-(1,3-benzothiazol-2-ylcarbamoyl)-3,4-dihydroisoquinolin-2(1H)-yl]-3-[1-(2-cyclohexyl-1-phenylethyl)-1H-pyrazol-4-yl]pyridine-2-carboxylic acid

Example 96A 1-(2-cyclohexyl-1-phenylethyl)-1H-pyrazole

The title compound was prepared by substituting cyclohexylmethylbromide for 2-chloro-1,1-dimethoxyethane in EXAMPLE 77A.

Example 96B 1-(2-cyclohexyl-1-phenylethyl)-3-iodo-1H-pyrazole

The title compound was prepared by substituting EXAMPLE 96A for EXAMPLE 65E in EXAMPLE 65F.

Example 96C tert-butyl 6-(8-(benzo[d]thiazol-2-ylcarbamoyl)-3,4-dihydroisoquinolin-2(1H)-yl)-3-(1-(2-cyclohexyl-1-phenylethyl)-1H-pyrazol-4-yl)picolinate The title compound was prepared by substituting EXAMPLE 96B for EXAMPLE 77D in EXAMPLE 77E.

Example 96D

6-[8-(1,3-benzothiazol-2-ylcarbamoyl)-3,4-dihydroisoquinolin-2(1H)-yl]-3-[1-(2-cyclohexyl-1-phenylethyl)-1H-pyrazol-4-yl]pyridine-2-carboxylic acid The title compound was prepared by substituting EXAMPLE 96C for EXAMPLE 1E in EXAMPLE 1F. $^1$H NMR (300 MHz, dimethylsulfoxide-$d_6$) δ ppm 12.86 (s, 1H), 8.04 (d, 1H), 7.99 (s, 1H), 7.79 (d, 1H), 7.71 (d, 1H), 7.61 (d, 1H), 7.56 (s, 1H), 7.44-7.52 (m, 1H), 7.40-7.44 (m, 1H), 7.22-7.40 (m, 7H), 6.94 (d, 1H), 5.51 (dd, 1H), 4.94 (s, 2H), 3.86 (t, 2H), 2.99 (t, 2H), 2.15-2.32 (m, 1H), 1.85-1.99 (m, 1H), 1.80 (d, 1H), 1.48-1.71 (m, 4H), 0.86-1.14 (m, 6H).

Example 97

6-[8-(1,3-benzothiazol-2-ylcarbamoyl)-3,4-dihydroisoquinolin-2(1H)-yl]-3-(1-{[1-(3-methoxypropyl)cyclohexyl]methyl}-5-methyl-1H-pyrazol-4-yl)pyridine-2-carboxylic acid

Example 97A methyl 1-(3-methoxypropyl)cyclohexanecarboxylate

To a cooled (−78° C.) solution of lithium diisopropylamide (2.0 M, 12 mL) in tetrahydrofuran (10 mL) was added methyl cyclohexanecarboxylate (1.42 g) in tetrahydrofuran (10 mL). The mixture was stirred at −78° C. for 30 minutes and a solution of 1-bromo-3-methoxypropane (1.73 g) in tetrahydrofuran (10 mL) was added to the mixture. The mixture was stirred overnight and the temperature was allowed to warm up to room temperature. The mixture was quenched with aqueous $NH_4Cl$ and extracted with ethyl acetate (200 mL) and washed with water (3×), brine and dried over $Na_2SO_4$. Filtration and evaporation of the solvent gave the crude product which was used in the next reaction without further purification.

Example 97B (1-(3-methoxypropyl)cyclohexyl)methanol

A solution of EXAMPLE 97A (2.14 g) in diethyl ether (10 mL) was added dropwise to a suspension of $LiAlH_4$ (0.380 g) in diethyl ether (20 mL). Once the addition was finished, the mixture was refluxed for 90 minutes, and then cooled to 0° C. NaOH (2N, aqueous, 50 mL) was then added slowly. The mixture was extracted with ethyl acetate (300 mL) and washed with brine and dried over Na$_2$SO$_4$. Filtration and evaporation of the solvent gave the title compound.

Example 97C 1-((1-(3-methoxypropyl)cyclohexyl)methyl)-1H-pyrazole

The title compound was prepared by substituting EXAMPLE 97B for (3-(dimethylamino)phenyl)methanol and pyrazole for 4-(4,4,5,5-tetramethyl-1,3,2-dioxaborolan-2-yl)-1H-pyrazole in EXAMPLE 34A.

Example 97D 1-((1-(3-methoxypropyl)cyclohexyl)methyl)-5-methyl-1H-pyrazole

The title compound was prepared by substituting EXAMPLE 97C for EXAMPLE 63A in EXAMPLE 63B.

Example 97E 4-bromo-1-((1-(3-methoxypropyl)cyclohexyl)methyl)-5-methyl-1H-pyrazole The title compound was prepared by substituting EXAMPLE 97D for EXAMPLE 63B in EXAMPLE 63C.

Example 97F

6-[8-(1,3-benzothiazol-2-ylcarbamoyl)-3,4-dihydroisoquinolin-2(1H)-yl]-3-(1-{[1-(3-methoxypropyl)cyclohexyl]methyl}-5-methyl-1H-pyrazol-4-yl)pyridine-2-carboxylic acid The title compound was prepared by first substituting EXAMPLE 97E for EXAMPLE 86D in EXAMPLE 86E, and then substituting the product from that reaction for EXAMPLE 8B in EXAMPLE 8C. $^1$H NMR (300 MHz, dimethylsulfoxide-d$_6$) δ ppm 12.85 (s, 1H), 8.04 (d, 1H), 7.79 (d, 1H), 7.70 (m, 1H), 7.61 (d, 1H), 7.41 (m, 6H), 7.28 (s, 1H), 6.95 (d, 1H), 4.95 (s, 3H), 3.88 (m, 4H), 3.27 (t, 2H), 3.02 (m, 2H), 2.10 (s, 3H), 1.30 (m, 14H).

Example 98

6-[8-(1,3-benzothiazol-2-ylcarbamoyl)-3,4-dihydroisoquinolin-2(1H)-yl]-3-(1-{2-[3-hydroxy-2-(hydroxymethyl)-2-methylpropoxy]benzyl}-5-methyl-1H-pyrazol-4-yl)pyridine-2-carboxylic acid Example 98A 4-Iodo-5-methyl-1-(2-((3-methyloxetan-3-yl)methoxy)benzyl)-1H-pyrazole The title compound was prepared by substituting (3-methyloxetan-3-yl)methanol for 2-morpholinoethanol in EXAMPLE 79C.

Example 98B

6-[8-(1,3-benzothiazol-2-ylcarbamoyl)-3,4-dihydroisoquinolin-2(1H)-yl]-3-(1-{2-[3-hydroxy-2-(hydroxymethyl)-2-methylpropoxy]benzyl}-5-methyl-1H-pyrazol-4-yl)pyridine-2-carboxylic acid The title compound was prepared by first substituting EXAMPLE 98A for EXAMPLE 77D in EXAMPLE 77E, and then substituting the product from that reaction for EXAMPLE 1E in EXAMPLE 1F. $^1$H NMR (300 MHz, dimethylsulfoxide-d$_6$) δ ppm 12.85 (s, 1H), 8.03 (d, 1H), 7.79 (d, 1H), 7.61 (d, 1H), 7.48 (m, 3H), 7.36 (m, 3H), 7.22 (t, 1H), 6.97 (t, 2H), 6.82 (t, 1H), 6.47 (d, 1H), 5.26 (s, 2H), 4.96 (s, 2H), 3.41 (m, 4H), 3.01 (t, 2H), 2.06 (s, 3H), 0.94 (s, 3H).

Example 99

6-[8-(1,3-benzothiazol-2-ylcarbamoyl)-3,4-dihydroisoquinolin-2(1H)-yl]-3-{5-methyl-1-[2-(tetrahydro-2H-pyran-4-ylmethoxy)benzyl]-1H-pyrazol-4-yl}pyridine-2-carboxylic acid Example 99A 4-iodo-5-methyl-1-(2-((tetrahydro-2H-pyran-4-yl)methoxy)benzyl)-1H-pyrazole The title compound was prepared by substituting (tetrahydro-2H-pyran-4-yl)methanol for 2-morpholinoethanol in EXAMPLE 79C.

Example 99B tert-butyl 6-(8-(benzo[d]thiazol-2-ylcarbamoyl)-3,4-dihydroisoquinolin-2(1H)-yl)-3-(5-methyl-1-(2-((tetrahydro-2H-pyran-4-yl)methoxy)benzyl)-1H-pyrazol-4-yl)picolinate The title compound was prepared by substituting EXAMPLE 99A for EXAMPLE 77D in EXAMPLE 77E.

Example 99C

6-[8-(1,3-benzothiazol-2-ylcarbamoyl)-3,4-dihydroisoquinolin-2(1H)-yl]-3-{5-methyl-1-[2-(tetrahydro-2H-pyran-4-ylmethoxy)benzyl]-1H-pyrazol-4-yl}pyridine-2-carboxylic acid The title compound was prepared by substituting EXAMPLE 99B for EXAMPLE 1E in EXAMPLE 1F. $^1$H NMR (300 MHz, dimethylsulfoxide-d$_6$) δ ppm 12.86 (s, 1H), 8.03 (d, 1H), 7.78 (d, 1H), 7.61 (d, 1H), 7.42 (m, 6H), 7.24 (t, 1H), 6.98 (m, 2H), 6.85 (t, 1H), 6.61 (d, 1H), 5.23 (s, 2H), 4.95 (s, 2H), 3.87 (m, 7H), 3.32 (t, 2H), 3.02 (t, 2H), 2.08 (s, 3H), 1.69 (m, 2H), 1.36 (m, 2H).

Example 100

6-[8-(1,3-benzothiazol-2-ylcarbamoyl)-3,4-dihydroisoquinolin-2(1H)-yl]-3-{1-[2-(1,4-dioxan-2-ylmethoxy)benzyl]-5-methyl-1H-pyrazol-4-yl}pyridine-2-carboxylic acid Example 100A 1-(2-((1,4-dioxan-2-yl)methoxy)benzyl)-4-iodo-5-methyl-1H-pyrazole The title compound was prepared by substituting (1,4-dioxan-2-yl)methanol for 2-morpholinoethanol in EXAMPLE 79C.

Example 100B

Tert-butyl 3-(1-(2-((1,4-dioxan-2-yl)methoxy)benzyl)-5-methyl-1H-pyrazol-4-yl)-6-(8-(benzo[d]thiazol-2-ylcarbamoyl)-3,4-dihydroisoquinolin-2(1H)-yl)picolinate The title compound was prepared by substituting EXAMPLE 100A for EXAMPLE 77D in EXAMPLE 77E.

Example 100C

6-[8-(1,3-benzothiazol-2-ylcarbamoyl)-3,4-dihydroisoquinolin-2(1H)-yl]-3-{1-[2-(1,4-dioxan-2-ylmethoxy)benzyl]-5-methyl-1H-pyrazol-4-yl}pyridine-2-carboxylic acid The title compound was prepared by substituting EXAMPLE 100B for EXAMPLE 1E in EXAMPLE 1F. $^1$H NMR (300 MHz, dimethylsulfoxide-$d_6$) δ ppm 12.86 (s, 1H), 8.03 (d, 1H), 7.79 (d, 1H), 7.61 (d, 1H), 7.42 (m, 6H), 7.24 (t, 1H), 6.99 (m, 2H), 6.87 (t, 1H), 6.65 (d, 1H), 5.23 (s, 2H), 4.96 (m, 2H), 4.02 (m, 2H), 3.83 (m, 5H), 3.65 (m, 2H), 3.46 (m, 2H), 3.01 (t, 2H), 2.10 (s, 3H).

Example 101

6-[8-(1,3-benzothiazol-2-ylcarbamoyl)-3,4-dihydroisoquinolin-2(1H)-yl]-3-(1-{[1-(2-methoxyethoxy)cyclohexyl]methyl}-5-methyl-1H-pyrazol-4-yl)pyridine-2-carboxylic acid

Example 101A 1-oxaspiro[2.5]octane

To a solution of trimethylsulfonium iodide (35.7 g) in dry DMSO (300 mL) was added cyclohexanone (9.82 g) with stirring. The mixture was brought under $N_2$ atmosphere and a solution of potassium tert-butoxide (16.83 g) in dry DMSO (200 mL) was slowly added. The resulting solution was stirred at room temperature for 16 hours under $N_2$. The reaction mixture was quenched by addition of water (600 mL), and extracted with diethyl ether (3×200 mL). The combined organic layers were washed with water (200 mL), dried over $Na_2SO_4$, filtered, and concentrated under reduced pressure to provide the title compound.

Example 101B 1-((4-iodo-5-methyl-1H-pyrazol-1-yl)methyl)cyclohexanol

To a solution of 4-iodo-5-methyl-1H-pyrazole (2.08 g) in N,N-dimethylformamide (1 mL) was added EXAMPLE 101A (3.1 g) and $Cs_2CO_3$ (5.34 g). The mixture was stirred at 120° C. for 5 minutes in a Biotage Initiator microwave reactor. The reaction mixture was diluted with ethyl acetate (400 mL) and washed with water and brine and dried over $Na_2SO_4$. The mixture was filtered and concentrated under reduced pressure to give crude product which was loaded on a 120 g silica gel column and eluted with 10% ethyl acetate in hexane to provide the title compound.

Example 101C 4-iodo-1-((1-(2-methoxyethoxy)cyclohexyl)methyl)-5-methyl-1H-pyrazole To a solution of EXAMPLE 101B (260 mg) in tetrahydrofuran (15 mL) was added NaH (97 mg). The mixture was stirred for 30 minutes. 1-Bromo-2-methoxyethane (564 mg) was added to the mixture and the mixture was stirred for 3 hours. The mixture was then stirred at reflux for 2 hours. Hexamethylphosphoramide (5 mL) and additional NaH (200 mg) were added to the mixture and the mixture was stirred at reflux overnight. The reaction mixture was diluted with ethyl acetate (200 mL) and washed with water and brine and dried over $Na_2SO_4$. The residue, after filtration and evaporation of the solvent, was loaded on a 40 g column and eluted with 20% ethyl acetate in hexane to give the title compound.

Example 101D

6-[8-(1,3-benzothiazol-2-ylcarbamoyl)-3,4-dihydroisoquinolin-2(1H)-yl]-3-(1-{[1-(2-methoxyethoxy)cyclohexyl]methyl}-5-methyl-1H-pyrazol-4-yl)pyridine-2-carboxylic acid The title compound was prepared by first substituting EXAMPLE 101C for EXAMPLE 77D in EXAMPLE 77E, and then substituting the product from that reaction for EXAMPLE 1E in EXAMPLE 1F. $^1$H NMR (300 MHz, dimethylsulfoxide-$d_6$) δ ppm 12.85 (s, 1H), 8.04 (d, 1H), 7.79 (d, 1H), 7.61 (d, 1H), 7.40 (m, 6H), 7.28 (s, 1H), 6.95 (d, 1H), 4.95 (s, 3H), 4.05 (s, 2H), 3.89 (t, 2H), 3.46 (m, 4H), 3.25 (m, 3H), 3.01 (t, 2H), 2.14 (m, 3H), 1.33 (m, 10H).

Example 102

6-[8-(1,3-benzothiazol-2-ylcarbamoyl)-3,4-dihydroisoquinolin-2(1H)-yl]-3-(4-phenoxyphenyl)pyridine-2-carboxylic acid

Example 102A tert-butyl 6-(8-(benzo[d]thiazol-2-ylcarbamoyl)-3,4-dihydroisoquinolin-2(1H)-yl)-3-(4-phenoxyphenyl)picolinate The title compound was prepared by substituting 4-phenoxyphenylboronic acid for 1-benzyl-4-(4,5,5-tetramethyl-1,3,2-dioxaborolan-2-yl)-1H-pyrazole in EXAMPLE 1E.

Example 102B

6-[8-(1,3-benzothiazol-2-ylcarbamoyl)-3,4-dihydroisoquinolin-2(1H)-yl]-3-(4-phenoxyphenyl)pyridine-2-carboxylic acid The title compound was prepared by substituting EXAMPLE 102A for EXAMPLE 8B in EXAMPLE 8C. $^1$H NMR (400 MHz, dimethylsulfoxide-$d_6$) δ ppm 12.86 (s, 2H), 8.04 (d, 1H), 7.79 (d, 1H), 7.66 (d, 1H), 7.62 (d, 1H), 7.31-7.50 (m, 8H), 7.15 (t, 1H), 6.97-7.05 (m, 5H), 4.98 (s, 2H), 3.91 (t, 2H), 3.02 (t, 2H).

Example 103

6-[8-(1,3-benzothiazol-2-ylcarbamoyl)-3,4-dihydroisoquinolin-2(1H)-yl]-3-(3-phenoxyphenyl)pyridine-2-carboxylic acid

Example 103A tert-butyl 6-(8-(benzo[d]thiazol-2-ylcarbamoyl)-3,4-dihydroisoquinolin-2(1H)-yl)-3-(3-phenoxyphenyl)picolinate The title compound was prepared by substituting 3-phenoxyphenylboronic acid for 1-benzyl-4-(4,4,5,5-tetramethyl-1,3,2-dioxaborolan-2-yl)-1H-pyrazole in EXAMPLE 1E.

Example 103B

6-[8-(1,3-benzothiazol-2-ylcarbamoyl)-3,4-dihydroisoquinolin-2(1H)-yl]-3-(3-phenoxyphenyl)pyridine-2-carboxylic acid The title compound was prepared by substituting EXAMPLE 103A for EXAMPLE 8B in EXAMPLE 8C. $^1$H NMR (400 MHz, dimethylsulfoxide-$d_6$) δ ppm 12.86 (s, 2H), 8.04 (d, 1H), 7.79 (d, 1H), 7.66 (d, 1H), 7.62 (d, 1H), 7.33-7.50 (m, 7H), 7.08-7.17 (m, 2H), 7.03 (d, 2H), 6.90-6.99 (m, 3H), 4.98 (s, 2H), 3.90 (t, 2H), 3.01 (t, 2H).

Example 104

6-[8-(1,3-benzothiazol-2-ylcarbamoyl)-3,4-dihydroisoquinolin-2(1H)-yl]-3-[3-(4-nitrophenoxy)phenyl]pyridine-2-carboxylic acid

Example 104A

Methyl 6-(8-(benzo[d]thiazol-2-ylcarbamoyl)-3,4-dihydroisoquinolin-2(1H)-yl)-3-bromopicolinate The title compound was prepared by substituting methyl 3-bromo-6-chloropicolinate for tert-butyl 3-bromo-6-chloropicolinate in EXAMPLE 1D.

Example 104B

Methyl 6-(8-(benzo[d]thiazol-2-ylcarbamoyl)-3,4-dihydroisoquinolin-2(1H)-yl)-3-(3-(4-nitrophenoxy)phenyl)picolinate The title compound was prepared by substituting EXAMPLE 104A for EXAMPLE 1D and 3-(4-nitrophenoxy)phenylboronic acid for 1-benzyl-4-(4,4,5,5-tetramethyl-1,3,2-dioxaborolan-2-yl)-1H-pyrazole in EXAMPLE 1E.

Example 104C

6-[8-(1,3-benzothiazol-2-ylcarbamoyl)-3,4-dihydroisoquinolin-2(1H)-yl]-3-[3-(4-nitrophenoxy)phenyl]pyridine-2-carboxylic acid To an ambient solution of EXAMPLE 104B (75 mg) in tetrahydrofuran (1.5 mL) and water (0.5 mL) was added LiOH H$_2$O (13 mg). The reaction was stirred overnight, diluted with 2 mL water and 2 mL ethyl acetate, and acidified to pH ~3 with 10% aqueous HCl solution. The layers were separated, and the aqueous layer was extracted with additional ethyl acetate (2×8 mL). The combined organic layers were dried with anhydrous sodium sulfate, filtered and concentrated under reduced pressure to provide the title compound. $^1$H NMR (300 MHz, dimethylsulfoxide-$d_6$) δ ppm 12.85 (s, 1H), 8.26 (m, 2H), 8.03 (d, 1H), 7.79 (d, 1H), 7.71 (d, 1H), 7.62 (d, 1H), 7.43 (m, 5H), 7.26 (d, 1H), 7.14 (m, 4H), 7.00 (d, 1H), 4.99 (s, 2H), 3.91 (t, 2H), 3.01 (t, 2H).

Example 105

6-[8-(1,3-benzothiazol-2-ylcarbamoyl)-3,4-dihydroisoquinolin-2(1H)-yl]-3-[3-(4-chlorophenoxy)phenyl]pyridine-2-carboxylic acid

Example 105A 2-(3-(4-chlorophenoxy)phenyl)-4,4,5,5-tetramethyl-1,3,2-dioxaborolane 3-(4,4,5,5-Tetramethyl-1,3,2-dioxaborolan-2-yl)phenol (0.23 g), copper(II) acetate (0.19 g), triethylamine (0.218 g) and 4-chlorophenylboronic acid (0.237 g) were stirred at room temperature overnight. The solid was filtered off, and the solvent was removed under reduced pressure. The crude product was purified by flash chromatography (Varian, Superflash SF25-40 g column), eluting with 0-25% ethyl acetate/hexane, to provide the title compound.

Example 105B tert-butyl 6-(8-(benzo[d]thiazol-2-ylcarbamoyl)-3,4-dihydroisoquinolin-2(1H)-yl)-3-(3-(4-chlorophenoxy)phenyl)picolinate The title compound was prepared by substituting EXAMPLE 105A for 1-benzyl-4-(4,4,5,5-tetramethyl-1,3,2-dioxaborolan-2-yl)-1H-pyrazole in EXAMPLE 1E.

Example 105C

6-[8-(1,3-benzothiazol-2-ylcarbamoyl)-3,4-dihydroisoquinolin-2(1H)-yl]-3-[3-(4-chlorophenoxy)phenyl]pyridine-2-carboxylic acid The title compound was prepared by substituting EXAMPLE 105B for EXAMPLE 1E in EXAMPLE 1F. $^1$H NMR (300 MHz, dimethylsulfoxide-$d_6$) δ ppm 12.86 (s, 1H), 8.04 (d, 1H), 7.79 (d, 1H), 7.64 (m, 2H), 7.41 (m, 7H), 7.05 (m, 6H), 4.98 (s, 2H), 3.90 (t, 2H), 3.01 (t, 2H).

Example 106

6-[8-(1,3-benzothiazol-2-ylcarbamoyl)-3,4-dihydroisoquinolin-2(1H)-yl]-3-(3-benzylphenyl)pyridine-2-carboxylic acid

Example 106A tert-butyl 6-(8-(benzo[d]thiazol-2-ylcarbamoyl)-3,4-dihydroisoquinolin-2(1H)-yl)-3-(3-benzylphenyl)picolinate The title compound was prepared by substituting 3-benzylphenylboronic acid for 1-benzyl-4-(4,4,5,5-tetramethyl-1,3,2-dioxaborolan-2-yl)-1H-pyrazole in EXAMPLE 1E.

Example 106B

6-[8-(1,3-benzothiazol-2-ylcarbamoyl)-3,4-dihydroisoquinolin-2(1H)-yl]-3-(3-benzylphenyl)pyridine-2-carboxylic acid The title compound was prepared by substituting EXAMPLE 106A for EXAMPLE 88 in EXAMPLE 8C. $^1$H NMR (400 MHz, dimethylsulfoxide-$d_6$) δ ppm 12.87 (s, 2H), 8.04 (d, 1H), 7.80 (d, 1H), 7.62 (d, 2H), 7.41-7.50 (m, 2H), 7.33-7.39 (m, 2H), 7.20-7.31 (m, 6H), 7.12-7.19 (m, 3H), 6.98 (d, 1H), 4.98 (s, 2H), 3.86-3.96 (m, 4H), 3.01 (t, 2H).

Example 107

6-[8-(1,3-benzothiazol-2-ylcarbamoyl)-3,4-dihydroisoquinolin-2(1H)-yl]-3-[3-(cyclohexylmethyl)-2-methylphenyl]pyridine-2-carboxylic acid

Example 107A tert-butyl 6-(8-(benzo[d]thiazol-2-ylcarbamoyl)-3,4-dihydroisoquinolin-2(1H)-yl)-3-(3-chloro-2-methylphenyl)picolinate The title compound was prepared by substituting 3-chloro-2-methylphenylboronic acid for 1-benzyl-4-(4,4,5,5-tetramethyl-1,3,2-dioxaborolan-2-yl)-1H-pyrazole in EXAMPLE 1E.

Example 107B tert-butyl 6-(8-(benzo[d]thiazol-2-ylcarbamoyl)-3,4-dihydroisoquinolin-2(1H)-yl)-3-(3-(cyclohexylmethyl)-2-methylphenyl)picolinate A mixture of EXAMPLE 107A (60 mg), dicyclohexyl(2',6'-diisopropoxybiphenyl-2-yl)phosphine (RuPhos, 4.58 mg) and tris(dibenzylideneacetone)dipalladium(0) (2.25 mg) in tetrahydrofuran (0.5 mL) and 1-methyl-2-pyrrolidinone (0.5 mL) was stirred at room temperature for 5 minutes while bubbling $N_2$ through the reaction mixture. To this solution was added 0.5 M (cyclohexylmethyl)zinc(II) bromide (0.393 mL) at room temperature. The reaction mixture in a sealed tube was heated in a preheated oil bath at 100(C overnight and cooled. The reaction mixture was quenched with water and diluted with dichloromethane. The dichloromethane layer was washed with water and concentrated. The residue was purified by flash chromatography, and eluted with 5% ethyl acetate in dichloromethane to provide the title compound.

Example 107C

6-[8-(1,3-benzothiazol-2-ylcarbamoyl)-3,4-dihydroisoquinolin-2(1H)-yl]-3-[3-(cyclohexylmethyl)-2-methylphenyl]pyridine-2-carboxylic acid The title compound was prepared by substituting EXAMPLE 107B for EXAMPLE 8B in EXAMPLE 8C. $^1$H NMR (400 MHz, dimethylsulfoxide-$d_6$) δ ppm 12.85 (s, 1H), 8.03 (d, 1H), 7.79 (d, 1H), 7.62 (d, 1H), 7.42-7.49 (m, 3H), 7.32-7.40 (m, 2H), 7.02-7.06 (m, 2H), 6.97 (d, 1H), 6.84 (dd, 1H), 4.98 (d, 2H), 3.92 (t, 2H), 3.03 (t, 2H), 1.97 (s, 3H), 1.40-1.70 (m, 7H), 0.91-1.26 (m, 6H).

Example 108

6-[8-(1,3-benzothiazol-2-ylcarbamoyl)-3,4-dihydroisoquinolin-2(1H)-yl]-3-(4-methyl-3-phenoxyphenyl)pyridine-2-carboxylic acid

Example 108A 4-bromo-1-methyl-2-phenoxybenzene

A mixture of 5-bromo-2-methylphenol (1.0 g), phenylboronic acid (1.30 g), $Cu(OAc)_2$ (0.97 g), and triethylamine (2.98 mL) in dichloromethane (50 mL) was stirred for 4 days. The mixture was diluted with ethyl acetate, washed four times with 1M aqueous NaOH solution and once with brine, dried over $Na_2SO_4$, filtered, and concentrated. The crude product was chromatographed on silica gel using 2% ethyl acetate in hexanes to afford the title compound.

Example 108B tert-butyl 6-(8-(benzo[d]thiazol-2-ylcarbamoyl)-3,4-dihydroisoquinolin-2(1H)-yl)-3-(4-methyl-3-phenoxyphenyl)picolinate A mixture of EXAMPLE 30A (172 mg), EXAMPLE 108A (74 mg), and [1,1'-bis(diphenylphosphino)ferrocene]dichloropalladium(II) (10 mg) in dioxane (6 mL) and 2M aqueous $Na_2CO_3$ solution (3 mL) was stirred at 60° C. for 18 hours. The mixture was chromatographed on silica gel using 2-20% ethyl acetate in hexanes to afford the title compound.

Example 108C

6-[8-(1,3-benzothiazol-2-ylcarbamoyl)-3,4-dihydroisoquinolin-2(1H)-yl]-3-(4-methyl-3-phenoxyphenyl)pyridine-2-carboxylic acid The title compound was prepared by substituting EXAMPLE 108B for EXAMPLE 8B in EXAMPLE 8C. $^1$H NMR (300 MHz, dimethylsulfoxide-$d_6$) δ ppm 12.85 (br s, 2H), 8.04 (d, 1H), 7.79 (d, 1H), 7.62 (d, 2H), 7.49 (dd, 1H), 7.43 (dd, 1H), 7.30-7.38 (m, 3H), 7.25 (dd, 1H), 7.16 (dd, 1H), 7.06 (m, 2H), 6.95 (d, 1H), 6.91 (d, 1H), 6.87 (m, 2H), 4.96 (s, 2H), 3.88 (t, 2H), 2.99 (t, 2H), 2.16 (s, 3H).

Example 109

6-[8-(1,3-benzothiazol-2-ylcarbamoyl)-3,4-dihydroisoquinolin-2(1H)-yl]-3-(2-methyl-5-phenoxyphenyl)pyridine-2-carboxylic acid

Example 109A 2-bromo-1-methyl-4-phenoxybenzene

The title compound was prepared by substituting 3-bromo-4-methylphenol for 5-bromo-2-methylphenol in EXAMPLE 108A.

Example 109B tert-butyl 6-(8-(benzo[d]thiazol-2-ylcarbamoyl)-3,4-dihydroisoquinolin-2(1H)-yl)-3-(2-methyl-5-phenoxyphenyl)picolinate The title compound was prepared by substituting EXAMPLE 109A for EXAMPLE 108A in EXAMPLE 108B.

Example 109C

6-[8-(1,3-benzothiazol-2-ylcarbamoyl)-3,4-dihydroisoquinolin-2(1H)-yl]-3-(2-methyl-5-phenoxyphenyl)pyridine-2-carboxylic acid The title compound was prepared by substituting EXAMPLE 109B for EXAMPLE 8B in EXAMPLE 8C. $^1$H NMR (300 MHz, dimethylsulfoxide-$d_6$) δ ppm 12.55 (br s, 1H), 12.00 (br s, 1H), 8.03 (d, 1H), 7.79 (d, 1H), 7.62 (d, 1H), 7.51 (dd, 1H), 7.45 (dd, 2H), 7.35 (m, 4H), 7.23 (dd, 1H), 7.08

(t, 1H), 6.96 (m, 3H), 6.87 (dd, 1H), 6.68 (d, 1H), 4.97 (s, 2H), 3.91 (t, 2H), 3.02 (t, 2H), 2.04 (s, 3H).

Example 110

6-[8-(1,3-benzothiazol-2-ylcarbamoyl)-3,4-dihydroisoquinolin-2(1H)-yl]-3-(2-methyl-3-phenoxyphenyl)pyridine-2-carboxylic acid

Example 110A 1-bromo-2-methyl-3-phenoxybenzene

The title compound was prepared by substituting 3-bromo-2-methylphenol for 5-bromo-2-methylphenol in EXAMPLE 108A.

Example 110B tert-butyl 6-(8-(benzo[d]thiazol-2-ylcarbamoyl)-3,4-dihydroisoquinolin-2(1H)-yl)-3-(2-methyl-3-phenoxyphenyl)picolinate The title compound was prepared by substituting EXAMPLE 1100A for EXAMPLE 108A in EXAMPLE 108B.

Example 110C

6-[8-(1,3-benzothiazol-2-ylcarbamoyl)-3,4-dihydroisoquinolin-2(1H)-yl]-3-(2-methyl-3-phenoxyphenyl)pyridine-2-carboxylic acid The title compound was prepared by substituting EXAMPLE 110B for EXAMPLE 8B in EXAMPLE 8C. $^1$H NMR (300 MHz, dimethylsulfoxide-$d_6$) δ ppm 12.85 (br s, 1H), 12.00 (br s, 1H), 8.04 (d, 1H), 7.79 (d, 1H), 7.63 (d, 1H), 7.54 (d, 1H), 7.47 (dd, 2H), 7.34 (m, 4H), 7.24 (dd, 1H), 7.18 (dd, 1H), 7.06 (t, 1H), 7.01 (dd, 2H), 6.90 (m, 3H), 4.99 (s, 2H), 3.93 (t, 2H), 3.03 (t, 2H), 1.90 (s, 3H).

Example 111

6-[8-(1,3-benzothiazol-2-ylcarbamoyl)-3,4-dihydroisoquinolin-2(1H)-yl]-3-(2-methyl-4-phenoxyphenyl)pyridine-2-carboxylic acid

Example 111A 1-bromo-2-methyl-4-phenoxybenzene

The title compound was prepared by substituting 4-bromo-3-methylphenol for 5-bromo-2-methylphenol in EXAMPLE 108A.

Example 111B tert-butyl 6-(8-(benzo[d]thiazol-2-ylcarbamoyl)-3,4-dihydroisoquinolin-2(1H)-yl)-3-(2-methyl-4-phenoxyphenyl)picolinate The title compound was prepared by substituting EXAMPLE 111A for EXAMPLE 108A in EXAMPLE 108B.

Example 111C

6-[8-(1,3-benzothiazol-2-ylcarbamoyl)-3,4-dihydroisoquinolin-2(1H)-yl]-3-(2-methyl-4-phenoxyphenyl)pyridine-2-carboxylic acid The title compound was prepared by substituting EXAMPLE 111B for EXAMPLE 8B in EXAMPLE 8C. $^1$H NMR (300 MHz, dimethylsulfoxide-$d_6$) δ ppm 12.85 (br s, 1H), 12.00 (br s, 1H), 8.04 (d, 1H), 7.79 (d, 1H), 7.63 (d, 1H), 7.32-7.51 (m, 7H), 7.14 (t, 1H), 7.03 (m, 3H), 6.98 (d, 1H), 6.88 (d, 1H), 6.78 (dd, 1H), 4.98 (s, 2H), 3.92 (t, 2H), 3.03 (t, 2H), 1.91 (s, 3H).

Example 112

6-[8-(1,3-benzothiazol-2-ylcarbamoyl)-3,4-dihydroisoquinolin-2(1H)-yl]-3-[3-(cyclohexylmethoxy)-2-methylphenyl]pyridine-2-carboxylic acid

Example 112A

1-Bromo-3-cyclohexylmethoxy-2-methyl-benzene

The title compound was prepared by substituting cyclohexylmethanol for (3-(dimethylamino)phenyl)methanol and 3-bromo-2-methylphenol for 4-(4,4,5,5-tetramethyl-1,3,2-dioxaborolan-2-yl)-1H-pyrazole in EXAMPLE 34A.

Example 112B

6-[8-(1,3-benzothiazol-2-ylcarbamoyl)-3,4-dihydroisoquinolin-2(1H)-yl]-3-[3-(cyclohexylmethoxy)-2-methylphenyl]pyridine-2-carboxylic acid tert-butyl ester EXAMPLE 30A (125 mg), EXAMPLE 112A (87 mg), trans-dichlorobis(triphenylphosphine)palladium (II) (29 mg), and cesium carbonate (266 mg) were added to a microwave vial. N,N-dimethylformamide (0.9 mL), 1,4-dioxane (0.6 mL), and water (0.3 mL) were added. The vial was placed in a microwave reactor and subjected to 120° C. for 15 minutes. The solution was then added to water and extracted with 30% ethyl acetate in hexanes. The extract was washed with brine and dried over anhydrous sodium sulfate. The solution was filtered, concentrated and purified on silica gel using 30% ethyl acetate in hexanes.

Example 112C

6-[8-(1,3-benzothiazol-2-ylcarbamoyl)-3,4-dihydroisoquinolin-2(1H)-yl]-3-[3-(cyclohexylmethoxy)-2-methylphenyl]pyridine-2-carboxylic acid The title compound was prepared by substituting EXAMPLE 112B for EXAMPLE 7D in EXAMPLE 7E. $^1$H NMR (400 MHz, dimethylsulfoxide-$d_6$) δ ppm 12.86 (bs, 1H), 8.04 (d, 1H), 7.89 (d, 1H), 7.63 (d, 1H), 7.50-7.32 (m, 5H), 7.08 (t, 1H), 6.98 (d, 1H), 6.86 (d, 1H), 6.62 (d, 1H), 4.98 (s, 2H), 3.92 (t, 2H), 3.77 (d, 2H), 3.03 (t, 2H), 1.90 (s, 3H), 1.88-1.62 (m, 6H), 1.31-1.03 (m, 5H).

Example 113

6-[8-(1,3-benzothiazol-2-ylcarbamoyl)-3,4-dihydroisoquinolin-2(1H)-yl]-3-[4-(cyclohexyloxy)-2-methylphenyl]pyridine-2-carboxylic acid

Example 113A

1-bromo-4-cyclohexyloxy-2-methyl-benzene

The title compound was prepared by substituting cyclohexanol for (3-(dimethylamino)phenyl)methanol and 4-bromo-3-methylphenol for 4-(4,4,5,5-tetramethyl-1,3,2-dioxaborolan-2-yl)-1H-pyrazole in EXAMPLE 34A.

Example 113B

6-[8-(1,3-benzothiazol-2-ylcarbamoyl)-3,4-dihydroisoquinolin-2(1H)-yl]-3-[4-(cyclohexyloxy)-2-methylphenyl]pyridine-2-carboxylic acid tert-butyl ester The title compound was prepared by substituting EXAMPLE 113A for EXAMPLE 112A in EXAMPLE 112B.

Example 113C

6-[8-(1,3-benzothiazol-2-ylcarbamoyl)-3,4-dihydroisoquinolin-2(1H)-yl]-3-[4-(cyclohexyloxy)-2-methylphenyl]pyridine-2-carboxylic acid The title compound was prepared by substituting EXAMPLE 113B for EXAMPLE 7D in EXAMPLE 7E. $^1$H NMR (400 MHz, dimethylsulfoxide-$d_6$) δ ppm 12.86 (bs, 1H), 8.04 (d, 1H), 7.79 (d, 1H), 7.62 (d, 1H), 7.51-7.34 (m, 5H), 6.97-6.89 (m, 2H), 6.79 (dd, 1H), 6.71 (dd, 1H), 4.97 (s, 2H), 4.30 (m, 1H), 3.91 (t, 2H), 3.02 (t, 2H), 2.02 (s, 3H), 1.97-1.85 (m, 2H), 1.78-1.62 (m, 2H), 1.58-1.20 (m, 6H).

Example 114

6-[8-(1,3-benzothiazol-2-ylcarbamoyl)-3,4-dihydroisoquinolin-2(1H)-yl]-3-[3-(cyclohexyloxy)-2-methylphenyl]pyridine-2-carboxylic acid

Example 114A

1-bromo-3-cyclohexyloxy-2-methyl-benzene

The title compound was prepared by substituting cyclohexanol for (3-(dimethylamino)phenyl)methanol and 3-bromo-2-methylphenol for 4-(4,4,5,5-tetramethyl-1,3,2-dioxaborolan-2-yl)-1H-pyrazole in EXAMPLE 34A.

Example 114B

6-[8-(1,3-benzothiazol-2-ylcarbamoyl)-3,4-dihydroisoquinolin-2(1H)-yl]-3-[3-(cyclohexyloxy)-2-methylphenyl]pyridine-2-carboxylic acid tert-butyl ester The title compound was prepared by substituting EXAMPLE 114A for EXAMPLE 112A in EXAMPLE 112B.

Example 114C

6-[8-(1,3-benzothiazol-2-ylcarbamoyl)-3,4-dihydroisoquinolin-2(1H)-yl]-3-[3-(cyclohexyloxy)-2-methylphenyl]pyridine-2-carboxylic acid The title compound was prepared by substituting EXAMPLE 114B for EXAMPLE 7D in EXAMPLE 7E. $^1$H NMR (400 MHz, dimethylsulfoxide-$d_6$) δ ppm 12.85 (bs, 1H), 8.03 (d, 1H), 7.79 (d, 1H), 7.62 (d, 1H), 7.51-7.32 (m, 5H), 7.07 (t, 1H), 6.97 (d, 1H), 6.91 (d, 1H), 6.61 (d, 1H), 4.98 (s, 2H), 4.33 (m, 1H), 3.92 (t, 2H), 3.03 (t, 2H), 1.95-1.84 (m, 2H), 1.89 (s, 3H), 1.77-1.63 (m, 2H), 1.57-1.26 (m, 6H).

Example 115

6-[8-(1,3-benzothiazol-2-ylcarbamoyl)-3,4-dihydroisoquinolin-2(1H)-yl]-3-[4-(cyclohexylmethoxy)-2-methylphenyl]pyridine-2-carboxylic acid

Example 115A

1-Bromo-4-cyclohexylmethoxy-2-methyl-benzene

The title compound was prepared by substituting cyclohexylmethanol for (3-(dimethylamino)phenyl)methanol and 4-bromo-3-methylphenol for 4-(4,4,5,5-tetramethyl-1,3,2-dioxaborolan-2-yl)-1H-pyrazole in EXAMPLE 34A.

Example 115B

6-[8-(1,3-benzothiazol-2-ylcarbamoyl)-3,4-dihydroisoquinolin-2(1H)-yl]-3-[4-(cyclohexylmethoxy)-2-methylphenyl]pyridine-2-carboxylic acid tert-butyl ester The title compound was prepared by substituting EXAMPLE 115A for EXAMPLE 112A in EXAMPLE 112B.

Example 115C

6-[8-(1,3-benzothiazol-2-ylcarbamoyl)-3,4-dihydroisoquinolin-2(1H)-yl]-3-[4-(cyclohexylmethoxy)-2-methylphenyl]pyridine-2-carboxylic acid The title compound was prepared by substituting EXAMPLE 115B for EXAMPLE 7D in EXAMPLE 7E. $^1$H NMR (400 MHz, dimethylsulfoxide-$d_6$) δ ppm 12.85 (bs, 1H), 8.04 (d, 1H), 7.79 (d, 1H), 7.62 (d, 1H), 7.51-7.32 (m, 5H), 6.96 (d, 1H), 6.91 (d, 1H), 6.79 (d, 1H), 6.70 (d, 1H), 4.97 (s, 2H), 3.91 (t, 2H), 3.75 (d, 2H), 3.03 (t, 2H), 2.02 (s, 3H), 1.87-1.59 (m, 6H), 1.31-1.00 (m, 5H).

Example 116

6-[8-(1,3-benzothiazol-2-ylcarbamoyl)-3,4-dihydroisoquinolin-2(1H)-yl]-3-[2-cyano-3-(cyclohexyloxy)phenyl]pyridine-2-carboxylic acid

Example 116A

2-bromo-6-(cyclohexyloxy)benzonitrile

To a solution of cyclohexanol (0.275 g) in N,N-dimethylformamide (5 mL) was added sodium hydride (60%, 0.069 g). After 30 minutes, 2-bromo-6-fluorobenzonitrile (0.500 g)

was added and the reaction stirred at room temperature for 2 hours. The reaction mixture was diluted with ethyl acetate (25 mL), washed with water (20 mL) and brine (20 mL), dried over magnesium sulfate, filtered, and concentrated. Silica gel chromatography eluting with a gradient of 3% to 10% ethyl acetate/hexanes provided the title compound.

Example 116B

6-[8-(1,3-benzothiazol-2-ylcarbamoyl)-3,4-dihydroisoquinolin-2(1H)-yl]-3-[2-cyano-3-(cyclohexyloxy)phenyl]pyridine-2-carboxylic acid The title compound was prepared by first substituting EXAMPLE 116A for EXAMPLE 112A in EXAMPLE 112B, and then substituting the product from that reaction for EXAMPLE 8B in EXAMPLE 8C. $^1$H NMR (300 MHz, dimethylsulfoxide-$d_6$) δ ppm 12.79 (s, 2H), 8.03 (d, 1H), 7.79 (d, 1H), 7.63 (d, 2H), 7.55 (dd, 1H), 7.51-7.31 (m, 4H), 7.21 (d, 1H), 7.04 (d, 1H), 6.87 (d, 1H), 5.03 (s, 2H), 4.59 (s, 1H), 3.97 (d, 2H), 3.04 (s, 2H), 1.91 (s, 2H), 1.71 (s, 2H), 1.62-1.26 (m, 6H).

Example 117

6-[8-(1,3-benzothiazol-2-ylcarbamoyl)-3,4-dihydroisoquinolin-2(1H)-yl]-3-[2-chloro-3-(cyclohexyloxy)phenyl]pyridine-2-carboxylic acid Example 117A 1-bromo-2-chloro-3-(cyclohexyloxy)benzene The title compound was prepared by substituting for cyclohexanol for (3-(dimethylamino)phenyl)methanol and 3-bromo-2-chlorophenol for 4-(4,4,5,5-tetramethyl-1,3,2-dioxaborolan-2-yl)-1H-pyrazole in EXAMPLE 34A.

Example 117B

6-[8-(1,3-benzothiazol-2-ylcarbamoyl)-3,4-dihydroisoquinolin-2(1H)-yl]-3-[2-chloro-3-(cyclohexyloxy)phenyl]pyridine-2-carboxylic acid The title compound was prepared by first substituting EXAMPLE 117A for EXAMPLE 112A in EXAMPLE 112B, and then substituting the product from that reaction for EXAMPLE 8B in EXAMPLE 8C. $^1$H NMR (300 MHz, dimethylsulfoxide-$d_6$) δ ppm 12.79 (s, 2H), 8.03 (d, 1H), 7.79 (d, 1H), 7.63 (d, 2H), 7.55 (dd, 1H), 7.51-7.31 (m, 4H), 7.21 (d, 1H), 7.04 (d, 1H), 6.87 (d, 1H), 5.03 (s, 2H), 4.59 (s, 1H), 3.97 (d, 2H), 3.04 (s, 2H), 1.91 (s, 2H), 1.71 (s, 2H), 1.62-1.26 (m, 6H).

Example 118

6-[8-(1,3-benzothiazol-2-ylcarbamoyl)-3,4-dihydroisoquinolin-2(1H)-yl]-3-[3-(cyclohexylamino)-2-methylphenyl]pyridine-2-carboxylic acid Example 118A (3-Bromo-2-methyl-phenyl)-cyclohexyl-amine The title compound was prepared by substituting cyclohexanone for EXAMPLE 64B and 3-bromo-2-methylaniline for dimethylamine in EXAMPLE 68A.

Example 118B

6-[8-(1,3-benzothiazol-2-ylcarbamoyl)-3,4-dihydroisoquinolin-2(1H)-yl]-3-[3-(cyclohexylamino)-2-methylphenyl]pyridine-2-carboxylic acid tert-butyl ester The title compound was prepared by substituting EXAMPLE 118A for EXAMPLE 112A in EXAMPLE 112B.

Example 118C

6-[8-(1,3-benzothiazol-2-ylcarbamoyl)-3,4-dihydroisoquinolin-2(1H)-yl]-3-[3-(cyclohexylamino)-2-methylphenyl]pyridine-2-carboxylic acid The title compound was prepared by substituting EXAMPLE 118B for EXAMPLE 7D in EXAMPLE 7E. $^1$H NMR (400 MHz, dimethylsulfoxide-$d_6$) δ ppm 12.86 (bs, 1H), 8.03 (d, 1H), 7.79 (d, 1H), 7.63 (d, 1H), 7.50-7.32 (m, 6H), 7.26-7.10 (m, 2H), 6.99 (d, 1H), 4.99 (s, 2H), 3.93 (t, 2H), 3.29 (bs, 1H), 3.03 (t, 2H), 2.08-1.83 (m, 2H), 1.96 (bs, 3H), 1.80-1.70 (m, 2H), 1.66-1.57 (m, 1H), 1.45-1.15 (m, 5H).

Example 119

6-[8-(1,3-benzothiazol-2-ylcarbamoyl)-3,4-dihydroisoquinolin-2(1H)-yl]-3-[3-(cyclohexyloxy)-2-fluorophenyl]pyridine-2-carboxylic acid Example 119A 1-Bromo-3-cyclohexyloxy-2-fluoro-benzene The title compound was prepared by substituting cyclohexanol for (3-(dimethylamino)phenyl)methanol and 3-bromo-2-fluorophenol for 4-(4,4,5,5-tetramethyl-1,3,2-dioxaborolan-2-yl)-1H-pyrazole in EXAMPLE 34A.

Example 119B

6-[8-(1,3-benzothiazol-2-ylcarbamoyl)-3,4-dihydroisoquinolin-2(1H)-yl]-3-[3-(cyclohexyloxy)-2-fluorophenyl]pyridine-2-carboxylic acid tert-butyl ester The title compound was prepared by substituting EXAMPLE 119A for EXAMPLE 112A in EXAMPLE 112B.

Example 119C

6-[8-(1,3-benzothiazol-2-ylcarbamoyl)-3,4-dihydroisoquinolin-2(1H)-yl]-3-[3-(cyclohexyloxy)-2-fluorophenyl]pyridine-2-carboxylic acid The title compound was prepared by substituting EXAMPLE 119B for EXAMPLE 7D in EXAMPLE 7E. $^1$H NMR (400 MHz, dimethylsulfoxide-$d_6$) δ ppm 12.85 (bs, 1H), 8.04 (d, 1H), 7.80 (d, 1H), 7.65-7.58 (m, 2H), 7.51-7.32 (m, 5H), 7.15-6.99 (m, 2H), 6.80 (td, 1H), 5.00 (s, 2H), 4.32 (m, 1H), 3.94 (t, 2H), 3.02 (t, 2H), 1.98-1.87 (m, 2H), 1.77-1.66 (m, 2H), 1.58-1.22 (m, 6H).

Example 120

6-[8-(1,3-benzothiazol-2-ylcarbamoyl)-3,4-dihydroisoquinolin-2(1H)-yl]-3-[3-(cyclohexyloxy)-2-(trifluoromethyl)phenyl]pyridine-2-carboxylic acid

Example 120A

1-Bromo-3-cyclohexyloxy-2-trifluoromethyl-benzene

Cyclohexanol (214 mg) was added to N,N-dimethylacetamide (10 mL), and sodium hydride (60% in mineral oil, 86 mg) was added. The solution was mixed at room temperature for 15 minutes after which time 1-bromo-3-fluoro-2-(trifluoromethyl)benzene (400 mg) was added. The solution was then heated at 100° C. for 1 hour. The solution was cooled, added to water, and extracted with diethyl ether. The extract was washed with brine, dried over anhydrous sodium sulfate, and filtered. The filtrate was concentrated and purified on silica gel using 5% ethyl acetate in hexanes.

Example 120B

6-[8-(1,3-benzothiazol-2-ylcarbamoyl)-3,4-dihydroisoquinolin-2(1H)-yl]-3-[3-(cyclohexyloxy)-2-(trifluoromethyl)phenyl]pyridine-2-carboxylic acid tert-butyl ester The title compound was prepared by substituting EXAMPLE 120A for EXAMPLE 112A in EXAMPLE 112B.

Example 120C

6-[8-(1,3-benzothiazol-2-ylcarbamoyl)-3,4-dihydroisoquinolin-2(1H)-yl]-3-[3-(cyclohexyloxy)-2-(trifluoromethyl)phenyl]pyridine-2-carboxylic acid The title compound was prepared by substituting EXAMPLE 120B for EXAMPLE 7D in EXAMPLE 7E. $^1$H NMR (400 MHz, dimethylsulfoxide-$d_6$) δ ppm 12.85 (bs, 1H), 8.03 (d, 1H), 7.79 (d, 1H), 7.62 (d, 1H), 7.50-7.32 (m, 6H), 7.22 (d, 1H), 6.99 (d, 1H), 6.64 (d, 1H), 4.99 (s, 2H), 4.57 (m, 1H), 3.94 (t, 2H), 3.03 (t, 2H), 1.93-1.80 (m, 2H), 1.78-1.63 (m, 2H), 1.60-1.18 (m, 6H).

Example 121

6-[8-(1,3-benzothiazol-2-ylcarbamoyl)-3,4-dihydroisoquinolin-2(1H)-yl]-3-{3-[(3,3-dimethylcyclohexyl)oxy]-2-methylphenyl}pyridine-2-carboxylic acid

Example 121A 1-bromo-3-(3,3-dimethyl-cyclohexyloxy)-2-methylbenzene

The title compound was prepared by substituting 3,3-dimethylcyclohexanol for (3-(dimethylamino)phenyl)methanol and 3-bromo-2-methylphenol for 4-(4,4,5,5-tetramethyl-1,3,2-dioxaborolan-2-yl)-1H-pyrazole in EXAMPLE 34A.

Example 121B

6-[8-(1,3-benzothiazol-2-ylcarbamoyl)-3,4-dihydroisoquinolin-2(1H)-yl]-3-{3-[(3,3-dimethylcyclohexyl)oxy]-2-methylphenyl}pyridine-2-carboxylic acid tert-butyl ester The title compound was prepared by substituting EXAMPLE 121A for EXAMPLE 112A in EXAMPLE 112B.

Example 121C

6-[8-(1,3-benzothiazol-2-ylcarbamoyl)-3,4-dihydroisoquinolin-2(1H)-yl]-3-{3-[(3,3-dimethylcyclohexyl)oxy]-2-methylphenyl}pyridine-2-carboxylic acid The title compound was prepared by substituting EXAMPLE 121B for EXAMPLE 7D in EXAMPLE 7E. $^1$H NMR (400 MHz, dimethylsulfoxide-$d_6$) δ ppm 12.85 (bs, 1H), 8.03 (d, 1H), 7.79 (d, 1H), 7.62 (d, 1H), 7.56-7.32 (m, 5H), 7.08 (t, 1H), 6.97 (d, 1H), 6.91 (d, 1H), 6.61 (d, 1H), 4.98 (s, 2H), 4.40 (m, 1H), 3.92 (t, 2H), 3.03 (t, 2H), 2.08-1.98 (m, 2H), 1.86 (s, 3H), 1.81-1.72 (m, 2H), 1.69-1.45 (m, 2H), 1.37-1.20 (m, 2H), 0.96 (s, 6H).

Example 122

6-[8-(1,3-benzothiazol-2-ylcarbamoyl)-3,4-dihydroisoquinolin-2(1H)-yl]-3-(1-benzyl-1H-1,2,3-triazol-4-yl)pyridine-2-carboxylic acid

Example 122A tert-butyl 6-(8-(benzo[d]thiazol-2-ylcarbamoyl)-3,4-dihydroisoquinolin-2(1H)-yl)-3-ethynylpicolinate To a 50 mL pressure flask was added EXAMPLE 1D (1.0 g), ethynyltrimethylsilane (2.50 mL), and triethylamine (1.23 mL) in tetrahydrofuran (18 mL). Bis(triphenylphosphine)palladium(II) dichloride (0.124 g) and CuI (0.034 g) were added, and the flask was flushed with nitrogen and sealed. The reaction was heated to 85° C. for 36 hours, cooled and passed through a plug of silica gel. After rinsing the silica gel with dichloromethane, the combined filtrates were concentrated by rotary evaporation, taken up in tetrahydrofuran (20 mL). tetra-n-Butylammonium fluoride (1M in tetrahydrofuran, 1.48 mL) was added dropwise at room temperature. The reaction was allowed to stir for 2 hours. Saturated aqueous NH$_4$Cl solution was added and the aqueous portion was extracted three times with dichloromethane. The combined organics were dried over Na$_2$SO$_4$, filtered and concentrated. The residue was purified by regular phase flash column chromatography (Analogix, 0-100% ethyl acetate in hexanes) to provide the title compound.

Example 122B tert-butyl 6-(8-(benzo[d]thiazol-2-ylcarbamoyl)-3,4-dihydroisoquinolin-2(1H)-yl)-3-(1-benzyl-1H-1,2,3-triazol-4-yl)picolinate To a 4 mL vial was added EXAMPLE 122A (30 mg), benzyl bromide (10.05 mg), and NaN$_3$ (4.58 mg) in N,N- dimethylformamide (0.5 mL) and water (0.12 mL). Sodium ascorbate (1.7 mg) and copper (II) sulfate pentahydrate (0.733 mg) was added and the mixture was heated at 70° C. overnight, cooled, and chromatographed by regular phase flash column chromatography (Analogix, 0-100% ethyl acetate in hexanes) to provide the title compound.

Example 122C

6-[8-(1,3-benzothiazol-2-ylcarbamoyl)-3,4-dihydroisoquinolin-2(1H)-yl]-3-(1-benzyl-1H-1,2,3-triazol-4-yl)pyridine-2-carboxylic acid To a 10 mL round-bottomed flask was added EXAMPLE 122B (150 mg) in dichloromethane (2.3 mL). TFA (1.2 mL) was added and the mixture was stirred for 2 hours. The volatiles were removed under a stream of $N_2$. The residue was placed on high-vacuum for 1 hour and then purified by regular phase flash column chromatography (Analogix, 0-100% ethyl acetate in hexanes) to provide the title compound. $^1$H NMR (300 MHz, dimethylsulfoxide-$d_6$) δ ppm 13.07 (s, 1H), 8.21 (s, 1H), 8.04 (d, 1H), 7.98 (d, 1H), 7.79 (d, 1H), 7.62 (d, 1H), 7.51-7.27 (m, 9H), 6.98 (d, 1H), 5.62 (s, 2H), 4.98 (s, 2H), 3.90 (t, 2H), 3.01 (t, 2H).

Example 123

6-[8-(1,3-benzothiazol-2-ylcarbamoyl)-3,4-dihydroisoquinolin-2(1H)-yl]-3-[1-benzyl-5-(ethoxycarbonyl)-2-methyl-1H-pyrrol-3-yl]pyridine-2-carboxylic acid Example 123A ethyl 1-benzyl-5-methyl-1H-pyrrole-2-carboxylate Ethyl 5-methyl-1H-pyrrole-2-carboxylate (1.1 g) and benzyl bromide (1.35 g) in N,N-dimethylformamide (30 mL) was treated with NaH (95%, 0.5 g) overnight. The reaction was quenched with ice water. The mixture was diluted with ethyl acetate and washed with brine. The organic layer was dried over $Na_2SO_4$, filtered, and concentrated to provide the title compound.

Example 123B ethyl 1-benzyl-4-iodo-5-methyl-1H-pyrrole-2-carboxylate

To a solution of EXAMPLE 123A (564 mg) in acetone (8 mL) at 0° C. was added N-iodosuccinimide (600 mg). The mixture was stirred at room temperature overnight, and diluted with ethyl acetate and washed with water. The organic layer was concentrated and the residue was purified by flash chromatography, and eluted with 50% dichloromethane in hexane to provide the title compound.

Example 123C tert-butyl 6-(8-(benzo[d]thiazol-2-ylcarbamoyl)-3,4-dihydroisoquinolin-2(1H)-yl)-3-(1-benzyl-5-(ethoxycarbonyl)-2-methyl-1H-pyrrol-3-yl)picolinate The title compound was prepared by substituting EXAMPLE 123B for EXAMPLE 112A in EXAMPLE 112B.

Example 123D

6-[8-(1,3-benzothiazol-2-ylcarbamoyl)-3,4-dihydroisoquinolin-2(1H)-yl]-3-[1-benzyl-5-(ethoxycarbonyl)-2-methyl-1H-pyrrol-3-yl]pyridine-2-carboxylic acid The title compound was prepared by substituting EXAMPLE 123C for EXAMPLE 8B in EXAMPLE 8C. $^1$H NMR (400 MHz, dimethylsulfoxide-$d_6$) δ ppm 12.86 (s, 2H), 8.04 (d, 1H), 7.79 (d, 1H), 7.62 (d, 1H), 7.52 (d, 1H), 7.42-7.50 (m, 2H), 7.27-7.40 (m, 4H), 7.22 (t, 1H), 6.91-6.96 (m, 3H), 6.86 (s, 1H), 5.63 (s, 2H), 4.96 (s, 2H), 4.12 (q, 2H), 3.89 (t, 2H), 3.01 (t, 2H), 2.01 (s, 3H), 1.19 (t, 3H).

Example 124

6-[8-(1,3-benzothiazol-2-ylcarbamoyl)-3,4-dihydroisoquinolin-2(1H)-yl]-3-(1-benzyl-5-carboxy-2-methyl-1H-pyrrol-3-yl)pyridine-2-carboxylic acid EXAMPLE 123D (30 mg) in tetrahydrofuran (3 mL) and methanol (3 mL) was treated with 2N aqueous NaOH (3 mL) overnight. The mixture was acidified to a pH of 5 with 1 M aqueous HCl and concentrated. The residue was purified by RP-HPLC to provide the title compound. $^1$H NMR (400 MHz, dimethylsulfoxide-$d_6$) δ ppm 12.86 (s, 2H), 8.04 (d, 1H), 7.79 (d, 1H), 7.61 (d, 1H), 7.41-7.53 (m, 3H), 7.27-7.39 (m, 4H), 7.22 (t, 1H), 6.91-6.97 (m, 3H), 6.83 (s, 1H), 5.65 (s, 2H), 4.95 (s, 2H), 3.89 (t, 2H), 3.01 (t, 2H), 1.99 (s, 3H).

Example 125

6-[8-(1,3-benzothiazol-2-ylcarbamoyl)-3,4-dihydroisoquinolin-2(1H)-yl]-3-(1-benzyl-1H-pyrrol-3-yl)pyridine-2-carboxylic acid Example 125A 1-benzyl-3-(4,4,5,5-tetramethyl-1,3,2-dioxaborolan-2-yl)-1H-pyrrole The title compound was prepared by substituting 3-(4,4,5,5-tetramethyl-1,3,2-dioxaborolan-2-yl)-1H-pyrrole for and 4-(4,4,5,5-tetramethyl-1,3,2-dioxaborolan-2-yl)-1H-pyrazole and benzyl bromide for EXAMPLE 4A in EXAMPLE 4B.

Example 125B tert-butyl 6-(8-(benzo[d]thiazol-2-ylcarbamoyl)-3,4-dihydroisoquinolin-2(1H)-yl)-3-(1-benzyl-1H-pyrrol-3-yl)picolinate The title compound was prepared by substituting EXAMPLE 125A for 1-benzyl-4-(4,4,5,5-tetramethyl-1,3,2-dioxaborolan-2-yl)-1H-pyrazole in EXAMPLE 1E.

Example 125C

6-[8-(1,3-benzothiazol-2-ylcarbamoyl)-3,4-dihydroisoquinolin-2(1H)-yl]3-(1-benzyl-1H-pyrrol-3-yl)pyridine-2-carboxylic acid The title compound was prepared by substituting EXAMPLE 125B for EXAMPLE 1E in EXAMPLE 1F. $^1$H NMR (400 MHz, dimethylsulfoxide-$d_6$) δ ppm 12.86 (s, 1H), 8.04 (d, 1H), 7.79 (d, 1H), 7.67 (d, 1H), 7.60 (d, 1H), 7.45 (m, 2H), 7.34 (m, 4H), 7.23 (m, 3H), 6.96 (t, 1H), 6.89 (d, 1H), 6.81 (m, 1H), 6.19 (m, 1H), 5.08 (s, 2H), 4.91 (s, 2H), 3.84 (t, 2H), 2.99 (t, 2H).

Example 126

6-[8-(1,3-benzothiazol-2-ylcarbamoyl)-3,4-dihydroisoquinolin-2(1H)-yl]-3-{1-[(4-methylphenyl)sulfonyl]-1H-pyrrol-3-yl}pyridine-2-carboxylic acid

Example 126A tert-butyl 6-(8-(benzo[d]thiazol-2-ylcarbamoyl)-3,4-dihydroisoquinolin-2(1H)-yl)-3-(1-tosyl-1H-pyrrol-3-yl)picolinate The title compound was prepared by substituting 3-(4,4,5,5-tetramethyl-1,3,2-dioxaborolan-2-yl)-1-tosyl-1H-pyrrole for 1-benzyl-4-(4,4,5,5-tetramethyl-1,3,2-dioxaborolan-2-yl)-1H-pyrazole in EXAMPLE 1E.

Example 126B

6-[8-(1,3-benzothiazol-2-ylcarbamoyl)-3,4-dihydroisoquinolin-2(1H)-yl]-3-{1-[(4-methylphenyl)sulfonyl]-1H-pyrrol-3-yl}pyridine-2-carboxylic acid The title compound was prepared by substituting EXAMPLE 126A for EXAMPLE 1E in EXAMPLE 1F. $^1$H NMR (300 MHz, dimethylsulfoxide-$d_6$) δ ppm 12.84 (s, 1H), 8.03 (d, 1H), 7.78 (m, 4H), 7.60 (d, 1H), 7.41 (m, 9H), 6.90 (d, 1H), 6.49 (m, 1H), 4.94 (s, 2H), 3.86 (t, 2H), 2.99 (t, 2H), 2.37 (s, 3H).

Example 127

6-[8-(1,3-benzothiazol-2-ylcarbamoyl)-3,4-dihydroisoquinolin-2(1H)-yl]-3-(1-benzoyl-1H-pyrrol-3-yl)pyridine-2-carboxylic acid

Example 127A tert-butyl 6-(8-(benzo[d]thiazol-2-ylcarbamoyl)-3,4-dihydroisoquinolin-2(1H)-yl)-3-(1-benzoyl-1H-pyrrol-3-yl)picolinate The title compound was prepared by substituting phenyl (3-(4,4,5,5-tetramethyl-1,3,2-dioxaborolan-2-yl)-1H-pyrrol-1-yl)methanone for 1-benzyl-4-(4,4,5,5-tetramethyl-1,3,2-dioxaborolan-2-yl)-1H-pyrazole in EXAMPLE 1E.

Example 127B

6-[8-(1,3-benzothiazol-2-ylcarbamoyl)-3,4-dihydroisoquinolin-2(1H)-yl]-3-(1-benzoyl-1H-pyrrol-3-yl)pyridine-2-carboxylic acid The title compound was prepared by substituting EXAMPLE 127A for EXAMPLE 1E in EXAMPLE 1F. $^1$H NMR (300 MHz, dimethylsulfoxide-$d_6$) δ ppm 12.86 (s, 1H), 8.04 (d, 1H), 7.70 (m, 8H), 7.38 (m, 6H), 6.94 (d, 1H), 6.57 (m, 1H), 4.95 (s, 2H), 3.87 (t, 2H), 3.01 (t, 2H).

Example 128

6-[8-(1,3-benzothiazol-2-ylcarbamoyl)-3,4-dihydroisoquinolin-2(1H)-yl]-3-[1-(phenylsulfonyl)-1H-pyrrol-3-yl]pyridine-2-carboxylic acid

Example 128A tert-butyl 6-(8-(benzo[d]thiazol-2-ylcarbamoyl)-3,4-dihydroisoquinolin-2(1H)-yl)-3-(1-(phenylsulfonyl)-1H-pyrrol-3-yl)picolinate The title compound was prepared by substituting 1-(phenylsulfonyl)-3-(4,4,5,5-tetramethyl-1,3,2-dioxaborolan-2-yl)-1H-pyrrole for 1-benzyl-4-(4,4,5,5-tetramethyl-1,3,2-dioxaborolan-2-yl)-1H-pyrazole in EXAMPLE 1E.

Example 128B

6-[8-(1,3-benzothiazol-2-ylcarbamoyl)-3,4-dihydroisoquinolin-2(1H)-yl]-3-[1-(phenylsulfonyl)-1H-pyrrol-3-yl]pyridine-2-carboxylic acid The title compound was prepared by substituting EXAMPLE 128A for EXAMPLE 1E in EXAMPLE 1F. $^1$H NMR (300 MHz, dimethylsulfoxide-$d_6$) δ ppm 12.83 (s, 1H), 8.04 (d, 1H), 7.95 (m, 2H), 7.76 (m, 3H), 7.63 (m, 3H), 7.41 (m, 6H), 6.91 (d, 1H), 6.51 (m, 1H), 4.94 (s, 2H), 3.86 (t, 2H), 2.99 (t, 2H).

Example 129

6-[8-(1,3-benzothiazol-2-ylcarbamoyl)-3,4-dihydroisoquinolin-2(1H)-yl]-3-(1-benzyl-5-cyano-2-methyl-1H-pyrrol-3-yl)pyridine-2-carboxylic acid

Example 129A 1-benzyl-4-iodo-5-methyl-1H-pyrrole-2-carboxylic acid

EXAMPLE 123B (0.5 g) in tetrahydrofuran (20 mL) and methanol (10 mL) was treated with 2 N NaOH (10 mL) overnight. The reaction mixture was cooled to 0° C., acidified to pH 5, diluted with water (30 mL) and concentrated to remove the organic solvent. The precipitates were collected by filtration, washed with water and dried over sodium sulfate to provide the title compound.

Example 129B 1-benzyl-4-iodo-5-methyl-1H-pyrrole-2-carboxamide

To a solution of EXAMPLE 129A (450 mg) in tetrahydrofuran (12 mL) at 0° C. was added carbonyldiimidazole (642 mg). The resulting mixture was stirred at room temperature for 2 hours. The reaction mixture was cooled to 0° C. and ammonium hydroxide (3 mL) was added. The mixture was stirred at room temperature for 2 hours and concentrated. The residue was dissolved in ethyl acetate, washed with brine and concentrated to provide the title compound.

Example 129C 1-benzyl-4-iodo-5-methyl-1H-pyrrole-2-carbonitrile

To a solution of EXAMPLE 129B (400 mg) in N,N-dimethylformamide (6 mL) and pyridine (0.6 mL) at (PC was added dropwise oxalyl chloride (0.31 mL). The mixture was stirred at room temperature for 30 minutes, diluted with ethyl acetate and washed with saturated NaHCO$_3$ and water extensively. The organic layer was dried over Na$_2$SO$_4$, filtered, and concentrated. The residue was purified by flash chromatography, and eluted with dichloromethane to provide the title compound.

Example 129D tert-butyl 6-(8-(benzo[d]thiazol-2-ylcarbamoyl)-3,4-dihydroisoquinolin-2(1H)-yl)-3-(1-benzyl-5-cyano-2-methyl-1H-pyrrol-3-yl)picolinate The title compound was prepared by substituting EXAMPLE 129C for EXAMPLE 112A in EXAMPLE 112B.

Example 129E

6-[8-(1,3-benzothiazol-2-ylcarbamoyl)-3,4-dihydroisoquinolin-2(1H)-yl]-3-(1-benzyl-5-cyano-2-methyl-1H-pyrrol-3-yl)pyridine-2-carboxylic acid The title compound was prepared by substituting EXAMPLE 129D for EXAMPLE 8B in EXAMPLE 8C. $^1$H NMR (400 MHz, dimethylsulfoxide-d$_6$) δ ppm 12.85 (s, 1H), 8.03 (d, 1H), 7.79 (d, 1H), 7.61 (d, 1H), 7.52 (d, 1H), 7.41-7.50 (m, 2H), 7.28-7.40 (m, 5H), 7.04 (d, 2H), 6.96 (d, 1H), 6.90 (s, 1H), 5.30 (s, 2H), 4.96 (s, 2H), 3.89 (t, 2H), 3.01 (t, 2H), 2.05 (s, 3H).

Example 130

6-[8-(1,3-benzothiazol-2-ylcarbamoyl)-3,4-dihydroisoquinolin-2(1H)-yl]-3-[5-cyano-1-(cyclohexylmethyl)-2-methyl-1H-pyrrol-3-yl]pyridine-2-carboxylic acid

Example 130A ethyl 4-iodo-5-methyl-1H-pyrrole-2-carboxylate

The title compound was prepared by following the procedure described for EXAMPLE 123B, replacing EXAMPLE 123A with ethyl 5-methyl-1H-pyrrole-2-carboxylate.

Example 130B 4-iodo-5-methyl-1H-pyrrole-2-carboxylic acid

The title compound was prepared by following the procedure described for EXAMPLE 129A and replacing EXAMPLE 123B with EXAMPLE 130A.

Example 130C 4-iodo-5-methyl-1H-pyrrole-2-carboxamide

The title compound was prepared by following the procedure described for EXAMPLE 129B and replacing EXAMPLE 129A with EXAMPLE 130B.

Example 130D 4-iodo-5-methyl-1H-pyrrole-2-carbonitrile

The title compound was prepared by following the procedure described for EXAMPLE 129C, replacing EXAMPLE 129B with EXAMPLE 130C.

Example 130E 1-(cyclohexylmethyl)-4-iodo-5-methyl-1H-pyrrole-2-carbonitrile

EXAMPLE 130D (100 mg), (bromomethyl)cyclohexane (382 mg) and tetrabutylammonium bromide (159 mg) in N,N-dimethylformamide was treated with sodium hydride (86 mg) and stirred at 50° C. overnight. The reaction mixture was cooled, diluted with ethyl acetate and washed with brine. The organic layer was concentrated. The residue was purified by flash chromatography (40% dichloromethane in hexanes) to provide the title compound.

Example 130F tert-butyl 6-(8-(benzo[d]thiazol-2-ylcarbamoyl)-3,4-dihydroisoquinolin-2(1H)-yl)-3-(5-cyano-1-(cyclohexylmethyl)-2-methyl-1H-pyrrol-3-yl)picolinate The title compound was prepared by substituting EXAMPLE 130E for EXAMPLE 112A in EXAMPLE 112B.

Example 130G

6-[8-(1,3-benzothiazol-2-ylcarbamoyl)-3,4-dihydroisoquinolin-2(1H)-yl]-3-[5-cyano-1-(cyclohexylmethyl)-2-methyl-1H-pyrrol-3-yl]pyridine-2-carboxylic acid The title compound was prepared by substituting EXAMPLE 130F for EXAMPLE 8B in EXAMPLE 8C. $^1$H NMR (400 MHz, dimethylsulfoxide-d$_6$) δ ppm 12.86 (s, 1H), 8.04 (d, 1H), 7.79 (d, 1H), 7.62 (d, 1H), 7.41-7.52 (m, 3H), 7.31-7.40 (m, 2H), 6.95 (d, 1H), 6.79 (s, 1H), 4.96 (s, 2H), 3.80-3.94 (m, 4H), 3.01 (t, 2H), 2.09 (s, 3H), 1.45-1.77 (m, 6H), 1.10-1.24 (m, 3H), 0.94-1.06 (m, 2H).

Example 131

6-[8-(1,3-benzothiazol-2-ylcarbamoyl)-3,4-dihydroisoquinolin-2(1H)-yl]-3-(5-cyano-2-methyl-1-[1-(piperidin-1-yl)cyclohexyl]methyl)-1H-pyrrol-3-yl)pyridine-2-carboxylic acid

Example 131A (1-(piperidin-1-yl)cyclohexyl)methanol

The title compound was prepared by substituting 1-phenylcyclohexanecarboxylic acid with 1-(piperidin-1-yl)cyclohexanecarboxylic acid in EXAMPLE 67A.

Example 131B 4-iodo-5-methyl-1-((1-(piperidin-1-yl)cyclohexyl)methyl)-1H-pyrrole-2-carbonitrile The title compound was prepared by substituting EXAMPLE 131A for (3-(dimethylamino)phenyl)methanol and EXAMPLE 130D for 4-(4,4,5,5-tetramethyl-1,3,2-dioxaborolan-2-yl)-1H-pyrazole in EXAMPLE 34A.

Example 131C tert-butyl 6-(8-(benzo[d]thiazol-2-ylcarbamoyl)-3,4-dihydroisoquinolin-2(1H)-yl)-3-(5-cyano-2-methyl-1-((1-(piperidin-1-yl)cyclohexyl)methyl)-1H-pyrrol-3-yl)picolinate The title compound was prepared by substituting EXAMPLE 131B for EXAMPLE 112A in EXAMPLE 112B

Example 131D

6-[8-(1,3-benzothiazol-2-ylcarbamoyl)-3,4-dihydroisoquinolin-2(1H)-yl]-3-(5-cyano-2-methyl-1-{[1-(piperidin-1-yl)cyclohexyl]methyl}-1H-pyrrol-3-yl)pyridine-2-carboxylic acid The title compound was prepared by substituting EXAMPLE 131C for EXAMPLE 1E in EXAMPLE 1F. $^1$H NMR (500 MHz, dimethylsulfoxide-$d_6$) δ ppm 12.86 (s, 2H), 8.26 (s, 1H), 8.04 (d, 1H), 7.79 (d, 1H), 7.62 (d, 1H), 7.52 (d, 1H), 7.42-7.50 (m, 2H), 7.33-7.40 (m, 2H), 6.97 (d, 2H), 4.90-5.06 (m, 2H), 4.46 (s, 2H), 3.90 (t, 2H), 3.25 (s, 2H), 3.02 (t, 2H), 1.92-2.20 (m, 7H), 1.57-1.93 (m, 6H), 1.19-1.55 (m, 5H).

Example 132

6,6'-bis[8-(1,3-benzothiazol-2-ylcarbamoyl)-3,4-dihydroisoquinolin-2(1H)-yl]-3,3'-bipyridine-2,2'-dicarboxylic acid

Example 132A di-tert-butyl 6,6'-bis(8-(benzo[d]thiazol-2-ylcarbamoyl)-3,4-dihydroisoquinolin-2(1H)-yl)-3,3'-bipyridine-2,2'-dicarboxylate The title compound was isolated during the synthesis of EXAMPLE 79D as a byproduct.

Example 132B 6,6'-bis[8-(1,3-benzothiazol-2-ylcarbamoyl)-3,4-dihydroisoquinolin-2(1H)-yl]-3,3'-bipyridine-2,2'-dicarboxylic acid The title compound was prepared by substituting EXAMPLE 132A for EXAMPLE 1E in EXAMPLE 1F. $^1$H NMR (300 MHz, dimethylsulfoxide-$d_6$) δ ppm 12.83 (br.s, 2H), 8.02 (d, 2H), 7.77 (d, 2H), 7.60 (d, 2H), 7.40 (m, 10H), 6.97 (d, 2H), 4.97 (s, 4H), 3.92 (t, 4H), 3.01 (t, 4H).

Example 133

6-[8-(1,3-benzothiazol-2-ylcarbamoyl)-3,4-dihydroisoquinolin-2(1H)-yl]-3-(2-benzyl-1,2,3,4-tetrahydroisoquinolin-6-yl)pyridine-2-carboxylic acid

Example 133A tert-butyl 6-(8-(benzo[d]thiazol-2-ylcarbamoyl)-3,4-dihydroisoquinolin-2(1H)-yl)-3-(1,2,3,4-tetrahydroisoquinolin-6-yl)picolinate The title compound was prepared by substituting 6-bromo-1,2,3,4-tetrahydroisoquinoline hydrochloride for EXAMPLE 75A in EXAMPLE 75B.

Example 133B tert-butyl 6-(8-(benzo[d]thiazol-2-ylcarbamoyl)-3,4-dihydroisoquinolin-2(1H)-yl)-3-(2-benzyl-1,2,3,4-tetrahydroisoquinolin-6-yl)picolinate A suspension of EXAMPLE 133A (20 mg), benzaldehyde (6.58 μL), MP-CNBH$_3$ (100 mg, 2.47 mmol/g), acetic acid (2 μL) in dichloromethane (2 mL)/methanol (2 mL) was shaken at room temperature for 18 hours. The reaction mixture was filtered, washed with methanol/dichloromethane, concentrated and purified by RP HPLC (C8, 30-100% CH$_3$CN/water/0.1% TFA) to provide the title compound.

Example 133C

6-[8-(1,3-benzothiazol-2-ylcarbamoyl)-3,4-dihydroisoquinolin-2(1H)-yl]-3-(2-benzyl-1,2,3,4-tetrahydroisoquinolin-6-yl)pyridine-2-carboxylic acid The title compound was prepared by substituting EXAMPLE 133B for EXAMPLE 1E in EXAMPLE 1F. $^1$H NMR (300 MHz, dimethylsulfoxide-$d_6$) δ ppm 12.96 (s, 1H), 12.86 (s, 1H), 10.10 (s, 1H), 8.03 (d, 1H), 7.79 (d, 1H), 7.63 (d, 2H), 7.60-7.41 (m, 7H), 7.36 (m, 2H), 7.26-7.15 (m, 3H), 6.99 (d, 1H), 4.98 (s, 2H), 4.49 (d, 2H), 4.36 (s, 2H), 3.90 (t, 2H), 3.43-3.28 (m, 2H), 3.10 (s, 2H), 3.02 (t, 2H).

Example 134

6-[8-(1,3-benzothiazol-2-ylcarbamoyl)-3,4-dihydroisoquinolin-2(1H)-yl]-3-(1-{[1-(2-methoxyethyl)cycloheptyl]methyl}-5-methyl-1H-pyrazol-4-yl)pyridine-2-carboxylic acid

Example 134A methyl cycloheptanecarboxylate

To a solution of 25.0 g cycloheptanecarboxylic acid in methanol (300 mL) was added concentrated H$_2$SO$_4$ (0.5 g) and the mixture was stirred at reflux overnight. The reaction mixture was concentrated under vacuum and the residue was diluted with ethyl ether (500 mL). The mixture was washed with water and brine, dried over Na$_2$SO$_4$, filtered, and concentrated under reduced pressure to give the title compound.

Example 134B methyl 1-(2-methoxyethyl)cycloheptanecarboxylate

To a cooled (−78° C.) solution of lithium diisopropylamide (2.0M, 6 mL) in tetrahydrofuran (10 mL) was added EXAMPLE 134A (1.60 g) in tetrahydrofuran (10 mL). The mixture was stirred at −78° C. for 30 minutes and a solution of 1-bromo-2-methoxyethane (1.73 g) in tetrahydrofuran (10 mL) was added to the mixture. The mixture was stirred overnight and allowed to warm up to room temperature. The mixture was quenched with aqueous $NH_4Cl$, extracted with ethyl acetate (200 mL), washed with water (3 times) and brine, and dried over $Na_2SO_4$. Filtration and concentration gave the crude product which was used in the next reaction without further purification.

Example 134C (1-(2-methoxyethyl)cycloheptyl)methanol

A solution of EXAMPLE 134B (2.25 g) in diethyl ether (10 mL) was added dropwise to a suspension of $LiAlH_4$ (0.40 g) in diethyl ether (20 mL). Once the addition was finished, the mixture was refluxed for 90 minutes, and cooled to 0° C. Aqueous NaOH (2N, 50 mL) was added slowly. The mixture was then extracted with ethyl acetate (300 mL) and the organic layer was washed with brine and dried over $Na_2SO_4$. Filtration and concentration provided the title compound.

Example 134D 1-((1-(2-methoxyethyl)cycloheptyl)methyl)-1H-pyrazole

The title compound was prepared by substituting EXAMPLE 134C for (3-(dimethylamino)phenyl)methanol and 1H-pyrazole for 4-(4,4,5,5-tetramethyl-1,3,2-dioxaborolan-2-yl)-1H-pyrazole in EXAMPLE 34A.

Example 134E 1-((1-(3-methoxypropyl)cycloheptyl)methyl)-5-methyl-1H-pyrazole The title compound was prepared by substituting EXAMPLE 134D for EXAMPLE 63A in EXAMPLE 63B.

Example 134F 4-iodo-1-((1-(2-methoxyethyl)cycloheptyl)methyl)-5-methyl-1H-pyrazole The title compound was prepared by substituting EXAMPLE 134E for EXAMPLE 65E in EXAMPLE 65F.

Example 134G

6-[8-(1,3-benzothiazol-2-ylcarbamoyl)-3,4-dihydroisoquinolin-2(1H)-yl]-3-(1-{[1-(2-methoxyethyl)cycloheptyl]methyl}-5-methyl-1H-pyrazol-4-yl)pyridine-2-carboxylic acid The title compound was prepared by substituting EXAMPLE 134F for EXAMPLE 75A in EXAMPLE 75B, and then substituting that product for EXAMPLE 8B in EXAMPLE 8C. $^1$H NMR (300 MHz, dimethylsulfoxide-$d_6$) δ ppm 12.85 (s, 1H), 8.04 (d, 1H), 7.79 (d, 1H), 7.61 (d, 1H), 7.40 (m, 6H), 6.95 (d, 1H), 4.95 (s, 2H), 3.89 (t, 2H), 3.83 (s, 2H), 3.41 (t, 2H), 3.20 (s, 3H), 3.01 (t, 2H), 2.11 (s, 3H), 1.43 (m, 16H)

Example 135

6-[8-(1,3-benzothiazol-2-ylcarbamoyl)-3,4-dihydroisoquinolin-2(1H)-yl]-3-[1-(piperidin-4-ylmethyl)-1H-pyrazol-4-yl]pyridine-2-carboxylic acid The title compound was prepared by substituting EXAMPLE 78B for EXAMPLE 1E in EXAMPLE 1F. $^1$H NMR (300 MHz, dimethylsulfoxide-dt) δ ppm 13.06 (s, 1H), 12.86 (s, 1H), 8.45 (d, 1H), 8.15 (d, 1H), 8.04 (d, 1H), 7.80 (d, 2H), 7.70 (d, 1H), 7.62 (d, 1H), 7.57 (d, 1H), 7.52-7.45 (m, 1H), 7.45-7.30 (m, 3H), 6.95 (d, 1H), 4.95 (s, 2H), 4.05 (d, 2H), 3.87 (t, 2H), 3.25 (d, 2H), 3.00 (t, 2H), 2.84 (dd, 2H), 2.10 (dd, 1H), 1.66 (d, 2H), 1.33 (td, 2H).

Example 136

6-[8-(1,3-benzothiazol-2-ylcarbamoyl)-3,4-dihydroisoquinolin-2(1H)-yl]-3-[2-(pyridin-2-ylmethyl)-1,2,3,4-tetrahydroisoquinolin-6-yl]pyridine-2-carboxylic acid

Example 136A tert-butyl 6-(8-(benzo[d]thiazol-2-ylcarbamoyl)-3,4-dihydroisoquinolin-2(1H)-yl)-3-(2-(pyridin-2-ylmethyl)-1,2,3,4-tetrahydroisoquinolin-6-yl)picolinate The title compound was prepared by substituting picolinaldehyde for benzaldehyde in EXAMPLE 133B.

Example 136B

6-[8-(1,3-benzothiazol-2-ylcarbamoyl)-3,4-dihydroisoquinolin-2(1H)-yl]-3-[2-(pyridin-2-ylmethyl)-1,2,3,4-tetrahydroisoquinolin-6-yl]pyridine-2-carboxylic acid The title compound was prepared by substituting EXAMPLE 136A for EXAMPLE 1E in EXAMPLE 1F. $^1$H NMR (300 MHz, dimethylsulfoxide-$d_6$) δ ppm 13.00 (s, 1H), 12.86 (s, 1H), 10.56 (s, 1H), 8.71 (dd, 1H), 8.04 (d, 1H), 7.96 (td, 1H), 7.79 (d, 1H), 7.68-7.56 (m, 3H), 7.55-7.42 (m, 3H), 7.36 (ddd, 2H), 7.21 (d, 3H), 7.00 (d, 2H), 4.99 (s, 2H), 4.63 (s, 2H), 4.47 (s, 2H), 3.93-3.88 (m, 2H), 3.63-3.55 (m, 2H), 3.13 (t, 2H), 3.02 (t, 2H).

Example 137

6-[8-(1,3-benzothiazol-2-ylcarbamoyl)-3,4-dihydroisoquinolin-2(1H)-yl]-3-[2-(cyclohexylethyl)-1,2,3,4-tetrahydroisoquinolin-6-yl]pyridine-2-carboxylic acid

Example 137A tert-butyl 6-(8-(benzo[d]thiazol-2-ylcarbamoyl)-3,4-dihydroisoquinolin-2(1H)-yl)-3-[2-(cyclohexylmethyl)-1,2,3,4-tetrahydroisoquinolin-6-yl)picolinate The title compound was prepared by substituting cyclohexanecarbaldehyde for benzaldehyde in EXAMPLE 133B.

Example 137B

6-[8-(1,3-benzothiazol-2-ylcarbamoyl)-3,4-dihydroisoquinolin-2(1H)-yl]-3-[2-(cyclohexylmethyl)-1,2,3,4-tetrahydroisoquinolin-6-yl]pyridine-2-carboxylic acid The title compound was prepared by substituting EXAMPLE 137A for EXAMPLE 1E in EXAMPLE 1F. $^1$H NMR (300 MHz, dimethylsulfoxide-d$_6$) δ ppm 12.97 (s, 1H), 12.87 (s, 1H), 9.42 (s, 1H), 8.04 (d, 1H), 7.79 (d, 1H), 7.67-7.59 (m, 2H), 7.52-7.42 (m, 2H), 7.36 (ddd, 2H), 7.22 (s, 3H), 7.00 (d, 1H), 4.99 (s, 2H), 4.58 (d, 1H), 4.30 (dd, 1H), 3.91 (t, 2H), 3.55 (d, 2H), 3.40-3.25 (m, 2H), 3.18 (s, 1H), 3.12-2.98 (m, 4H), 1.96-1.55 (m, 6H), 1.32-1.12 (m, 2H), 1.09-0.89 (m, 2H).

Example 138

6-[8-(1,3-benzothiazol-2-ylcarbamoyl)-3,4-dihydroisoquinolin-2(1H)-yl]-2'-(cyclohexyloxy)-3'-methyl-3,4'-bipyridine-2-carboxylic acid

Example 138A 2-(cyclohexyloxy)-4-iodo-3-methylpyridine

Cyclohexanol (0.501 g) in tetrahydrofuran (3.5 mL) was treated with NaH (0.1 g) until gas evolution ceased. 2-Fluoro-4-iodo-3-methylpyridine (0.237 g) in tetrahydrofuran (1.5 mL) was added. The reaction mixture was stirred at room temperature for 0.5 hours and was quenched with ice-water. The resulting mixture was extracted with ethyl acetate. The combined organic layer was washed with brine, dried over Na$_2$SO$_4$, filtered, and concentrated. The residue was purified by preparative TLC, and was eluted with petroleum ether to provide the title compound.

Example 138B tert-butyl 6-(8-(benzo[d]thiazol-2-ylcarbamoyl)-3,4-dihydroisoquinolin-2(1H)-yl)-2'-(cyclohexyloxy)-3'-methyl-3,4'-bipyridine-2-carboxylate The title compound was prepared by substituting EXAMPLE 138A for EXAMPLE 1D and EXAMPLE 30A for EXAMPLE 82D in EXAMPLE 82E.

Example 138C

6-[8-(1,3-benzothiazol-2-ylcarbamoyl)-3,4-dihydroisoquinolin-2(1H)-yl]-2'-(cyclohexyloxy)-3'-methyl-3,4'-bipyridine-2-carboxylic acid The title compound was prepared by substituting EXAMPLE 138B for EXAMPLE 8B in EXAMPLE 8C. $^1$H NMR (400 MHz, dimethylsulfoxide-d$_6$) δ ppm 7.86-7.88 (m, 1H), 7.73-7.74 (m, 1H), 7.23-7.48 (m, 7H), 6.95 (d, 1H), 6.50 (d, 1H), 5.04-5.12 (m, 3H), 3.90-3.93 (m, 2H), 3.10-3.13 (m, 2H), 1.86-1.90 (m, 2H), 1.85 (s, 3H), 1.66-1.68 (m, 2H), 1.17-1.50 (m, 6H).

Example 139

6-[8-(1,3-benzothiazol-2-ylcarbamoyl)-3,4-dihydroisoquinolin-2(1H)-yl]-2'-(cyclohexyloxy)-3,4'-bipyridine-2-carboxylic acid

Example 139A 2-(cyclohexyloxy)-4-iodopyridine

The title compound was prepared by substituting 2-fluoro-4-iodo-pyridine for 2-fluoro-4-iodo-3-methylpyridine in EXAMPLE 138A.

Example 139B tert-butyl 6-(8-(benzo[d]thiazol-2-ylcarbamoyl)-3,4-dihydroisoquinolin-2(1H)-yl)-2'-(cyclohexyloxy)-3,4'-bipyridine-2-carboxylate The title compound was prepared by substituting EXAMPLE 139A for EXAMPLE 1D and EXAMPLE 30A for EXAMPLE 82D in EXAMPLE 82E.

Example 139C

6-[8-(1,3-benzothiazol-2-ylcarbamoyl)-3,4-dihydroisoquinolin-2(1H)-yl]-2'-(cyclohexyloxy)-3,4'-bipyridine-2-carboxylic acid The title compound was prepared by substituting EXAMPLE 139B for EXAMPLE 8B in EXAMPLE 8C. $^1$H NMR (400 MHz, dimethylsulfoxide-d$_6$) δ ppm 12.89 (s, 1H), 8.11 (d, 1H), 8.04 (d, 1H), 7.76 (d, 1H), 7.73 (d, 1H), 7.63 (d, 1H), 7.43-7.49 (m, 2H), 7.34-7.39 (m, 2H), 6.99 (d, 1H), 6.89 (d, 1H), 6.67 (s, 1H), 5.01 (s, 3H), 3.92 (s, 2H), 3.02 (s, 2H), 1.95-1.98 (m, 2H), 1.71-1.78 (m, 2H), 1.54-1.56 (m, 1H), 1.35-1.45 (m, 4H), 1.23-1.30 (m, 1H).

Example 140

6-[8-(1,3-benzothiazol-2-ylcarbamoyl)-3,4-dihydroisoquinolin-2(1H)-yl]-2'-phenoxy-3,4'-bipyridine-2-carboxylic acid

Example 140A 4-iodo-2-phenoxypyridine

Phenol (0.464 g) in N,N-dimethylformamide (5 mL) was treated with sodium hydride (60% in mineral oil, 0.057 g). After the gas evolution ceased, 2-fluoro-4-iodopyridine (0.22 g) was added slowly to the solution. The mixture was heated at 100° C. overnight under nitrogen atmosphere, cooled, diluted with ethyl acetate and washed with aqueous NaOH. The organic layer was concentrated and purified by preparative TLC, eluting with petroleum ether/ethyl acetate (10/1).

Example 140B tert-butyl 6-(8-(benzo[d]thiazol-2-ylcarbamoyl)-3,4-dihydroisoquinolin-2(1H)-yl)-2'-phenoxy-3,4'-bipyridine-2-carboxylate The title compound was prepared by substituting EXAMPLE 140A for EXAMPLE 1D and EXAMPLE 30A for EXAMPLE 82D in EXAMPLE 82E.

Example 140C

6-[8-(1,3-benzothiazol-2-ylcarbamoyl)-3,4-dihydroisoquinolin-2(1H)-yl]-2'-phenoxy-3,4'-bipyridine-2-carboxylic acid The title compound was prepared by substituting EXAMPLE 140B for EXAMPLE 8B in EXAMPLE 8C. $^1$H NMR (400 MHz, dimethylsulfoxide-$d_6$) δ ppm 12.89 (s, 1H), 8.03-8.12 (m, 2H), 7.78 (t, 2H), 7.63 (d, 1H), 7.34-7.49 (m, 6H), 7.18-7.22 (m, 1H), 7.13 (d, 2H), 7.08 (d, 1H), 7.03 (d, 1H), 6.96 (s, 1H), 4.95-5.06 (m, 2H), 3.93 (t, 2H), 3.01-3.04 (m, 2H).

Example 141

6-[8-(1,3-benzothiazol-2-ylcarbamoyl)-3,4-dihydroisoquinolin-2(1H)-yl]-3-(1-benzyl-1H-pyrrolo[2,3-b]pyridin-3-yl)pyridine-2-carboxylic acid

Example 141A 1-benzyl-3-bromo-1H-pyrrolo[2,3-b]pyridine

To a solution of 3-bromo-1H-pyrrolo[2,3-b]pyridine (500 mg) in N,N-dimethylformamide (10 mL) was added NaH (70 mg). The mixture was stirred for 50 minutes, and (bromomethyl)benzene (0.290 mL) was added dropwise. The reaction was stirred for 48 hours and quenched by the addition of water and ethyl acetate. The layers were separated, and the organic layer was washed with brine, dried with $Na_2SO_4$, filtered and concentrated. The residue was purified by silica gel chromatography, eluting with 2:1 hexane to ethyl acetate, to give the title compound.

Example 141B 1-benzyl-3-(4,4,5,5-tetramethyl-1,3,2-dioxaborolan-2-yl)-1H-pyrrolo[2,3-b]pyridine The title compound was prepared by substituting EXAMPLE 141A for EXAMPLE 84C in EXAMPLE 84D.

Example 141C tert-butyl 6-(8-(benzo[d]thiazol-2-ylcarbamoyl)-3,4-dihydroisoquinolin-2(1H)-yl)-3-(1-benzyl-1H-pyrrolo[2,3-b]pyridin-3-yl)picolinate The title compound was prepared by substituting EXAMPLE 141B for EXAMPLE 22A in EXAMPLE 22B.

Example 141D

6-[8-(1,3-benzothiazol-2-ylcarbamoyl)-3,4-dihydroisoquinolin-2(1H)-yl]-3-(1-benzyl-1H-pyrrolo[2,3-b]pyridin-3-yl)pyridine-2-carboxylic acid The title compound was prepared by substituting EXAMPLE 141C for EXAMPLE 88 in EXAMPLE 8C. $^1$H NMR (400 MHz, dimethylsulfoxide-$d_6$) δ ppm 12.86 (v br s, 1H), 8.28 (s, 1H), 8.03 (d, 1H), 7.87 (d, 1H), 7.80 (d, 1H), 7.75 (d, 1H), 7.63 (d, 1H), 7.62 (s, 1H), 7.46 (m, 2H), 7.40-7.20 (m, 7H) 7.12 (m, 1H), 6.99 (d, 1H), 5.51 (s, 2H), 4.99 (s, 2H), 3.92 (br t, 2H), 3.03 (br t, 2H).

Example 142

6-[8-(1,3-benzothiazol-2-ylcarbamoyl)-3,4-dihydroisoquinolin-2(1H)-yl]-3'-methyl-2'-phenoxy-3,4'-bipyridine-2-carboxylic acid

Example 142A 4-iodo-3-methyl-2-phenoxypyridine

The title compound was prepared by substituting phenol for cyclohexanol in EXAMPLE 138A.

Example 142B tert-butyl 6-(8-(benzo[d]thiazol-2-ylcarbamoyl)-3,4-dihydroisoquinolin-2(1H)-yl)-3'-methyl-2'-phenoxy-3,4'-bipyridine-2-carboxylate The title compound was prepared by substituting EXAMPLE 142A for EXAMPLE 1D and EXAMPLE 30A for EXAMPLE 82D in EXAMPLE 82E.

Example 142C

6-[8-(1,3-benzothiazol-2-ylcarbamoyl)-3,4-dihydroisoquinolin-2(1H)-yl]-3'-methyl-2'-phenoxy-3,4'-bipyridine-2-carboxylic acid The title compound was prepared by substituting EXAMPLE 142B for EXAMPLE 8B in EXAMPLE 8C. $^1$H NMR (400 MHz, dimethylsulfoxide-$d_6$) δ ppm 7.88 (d, 1H), 7.72 (s, 1H), 7.47 (d, 1H), 7.38 (d, 1H), 7.28-7.32 (m, 4H), 7.24-7.28 (m, 3H), 7.05-7.10 (m, 3H), 6.97 (d, 1H), 6.67 (d, 1H), 5.09-5.13 (m, 2H), 3.84 (s, 2H), 3.04 (s, 2H), 2.01 (s, 3H).

Example 143

6-[8-(1,3-benzothiazol-2-ylcarbamoyl)-3,4-dihydroisoquinolin-2(1H)-yl]-3'-methyl-2'-[methyl(phenyl)amino]-3,4'-bipyridine-2-carboxylic acid

Example 143A 4-iodo-N,3-dimethyl-N-phenylpyridin-2-amine

2-Fluoro-4-iodo-3-methylpyridine (700 mg) in N-methylaniline (2.5 mL) was heated at 18° C. in a Biotage Initiator microwave reactor for 18 hours. The reaction mixture was loaded onto a silica gel cartridge, and was eluted with 0-100% dichloromethane in hexanes to provide the title compound.

Example 143B tert-butyl 6-(8-(benzo[d]thiazol-2-ylcarbamoyl)-3,4-dihydroisoquinolin-2(1H)-yl)-3'-methyl-2'-(methyl(phenyl)amino)-3,4'-bipyridine-2-carboxylate The title compound was prepared by substituting EXAMPLE 143A for EXAMPLE 1D and EXAMPLE 30A for EXAMPLE 82D in EXAMPLE 82E.

Example 143C

6-[8-(1,3-benzothiazol-2-ylcarbamoyl)-3,4-dihydroisoquinolin-2(1H)-yl]-3'-methyl-2'-[methyl(phenyl)amino]-3,4'-bipyridine-2-carboxylic acid The title compound was prepared by substituting EXAMPLE 143B for EXAMPLE 8B in EXAMPLE 8C. $^1$H NMR (400 MHz, DMSO-$d_6$) δ ppm 8.24 (d, 1H), 7.76 (d, 1H), 7.49 (d, 1H), 7.32-7.41 (m, 4H), 7.19-7.29 (m, 3H), 7.13-7.15 (m, 2H), 6.96 (d, 1H), 6.71-6.77 (m, 4H), 5.07-5.13 (m, 2H), 3.80-3.83 (m, 2H), 3.37 (s, 3H), 3.05 (t, 2H), 1.64 (s, 3H).

Example 144

6-[8-(1,3-benzothiazol-2-ylcarbamoyl)-3,4-dihydroisoquinolin-2(1H)-yl]-3-(1-{[1-(methoxymethyl)cyclohexyl]methyl}-5-methyl-1H-pyrazol-4-yl)pyridine-2-carboxylic acid

Example 144A methyl 1-(methoxymethyl)cyclohexanecarboxylate

The title compound was prepared by substituting bromomethylmethyl ether for 1-bromo-2-methoxyethane and methyl cyclohexanecarboxylate for EXAMPLE 134A in EXAMPLE 134B.

Example 144B (1-(methoxymethyl)cyclohexyl)methanol

The title compound was prepared by substituting EXAMPLE 144A for EXAMPLE 134B in EXAMPLE 134C.

Example 144C 1-((1-(methoxymethyl)cyclohexyl)methyl)-1H-pyrazole

The title compound was prepared by substituting EXAMPLE 144B for (3-(dimethylamino)phenyl)methanol and 1H-pyrazole for 4-(4,4,5,5-tetramethyl-1,3,2-dioxaborolan-2-yl)-1H-pyrazole in EXAMPLE 34A.

Example 144D 1-((1-(methoxymethyl)cyclohexyl)methyl)-5-methyl-1H-pyrazole

The title compound was prepared by substituting EXAMPLE 144C for EXAMPLE 63A in EXAMPLE 63B.

Example 144E 4-iodo-1-((1-(methoxymethyl)cyclohexyl)methyl)-5-methyl-1H-pyrazole The title compound was prepared by substituting EXAMPLE 144D for EXAMPLE 65E in EXAMPLE 65F.

Example 144F

6-[8-(1,3-benzothiazol-2-ylcarbamoyl)-3,4-dihydroisoquinolin-2(1H)-yl]-3-(1-{[1-(methoxymethyl)cyclohexyl]methyl}-5-methyl-1H-pyrazol-4-yl)pyridine-2-carboxylic acid The title compound was prepared by substituting EXAMPLE 144E for EXAMPLE 75A in EXAMPLE 75B, and then substituting that product for EXAMPLE 8B in EXAMPLE 8C. $^1$H NMR (300 MHz, dimethylsulfoxide-$d_6$) δ ppm 12.86 (s, 1H), 8.04 (d, 1H), 7.54 (m, 8H), 6.94 (d, 1H), 4.94 (s, 2H), 3.86 (t, 2H), 3.28 (m, 4H), 3.03 (m, 4H), 1.23 (m, 10H).

Example 145

6-[8-(1,3-benzothiazol-2-ylcarbamoyl)-3,4-dihydroisoquinolin-2(1H)-yl]-3-(1-{[3,3-dimethyl-1-(morpholin-4-yl)cyclohexyl]methyl}-5-methyl-1H-pyrazol-4-yl)pyridine-2-carboxylic acid

Example 145A 1-amino-3,3-dimethylcyclohexanecarbonitrile

To a solution of 3,3-dimethylcyclohexanone (1.89 g) in water (3.8 mL) and ethanol (4.5 mL) was added ammonium chloride (920 mg), followed by concentrated ammonium hydroxide solution (2 mL) and trimethylsilanecarbonitrile (1.71 g). The reaction was heated to 70° C. for 18 hours. The reaction was concentrated to dryness, and was partitioned between water and methylene chloride. The layers were separated, and the aqueous layer was extracted with additional methylene chloride (3×25 mL). The combined organic layers were dried over MgSO$_4$, filtered and concentrated. The residue was purified by silica gel chromatography, eluting with 40% ethyl acetate in petroleum ether, to give the title compound.

Example 145B 1-amino-3,3-dimethylcyclohexanecarboxamide

A solution of EXAMPLE 145A (4.6 g) in concentrated H$_2$SO$_4$ (9 mL) was heated to 70° C. for 20 minutes. The reaction mixture was cooled to about 0° C. in an ice bath and diluted with water. The pH of the solution was adjusted to pH 7-8 by addition of concentrated aqueous ammonia solution. The aqueous layer was extracted with methylene chloride (2×50 mL). The combined organic layers were washed with water (1×20 mL), dried over MgSO$_4$, filtered, and concentrated to give the title compound, which was used in the next step without further purification.

Example 145C ethyl 1-amino-3,3-dimethylcyclohexanecarboxylate

To a solution of EXAMPLE 145B (3.8 g) in water (25 mL) was added concentrated hydrochloric acid (25 mL). The reaction mixture was heated to 110° C. for 3 hours, and then evaporated to dryness. The residue (3.5 g) was dissolved in ethanol (30 mL), and sulfurous dichloride (10 g) was added. The resulting mixture was heated to 80° C. for about 18 hours, after which it was concentrated to dryness. The residue was diluted with saturated aqueous NaHCO$_3$ solution and extracted with methylene chloride (2×25 mL). The organic layer was dried over MgSO$_4$, filtered and concentrated. The residue was purified by silica gel chromatography, eluting with 2:1 petroleum ether/ethyl acetate, to give the title compound.

Example 145D ethyl 3,3-dimethyl-1-morpholinocyclohexanecarboxylate

To a solution of EXAMPLE 145C (3.5 g) in N,N-dimethylformamide (30 mL) was added 1-bromo-2-(2-bromoethoxy)ethane (5.8 g) and K$_2$CO$_3$ (6.5 g). The reaction mixture was heated to 95° C. for 18 hours. The mixture was cooled to room temperature, diluted with water, and extracted with methylene chloride (3×50 mL). The combined organic layers were washed with saturated NaCl solution (1×25 mL), dried over Na$_2$SO$_4$, filtered, and concentrated. The residue was purified by silica gel chromatography, eluting with 4:1 petroleum ether/ethyl acetate solution, to give the title compound.

Example 145E (3,3-dimethyl-1-morpholinocyclohexyl)methanol

To a cooled (0° C.) solution of EXAMPLE 145D (3.7 g) in tetrahydrofuran (20 mL) was added lithium aluminum hydride (720 mg). The cooling bath was removed, and the reaction mixture was stirred at room temperature for 3 hours. The reaction was quenched by the sequential addition of water (0.8 mL) and 15% aqueous NaOH solution (2 mL). The mixture was dried with MgSO$_4$, filtered and concentrated to give the title compound, which was used in the subsequent step without further purification.

Example 145F 4-((1H-pyrazol-1-yl)methyl)-3,3-dimethylcyclohexyl)morpholine

The title compound was prepared by substituting EXAMPLE 145E for (3-(dimethylamino)phenyl)methanol and 1H-pyrazole for 4-(4,4,5,5-tetramethyl-1,3,2-dioxaborolan-2-yl)-1H-pyrazole in EXAMPLE 34A.

Example 145G 4-(1-((4-bromo-5-methyl-1H-pyrazol-1-yl)methyl)-3,3-dimethylcyclohexyl)morpholine A solution of EXAMPLE 145F (0.53 g) in tetrahydrofuran (15 mL) was cooled to 0° C., and nBuLi (0.917 ml) was added dropwise. The reaction was stirred at 0° C. for 30 minutes, and iodomethane (0.155 mL) was added. The cooling bath was removed, and the reaction mixture was warmed to room temperature. The reaction mixture was diluted with methylene chloride (50 mL) and washed with water (2×25 mL). The organic layer was dried over magnesium sulfate, filtered, and concentrated. The residue was dissolved in N,N-dimethylformamide (10 mL) and treated with N-bromosuccinimide (0.136 g). After 1 hour, the reaction mixture was diluted with methylene chloride (50 mL) and washed with water (2×25 mL). The organic layer was dried over magnesium sulfate, filtered, and concentrated. The residue was purified by silica gel chromatography, eluting with a gradient of 0 to 75% ethyl acetate in hexanes, to give the title compound.

Example 145H

6-[8-(1,3-benzothiazol-2-ylcarbamoyl)-3,4-dihydroisoquinolin-2(1H)-yl]-3-(1-{[3,3-dimethyl-1-(morpholin-4-yl)cyclohexyl]methyl}-5-methyl-1H-pyrazol-4-yl)pyridine-2-carboxylic acid A mixture of EXAMPLE 30A (0.192 g), EXAMPLE 145G (0.083 g), 1,3,5,7-tetramethyl-6-tetradecane-2,4,8-trioxa-6-phosphaadamantane (9.25 mg), potassium phosphate (0.167 g) and), and tris(dibenzylideneacetone)dipalladium(0) chloroform adduct (0.012 g) was dissolved in tetrahydrofuran (2 mL) and water (0.66 mL). The reaction mixture was flushed with nitrogen and then heated under microwave conditions (Biotage) to 140° C. for 5 minutes. The reaction was diluted with ethyl acetate (50 mL), washed with water (25 mL) and brine (25 mL), dried over magnesium sulfate, filtered, and concentrated. The residue was purified by silica gel chromatography, eluting with a gradient of 5% to 100% ethyl acetate in hexane, to give the intermediate ester. The residue was dissolved in methylene chloride (0.5 mL) and treated with TFA (0.5 mL). The reaction mixture was stirred overnight and concentrated to dryness. The residue was purified by RP-HPLC, eluting with 10% to 70% acetonitrile in water containing 0.1% v/v TFA, to give the title compound. $^1$H NMR (300 MHz, dimethylsulfoxide-d$_6$) δ 12.85 (s, 1H), 9.54 (s, 1H), 8.03 (d, 1H), 7.79 (d, 1H), 7.62 (d, 1H), 7.58-7.41 (m, 4H), 7.41-7.30 (m, 2H), 6.98 (d, 1H), 4.97 (s, 3H), 4.57 (s, 6H), 4.02 (s, 1H), 3.90 (t, 2H), 3.81-3.31 (m, 3H), 3.02 (t, 2H), 2.73 (s, 1H), 2.20 (s, 2H), 2.01-1.39 (m, 4H), 1.33-0.70 (m, 6H).

Example 146

6-[8-(1,3-benzothiazol-2-ylcarbamoyl)-3,4-dihydroisoquinolin-2(1H)-yl]-3-(1-{[1-(2-methoxyethyl)-3,3-dimethylcyclohexyl]methyl}-5-methyl-1H-pyrazol-4-yl)pyridine-2-carboxylic acid Example 146A 2-(3,3-dimethylcyclohexylidene)-1,3-dithiane To a solution of (1,3-dithian-2-yl)trimethylsilane (5.0 g) in tetrahydrofuran at −78° C. was added n-butyllithium (1.6M, 16.24 mL). After stirring for 30 minutes, 3,3-dimethylcyclohexanone (3.3 g) was added as a solution in tetrahydrofuran and the reaction mixture was allowed to warm to room temperature. The reaction mixture was diluted with diethyl ether (100 mL), washed with water (50 mL) and brine (50 mL), dried over magnesium sulfate, filtered, and concentrated. Silica gel chromatography eluting with a gradient of 0.13% to 2.5% ether/hexanes gave the title compound.

Example 146B methyl 3,3-dimethylcyclohexanecarboxylate

EXAMPLE 146A (2.00 g) and copper(II) sulfate pentahydrate (6.56 g) in methanol (25 mL) were heated to 65° C. and stirred overnight. The reaction mixture was filtered, rinsed with ether and concentrated. The residue was loaded onto

Example 146C methyl 1-(2-methoxyethyl)-3,3-dimethylcyclohexanecarboxylate

A solution of EXAMPLE 146B (0.60 g) in tetrahydrofuran (5 mL) was added to lithium diisopropylamide (2.0 M, 2.10 mL) at −78° C. After stirring for 30 minutes, 1-bromo-2-methoxyethane (0.64 g) was added and the reaction mixture was allowed to warm to room temperature. The reaction mixture was diluted with ether (75 mL), washed with water (50 mL) and brine (50 mL), dried over magnesium sulfate, filtered, and concentrated. Silica gel chromatography eluting with 1-20% ethyl acetate in hexanes provided the title compound.

Example 146D 1-((1-(2-methoxyethyl)-3,3-dimethylcyclohexyl)methyl)-1H-pyrazole To a solution of EXAMPLE 146C (0.37 g) in diethyl ether (5 mL) was added LiAlH$_4$ (11.0M, 1.61 mL) dropwise. The reaction was stirred for 2 hours at room temperature. The reaction mixture was cooled to 0° C., quenched with water (0.062 mL), 15% aqueous NaOH (0.062 mL), and then more water (0.17 mL) was added. The reaction mixture was stirred for 1 hour, magnesium sulfate was added, and the mixture was filtered and concentrated. The residue was dissolved in toluene (5 mL), 1H-pyrazole (0.17 g) and cyanomethylenetributylphosphorane (0.47 g) were added and the mixture was heated to 85° C. overnight. The reaction mixture was cooled, loaded onto silica gel and eluted with 1-10% ethyl acetate in hexanes to give the title compound.

Example 146E 1-((1-(2-methoxyethyl)-3,3-dimethylcyclohexyl)methyl)-5-methyl-1H-pyrazole The title compound was prepared by substituting EXAMPLE 146D for EXAMPLE 63A in EXAMPLE 63B.

Example 146F 4-iodo-1-((1-(2-methoxyethyl)-3,3-dimethylcyclohexyl)methyl)-5-methyl-1H-pyrazole The title compound was prepared by substituting EXAMPLE 146E for EXAMPLE 66B in EXAMPLE 66C.

Example 146G tert-butyl 6-(8-(benzo[d]thiazol-2-ylcarbamoyl)-3,4-dihydroisoquinolin-2(1H)-yl)-3-(1-((1-(2-methoxyethyl)-3,3-dimethylcyclohexyl)methyl)-5-methyl-1H-pyrazol-4-yl)picolinate The title compound was prepared by substituting EXAMPLE 146F for EXAMPLE 77D in EXAMPLE 77E.

Example 146H

6-[8-(1,3-benzothiazol-2-ylcarbamoyl)-3,4-dihydroisoquinolin-2(1H)-yl]-3-(1-{[1-(2-methoxyethyl)-3,3-dimethylcyclohexyl]methyl}-5-methyl-1H-pyrazol-4-yl)pyridine-2-carboxylic acid The title compound was prepared by substituting EXAMPLE 146G for EXAMPLE 8B in EXAMPLE 8C. $^1$H NMR (300 MHz, dimethylsulfoxide-d$_6$) δ 12.85 (s, 1H), 8.04 (d, 1H), 7.79 (d, 1H), 7.61 (d, 1H), 7.48 (dd, 2H), 7.46-7.41 (m, 1H), 7.36 (ddd, 2H), 7.29 (s, 1H), 6.95 (d, 1H), 4.95 (s, 2H), 3.96-3.73 (m, 4H), 3.20 (s, 3H), 3.00 (dd, 2H), 2.10 (s, 3H), 1.77-1.39 (m, 4H), 1.36-0.99 (m, 8H), 0.93 (d, 6H).

Example 147

6-[8-(1,3-benzothiazol-2-ylcarbamoyl)-3,4-dihydroisoquinolin-2(1H)-yl]-3-(1-{[1-(3-methoxypropyl)cycloheptyl]methyl}-5-methyl-1H-pyrazol-4-yl)pyridine-2-carboxylic acid

Example 147A methyl 1-(3-methoxypropyl)cycloheptanecarboxylate

The title compound was prepared by substituting 1-bromo-3-methoxypropane for 1-bromo-2-methoxyethane in EXAMPLE 134B.

Example 147B (1-(3-methoxypropyl)cycloheptyl)methanol

The title compound was prepared by substituting EXAMPLE 147A for EXAMPLE 134B in EXAMPLE 134C.

Example 147C 1-((1-(3-methoxypropyl)cycloheptyl)methyl)-1H-pyrazole

The title compound was prepared by substituting EXAMPLE 147B for (3-(dimethylamino)phenyl)methanol and 1H-pyrazole for 4-(4,4,5,5-tetramethyl-1,3,2-dioxaborolan-2-yl)-1H-pyrazole in EXAMPLE 34A.

Example 147D 1-((1-(3-methoxypropyl)cycloheptyl)methyl)-5-methyl-1H-pyrazole The title compound was prepared by substituting EXAMPLE 147C for EXAMPLE 63A in EXAMPLE 63B.

Example 147E 4-iodo-1-((1-(3-methoxypropyl)cycloheptyl)methyl)-5-methyl-1H-pyrazole The title compound was prepared by substituting EXAMPLE 147D for EXAMPLE 65E in EXAMPLE 65F.

Example 147F

6-[8-(1,3-benzothiazol-2-ylcarbamoyl)-3,4-dihydroisoquinolin-2(1H)-yl]-3-(1-{[1-(3-methoxypropyl)cycloheptyl]methyl}-5-methyl-1H-pyrazol-4-yl)pyridine-2-carboxylic acid The title compound was prepared by substituting EXAMPLE 147E for EXAMPLE 75A in EXAMPLE 75B, and then substituting that product for EXAMPLE 8B in EXAMPLE 8C. $^1$H NMR (300 MHz, dimethylsulfoxide-$d_6$) δ ppm 12.86 (s, 1H), 8.04 (d, 1H), 7.79 (d, 1H), 7.61 (d, 1H), 7.40 (m, 5H), 7.27 (s, 1H), 6.95 (d, 1H), 4.95 (s, 2H), 3.80 (s, 3H), 3.27 (t, 2H), 3.21 (s, 3H), 3.01 (t, 2H), 2.11 (s, 3H), 1.39 (m, 18H).

Example 148

N-(1,3-benzothiazol-2-yl)-2-{5-(1-{[1-(2-methoxyethyl)cycloheptyl]methyl}-5-methyl-1H-pyrazol-4-yl)-6-[(methylsulfonyl)carbamoyl]pyridin-2-yl}-1,2,3,4-tetrahydroisoquinoline-8-carboxamide To a solution of EXAMPLE 134G (50 mg) in dichloromethane (2 mL) was added methanesulfonamide (7.4 mg), 1-ethyl-3-[3-(dimethylamino)propyl]-carbodiimide hydrochloride (28 mg) and 4-dimethylaminopyridine (18 mg). The mixture was stirred overnight. The mixture was loaded on a silica gel column and eluted with 5% methanol in dichloromethane to give the pure product. $^1$H NMR (300 MHz, dimethylsulfoxide-$d_6$) δ ppm 8.03 (d, 1H), 7.79 (d, 1H), 7.60 (s, 1H), 7.41 (m, 5H), 7.30 (s, 1H), 7.00 (d, 1H), 4.96 (s, 2H), 3.94 (m, 2H), 3.83 (s, 2H), 3.42 (t, 2H), 3.41 (s, 3H), 3.27 (s, 3H), 3.21 (m, 3H), 3.11 (m, 2H), 2.12 (s, 3H), 1.45 (m, 16H)

Example 149

6-[8-(1,3-benzothiazol-2-ylcarbamoyl)-3,4-dihydroisoquinolin-2(1H)-yl]-3-[1-(tetrahydro-2H-pyran-2-ylmethyl)-1H-pyrazol-4-yl]pyridine-2-carboxylic acid

Example 149A 1-((tetrahydro-2H-pyran-2-yl)methyl)-4-(4,4,5,5-tetramethyl-1,3,2-dioxaborolan-2-yl)-1H-pyrazole The title compound was prepared by substituting (tetrahydro-2H-pyran-2-yl)methanol for (3-(dimethylamino)phenyl)methanol in EXAMPLE 34A.

Example 149B tert-butyl 6-(8-(benzo[d]thiazol-2-ylcarbamoyl)-3,4-dihydroisoquinolin-2(1H)-yl)-3-(1-((tetrahydro-2H-pyran-2-yl)methyl)-1H-pyrazol-4-yl)picolinate The title compound was prepared by substituting EXAMPLE 149A for EXAMPLE 82D in EXAMPLE 82E.

Example 149C

6-[8-(1,3-benzothiazol-2-ylcarbamoyl)-3,4-dihydroisoquinolin-2(1H)-yl]-3-[1-(tetrahydro-2H-pyran-2-ylmethyl)-1H-pyrazol-4-yl]pyridine-2-carboxylic acid The title compound was prepared by substituting EXAMPLE 149B for EXAMPLE 8B in EXAMPLE 8C. $^1$H NMR (300 MHz, dimethylsulfoxide-$d_6$) δ ppm 12.96-13.25 (m, 1H), 12.85 (s, 1H), 8.04 (d, 1H), 7.79 (d, 1H), 7.76 (s, 1H), 7.71 (d, 1H), 7.61 (d, 1H), 7.53 (s, 1H), 7.32-7.51 (m, 4H), 6.94 (d, 1H), 4.94 (s, 2H), 4.08 (d, 2H), 3.80-3.90 (m, 3H), 3.58-3.67 (m, 1H), 3.24-3.34 (m, 1H), 3.00 (t, 2H), 1.73-1.80 (m, 1H), 1.49-1.57 (m, 1H), 1.36-1.49 (m, 3H), 1.09-1.24 (m, 1H).

Example 150

6-[8-(1,3-benzothiazol-2-ylcarbamoyl)-3,4-dihydroisoquinolin-2(1H)-yl]-3-(1-{[(1R,2R,3R,5S)-2-(2-methoxyethyl)-6,6-dimethylbicyclo[3.1.1]hept-3-yl]methyl}-1H-pyrazol-4-yl)pyridine-2-carboxylic acid

Example 150A (1R,2R,3R,5S)-2-(2-methoxyethyl)-6,6-dimethylbicyclo[3.1.1]heptane-3-carbaldehyde To a solution of (1S,5R)-2-(2-methoxyethyl)-6,6-dimethylbicyclo[3.1.1]hept-2-ene (940 mg) in tetrahydrofuran (5 mL) was added dropwise 9-borabicyclo[3.3.1]nonane (0.5 M in tetrahydrofuran, 10.43 mL). The reaction mixture was heated to reflux overnight, then cooled to –35° C. and then placed under a CO atmosphere (1 atm). LiAl(OtBu)$_3$H (1M in tetrahydrofuran, 5.21 mL) was added dropwise over 30 minutes. Following the addition, the reaction mixture was stirred for 1.5 hours under CO (1 atm), during which time the reaction temperature was increased to 0° C. The mixture was warmed to room temperature and stirred for 45 minutes, then the system was flushed with argon and a buffer solution (5.28 g NaH$_2$PO$_4$ and 6.86 g K$_2$HPO$_4$ in 20 mL water) was added. The flask was chilled in a –10° C. cooling bath and the reaction was quenched by dropwise addition of 30% aqueous H$_2$O$_2$ solution (2.2 mL), then warmed to room temperature and stirred for 15 minutes. The reaction mixture was partitioned between water (50 mL) and ethyl acetate (3×75 mL). The organic phase was then washed with 10% Na$_2$S$_2$O$_3$ (3×50 mL) and brine (50 mL), then dried (MgSO$_4$), filtered, and concentrated. The crude product was purified by flash chromatography on silica gel eluting with 0 to 50% ethyl acetate in hexanes to give the title compound.

Example 150B ((1R,2R,3R,5S)-2-(2-methoxyethyl)-6,6-dimethylbicyclo[3.1.1]heptan-3-yl)methanol To a solution of EXAMPLE 150A (407 mg) in tetrahydrofuran (10 mL), which was cooled in a room temperature water bath, was added dropwise LAH (1.0M in tetrahydrofuran, 2.3 mL). The reaction was stirred at room temperature for 1 hour then quenched with water (25 mL). The resulting suspension was filtered through diatomaceous earth, and the filter cake was rinsed with ether (50 mL). The layers were separated and the aqueous layer was extracted with ether (2×25 mL). The extracts were washed with brine (25 mL), dried (MgSO$_4$), filtered, and concentrated to give the title compound, which was used without further purification.

Example 150C 1-(((1R,2R,3R,5S)-2-(2-methoxyethyl)-6,6-dimethylbicyclo[3.1.1]heptan-3-yl)methyl)-4-(4,4,5,5-tetramethyl-1,3,2-dioxaborolan-2-yl)-1H-pyrazole The title compound was prepared by substituting EXAMPLE 150B for (3-(dimethylamino)phenyl)methanol in EXAMPLE 34A.

Example 150D tert-butyl 6-(8-(benzo[d]thiazol-2-ylcarbamoyl)-3,4-dihydroisoquinolin-2(1H)-yl)-3-(1-(((1R,2R,3R,5S)-2-(2-methoxyethyl)-6,6-dimethylbicyclo[3.1.1]heptan-3-yl)methyl)-1H-pyrazol-4-yl)picolinate The title compound was prepared by substituting EXAMPLE 150C for EXAMPLE 82D in EXAMPLE 82E.

Example 150E

6-[8-(1,3-benzothiazol-2-ylcarbamoyl)-3,4-dihydroisoquinolin-2(1H)-yl]-3-(1-{[(1R,2R,3R,5S)-2-(2-methoxyethyl)-6,6-dimethylbicyclo[3.1.1]hept-3-yl]methyl}-1H-pyrazol-4-yl)pyridine-2-carboxylic acid The title compound was prepared by substituting EXAMPLE 150D for EXAMPLE 8B in EXAMPLE 8C. $^1$H NMR (300 MHz, DMSO-d) δ ppm 12.89-13.24 (m, 1H), 12.85 (s, 1H), 8.04 (d, 1H), 7.87 (s, 1H), 7.79 (d, 1H), 7.70 (d, 1H), 7.61 (d, 1H), 7.54 (s, 1H), 7.45-7.51 (m, 1H), 7.40-7.45 (m, 1H), 7.32-7.39 (m, 2H), 6.95 (d, 1H), 4.94 (s, 2H), 3.90-4.10 (m, 2H), 3.87 (t, 2H), 3.20-3.31 (m, 2H), 3.15 (s, 3H), 3.00 (t, 2H), 2.19-2.31 (m, 2H), 1.81-1.93 (m, 3H), 1.71-1.80 (m, 1H), 1.47-1.63 (m, 2H), 1.31-1.44 (m, 1H), 1.16 (s, 3H), 0.94 (s, 3H), 0.75 (d, 1H).

Example 151

6-[8-(1,3-benzothiazol-2-ylcarbamoyl)-3,4-dihydroisoquinolin-2(1H)-yl]-3-(1-{[1-(2-methoxyethoxy)cycloheptyl]methyl}-5-methyl-1H-pyrazol-4-yl)pyridine-2-carboxylic acid

Example 151A 1-oxaspiro[2.6]nonane

To a mixture of trimethylsulfonium iodide (35.7 g) in 300 mL dry DMSO was added 11.2 g of cycloheptanone with stirring. A solution of potassium tert-butoxide (16.83 g) in 200 mL dry DMSO was slowly added. The resulting solution was stirred at room temperature for 16 hours. The reaction mixture was quenched by addition of water (600 mL), and extracted with diethyl ether (3×200 mL). The combined organic layers were washed with water (200 mL), dried over Na$_2$SO$_4$, filtered, and concentrated under reduced pressure to give the product.

Example 151B 1-((4-iodo-5-methyl-1H-pyrazol-1-yl)methyl)cycloheptanol

The title compound was prepared by substituting EXAMPLE 151A for EXAMPLE 141A in EXAMPLE 141B.

Example 151C 4-iodo-1-((1-(2-methoxyethoxy)cycloheptyl)methyl)-5-methyl-1H-pyrazole To a solution of EXAMPLE 151B (356 mg) in N,N-dimethylacetamide (6 mL) was added NaH (128 mg, 60% in mineral oil). The mixture was stirred for 30 minutes. Then, 1-bromo-2-methoxyethane (740 mg) was added to the mixture, which was stirred overnight. The reaction mixture was diluted with ethyl acetate (200 mL) and washed with water, brine and dried over Na$_2$SO$_4$. After filtration and concentration, the residue containing the crude title compound was used in the next reaction without further purification.

Example 151D

6-[8-(1,3-benzothiazol-2-ylcarbamoyl)-3,4-dihydroisoquinolin-2(1H)-yl]-3-(1-{[1-(2-methoxyethoxy)cycloheptyl]methyl}-5-methyl-1H-pyrazol-4-yl)pyridine-2-carboxylic acid The title compound was prepared by substituting EXAMPLE 151C for EXAMPLE 75A in EXAMPLE 75B, and then substituting that product for EXAMPLE 8B in EXAMPLE 8C. $^1$H NMR (300 MHz, dimethylsulfoxide-d$_6$) δ ppm 12.85 (s, 1H), 8.03 (d, 1H), 7.79 (d, 1H), 7.61 (d, 1H), 7.41 (m, 5H), 7.27 (s, 1H), 6.95 (d, 1H), 4.95 (s, 2H), 4.03 (s, 2H), 3.89 (t, 2H), 3.39 (t, 2H), 3.21 (m, 3H), 3.01 (t, 2H), 2.13 (s, 3H), 1.43 (m, 14H).

Example 152

6-[8-(1,3-benzothiazol-2-ylcarbamoyl)-3,4-dihydroisoquinolin-2(1H)-yl]-3-{1-[1-cyclohexyl-3-(morpholin-4-yl)propyl]-5-methyl-1H-pyrazol-4-yl}pyridine-2-carboxylic acid

Example 152A 3-cyclohexyl-3-(1H-pyrazol-1-yl)propanal

A solution of (E)-3-cyclohexylacrylaldehyde (4.94 g) (made according to Organic Letters (2011), 13(1), 70-73), 2-(bis(3,5-bis(trifluoromethyl)phenyl)-(trimethylsilyloxy)methyl)pyrrolidine (0.712 g) and 4-nitrobenzoic acid (0.124 mL) in toluene (60 mL) was stirred at room temperature for 10 minutes and 1H-pyrazole (1.622 g) was added. The reaction mixture was stirred for 3 days, and purified by flash chromatography (silica gel, 0-50% ethyl acetate/hexanes).

Example 152B 4-(3-cyclohexyl-3-(1H-pyrazol-1-yl)propyl)morpholine

The title compound was prepared by substituting EXAMPLE 152A for benzaldehyde and morpholine for EXAMPLE 133A in EXAMPLE 133B.

Example 152C 4-(3-cyclohexyl-3-(5-methyl-1H-pyrazol-1-yl)propyl)morpholine

The title compound was prepared by substituting EXAMPLE 152B for EXAMPLE 63A in EXAMPLE 63B.

Example 152D 4-(3-(4-bromo-5-methyl-1H-pyrazol-1-yl)-3-cyclohexylpropyl)morpholine The title compound was prepared by substituting EXAMPLE 152C for EXAMPLE 63B in EXAMPLE 63C.

Example 152E tert-butyl 6-(8-(benzo[d]thiazol-2-ylcarbamoyl)-3,4-dihydroisoquinolin-2(1H)-yl)-3-(1-(1-cyclohexyl-3-morpholinopropyl)-5-methyl-1H-pyrazol-4-yl)picolinate The title compound was prepared by substituting EXAMPLE 152D for EXAMPLE 77D in EXAMPLE 77E.

Example 152F

6-[8-(1,3-benzothiazol-2-ylcarbamoyl)-3,4-dihydroisoquinolin-2(1H)-yl]-3-{1-[1-cyclohexyl-3-(morpholin-4-yl)propyl]-5-methyl-1H-pyrazol-4-yl}pyridine-2-carboxylic acid The title compound was prepared by substituting EXAMPLE 152E for EXAMPLE 1E in EXAMPLE 1F. $^1$H NMR (300 MHz, dimethylsulfoxide-$d_6$) δ ppm 12.86 (s, 1H), 9.63 (s, 1H), 8.03 (d, 1H), 7.79 (d, 1H), 7.62 (d, 1H), 7.53-7.42 (m, 3H), 7.36 (dd, 3H), 6.97 (d, 1H), 6.51 (s, 1H), 4.97 (s, 2H), 4.00-3.85 (m, 5H), 3.58 (t, 2H), 3.02 (t, 2H), 2.31-2.18 (m, 2H), 1.93-1.69 (m, 4H), 1.60 (d, 2H), 1.28-0.79 (m, 8H).

Example 153

6-[8-(1,3-benzothiazol-2-ylcarbamoyl)-3,4-dihydroisoquinolin-2(1H)-yl]3-(1-benzyl-1H-indazol-5-yl)pyridine-2-carboxylic acid

Example 153A 1-benzyl-5-(4,4,5,5-tetramethyl-1,3,2-dioxaborolan-2-yl)-1H-indazole The title compound was prepared by substituting 5-(4,4,5,5-tetramethyl-1,3,2-dioxaborolan-2-yl)-1H-indazole for 4-(4,4,5,5-tetramethyl-1,3,2-dioxaborolan-2-yl)-1H-pyrazole and benzyl bromide for EXAMPLE 4A in EXAMPLE 4B.

Example 153B tert-butyl 6-(8-(benzo[d]thiazol-2-ylcarbamoyl)-3,4-dihydroisoquinolin-2(1H)-yl)-3-(1-benzyl-1H-indazol-5-yl)picolinate The title compound was prepared by substituting EXAMPLE 153A for EXAMPLE 22A in EXAMPLE 22B.

Example 153C

6-[8-(1,3-benzothiazol-2-ylcarbamoyl)-3,4-dihydroisoquinolin-2(1H)-yl]-3-(1-benzyl-1H-indazol-5-yl)pyridine-2-carboxylic acid The title compound was prepared by substituting EXAMPLE 153B for EXAMPLE 1E in EXAMPLE 1F. $^1$H NMR (400 MHz, dimethylsulfoxide-$d_6$) δ ppm 12.86 (v br s, 1H), 8.12 (s, 1H), 8.03 (d, 1H), 7.79 (d, 1H), 7.69 (m, 3H), 7.62 (d, 1H), 7.46 (m, 2H), 7.39-7.20 (m, 8H), 6.99 (d, 1H), 5.66 (s, 2H), 4.99 (s, 2H), 3.91 (br t, 2H), 3.02 (br t, 2H).

Example 154

6-[8-(1,3-benzothiazol-2-ylcarbamoyl)-3,4-dihydroisoquinolin-2(1H)-yl]-3-[5-methyl-1-(tetrahydro-2H-pyran-2-ylmethyl)-1H-pyrazol-4-yl]pyridine-2-carboxylic acid

Example 154A 4-bromo-1-((tetrahydro-2H-pyran-2-yl)methyl)-1H-pyrazole

The title compound was prepared by substituting (tetrahydro-2H-pyran-2-yl)methanol for (3-(dimethylamino)phenyl)methanol and 4-bromo-1H-pyrazole for 4-(4,4,5,5-tetramethyl-1,3,2-dioxaborolan-2-yl)-1H-pyrazole in EXAMPLE 34A.

Example 154B 4-bromo-1-((tetrahydro-2H-pyran-2-yl)methyl)-1H-pyrazole

A solution of EXAMPLE 154A (0.25 g) in tetrahydrofuran (2 mL) was cooled to −78° C. and treated with lithium diisopropylamide (prepared from diisopropylamine (0.12 g) and n-butyllithium (0.77 mL, 1.6 M). After stirring for 1 hour, methyl iodide (0.19 mL) was added and the reaction mixture was allowed to warm to room temperature. The reaction was diluted with ether (100 mL) and washed with water (3×75 mL) and brine (75 mL), dried over magnesium sulfate, filtered, and concentrated. Silica gel chromatography eluting with a gradient of 5% to 30% ethyl acetate/hexanes provided the title compound.

Example 154C tert-butyl 6-(8-(benzo[d]thiazol-2-ylcarbamoyl)-3,4-dihydroisoquinolin-2(1H)-yl)-3-(5-methyl-1-((tetrahydro-2H-pyran-2-yl)methyl)-1H-pyrazol-4-yl)picolinate The title compound was prepared by substituting EXAMPLE 154B for EXAMPLE 77D in EXAMPLE 77E.

Example 154D

6-[8-(1,3-benzothiazol-2-ylcarbamoyl)-3,4-dihydroisoquinolin-2(1H)-yl]-3-[5-methyl-1-(tetrahydro-2H-pyran-2-ylmethyl)-1H-pyrazol-4-yl]pyridine-2-carboxylic acid The title compound was prepared by substituting EXAMPLE 154C for EXAMPLE 8B in EXAMPLE 8C. $^1$H NMR (300 MHz, dimethylsulfoxide-$d_6$) δ ppm 12.85 (s, 2H), 8.04 (d, 1H), 7.79 (d, 1H), 7.61 (d, 1H), 7.52-7.41 (m, 3H), 7.36 (m, 2H), 7.28 (s, 1H), 6.95 (d, 1H), 4.95 (s, 2H), 4.15-

3.76 (m, 5H), 3.73-3.55 (m, 1H), 3.27 (m, 1H), 3.01 (t, 2H), 2.12 (s, 3H), 1.77 (m, 1H), 1.60-1.33 (m, 4H), 1.24 (m, 1H).

Example 155

6-[8-(1,3-benzothiazol-2-ylcarbamoyl)-3,4-dihydroisoquinolin-2(1H)-yl]-3-[5-methyl-1-{(1-[3-(morpholin-4-yl)propoxy]cycloheptyl}methyl)-1H-pyrazol-4-yl]pyridine-2-carboxylic acid Example 155A 1-((1-(allyloxy)cycloheptyl)methyl)-4-iodo-5-methyl-1H-pyrazole The title compound was prepared by substituting 3-bromoprop-1-ene for 1-bromo-2-methoxyethane in EXAMPLE 151C.

Example 155B 3-(1-((4-iodo-5-methyl-1H-pyrazol-1-yl)methyl)cycloheptyloxy)propan-1-ol To a solution of EXAMPLE 155A (1.7 g) in tetrahydrofuran (20 mL) was added a 0.5 M 9-borabicyclo[3.3.1]nonane-tetrahydrofuran solution (50 mL, 0.5 M) at 0° C. After the reaction mixture was stirred for 24 hours at room temperature, a 0.5 M NaOH aqueous solution (30 mL) and 30% $H_2O_2$ aqueous solution (5.5 mL) were added. After the reaction mixture was stirred for 16 hours, the reaction was then quenched by adding water (15 mL). The reaction mixture was extracted with ethyl acetate, and the organic layer was washed with water and a saturated aqueous NaCl solution. After the organic layer was dried over $Na_2SO_4$, and filtered, the solvent was evaporated under reduced pressure. The crude product was purified on a silica gel column, eluting with 10-50% ethyl acetate in hexanes, to provide the title compound.

Example 155C 3-(1-((4-iodo-5-methyl-1H-pyrazol-1-yl)methyl)cycloheptyloxy)propanal To a solution of EXAMPLE 155B (393 mg) in dichloromethane (20 mL) was added Dess-Martin Periodinane (425 mg). After the reaction mixture was stirred for 4 hours at room temperature, 2N NaOH aqueous solution (10 mL) was added and the reaction mixture was extracted with ethyl acetate. The organic layer was washed with water and a saturated NaCl solution. After the organic layer was dried over $Na_2SO_4$ and filtered, the solvent was removed under reduced pressure. The crude product was used in the next step without further purification.

Example 155D 4-(3-(1-((4-iodo-5-methyl-1H-pyrazol-1-yl)methyl)cycloheptyloxy)propyl)morpholine To a solution of EXAMPLE 155C (393 mg) in dichloromethane (20 mL) was added morpholine (263 mg) and sodium triacetoxyborohydride (427 mg). After the reaction mixture was stirred overnight at room temperature, 2N NaOH aqueous solution (10 mL) was added and the reaction mixture was extracted with ethyl acetate, and the organic layer was washed with water and a saturated NaCl solution. After the organic layer was dried over $Na_2SO_4$, it was filtered and the solvent was evaporated under reduced pressure. The crude product was used in the next reaction without further purification.

Example 155E

6-[8-(1,3-benzothiazol-2-ylcarbamoyl)-3,4-dihydroisoquinolin-2(1H)-yl]-3-[5-methyl-1-({1-[3-(morpholin-4-yl)propoxy]cycloheptyl}methyl)-1H-pyrazol-4-yl]pyridine-2-carboxylic acid The title compound was prepared by substituting EXAMPLE 155D for EXAMPLE 75A in EXAMPLE 75B, and then substituting that product for EXAMPLE 8B in EXAMPLE 8C. $^1$H NMR (300 MHz, dimethylsulfoxide-$d_6$) δ ppm 12.86 (s, 1H), 9.28 (m, 1H), 8.03 (d, 1H), 7.79 (d, 1H), 7.62 (d, 1H), 7.41 (m, 5H), 6.96 (d, 1H), 4.97 (m, 2H), 3.99 (m, 5H), 3.09 (m, 6H), 2.15 (m, 3H), 1.91 (s, 2H), 1.53 (m, 14H).

Example 156

6-[8-(1,3-benzothiazol-2-ylcarbamoyl)-3,4-dihydroisoquinolin-2(1H)-yl]-3-{2-methyl-3-[methyl(phenyl)amino]phenyl}pyridine-2-carboxylic acid Example 156A (3-bromo-2-methyl-phenyl)-methyl-phenyl-amine 1,3-Dibromo-2-methylbenzene (5.01 g) and N-methylaniline (1.00 g) were added to toluene (65 mL). The solution was degassed and flushed with nitrogen three times. Cesium carbonate (9.12 g), 2,2'-bis(diphenylphosphino)-1,1'-binaphthyl (0.872 g), and palladium (II) acetate (0.314 g) were added. The solution was degassed and flushed with nitrogen and then heated to 85° C. for 72 hours. The solution was cooled, added to 1 M aqueous HCl, and extracted with diethyl ether. The extract was washed with brine, dried on anhydrous sodium sulfate, filtered, and concentrated under vacuum. The crude material was purified on silica gel using 2% ethyl acetate in hexanes.

Example 156B

6-[8-(1,3-benzothiazol-2-ylcarbamoyl)-3,4-dihydroisoquinolin-2(1H)-yl]-3-{2-methyl-3-[methyl(phenyl)amino]phenyl}pyridine-2-carboxylic acid tert-butyl ester The title compound was prepared by substituting EXAMPLE 156A for EXAMPLE 112A in EXAMPLE 112B.

Example 156C

6-[8-(1,3-benzothiazol-2-ylcarbamoyl)-3,4-dihydroisoquinolin-2(1H)-yl]-3-{2-methyl-3-[methyl(phenyl)amino]phenyl}pyridine-2-carboxylic acid The title compound was prepared by substituting EXAMPLE 156B for EXAMPLE 7D in EXAMPLE 7E. $^1$H NMR (400 MHz, dimethylsulfoxide-$d_6$) δ ppm 12.84 (bs, 1H), 8.04 (d, 1H), 7.79 (d, 1H), 7.65-7.57 (m, 1H), 7.55-7.23

(m, 8H), 7.11 (m, 2H), 6.99 (m, 2H), 6.63 (t, 1H), 6.49 (d, 1H), 4.99 (bs, 2H), 3.93 (t, 2H), 3.18 (s, 3H), 3.03 (t, 2H), 1.80 (s, 3H).

Example 157

6-[8-(1,3-benzothiazol-2-ylcarbamoyl)-3,4-dihydroisoquinolin-2(1H)-yl]-3-{1-[(1-methoxy-3,3-dimethylcyclohexyl)methyl]-5-methyl-1H-pyrazol-4-yl}pyridine-2-carboxylic acid

Example 157A 3,3-dimethyl-1-((5-methyl-1H-pyrazol-1-yl)methyl)cyclohexanol

A solution of n-butyllithium (2.5 M, 12.48 mL) in tetrahydrofuran (40 mL) was cooled to −78° C. and a solution of 1,5-dimethyl-1H-pyrazole (3.00 g) in tetrahydrofuran (3 mL) was added dropwise. After stirring for 1 hour, a solution of 3,3-dimethylcyclohexanone (3.94 g) in tetrahydrofuran (3 mL) was added dropwise and the reaction allowed to warm to 0° C. After stirring for 1 hour, the reaction was diluted with ether (100 mL), washed with water (50 mL) and brine (50 mL), dried over magnesium sulfate, filtered, and concentrated. Silica gel chromatography eluting with a gradient of 3% to 25% ethyl acetate/hexanes provided the title compound.

Example 157B 1-((4-bromo-5-methyl-1H-pyrazol-1-yl)methyl)-3,3-dimethylcyclohexanol The title compound was prepared by substituting EXAMPLE 157A for EXAMPLE 63B in EXAMPLE 63C.

Example 157C 4-bromo-1-((1-methoxy-3,3-dimethylcyclohexyl)methyl)-5-methyl-1H-pyrazole A solution of EXAMPLE 157B (0.62 g) was dissolved in N,N-dimethylformamide (10 mL) and treated with NaH (0.062 g, 60% in mineral oil). After 10 minutes, iodomethane (0.16 mL) was added. After 1 hour, additional sodium hydride (0.5 eq.) and iodomethane (0.5 eq.) were added and stirring was continued at room temperature for 3 hours. The reaction was diluted with ether (75 mL) and washed with water (50 mL) and brine (50 mL), dried over magnesium sulfate, filtered, and concentrated. Silica gel chromatography eluting with a gradient of 1.5% to 15% ethyl acetate/hexanes provided the title compound.

Example 157D 1-((1-methoxy-3,3-dimethylcyclohexyl)methyl)-5-methyl-4-(4,4,5,5-tetramethyl-1,3,2-dioxaborolan-2-yl)-1H-pyrazole The title compound was prepared by substituting EXAMPLE 157C for EXAMPLE 84C in EXAMPLE 84D.

Example 157E

6-[8-(1,3-benzothiazol-2-ylcarbamoyl)-3,4-dihydroisoquinolin-2(1H)-yl]-3-{1-[(1-methoxy-3,3-dimethylcyclohexyl)methyl]-5-methyl-1H-pyrazol-4-yl}pyridine-2-carboxylic acid A solution of a 1:1 ratio of 1,4-dioxane and water was degassed with nitrogen for 45 minutes. This solution (5 mL) was added to EXAMPLE 1D (0.375 g), EXAMPLE 157D (0.30 g), potassium phosphate (0.62 g), tris(dibenzylideneacetone)dipalladium(0) chloroform adduct (0.021 g) and 1,3,5,7-tetramethyl-6-tetradecane-2,4,8-trioxa-6-phosphaadamantane (0.034 g), degassed then heated to 90° C. under nitrogen for 4 hours. The reaction mixture was cooled, diluted with ether (75 mL) and washed with water (3×50 mL) and brine (50 mL), dried over magnesium sulfate, filtered, and concentrated. Silica gel chromatography eluting with a gradient of 10% to 50% ethyl acetate/hexanes gave the desired ester. The ester was dissolved in dichloromethane (1 mL) and TFA was added (1 mL) and the mixture was stirred overnight. The reaction mixture was concentrated, loaded onto silica gel and eluted with a gradient of 0.5% to 4% methanol/dichloromethane to provide the title compound. $^1$H NMR (300 MHz, dimethylsulfoxide-$d_6$) δ ppm 12.88 (s, 1H), 8.04 (d, 1H), 7.79 (d, 1H), 7.62 (d, 1H), 7.53-7.41 (m, 3H), 7.41-7.32 (m, 2H), 7.28 (s, 1H), 6.95 (d, 1H), 4.95 (s, 2H), 3.98 (s, 2H), 3.89 (t, 2H), 3.15 (s, 3H), 3.01 (t, 2H), 2.12 (s, 3H), 1.77-1.00 (m, 8H), 0.97 (s, 3H), 0.84 (s, 3H).

Example 158

6-[8-(1,3-benzothiazol-2-ylcarbamoyl)-3,4-dihydroisoquinolin-2(1H)-yl]-3-(1-{[(1S,2R,5S)-6,6-dimethylbicyclo[3.1.1]hept-2-yl]methyl}-5-methyl-1H-1,2,3-triazol-4-yl)pyridine-2-carboxylic acid

Example 158A (1S,2R,5S)-2-(azidomethyl)-6,6-dimethylbicyclo[3.1.1]heptane ((1S,2R,5S)-6,6-dimethylbicyclo[3.1.1]heptan-2-yl)methanol (500 mg) was dissolved in dichloromethane (15 mL). The solution was chilled in an ice bath and triethylamine (0.633 mL) was added, followed by methanesulfonyl chloride (0.278 mL). The reaction was stirred for 2 hours at 0° C., and was transferred to a separatory funnel and washed with 1N aqueous HCl (15 mL), saturated aqueous NaHCO$_3$ (20 mL) and brine (15 mL), then dried (Na$_2$SO$_4$), filtered and concentrated to give a crude oil, which was dissolved in N,N-dimethylformamide (7.5 mL). Sodium azide (1054 mg) was added and the mixture was heated to 110° C. for 1.5 hours, and was cooled and partitioned between water (30 mL) and ethyl acetate (3×25 mL). The organic extracts were washed with brine (25 mL), dried (Na$_2$SO$_4$), filtered, and concentrated to give a crude oil, which was purified by flash chromatography on silica gel eluting with 50 to 100% dichloromethane in hexanes to provide the title compound.

Example 158B 1-(((1S,2R,5S)-6,6-dimethylbicyclo[3.1.1]heptan-2-yl)methyl)-5-methyl-4-(tributylstannyl)-1H-1,2,3-triazole EXAMPLE 158A (200 mg), tributyl-n-propynyltin (367 mg) and toluene (1 mL) were combined in a sealed reaction vessel which was heated to 130° C. overnight. The reaction mixture was placed atop a column and purified by flash chromatography on silica gel eluting with 0 to 20% ethyl acetate in hexanes to provide the title compound.

Example 158C methyl 6-amino-3-bromopicolinate

To a solution of 6-amino-3-bromopicolinic acid (30 g) in ethyl acetate (300 mL) and methanol (300 mL) was added TMS-diazomethane (70 mL, 2M in hexanes) and the reaction mixture was stirred for 3 days. The mixture was concentrated, taken up in ether (500 mL) and washed with aqueous saturated $Na_2CO_3$ solution (twice) and brine, then dried over sodium sulfate, filtered and concentrated to provide the title compound.

Example 158D methyl 3-bromo-6-fluoropicolinate

To a solution of nitrosonium terafluoroborate (17.8 g) in dichloromethane (100 mL) at 5° C. was added EXAMPLE 158C (26.1 g) in dichloromethane (250 mL) over 1 hour. The reaction mixture was stirred an for additional 30 minutes at 5° C., and then allowed to warm to room temperature overnight. The reaction mixture was quenched with pH 7 buffer (100 mL), and then neutralized with solid potassium carbonate. The resulting mixture was extracted with ether (twice), and the combined extracts were washed with brine, dried over sodium sulfate, filtered and concentrated. The residue was purified by flash chromatography on silica gel eluting with 1 to 10% ethyl acetate in hexanes to provide the title compound.

Example 158E methyl 3-(1-(((1S,2R,5S)-6,6-dimethylbicyclo[3.1.1]hept-2-yl)methyl)-5-methyl-1H-1,2,3-triazol-4-yl)-6-fluoropicolinate EXAMPLE 158B (75 mg), EXAMPLE 158D (35 mg) and $PdCl_2(PPh_3)_2$ (8.8 mg) were combined in a sealed tube with N,N-dimethylformamide (0.6 mL) and the mixture was sparged with nitrogen and then heated to 100° C. overnight. Saturated aqueous KF (2 mL) and ethyl acetate (2 mL) were added and the mixture was stirred for 1 hour, then filtered through diatomaceous earth, rinsing the filter cake with ethyl acetate (15 mL). The layers were separated and the aqueous layer was extracted with ethyl acetate (2×15 mL). The extracts were dried ($Na_2SO_4$), filtered and concentrated, then purified by flash chromatography on silica gel using 0 to 50% ethyl acetate in hexanes to provide the title compound.

Example 158F methyl 6-(8-(benzo[d]thiazol-2-ylcarbamoyl)-3,4-dihydroisoquinolin-2(1H)-yl)-3-(1-(((1S,2R,5S)-6,6-dimethylbicyclo[3.1.1]heptan-2-yl)methyl)-5-methyl-1H-1,2,3-triazol-4-yl)picolinate EXAMPLE 1B (30 mg), EXAMPLE 158E (25 mg) and cesium carbonate (26.0 µL) were combined in DMSO (336 µL) and the mixture was heated to 65° C. overnight. The reaction mixture was then partitioned between ethyl acetate (3×10 mL) and water (10 mL). The extracts were dried ($Na_2SO_4$), filtered, and concentrated, then purified by flash chromatography using 0 to 50% ethyl acetate in hexanes to provide the title compound.

Example 158G

6-[8-(1,3-benzothiazol-2-ylcarbamoyl)-3,4-dihydroisoquinolin-2(1H)-yl]-3-(1-{[(1S,2R,5S)-6,6-dimethylbicyclo[3.1.1]hept-2-yl]methyl}-5-methyl-1H-1,2,3-triazol-4-yl)pyridine-2-carboxylic acid EXAMPLE 158F (18 mg) was dissolved in dioxane (1 mL) and 1M aqueous LiOH (0.2 mL) was added. The reaction was heated to 60° C. for 3 hours, then cooled to room temperature, diluted with 1N aqueous HCl (5 mL) and extracted with ethyl acetate (3×10 mL). The organic extracts were dried ($Na_2SO_4$), filtered, and concentrated. The residue was purified by flash chromatography using 0 to 10% methanol in dichloromethane, to provide the title compound. $^1$H NMR (300 MHz, dimethylsulfoxide-$d_6$) δ ppm 12.65-12.94 (br m, 2H), 8.03 (d, 1H), 7.79 (d, 1H), 7.60-7.67 (m, 2H), 7.41-7.51 (m, 2H), 7.31-7.40 (m, 2H), 6.99 (d, 1H), 4.99 (s, 2H), 4.16-4.31 (m, 2H), 3.92 (t, 2H), 3.02 (t, 2H), 2.22-2.35 (m, 1H), 2.18 (s, 3H), 1.77-1.96 (m, 4H), 1.69-1.76 (m, 1H), 1.49-1.63 (m, 1H), 1.18 (s, 3H), 1.13 (s, 3H), 0.88 (d, 1H).

Example 159

6-[8-(1,3-benzothiazol-2-ylcarbamoyl)-3,4-dihydroisoquinolin-2(1H)-yl]-3-{3-[(3,3-dimethylcyclohexyl)methyl)amino]-2-methylphenyl}pyridine-2-carboxylic acid Example 159A (3-Bromo-2-methyl-phenyl)-(3,3-dimethyl-cyclohexyl)-amine 3-Bromo-2-methylaniline (1000 mg) and 3,3-dimethylcyclohexanone (780 mg) were added to dichloromethane (25 mL) and the mixture was stirred at room temperature for 15 minutes. Sodium triacetoxyborohydride (1367 mg) was then added and the solution was stirred at room temperature for 16 hours. Additional 3,3-dimethylcyclohexanone (780 mg) and sodium triacetoxyborohydride (1367 mg) were added, and the mixture was stirred for another 16 hours. The mixture was then washed with a saturated sodium bicarbonate solution and brine, dried over anhydrous sodium sulfate, filtered, and concentrated under vacuum. The crude material was purified on silica gel using 2.5% ethyl acetate in hexanes to provide the title compound.

Example 159B (3-Bromo-2-methyl-phenyl)-(3,3-dimethyl-cyclohexyl)-methyl-amine

EXAMPLE 159A (400 mg), methyl iodide (230 mg), and potassium carbonate (224 mg) were added to N,N-dimethylformamide (5 mL) and the mixture was stirred at room temperature for 16 hours. The mixture was added to water and extracted with diethyl ether. The organic extract was washed with brine, dried over anhydrous sodium sulfate, and filtered. The solvent was removed under vacuum to provide the title compound without further purification.

Example 159C

6-[8-(1,3-benzothiazol-2-ylcarbamoyl)-3,4-dihydroisoquinolin-2(1H)-yl]-3-{3-[(3,3-dimethylcyclohexyl)methyl)amino]-2-methylphenyl}pyridine-2-carboxylic acid tert-butyl ester The title compound was prepared by substituting EXAMPLE 159B for EXAMPLE 112A in EXAMPLE 112B.

Example 159D

6-[8-(1,3-benzothiazol-2-ylcarbamoyl)-3,4-dihydroisoquinolin-2(1H)-yl]-3-{3-[(3,3-dimethylcyclohexyl)(methyl)amino]-2-methylphenyl}pyridine-2-carboxylic acid The title compound was prepared by substituting EXAMPLE 159C for EXAMPLE 7D in EXAMPLE 7E. $^1$H NMR (400 MHz, dimethylsulfoxide-$d_6$) δ ppm 12.90 (bs, 1H), 8.04 (d, 1H), 7.80 (d, 1H), 7.63 (d, 1H), 7.52-7.43 (m, 4H), 7.38 (m, 3H), 7.06-6.95 (m, 2H), 5.00 (bs, 2H), 3.93 (t, 2H), 3.03 (t, 2H), 2.15-1.92 (m, 3H), 1.74-1.50 (m, 2H), 1.48-1.15 (m, 5H), 1.10-0.75 (m, 11H).

Example 160

6-[8-(1,3-benzothiazol-2-ylcarbamoyl)-3,4-dihydroisoquinolin-2(1H)-yl]-3-(5-methyl-1-{[1-(morpholin-4-yl)cyclohexyl]methyl}-1H-pyrazol-4-yl)pyridine-2-carboxylic acid

Example 160A ethyl 1-morpholinocyclohexanecarboxylate

Ethyl 1-aminocyclohexancarboxylate hydrogen chloride (5.800 g), triethylamine (13.62 mL) and 1-bromo-2-(2-bromoethoxy)ethane (4.21 mL) were stirred together in N,N-dimethylformamide (50 mL) at 95° C. overnight. The reaction mixture was diluted with ethyl acetate (150 mL), washed with water (100 mL) and brine (100 mL), dried over magnesium sulfate, filtered, and concentrated. Silica gel chromatography eluting with a gradient of 5% to 25% ethyl acetate/hexanes provided the title compound.

Example 160B (1-morpholinocyclohexyl)methanol

The title compound was prepared by substituting EXAMPLE 160A for ethyl 4,4-difluorocyclohexanecarboxylate in EXAMPLE 73A.

Example 160C 4-(1-((1H-pyrazol-1-yl)methyl)cyclohexyl)morpholine

The title compound was prepared by substituting EXAMPLE 160B for (3-(dimethylamino)phenyl)methanol and 1H-pyrazole for 4-(4,4,5,5-tetramethyl-1,3,2-dioxaborolan-2-yl)-1H-pyrazole in EXAMPLE 34A.

Example 160D 4-(1-((5-methyl-1H-pyrazol-1-yl)methyl)cyclohexyl)morpholine

The title compound was prepared by substituting EXAMPLE 160C for EXAMPLE 63A in EXAMPLE 63B.

Example 160E 4-(1-((4-bromo-5-methyl-1H-pyrazol-1-yl)methyl)cyclohexyl)morpholine The title compound was prepared by substituting EXAMPLE 160D for EXAMPLE 63B in EXAMPLE 63C.

Example 160F tert-butyl 6-(8-(benzo[d]thiazol-2-ylcarbamoyl)-3,4-dihydroisoquinolin-2(1H)-yl)-3-(5-methyl-1-((1-morpholinocyclohexyl)methyl)-1H-pyrazol-4-yl)picolinate The title compound was prepared by substituting EXAMPLE 160E for EXAMPLE 77D in EXAMPLE 77E.

Example 160G

6-[8-(1,3-benzothiazol-2-ylcarbamoyl)-3,4-dihydroisoquinolin-2(1H)-yl]-3-(5-methyl-1-{[1-(morpholin-4-yl)cyclohexyl]methyl}-1H-pyrazol-4-yl)pyridine-2-carboxylic acid The title compound was prepared by substituting EXAMPLE 160F for EXAMPLE 8B in EXAMPLE 8C. $^1$H NMR (300 MHz, dimethylsulfoxide-$d_6$) δ ppm 12.85 (s, 2H), 9.50 (d, 1H), 8.03 (d, 1H), 7.79 (d, 1H), 7.62 (d, 1H), 7.57-7.41 (m, 4H), 7.41-7.30 (m, 2H), 6.98 (d, 1H), 4.97 (s, 2H), 4.59 (s, 1H), 4.10-3.51 (m, 8H), 2.95 (m, 6H), 2.42-2.03 (m, 4H), 2.00-0.97 (m, 8H).

Example 161

6-[8-(1,3-benzothiazol-2-ylcarbamoyl)-3,4-dihydroisoquinolin-2(1H)-yl]-2'-[cyclohexyl(methy)amino]-methyl-3'-methyl-34'-bipyridine-2-carboxylic acid

Example 161A

N-cyclohexyl-4-iodo-N,3-dimethylpyridin-2-amine

2-Fluoro-4-iodo-3-methylpyridine (700 mg) in N-methylcyclohexanamine (2.2 ml) was heated at 180(C in a Biotage Initiator microwave reactor for 18 hours. The reaction mixture was loaded onto a silica gel cartridge, and was eluted with 0-100% dichloromethane in hexanes to provide the title compound.

Example 161B tert-butyl 6-(8-(benzo[d]thiazol-2-ylcarbamoyl)-3,4-dihydroisoquinolin-2(1H)-yl)-2'-(cyclohexyl(methyl)amino)-3'-methyl-3,4'-bipyridine-2-carboxylate The title compound was prepared by substituting EXAMPLE 161A for EXAMPLE 12A in EXAMPLE 112B.

Example 161C

6-[8-(1,3-benzothiazol-2-ylcarbamoyl)-3,4-dihydroisoquinolin-2(1H)-yl]-2'-[cyclohexyl(methyl)amino]-3'-methyl-3,4'-bipyridine-2-carboxylic acid The title compound was prepared by substituting EXAMPLE 161B for EXAMPLE 1E in EXAMPLE 1F. $^1$H NMR (400 MHz, dimethylsulfoxide-$d_6$) δ ppm 12.90 (s, 1H), 8.07 (d, 1H), 8.04 (d, 1H), 7.79 (d, 1H), 7.64 (d, 2H), 7.44-7.51 (m, 2H), 7.32-7.42 (m, 2H), 7.10 (d, 1H), 7.03 (d, 1H), 5.05 (s, 2H), 3.97 (t, 2H), 3.44 (t, 1H), 3.05 (t, 2H), 2.96 (s, 3H), 2.06 (s, 3H), 1.69 (d, 7H), 1.31 (d, 2H), 1.12 (q, 1H)

Example 162

N-(1,3-benzothiazol-2-yl)-2-(5-{1-[(1-methoxy-3,3-dimethylcyclohexyl)methyl]-5-methyl-1H-pyrazol-4-yl}-6-[(methylsulfonyl)carbamoyl]pyridin-2-yl)-1,2,3,4-tetrahydroisoquinoline-8-carboxamide A solution of EXAMPLE 157E (0.051 g), methanesulfonamide (0.015 g), 1-ethyl-3-[3-(dimethylamino)propyl]-carbodiimide hydrochloride.HCl (0.037 g) and 4-dimethylaminopyridine (0.019 g) were stirred together in dichloromethane (1 mL) at room temperature overnight. The reaction mixture was loaded onto silica gel and eluted using a gradient of 0.5% to 3.25% methanol/dichloromethane to provide the title compound. $^1$H NMR (300 MHz, dimethylsulfoxide-$d_6$) δ ppm 12.84 (s, 1H), 11.81 (s, 1H), 8.03 (d, 1H), 7.79 (d, 1H), 7.62 (d, 1H), 7.56-7.41 (m, 3H), 7.41-7.32 (m, 2H), 7.29 (s, 1H), 7.00 (d, 1H), 4.96 (s, 2H), 4.00 (d, 2H), 3.93 (t, 2H), 3.16 (s, 3H), 3.11 (s, 3H), 3.03 (t, 2H), 2.13 (s, 3H), 1.71 (d, 1H), 1.58-1.00 (m, 7H), 0.96 (s, 3H), 0.84 (s, 3H).

Example 163

6-[8-(1,3-benzothiazol-2-ylcarbamoyl)-1-methyl-3,4-dihydroisoquinolin-2(1H)-yl]-3-{5-methyl-1-[(1-methylcyclohexyl)methyl]-1H-pyrazol-4-yl}pyridine-2-carboxylic acid

Example 163A 2-(tert-butoxycarbonyl)-1-methyl-1,2,3,4-tetrahydroisoquinoline-8-carboxylic acid To a solution of 2-(tert-butoxycarbonyl)-1,2,3,4-tetrahydroisoquinoline-8-carboxylic acid (2.25 g) and tetramethylethylenediamine (1.347 mL) in tetrahydrofuran (40 mL) was added dropwise t-butyllithium (1.6M, 15.21 mL) at −78° C. The mixture was stirred at −78° C. for 40 minutes. To the resulting mixture was added iodomethane (5.07 mL) dropwise and the mixture was stirred at −78° C. for 3 hours, followed by stirring at room temperature overnight. The reaction mixture was quenched with saturated ammonium chloride. The reaction mixture was extracted with ethyl acetate (150 mL), and the organic layer was washed with brine (40 mL×3), dried over $Na_2SO_4$, filtered, and concentrated. The crude product was purified by flask chromotography (silica gel, 10% methanol/dichloromethane).

Example 163B tert-butyl 8-(benzo[d]thiazol-2-ylcarbamoyl)-1-methyl-3,4-dihydroisoquinoline-2(1H)-carboxylate A mixture of EXAMPLE 163A (400 mg), benzotriazol-1-yloxytripyrrolidinophosphonium hexafluorophosphate (714 mg), triethylamine (0.383 mL) and benzo[d]thiazol-2-amine (247 mg) in dichloromethane (10 mL) was stirred overnight at room temperature. The mixture was diluted with ethyl acetate (100 mL), washed with brine (30 mL×3), dried over $Na_2SO_4$, filtered, concentrated and purified by flash chromotography (silica gel, petroleum ether/ethyl acetate=1/1).

Example 163C

N-(benzo[d]thiazol-2-yl)-1-methyl-1,2,3,4-tetrahydroisoquinoline-8-carboxamide

A solution of EXAMPLE 163B (150 mg) in dichloromethane (10 mL) was treated with TFA (1 mL). The reaction mixture was stirred for 2 hours at 30° C. The reaction mixture was diluted with ethyl acetate (100 mL), washed with saturated aqueous $NaHCO_3$, brine, dried over $Na_2SO_4$, filtered, and concentrated. The crude product was purified by flash chromotography (silica gel, dichloromethane/methanol=10/1).

Example 163D methyl 6-(8-(benzo[d]thiazol-2-ylcarbamoyl)-1-methyl-3,4-dihydroisoquinolin-2(1H)-yl)-3-bromopicolinate A solution of EXAMPLE 163C (1 g), methyl 3-bromo-6-fluoropicolinate (0.715 g) and triethylamine (0.775 mL) in 12 mL DMSO was heated at 70° C. overnight followed by heating at 105° C. for 4 hours. The reaction mixture was diluted with ethyl acetate, washed three times with water and brine, dried over $Na_2SO_4$, filtered, and concentrated. The product was purified by flash chromatography (silica gel, 5-25% ethyl acetate/hexanes).

Example 163E methyl 6-(8-(benzo[d]thiazol-2-ylcarbamoyl)-1-methyl-3,4-dihydroisoquinolin-2(1H)-yl)-3-(5-methyl-1-((1-methylcyclohexyl)methyl)-1H-pyrazol-4-yl)picolinate The title compound was prepared by substituting EXAMPLE 163D for EXAMPLE 77D and EXAMPLE 82D for EXAMPLE 30A in EXAMPLE 77E.

Example 163F

6-[8-(1,3-benzothiazol-2-ylcarbamoyl)-1-methyl-3,4-dihydroisoquinolin-2(1H)-yl]-3-{5-methyl-1-[(1-methylcyclohexyl)methyl]-1H-pyrazol-4-yl}pyridine-2-carboxylic acid The title compound was prepared by substituting EXAMPLE 163E for EXAMPLE 75B in EXAMPLE 75C.

¹H NMR (300 MHz, dimethylsulfoxide-d₆) δ ppm 13.02-12.79 (m, 1H), 8.04 (d, 1H), 7.79 (d, 1H), 7.54 (d, 1H), 7.52 (d, 1H), 7.50-7.42 (m, 2H), 7.40-7.32 (m, 2H), 7.28 (s, 1H), 6.86 (d, 1H), 6.06 (q, 1H), 4.06-3.94 (m, 1H), 3.86 (s, 2H), 3.65 (dt, 1H), 3.14-3.01 (m, 2H), 2.12 (s, 3H), 1.58-1.33 (m, 10H), 1.33-1.18 (m, 3H), 0.85 (s, 3H).

Example 164

6-[8-(1,3-benzothiazol-2-ylcarbamoyl)-3,4-dihydroisoquinolin-2(1H)-yl]-3'-cyano-2'-[cyclohexyl(methyl)amino]-3,4'-bipyridine-2-carboxylic acid Example 164A 2-(cyclohexyl(methyl)amino)-4-iodonicotinonitrile The title compound was prepared by substituting 2-fluoro-4-iodonicotinonitrile for 2-fluoro-4-iodo-3-methylpyridine in EXAMPLE 161A.

Example 164B tert-butyl 6-(8-(benzo[d]thiazol-2-ylcarbamoyl)-3,4-dihydroisoquinolin-2(1H)-yl)-3'-cyano-2'-(cyclohexyl(methyl)amino)-3,4'-bipyridine-2-carboxylate The title compound was prepared by substituting EXAMPLE 164A for EXAMPLE 112A in EXAMPLE 112B.

Example 164C

6-[8-(1,3-benzothiazol-2-ylcarbamoyl)-3,4-dihydroisoquinolin-2(1H)-yl]-3'-cyano-2'-[cyclohexyl(methyl)amino]-3,4'-bipyridine-2-carboxylic acid The title compound was prepared by substituting EXAMPLE 164B for EXAMPLE 1E in EXAMPLE 1F. ¹H NMR (400 MHz, dimethylsulfoxide-d₆) δ ppm 12.90 (s, 1H), 8.07 (d, 1H), 8.04 (d, 1H), 7.79 (d, 1H), 7.64 (d, 2H), 7.44-7.51 (m, 2H), 7.33-7.42 (m, 2H), 7.10 (d, 1H), 7.03 (d, 1H), 5.05 (s, 2H), 3.97 (t, 2H), 3.44 (t, 1H), 3.05 (t, 2H), 2.96 (s, 3H), 2.06 (s, 3H), 1.54-1.84 (m, 7H), 1.21-1.42 (m, 2H), 1.06-1.19 (m, 1H).

Example 165

6-[8-(1,3-benzothiazol-2-ylcarbamoyl)-3,4-dihydroisoquinolin-2(1H)-yl]-3-{1-[(1-methoxycyclohexyl)methyl]-5-methyl-1H-pyrazol-4-yl}pyridine-2-carboxylic acid Example 165A 1-((5-methyl-1H-pyrazol-1-yl)methyl)cyclohexanol To a cold (−78° C.) solution of n-butyllithium (25 mL, 2.5M) in tetrahydrofuran (30 mL) was added 1,5-dimethyl-1H-pyrazole (5.0 g) in tetrahydrofuran (20 mL) dropwise via syringe. After 1 hour, cyclohexanone (5.1 g) in tetrahydrofuran (20 mL) was added dropwise and the reaction mixture was allowed to warm to room temperature. The mixture was quenched by the addition of saturated ammonium chloride solution and ethyl acetate. The layers were separated and the aqueous layer was extracted with additional ethyl acetate (twice). The combined organics were dried over Na₂SO₄, filtered, and concentrated to provide the crude title compound.

Example 165B 1-((1-methoxycyclohexyl)methyl)-5-methyl-1H-pyrazole

The title compound was prepared by substituting CH₃I for 1-bromo-2-methoxyethane and EXAMPLE 165A for EXAMPLE 151B in EXAMPLE 151C.

Example 165C 4-iodo-1-((1-methoxycyclohexyl)methyl)-5-methyl-1H-pyrazole

The title compound was prepared by substituting EXAMPLE 165B for EXAMPLE 65E in EXAMPLE 65F.

Example 165D

6-[8-(1,3-benzothiazol-2-ylcarbamoyl)-3,4-dihydroisoquinolin-2(1H)-yl]-3-{1-[(1-methoxycyclohexyl)methyl]-5-methyl-1H-pyrazol-4-yl}pyridine-2-carboxylic acid The title compound was prepared by substituting EXAMPLE 165C for EXAMPLE 75A in EXAMPLE 75B, and then substituting that product for EXAMPLE 8B in EXAMPLE 8C. ¹H NMR (300 MHz, dimethylsulfoxide-d₆) δ ppm 12.85 (s, 1H), 8.04 (d, 1H), 7.79 (d, 1H), 7.61 (d, 1H), 7.40 (m, 5H), 7.27 (s, 1H), 6.94 (d, 1H), 4.95 (s, 2H), 4.03 (m, 2H), 3.89 (t, 2H), 3.15 (m, 3H), 3.01 (t, 2H), 2.12 (s, 3H), 1.36 (m, 10H)

Example 166

6-[8-(1,3-benzothiazol-2-ylcarbamoyl)-3,4-dihydroisoquinolin-2(1H)-yl]-3-{1-[(1-methoxy-3,3-dimethylcyclohexyl)methyl]-5-methyl-1H-1,2,3-triazol-4-yl}pyridine-2-carboxylic acid Example 166A 5,5-dimethyl-1-oxaspiro[2.5]octane The title compound was prepared by substituting 3,3-dimethylcyclohexanone for cyclohexanone in EXAMPLE 101A.

Example 166B 1-(azidomethyl)-3,3-dimethylcyclohexanol

EXAMPLE 166A (1.93 g), ammonium chloride (3.68 g) and sodium azide (4.47 g) were combined in a flask with methanol (40 mL) and water (16 mL) and the mixture was heated to reflux overnight, then cooled to room temperature, diluted with water (200 mL) and extracted with ethyl acetate (3×100 mL). The organic extracts were dried (Na₂SO₄), filtered, and concentrated. The crude material was purified by flash chromatography on silica gel using 0 to 10% ethyl acetate in hexanes to provide the title compound.

Example 166C 1-(azidomethyl)-1-methoxy-3,3-dimethylcyclohexane

A solution of EXAMPLE 166B (1.33 g) was added dropwise to a suspension of NaH (60% dispersion in mineral oil, 435 mg) in tetrahydrofuran (15 mL) at 0° C. The mixture was stirred for 10 minutes at 0° C. and for 30 minutes at room temperature. $CH_3I$ (1.55 g) was added dropwise. The resulting reaction mixture was stirred overnight at room temperature, and then quenched with water (100 mL) and extracted with ethyl acetate (3×50 mL). The extracts were washed with brine, dried ($Na_2SO_4$), and filtered. After concentration, the crude material was purified by flash chromatography on silica gel using 0 to 7% ethyl acetate in hexanes to afford the title compound.

Example 166D 1-((1-methoxy-3,3-dimethylcyclohexyl)methyl)-5-methyl-4-(tributylstannyl)-1H-1,2,3-triazole The title compound was prepared by substituting EXAMPLE 166C for EXAMPLE 158A in EXAMPLE 158B.

Example 166E tert-butyl 3-bromo-6-fluoropicolinate

The title compound was prepared by substituting 3-bromo-6-fluoropicolinic acid for 3-bromo-6-chloropicolinic acid in EXAMPLE 1C.

Example 166F tert-butyl 6-fluoro-3-(1-((1-methoxy-3,3-dimethylcyclohexyl)methyl)-5-methyl-1H-1,2,3-triazol-4-yl) picolinate The title compound was prepared by substituting EXAMPLE 166D for EXAMPLE 158B and EXAMPLE 166E for EXAMPLE 158D in EXAMPLE 158E.

Example 166G tert-butyl 6-(8-(benzo[d]thiazol-2-ylcarbamoyl)-3,4-dihydroisoquinolin-2(1H)-yl)-3-(1-((1-methoxy-3,3-dimethylcyclohexyl)methyl)-5-methyl-1H-1,2,3-triazol-4-yl)picolinate The title compound was prepared by substituting EXAMPLE 166F for EXAMPLE 158E in EXAMPLE 158F.

Example 166H

6-[8-(1,3-benzothiazol-2-ylcarbamoyl)-3,4-dihydroisoquinolin-2(1H)-yl]-3-{1-[(1-methoxy-3,3-dimethylcyclohexyl)methyl]-5-methyl-1H-1,2,3-triazol-4-yl}pyridine-2-carboxylic acid The title compound was prepared by substituting EXAMPLE 166G for EXAMPLE 88 in EXAMPLE 8C. $^1H$ NMR (300 MHz, DMSO-$d_6$) δ ppm 12.85 (s, 1H), 12.64-12.81 (br s, 1H), 8.04 (d, 1H), 7.79 (d, 1H), 7.66 (d, 1H), 7.62 (d, 1H), 7.42-7.51 (m, 2H), 7.32-7.41 (m, 2H), 7.01 (d, 1H), 5.00 (s, 2H), 4.25 (s, 2H), 3.93 (t, 2H), 3.22 (s, 3H), 3.03 (t, 2H), 2.18 (s, 3H), 1.66 (d, 1H), 1.28-1.56 (m, 4H), 1.02-1.24 (m, 3H), 0.96 (s, 3H), 0.86 (s, 3H).

Example 167

6-[8-(1,3-benzothiazol-2-ylcarbamoyl)-3,4-dihydroisoquinolin-2(1H)-yl]-3-[1-({1-[2-(1,1-dioxidothiomorpholin-4-yl)ethoxy]cyclohexyl}methyl)-5-methyl-1H-pyrazol-4-yl]pyridine-2-carboxylic acid

Example 167A 1-((4-bromo-5-methyl-1H-pyrazol-1-yl)methyl)cyclohexanol

To a solution of EXAMPLE 165B (10.6 g) in N,N-dimethylacetamide (30 mL) was added N-bromosuccinimide (9.72 g). The mixture was stirred at room temperature overnight. The mixture was diluted with ethyl acetate (400 mL) and washed with aqueous sodium bisulfite, water, and brine. Evaporation of the solvent gave the crude product which was used in the next reaction without further purification.

Example 167B 1-((1-(allyloxy)cyclohexyl)methyl)-4-bromo-5-methyl-1H-pyrazole The title compound was prepared by substituting allyl bromide for 1-bromo-2-methoxyethane and EXAMPLE 167A for EXAMPLE 151B in EXAMPLE 151C.

Example 167C 1-((1-(allyloxy)cyclohexyl)methyl)-5-methyl-4-(4,4,5,5-tetramethyl-1,3,2-dioxaborolan-2-yl)-1H-pyrazole To a solution of EXAMPLE 167B (1.25 g) in dioxane (30 mL) was added $PdCl_2$ (40 mg), S-Phos (0.328 g), pinacolborane (0.77 g) and triethylamine (1.22 g). The mixture was stirred at reflux under nitrogen for 3 hours. The reaction mixture was diluted with ethyl acetate (200 mL), washed with water and brine, dried over $Na_2SO_4$, filtered, and concentrated under reduced pressure. Flash column purification (20% ethyl acetate in hexane) provided the title compound.

Example 167D tert-butyl 3-(1-((1-(allyloxy)cyclohexyl)methyl)-5-methyl-1H-pyrazol-4-yl)-6-(8-(benzo[d]thiazol-2-ylcarbamoyl)-3,4-dihydroisoquinolin-2(1H)-yl)picolinate The title compound was prepared by substituting EXAMPLE 167C for EXAMPLE 30A and EXAMPLE 1D for EXAMPLE 75A in EXAMPLE 75B.

Example 167E tert-butyl 6-(8-(benzo[d]thiazol-2-ylcarbamoyl)-3,4-dihydroisoquinolin-2(1H)-yl)-3-(1-((1-(2,3-dihydroxypropoxy)cyclohexyl)methyl)-5-methyl-1H-pyrazol-4-yl)picolinate To a stirred solution of EXAMPLE 167D (600 mg) and N-methylmorpholine oxide (489 mg) in 50% aqueous dioxane (10 mL) was added a solution of osmium tetraoxide (1.2 mL, 0.12 M in t-butanol). After stirring for 1 hour, ethyl acetate was added followed by saturated sodium bisulfite. The reaction mixture was stirred for 20 minutes. The organic layer was separated and the aqueous layer was extracted with ethyl acetate (3×100 mL). The combined organic layers were dried (anhydrous $Na_2SO_4$), filtered, and concentrated under vacuum to give the crude product.

Example 167F tert-butyl 6-(8-(benzo[d]thiazol-2-ylcarbamoyl)-3,4-dihydroisoquinolin-2(1H)-yl)-3-(5-methyl-1-((1-(2-oxoethoxy)cyclohexyl)methyl)-1H-pyrazol-4-yl) picolinate A solution of EXAMPLE 167E (600 mg) in acetone (30 mL) was treated with a solution of sodium periodate (852 mg) in water (5 mL). After about 4 hours, the solvent was removed by distillation and the residue was extracted with ethyl acetate (3×100 mL). The combined organic layers were dried over $Na_2SO_4$, filtered, and concentrated under reduced pressure to give crude product which was purified by flash column chromatography (20% ethyl acetate in hexane) to give the pure product.

Example 167G

6-[8-(1,3-benzothiazol-2-ylcarbamoyl)-3,4-dihydroisoquinolin-2(1H)-yl]-3-[1-({1-[2-(1,1-dioxidothiomorpholin-4-yl)ethoxy]cyclohexyl}methyl)-5-methyl-1H-pyrazol-4-yl]pyridine-2-carboxylic acid To a solution of EXAMPLE 167F (72 mg) and thiomorpholine 1,1-dioxide (13.5 mg) in dichloromethane (3 mL) was added sodium triacetoxyborohydride (32 mg). The mixture was stirred overnight. The mixture was dissolved in ethyl acetate (200 mL) and washed with 2N aqueous NaOH and brine, and dried over $Na_2SO_4$. Filtration and evaporation of the solvent gave crude product which was dissolved in dichloromethane (2 mL) and TFA (2 mL). After stirring overnight, the solvent was evaporated. The residue was purified by reverse phase chromatography using a Gilson system, eluting with 20-80% acetonitrile in 0.1% TFA water solution to provide the title compound. $^1$H NMR (300 MHz, dimethylsulfoxide-$d_6$) δ ppm 12.86 (s, 1H), 8.04 (d, 1H), 7.79 (d, 1H), 7.62 (d, 1H), 7.42 (m, 5H), 6.97 (d, 1H), 4.96 (s, 2H), 4.10 (s, 3H), 3.53 (m, 8H), 3.02 (t, 2H), 2.13 (s, 3H), 1.43 (m, 10H).

Example 168

6-[8-(1,3-benzothiazol-2-ylcarbamoyl)-3,4-dihydroisoquinolin-2(1H)-yl]-3-(5-cyano-2-methyl-1-{[1-(morpholin-4-yl)cyclohexyl]methyl}-1H-pyrrol-3-yl)pyridine-2-carboxylic acid

Example 168A ethyl 4-iodo-5-methyl-1H-pyrrole-2-carboxylate

The title compound was prepared by substituting with ethyl 5-methyl-1H-pyrrole-2-carboxylate for EXAMPLE 65E in EXAMPLE 65F.

Example 168B 4-iodo-5-methyl-1H-pyrrole-2-carboxylic acid

EXAMPLE 168A (1 g) in tetrahydrofuran (30 mL) and methanol (10 mL) was treated with 2 N aqueous NaOH (20 mL) overnight. The reaction mixture was cooled to 0° C., acidified to pH 5, diluted with water (30 mL) and concentrated to remove the organic solvent. The precipitates were collected by filtration, washed with water and dried under vacuum to provide the title compound.

Example 168C 4-iodo-5-methyl-1H-pyrrole-2-carboxamide

To a solution of EXAMPLE 168B (7.7 g) in tetrahydrofuran (20 mL) at 0° C. was added carbonyldiimidazole (14.9 g). The resulting mixture was stirred at room temperature for 2 hours. The reaction mixture was cooled to 0° C. and ammonium hydroxide (3 mL) was added. The mixture was stirred at room temperature for 2 hours and concentrated. The residue was dissolved in ethyl acetate, washed with brine and concentrated to provide the title compound.

Example 168D 4-iodo-5-methyl-1H-pyrrole-2-carbonitrile

To a solution of EXAMPLE 168C (300 mg) in N,N-dimethylformamide (6 mL) and pyridine (0.6 mL) at 0° C. was added dropwise oxalyl chloride (0.35 mL). The mixture was stirred at room temperature for 30 minutes, diluted with ethyl acetate and washed with saturated $NaHCO_3$ and water extensively. The organic layer was dried over $Na_2SO_4$, filtered, and concentrated. The residue was purified by flash chromatography, and eluted with dichloromethane to provide the title compound.

Example 168E 4-iodo-5-methyl-1-((1-morpholinocyclohexyl)methyl)-1H-pyrrole-2-carbonitrile The title compound was prepared by substituting EXAMPLE 160B for (3-(dimethylamino)phenyl)methanol and EXAMPLE 168D for 4-(4,4,5,5-tetramethyl-1,3,2-dioxaborolan-2-yl)-1H-pyrazole in EXAMPLE 34A.

Example 168F

6-[8-(1,3-benzothiazol-2-ylcarbamoyl)-3,4-dihydroisoquinolin-2(1H)-yl]-3-(5-cyano-2-methyl-1-{[1-(morpholin-4-yl)cyclohexyl]methyl}-1H-pyrrol-3-yl)pyridine-2-carboxylic acid The title compound was prepared by substituting EXAMPLE 168E for EXAMPLE 75A in EXAMPLE 75B, and then substituting that product for EXAMPLE 88 in EXAMPLE 8C. $^1$H NMR (300 MHz, dimethylsulfoxide-$d_6$) δ ppm 12.85 (s, 1H), 8.03 (d, 1H), 7.79 (d, 1H), 7.62 (d, 1H), 7.41 (m, 5H), 6.95 (d, 1H), 6.83 (s, 1H), 4.96 (s, 2H), 4.01 (m, 2H), 3.89 (t, 2H), 3.01 (t, 2H), 2.69 (m, 3H), 2.10 (s, 3H), 1.95 (m, 3H), 1.56 (m, 3H), 1.27 (m, 4H), 0.96 (m, 3H).

Example 169

6-[8-(1,3-benzothiazol-2-ylcarbamoyl)-3,4-dihydroisoquinolin-2(1H)-yl]-3-(1-{[1-(2-hydroxyethoxy)cyclohexyl]methyl}-5-methyl-1H-pyrazol-4-yl)pyridine-2-carboxylic acid To a solution of EXAMPLE 167F (56 mg) in tetrahydrofuran (10 mL) was added $NaBH_4$ (15 mg). The mixture was stirred at room temperature overnight. The mixture was added to ethyl acetate (200 mL) and water (60 mL). The organic layer was washed with brine and dried over $Na_2SO_4$. Filtration and evaporation of the solvent gave crude product which was dissolved in dichloromethane (2 mL) and TFA (2 mL). After sitting on the bench overnight, the solvent was evaporated. The residue was purified by reverse phase chromatography using a Gilson system, eluting with 20-80% acetonitrile in 0.1% TFA water solution to provide the desired product. $^1$H NMR (300 MHz, dimethylsulfoxide-dc) δ ppm 12.85 (s, 1H), 8.03 (d, 1H), 7.79 (d, 1H), 7.61 (d, 1H), 7.41 (m, 5H), 7.29 (s, 1H), 6.95 (d, 1H), 4.95 (s, 2H), 4.04 (s, 3H), 3.49 (m, 3H), 3.01 (t, 2H), 2.14 (m, 3H), 1.37 (m, 11H).

Example 170

6-[8-(1,3-benzothiazol-2-ylcarbamoyl)-3,4-dihydroisoquinolin-2(1H)-yl]-3-(1-{[1-(2,3-dimethoxypropoxy)cycloheptyl]methyl}-5-methyl-1H-pyrazol-4-yl)pyridine-2-carboxylic acid Example 170A 1-((5-methyl-1H-pyrazol-1-yl)methyl)cycloheptanol The title compound was prepared by substituting cycloheptanone for cyclohexanone in EXAMPLE 165A.

Example 170B 1-((1-(allyloxy)cycloheptyl)methyl)-5-methyl-1H-pyrazole

The title compound was prepared by substituting allyl bromide for 1-bromo-2-methoxyethane and EXAMPLE 170A for EXAMPLE 151B in EXAMPLE 151C.

Example 170C 3-(1-((5-methyl-1H-pyrazol-1-yl)methyl)cycloheptyloxy)propane-1,2-diol To a stirred solution of EXAMPLE 170B (248 mg) and N-methylmorpholine oxide (586 mg) in 50% aqueous dioxane (10 mL) was added a solution of osmium tetraoxide (1 mL, 0.12 M). After stirring for 3 hours, ethyl acetate was added followed by saturated sodium bisulfite. The reaction mixture was stirred for 20 minutes. The organic layer was separated and the aqueous layer was extracted with ethyl acetate (3×60 mL). The combined organic layers were dried (anhydrous $Na_2SO_4$), filtered, and concentrated under vacuum to give the crude product.

Example 170D 1-((1-(2,3-dimethoxypropoxy)cycloheptyl)methyl)-5-methyl-1H-pyrazole The title compound was prepared by substituting methyl iodide for 1-bromo-2-methoxyethane and EXAMPLE 170C for EXAMPLE 151B in EXAMPLE 151C.

Example 170E 1-((1-(2,3-dimethoxypropoxy)cycloheptyl)methyl)-4-iodo-5-methyl-1H-pyrazole The title compound was prepared by substituting EXAMPLE 170D for EXAMPLE 65E in EXAMPLE 65F.

Example 170F

6-[8-(1,3-benzothiazol-2-ylcarbamoyl)-3,4-dihydroisoquinolin-2(1H)-yl]-3-(1-{[1-(2,3-dimethoxypropoxy)cycloheptyl]methyl}-5-methyl-1H-pyrazol-4-yl)pyridine-2-carboxylic acid The title compound was prepared by substituting EXAMPLE 170E for EXAMPLE 75A in EXAMPLE 75B, and then substituting that product for EXAMPLE 88 in EXAMPLE 8C. $^1$H NMR (300 MHz, dimethylsulfoxide-$d_6$) δ ppm 12.84 (s, 1H), 8.03 (d, 1H), 7.79 (d, 1H), 7.61 (d, 1H), 7.41 (m, 5H), 7.27 (s, 1H), 6.95 (d, 1H), 4.95 (s, 2H), 4.04 (m, 3H), 3.89 (t, 2H), 3.44 (d, 2H), 3.35 (m, 4H), 3.28 (s, 3H), 3.19 (m, 3H), 3.00 (t, 2H), 2.14 (s, 3H), 1.51 (m, 14H).

Example 171

N-(1,3-benzothiazol-2-yl)-2-{5-[5-cyano-4-(cyclohexylmethyl)-2-methyl-1H-pyrrol-3-yl]-6-[(methylsulfonyl)carbamoyl]pyridin-2-yl}-1,2,3,4-tetrahydroisoquinoline-8-carboxamide 1-Ethyl-3-[3-(dimethylamino)propyl]-carbodiimide hydrochloride (34.6 mg), 4-dimethylaminopyridine (55.2 mg), EXAMPLE 130G (95 mg), and methanesulfonamide (17.19 mg) in dichloromethane (2 mL) was stirred overnight and concentrated. The residue was purified by reverse phase chromatography, and eluted with 40-80% acetonitrile in 0.1% TFA water solution to provide the desired product. $^1$H NMR (400 MHz, dimethylsulfoxide-$d_6$) δ ppm 12.86 (s, 1H), 11.81 (s, 1H), 8.03 (d, 1H), 7.79 (d, 1H), 7.62 (d, 1H), 7.42-7.54 (m, 3H), 7.33-7.40 (m, 2H), 7.00 (d, 1H), 6.80 (s, 1H), 4.97 (s, 2H), 3.94 (t, 2H), 3.83 (d, 2H), 3.13 (s, 3H), 3.03 (t, 2H), 2.09 (s, 3H), 1.49-1.74 (m, 6H), 1.09-1.26 (m, 3H), 0.92-1.05 (m, 2H).

Example 172

6-[8-(1,3-benzothiazol-2-ylcarbamoyl)-3,4-dihydroisoquinolin-2(1H)-yl]-3-(5-cyano-1-{[1-(2-methoxyethoxy)cycloheptyl]methyl}-2-methyl-1H-pyrrol-3-yl)pyridine-2-carboxylic acid Example 172A 1-((1-hydroxycycloheptyl)methyl)-5-methyl-1H-pyrrole-2-carbonitrile 1-Oxaspiro[2,6]nonane (2.5 g), 5-methyl-1H-pyrrole-2-carbonitrile (2.1 g) and $Cs_2CO_3$ (6.45 g) in N,N-dimethylformamide (15 mL) was heated at 120° C. in a Biotage Initiator microwave reactor for 30 minutes. The reaction mixture was diluted with ethyl acetate, washed with water and concentrated. The residue was purified by reverse phase chromatography, and was eluted with 30%-70% acetonitrile in 0.1% TFA water solution to provide the title compound.

Example 172B 1-((1-(2-methoxyethoxy)cycloheptyl)methyl)-5-methyl-1H-pyrrole-2-carbonitrile The title compound was prepared by substituting EXAMPLE 172A for EXAMPLE 151B in EXAMPLE 151C.

Example 172C 4-bromo-1-((1-(2-methoxyethoxy)cycloheptyl)methyl)-5-methyl-1H-pyrrole-2-carbonitrile EXAMPLE 172B (218 mg) in acetonitrile (10 ml) was treated with N-bromosuccinimide (140 mg) for 15 minutes and concentrated. The residue was purified by flash chromatography, and was eluted with 0-100% hexanes in dichloromethane to provide the title compound.

Example 172D methyl 6-(8-(benzo[d]thiazol-2-ylcarbamoyl)-3,4-dihydroisoquinolin-2(1H)-yl)-3-bromopicolinate The title compound was prepared by substituting methyl 3-bromo-6-fluoropicolinate for EXAMPLE 1C in EXAMPLE 1D.

Example 172E methyl 6-(8-(benzo[d]thiazol-2-ylcarbamoyl)-3,4-dihydroisoquinolin-2(1H)-yl)-3-(4,4,5,5-tetramethyl-1,3,2-dioxaborolan-2-yl)picolinate The title compound was prepared by substituting EXAMPLE 172D for EXAMPLE 63C in EXAMPLE 63D.

Example 172F methyl 6-(8-(benzo[d]thiazol-2-ylcarbamoyl)-3,4-dihydroisoquinolin-2(1H)-yl)-3-(5-cyano-1-((1-(2-methoxyethoxy)cycloheptyl)methyl)-2-methyl-1H-pyrrol-3-yl)picolinate The title compound was prepared by substituting EXAMPLE 172E for EXAMPLE 30A and EXAMPLE 172C for EXAMPLE 112A in EXAMPLE 112B.

Example 172G

6-[8-(1,3-benzothiazol-2-ylcarbamoyl)-3,4-dihydroisoquinolin-2(1H)-yl]-3-(5-cyano-1-{[1-(2-methoxyethoxy)cycloheptyl]methyl}-2-methyl-1H-pyrrol-3-yl)pyridine-2-carboxylic acid EXAMPLE 172F (50 mg) in tetrahydrofuran (5 mL) and methanol (3 mL) was treated with 2 N aqueous NaOH (3 mL) overnight, acidified to pH 1, and concentrated. The residue was suspended in water and the precipitates were collected, washed with water and dried over $Na_2SO_4$ to give the title compound. $^1$H NMR (400 MHz, dimethylsulfoxide-$d_6$) δ ppm 12.86 (s, 2H), 8.04 (d, 1H), 7.79 (d, 1H), 7.62 (d, 1H), 7.41-7.50 (m, 3H), 7.33-7.39 (m, 2H), 6.95 (d, 1H), 6.79 (s, 1H), 4.96 (s, 2H), 3.99 (s, 2H), 3.89 (t, 2H), 3.44-3.51 (m, 2H), 3.21 (s, 2H), 3.01 (t, 2H), 2.12 (s, 3H), 1.37-1.70 (m, 12H).

Example 173

6-[8-(1,3-benzothiazol-2-ylcarbamoyl)-3,4-dihydroisoquinolin-2(1H)-yl]-3-(1-{[1-(1,4-dioxan-2-ylmethoxy)cycloheptyl]methyl}-5-methyl-1H-pyrazol-4-yl)pyridine-2-carboxylic acid

Example 173A 1-((1-((1,4-dioxan-2-yl)methoxy)cycloheptyl)methyl)-5-methyl-1H-pyrazole To a stirred solution of EXAMPLE 170C (315 mg) in dichloromethane (10 mL) was added NaH (80 mg) at 0° C. The mixture was stirred for 10 minutes. A solution of vinyl selenone (240 mg) in dichloromethane (5 mL) was added to the mixture and the mixture was stirred at room temperature for 3 hours. The mixture was quenched with aqueous $NH_4Cl$, extracted with dichloromethane (2×200 mL), washed with water and brine, and dried over $Na_2SO_4$. Filtration and evaporation of the solvent gave the crude product which was purified by column eluted with 50% ethyl acetate in hexane) to provide the title compound.

Example 173B 1-((1-((1,4-dioxan-2-yl)methoxy)cycloheptyl)methyl)-4-iodo-5-methyl-1H-pyrazole The title compound was prepared by substituting EXAMPLE 173A for EXAMPLE 65E in EXAMPLE 65F.

Example 173C

6-[8-(1,3-benzothiazol-2-ylcarbamoyl)-3,4-dihydroisoquinolin-2(1H)-yl]-3-(1-{[1-(1,4-dioxan-2-ylmethoxy)cycloheptyl]methyl}-5-methyl-1H-pyrazol-4-yl)pyridine-2-carboxylic acid The title compound was prepared by substituting EXAMPLE 173B for EXAMPLE 75A in EXAMPLE 75B, and then substituting that product for EXAMPLE 8B in EXAMPLE 8C. $^1$H NMR (300 MHz, dimethylsulfoxide-$d_6$) δ ppm 12.84 (s, 1H), 8.03 (d, 1H), 7.79 (d, 1H), 7.61 (d, 1H), 7.42 (m, 5H), 7.27 (s, 1H), 6.95 (d, 1H), 4.95 (s, 2H), 4.02 (m, 4H), 3.89 (m, 2H), 3.59 (m, 5H), 3.42 (m, 3H), 3.02 (m, 2H), 2.13 (s, 3H), 1.33 (m, 14H)

Example 174

6-[8-(1,3-benzothiazol-2-ylcarbamoyl)-3,4-dihydroisoquinolin-2(1H)-yl]-3-[5-methyl-1-({1-[2-(morpholin-4-yl)-2-oxoethoxy]cyclohexyl}methyl)-1H-pyrazol-4-yl]pyridine-2-carboxylic acid

Example 174A 2-(1-((4-bromo-5-methyl-1H-pyrazol-1-yl)methyl)cyclohexyloxy)acetaldehyde To a solution of EXAMPLE 167B (3.13 g) in dioxane/water (3:1, 40 mL) was added 2,6-lutidine (2.5 mL), $OsO_4$ (2.5% in tert-butanol, 2.75 mL), and $NaIO_4$ (8.55 g) under argon. The reaction mixture was stirred at room temperature for 4 hours, then water (50 mL) and dichloromethane (200 mL) were added. The organic layer was separated, and the water phase was extracted by dichloromethane (3×200 mL).

The combined organic layers were washed with brine (200 mL) and dried over Na$_2$SO$_4$. After filtration, the solvent was removed to give the crude product which was used in the next step without further purification.

Example 174B 2-(1-((4-bromo-5-methyl-1H-pyrazol-1-yl)methyl) cyclohexyloxy)acetic acid To a solution of EXAMPLE 174A (3.15 g) in t-butanol (200 mL) and tetrahydrofuran (50 mL) was added 2-methyl-2-butene (8 mL). The mixture was allowed to stir in an ice bath. NaClO$_2$ (1.2 g) and NaH$_2$PO$_4$ (3 g) were dissolved into water (75 mL), and the solution was added to the mixture. The mixture was allowed to stir in an ice bath for 15 minutes, and then stirred at room temperature for 12 hours. NH$_4$Cl was added, the mixture was extracted with ethyl acetate, and the organic layer was washed with brine, dried over anhydrous Na$_2$SO$_4$, filtered, and concentrated to dryness to provide the title compound.

Example 174C 2-(1-((4-bromo-5-methyl-1H-pyrazol-1-yl)methyl) cyclohexyloxy)-1-morpholinoethanone To a solution of EXAMPLE 174B (331 mg) in dichloromethane (10 mL) was added morpholine (174 mg), 4-dimethylaminopyridine (122 mg) and 1-ethyl-3-[3-(dimethylamino)propyl]-carbodiimide hydrochloride (287 mg). The mixture was stirred overnight. The mixture was diluted with ethyl acetate (200 mL) and washed with water and brine and dried over Na$_2$SO$_4$. Filtration and evaporation of the solvent gave the crude title compound.

Example 174D

6-[8-(1,3-benzothiazol-2-ylcarbamoyl)-3,4-dihydroisoquinolin-2(1H)-yl]-3-[5-methyl-1-({1-[2-(morpholin-4-yl)-2-oxoethoxy]cyclohexyl}methyl)-1H-pyrazol-4-yl]pyridine-2-carboxylic acid The title compound was prepared by substituting EXAMPLE 174C for EXAMPLE 75A in EXAMPLE 75B, and then substituting that product for EXAMPLE 8B in EXAMPLE 8C. $^1$H NMR (300 MHz, dimethylsulfoxide-d$_6$) δ ppm 12.84 (s, 1H), 8.03 (d, 1H), 7.79 (d, 1H), 7.61 (d, 1H), 7.42 (m, 5H), 7.29 (s, 1H), 6.96 (d, 1H), 4.95 (s, 2H), 4.09 (m, 4H), 3.89 (t, 2H), 3.01 (t, 2H), 2.13 (s, 3H), 1.65 (m, 2H), 1.35 (m, 10H).

Example 175

6-[8-(1,3-benzothiazol-2-ylcarbamoyl)-3,4-dihydroisoquinolin-2(1H)-yl]-3-(1-{[1-(2,3-dihydroxypropoxy)cycloheptyl]methyl}-5-methyl-1H-pyrazol-4-yl)pyridine-2-carboxylic acid Example 175A 3-(1-((4-iodo-5-methyl-1H-pyrazol-1-yl)methyl) cycloheptyloxy)propane-1,2-diol The title compound was prepared by substituting EXAMPLE 170C for EXAMPLE 65E in EXAMPLE 65F.

Example 175B

6-[8-(1,3-benzothiazol-2-ylcarbamoyl)-3,4-dihydroisoquinolin-2(1H)-yl]-3-(1-{[1-(2,3-dihydroxypropoxy)cycloheptyl]methyl}-5-methyl-1H-pyrazol-4-yl)pyridine-2-carboxylic acid The title compound was prepared by substituting EXAMPLE 175A for EXAMPLE 75A in EXAMPLE 75B, and then substituting that product for EXAMPLE 8B in EXAMPLE 8C, 134. $^1$H NMR (300 MHz, dimethylsulfoxide-d$_6$) δ ppm 12.85 (s, 1H), 8.04 (d, 1H), 7.79 (d, 1H), 7.62 (d, 1H), 7.42 (m, 6H), 7.28 (s, 1H), 6.95 (d, 1H), 4.95 (s, 2H), 4.34 (m, 2H), 3.89 (m, 2H), 3.38 (m, 6H), 3.13 (m, 4H), 3.01 (t, 2H), 2.13 (m, 3H), 1.43 (m, 12H).

Example 176

6-[8-(1,3-benzothiazol-2-ylcarbamoyl)-3,4-dihydroisoquinolin-2(1H)-yl]-3-(5-cyano-1-{[1-(dimethylamino)cyclohexyl]methyl}-2-methyl-1H-pyrrol-3-yl)pyridine-2-carboxylic acid Example 176A (1-(dimethylamino)cyclohexyl)methanol To a solution of (1-aminocyclohexyl)methanol (378 mg) in ethanol (10 mL) was added CH$_3$I (2.1 g) and NaHCO$_3$ (246 mg). The mixture was stirred for 24 hours. The mixture was dissolved in 2N aqueous NaOH (20 mL) and ethyl acetate (200 mL). The organic layer was dried over Na$_2$SO$_4$, filtered, and concentrated under vacuum to give the crude title compound.

Example 176B 1-((1-(dimethylamino)cyclohexyl)methyl)-4-iodo-5-methyl-1H-pyrrole-2-carbonitrile The title compound was prepared by substituting EXAMPLE 176A for (3-(dimethylamino)phenyl)methanol and EXAMPLE 168D for 4-(4,4,5,5-tetramethyl-1,3,2-dioxaborolan-2-yl)-1H-pyrazole in EXAMPLE 34A.

Example 176C

6-[8-(1,3-benzothiazol-2-ylcarbamoyl)-3,4-dihydroisoquinolin-2(1H)-yl]-3-(5-cyano-1-{[1-(dimethylamino)cyclohexyl]methyl}-2-methyl-1H-pyrrol-3-yl)pyridine-2-carboxylic acid The title compound was prepared by substituting EXAMPLE 176B for EXAMPLE 75A in EXAMPLE 75B, and then substituting that product for EXAMPLE 8B in EXAMPLE 8C. $^1$H NMR (300 MHz, dimethylsulfoxide-d$_6$) δ ppm 12.86 (s, 1H), 8.75 (m, 1H), 8.04 (d, 1H), 7.79 (d, 1H), 7.62 (d, 1H), 7.43 (m, 5H), 6.98 (d, 1H), 6.96 (s, 1H), 4.98 (s, 2H), 4.41 (s, 2H), 3.90 (t, 2H), 2.99 (m, 8H), 2.13 (m, 3H), 1.31 (m, 10H).

Example 177

6-[8-(1,3-benzothiazol-2-ylcarbamoyl)-3,4-dihydroisoquinolin-2(1H)-yl]-3-{3-[(cyclohexylcarbonyl)(methyl)amino]-2-methylphenyl}pyridine-2-carboxylic acid

Example 177A cyclohexanecarboxylic acid (3-bromo-2-methyl-phenyl)-methyl-amide 3-Bromo-N,2-dimethylaniline (150 mg) and diisopropylethylamine (291 mg) were added to dichloromethane (5 mL). Cyclohexanecarbonyl chloride (115 mg) was added and the solution was stirred at room temperature for 16 hours. The solution was diluted with ethyl acetate and washed two times with 1M aqueous HCl and once with brine. The solution was dried on anhydrous sodium sulfate, filtered, and the solvent was removed to provide the title compound which was used without further purification.

Example 177B

6-[8-(1,3-benzothiazol-2-ylcarbamoyl)-3,4-dihydroisoquinolin-2(1H)-yl]-3-{3-[(cyclohexylcarbonyl)(methyl)amino]-2-methylphenyl}pyridine-2-carboxylic acid tert-butyl ester The title compound was prepared by substituting EXAMPLE 177A for EXAMPLE 112A in EXAMPLE 112B.

Example 177C

6-[8-(1,3-benzothiazol-2-ylcarbamoyl)-3,4-dihydroisoquinolin-2(1H)-yl]-3-{3-[(cyclohexylcarbonyl)(methyl)amino]-2-methylphenyl}pyridine-2-carboxylic acid The title compound was prepared by substituting EXAMPLE 177B for EXAMPLE 7D in EXAMPLE 7E. $^1$H NMR (400 MHz, dimethylsulfoxide-$d_6$) δ ppm 8.03 (d, 1H), 7.79 (d, 1H), 7.63 (d, 1H), 7.55-7.42 (m, 3H), 7.36 (q, 2H), 7.28-7.18 (m, 2H), 7.07-7.01 (m, 2H), 5.00 (bs, 2H), 3.94 (t, 2H), 3.04 (bs, 5H), 2.00 (m, 1H), 1.85 (bs, 3H), 1.65-1.35 (m, 6H), (m, 3H), 1.11-0.99 (m, 2H), 0.96-0.80 (m, 2H).

Example 178

6-[8-(1,3-benzothiazol-2-ylcarbamoyl)-3,4-dihydroisoquinolin-2(1H)-yl]-3-[1-({3,3-dimethyl-1-[2-(methylsulfonyl)ethoxy]cyclohexyl}methyl)-5-methyl-1H-pyrazol-4-yl]pyridine-2-carboxylic acid

Example 178A 4-bromo-1-((3,3-dimethyl-1-(2-(methylsulfonyl)ethoxy)cyclohexyl)methyl)-5-methyl-1H-pyrazole To a solution of EXAMPLE 157B (0.218 g) in tetrahydrofuran (2.5 mL) was added sodium hydride (0.027 g) and the reaction mixture was stirred for 15 minutes at room temperature. Methylsulfonylethene (0.095 mL) was added and the reaction was stirred at room temperature overnight. The reaction was cooled and diluted with ethyl acetate (50 mL). The organic layer was washed with water (50 mL) and brine (50 mL), dried over magnesium sulfate, filtered, and concentrated. Silica gel chromatography eluting with a gradient of 1-20% ethyl acetate in hexanes provided the title compound.

Example 178B tert-butyl 6-(8-(benzo[d]thiazol-2-ylcarbamoyl)-3,4-dihydroisoquinolin-2(1H)-yl)-3-(1-((3,3-dimethyl-1-(2-(methylsulfonyl)ethoxy)cyclohexyl)methyl)-5-methyl-1H-pyrazol-4-yl)picolinate The title compound was prepared by substituting EXAMPLE 178A for EXAMPLE 77D in EXAMPLE 77E.

Example 178C

6-[8-(1,3-benzothiazol-2-ylcarbamoyl)-3,4-dihydroisoquinolin-2(1H)-yl]-3-[1-({3,3-dimethyl-1-[2-methylsulfonyl)ethoxy]cyclohexyl}methyl)-5-methyl-1H-pyrazol-4-yl]pyridine-2-carboxylic acid The title compound was prepared by substituting EXAMPLE 178B for EXAMPLE 8B in EXAMPLE 8C. $^1$H NMR (400 MHz, dimethylsulfoxide-$d_6$) δ ppm 6 (s, 2H), 8.04 (d, 1H), 7.79 (d, 1H), 7.62 (d, 1H), 7.56-7.41 (m, 3H), 7.40-7.33 (m, 2H), 7.32 (s, 1H), 6.96 (d, 1H), 4.96 (s, 2H), 4.16-3.96 (m, 2H), 3.95-3.79 (m, 3H), 3.79-3.68 (m, 1H), 3.32 (d, 3H), 3.01 (t, 2H), 2.94 (s, 3H), 2.14 (s, 3H), 1.74 (d, 1H), 1.52 (t, 2H), 1.45-1.27 (m, 2H), 1.27-1.02 (m, 5H), 1.00 (s, 3H), 0.86 (s, 3H).

Example 179

6-[8-(1,3-benzothiazol-2-ylcarbamoyl)-3,4-dihydroisoquinolin-2(1H)-yl]-3-(2-methyl-3-{methyl[(1-methylcyclohexyl)carbonyl]amino}phenyl)pyridine-2-carboxylic acid

Example 179A

1-Methyl-cyclohexanecarboxylic acid (3-bromo-2-methyl-phenyl)-methyl-amide

The title compound was prepared by substituting 1-methylcyclohexanecarbonyl chloride for cyclohexanecarbonyl chloride in EXAMPLE 177A.

Example 179B

6-[8-(1,3-benzothiazol-2-ylcarbamoyl)-3,4-dihydroisoquinolin-2(1H)-yl]-3-(2-methyl-3-{methyl[(1-methylcyclohexyl)carbonyl]amino}phenyl)pyridine-2-carboxylic acid tert-butyl ester The title compound was prepared by substituting EXAMPLE 179A for EXAMPLE 112A in EXAMPLE 112B.

Example 179C

6-[8-(1,3-benzothiazol-2-ylcarbamoyl)-3,4-dihydroisoquinolin-2(1H)-yl]-3-(2-methyl-3-{methyl[(1-methylcyclohexyl)carbonyl]amino}phenyl)pyridine-2-carboxylic acid The title compound was prepared by substituting EXAMPLE 179B for EXAMPLE 7D in EXAMPLE 7E. $^1$H NMR (400 MHz, dimethylsulfoxide-d$_6$) δ ppm (8.03, 1H), 7.79 (d, 1H), 7.63 (d, 1H), 7.50-7.32 (m, 5H), 7.18 (m, 2H), 7.02 (m, 2H), 4.99 (bs, 2H), 3.93 (t, 2H), 3.02 (bs, 5H), 1.91 (s, 3H), 1.85-1.62 (m, 2H), 1.44-1.10 (m, 8H), 0.95 (m, 3H).

Example 180

6-[8-(1,3-benzothiazol-2-ylcarbamoyl)-3,4-dihydroisoquinolin-2(1H)-yl]-3-(1-{[1-(2-methoxyethoxy)-3,3-dimethylcyclohhexyl]methyl}-5-methyl-1H-pyrazol-4-yl)pyridine-2-carboxylic acid Example 180A 1-((1-(allyloxy)-3,3-dimethylcyclohexyl)methyl)-4-bromo-5-methyl-1H-pyrazole To a solution of EXAMPLE 157B (2.73 g) in N,N-dimethylformamide (20 mL) was added NaH (1.45 g) and the reaction mixture was stirred for 30 minutes at room temperature. 3-Bromoprop-1-ene (1.53 mL) was added and the mixture was stirred at room temperature for 2 hours. The reaction mixture was diluted with diethyl ether (75 mL), washed with water (2×50 mL) and brine (50 mL), dried over magnesium sulfate, filtered, and concentrated. Silica gel chromatography eluting with a gradient of 1.5% to 15% ethyl acetate/hexanes provided the title compound.

Example 180B 2-(1-((4-bromo-5-methyl-1H-pyrazol-1-yl)methyl)-3,3-dimethylcyclohexyloxy)ethanol A solution of EXAMPLE 180A (2.80 g) in dioxane/water (30 mL/10 mL) was added to 2,6-dimethylpyridine (1.909 mL) and sodium periodate (7.02 g) followed by the addition of osmium tetroxide (2.5% solution, 1.0 mL) and the reaction mixture was stirred for 30 minutes at room temperature. The reaction mixture was diluted with ethyl acetate (50 mL), washed with water (50 mL) and brine (50 mL), dried over magnesium sulfate, filtered, and concentrated. The residue was dissolved in methanol (20 mL) and sodium borohydride (0.16 g) was added. The mixture was stirred at room temperature for 1 hour. An aqueous work up followed by silica gel chromatography using 2-30% ethyl acetate in hexanes provided the title compound.

Example 180C 4-bromo-1-((1-(2-methoxyethoxy)-3,3-dimethylcyclohexyl)methyl)-5-methyl-1H-pyrazole To a solution of EXAMPLE 180B (2.2 g) in N,N-dimethylformamide (20 mL) was added sodium hydride (0.38 g). After stirring for 30 minutes, methyl iodide (0.60 mL) was added. The reaction mixture was stirred for 2 hours at room temperature, diluted with ether (100 mL) and washed with water (2×75 mL) and brine (75 mL), dried over magnesium sulfate, filtered, and concentrated. Silica gel chromatography eluting with a gradient of 3% to 25% ethyl acetate/hexanes provided the title compound.

Example 180D 1-((1-(2-methoxyethoxy)-3,3-dimethylcyclohexyl)methyl)-5-methyl-4-(4,4,5,5-tetramethyl-1,3,2-dioxaborolan-2-yl)-1H-pyrazole The title compound was prepared by substituting EXAMPLE 180C for EXAMPLE 63C in EXAMPLE 63D.

Example 180E

6-[8-(1,3-benzothiazol-2-ylcarbamoyl)-3,4-dihydroisoquinolin-2(1H)-yl]-3-(1-{[1-(2-methoxyethoxy)-3,3-dimethylcyclohexyl]methyl}-5-methyl-1H-pyrazol-4-yl)pyridine-2-carboxylic acid The title compound was prepared by substituting EXAMPLE 180D for EXAMPLE 157D in EXAMPLE 157E. $^1$H NMR (300 MHz, dimethylsulfoxide-d$_6$) δ ppm 12.84 (s, 1H), 8.03 (d, 1H), 7.79 (d, 1H), 7.62 (d, 1H), 7.53-7.40 (m, 3H), 7.36 (m, 2H), 7.28 (s, 1H), 6.95 (d, 1H), 4.95 (s, 2H), 4.10-3.93 (m, 2H), 3.89 (t, 2H), 3.62-3.45 (m, 4H), 3.23 (s, 3H), 3.01 (t, 2H), 2.12 (s, 3H), 1.79 (d, 1H), 1.63-1.01 (m, 7H), 0.99 (s, 3H), 0.84 (s, 3H).

Example 181

6-[8-(1,3-benzothiazol-2-ylcarbamoyl)-3,4-dihydroisoquinolin-2(1H)-yl]-3-{2-cyano-3-[(cyclohexylsulfonyl)(methyl)amino]phenyl}pyridine-2-carboxylic acid Example 181A cyclohexanesulfonic acid methylamide Cyclohexanesulfonyl chloride (500 mg) was added to methylamine (12.3 mL, 2M solution in tetrahydrofuran) and the reaction mixture was stirred at room temperature for one hour. The solution was added to 1M aqueous HCl and extracted with ethyl acetate. The extract was washed with brine and dried over anhydrous sodium sulfate. After filtration, the solvent was removed under vacuum to yield the product.

Example 181B cyclohexanesulfonic acid (3-bromo-2-cyano-phenyl)-methyl-amide

2-Bromo-6-fluorobenzonitrile (500) mg), EXAMPLE 181A (487 mg), and potassium carbonate (415 mg) were added to N,N-dimethylacetamide (15 mL) and the mixture was heated to 85° C. for three days. The mixture was cooled, added to 1M aqueous HCl, extracted with 70% ethyl acetate (hexanes), washed with water, washed with brine, and dried over anhydrous sodium sulfate. After filtration, the solvent was removed under vacuum, and the crude material was recrystallized from ethyl acetate to provide the title compound.

Example 181C

6-[8-(1,3-benzothiazol-2-ylcarbamoyl)-3,4-dihydroisoquinolin-2(1H)-yl]-3-{2-cyano-3-[(cyclohexylsulfonyl)(ethyl)amino]phenyl}pyridine-2-carboxylic acid tert-butyl ester The title compound was prepared by substituting EXAMPLE 181B for EXAMPLE 112A in EXAMPLE 112B.

Example 181D

6-[8-(1,3-benzothiazol-2-ylcarbamoyl)-3,4-dihydroisoquinolin-2(1H)-yl]-3-{2-cyano-3-[(cyclohexylsulfonyl)(ethyl)amino]phenyl}pyridine-2-carboxylic acid The title compound was prepared by substituting EXAMPLE 181C for EXAMPLE 7D in EXAMPLE 7E. $^1$H NMR (400 MHz, dimethylsulfoxide-d$_6$) δ ppm 12.85 (bs, 1H), 8.03 (d, 1H), 7.79 (d, 1H), 7.71 (dd, 1H), 7.63 (d, 1H), 7.60 (dd, 1H), 7.49-7.32 (m, 6H), 7.10 (d, 1H), 5.05 (bs, 2H), 3.98 (t, 2H), 3.28 (s, 3H), 3.04 (t, 2H), 2.14 (d, 2H), 1.79 (d, 2H), 1.62 (d, 1H), 1.51-1.10 (m, 6H).

Example 182

6-[8-(1,3-benzothiazol-2-ylcarbamoyl)-3,4-dihydroisoquinolin-2(1H)-yl]-3-{2-cyano-3-[2-(tricyclo[3.3.1.1$^{3,7}$]dec-1-yl)pyrrolidin-1-yl]phenyl}pyridine-2-carboxylic acid

Example 182A 2-(2-adamantan-1-yl-pyrrolidin-1-yl)-6-bromo-benzonitrile

2-Bromo-6-fluorobenzonitrile (900 mg), 2-adamantan-1-yl-pyrrolidine (924 mg), and potassium carbonate (1244 mg) were added to dimethyl sulfoxide and the mixture was heated at 130° C. for 16 hours. The solution was cooled, diluted with ethyl acetate, washed twice with 1M HCl, washed with brine, and dried over anhydrous sodium sulfate. After filtration, the crude material was concentrated under vacuum and purified on silica gel using 5% ethyl acetate (hexanes) to provide the title compound.

Example 182B

6-[8-(1,3-benzothiazol-2-ylcarbamoyl)-3,4-dihydroisoquinolin-2(1H)-yl]-3-(2-cyano-3-{2-[tricyclo[3.3.1.1$^{3,7}$]dec-1-yl]pyrrolidin-1-yl}phenyl)pyridine-2-carboxylic acid tert-butyl ester The title compound was prepared by substituting EXAMPLE 182A for EXAMPLE 112A in EXAMPLE 112B.

Example 182C

6-[8-(1,3-benzothiazol-2-ylcarbamoyl)-3,4-dihydroisoquinolin-2(1H)-yl]-3-{2-cyano-3-[2-(tricyclo[3.3.1.1$^{3,7}$]dec-1-yl)pyrrolidin-1-yl]phenyl}pyridine-2-carboxylic acid The title compound was prepared by substituting EXAMPLE 182B for EXAMPLE 7D in EXAMPLE 7E. $^1$H NMR (400 MHz, dimethylsulfoxide-d$_6$) δ ppm 12.85 (bs, 1H), 12.68 (bs, 1H), 8.03 (d, 1H), 7.79 (d, 1H), 7.65 (d, 1H), 7.62 (d, 1H), 7.50-7.44 (m, 2H), 7.40-7.27 (m, 4H), 7.03 (d, 1H), 6.65 (d, 1H), 5.02 (bs, 2H), 3.96 (m, 2H), 3.63 (m, 1H), 3.18 (m, 2H), 3.04 (t, 2H), 1.91-1.82 (m, 5H), 1.68-1.42 (m, 12H), 1.24 (bs, 2H).

Example 183

6-[8-(1,3-benzothiazol-2-ylcarbamoyl)-3,4-dihydroisoquinolin-2(1H)-yl]-3'-methyl-2'-(piperidin-1-yl)-3,4'-bipyridine-2-carboxylic acid

Example 183A tert-butyl 6-(8-(benzo[d]thiazol-2-ylcarbamoyl)-3,4-dihydroisoquinolin-2(1H)-yl)-2'-chloro-3'-methyl-3,4'-bipyridine-2-carboxylate To a solution of EXAMPLE 30A (1.22 g) in dioxane (4 mL), and aqueous NaHCO$_3$ (2 mL) was added 2-chloro-4-iodo-3-methylpyridine (505 mg), and tetrakis(triphenylphosphine)palladium(0) (115 mg). The mixture was stirred at 120° C. for 20 minutes in a Biotage Initiator microwave reactor. The mixture was diluted with ethyl acetate (300 mL) and washed with water (3 times) and brine, and dried over Na$_2$SO$_4$. Filtration and evaporation of the solvent gave crude product which was loaded on a silica gel column and eluted with 20% ethyl acetate in dichloromethane to provide the title compound.

Example 183B

6-[8-(1,3-benzothiazol-2-ylcarbamoyl)-3,4-dihydroisoquinolin-2(1H)-yl]-3'-methyl-2'-(piperidin-1-yl)-3,4'-bipyridine-2-carboxylic acid To a solution of EXAMPLE 183A (200 mg) in N,N-dimethylacetamide (15 mL) was added piperidine (110 mg), K$_3$PO$_4$ (218 mg), and bis(tri-tert-butylphosphine)palladium (7.01 mg). The mixture was stirred at 100° C. overnight under nitrogen. The mixture was diluted with ethyl acetate (300 mL), washed with water and brine, and dried over Na$_2$SO$_4$. Filtration and evaporation of the solvent gave crude product which was purified by flash chromatography to give the pure ester which was dissolved in dichloromethane/TFA (1:1, 6 mL) and stirred overnight. The solvent was evaporated under vacuum and the residue was dissolved in DMSO/methanol (1:1, 10 ml). The residue was purified by reverse phase chromatography using a Gilson system, eluting with 20-80% acetonitrile in 0.1% TFA water solution to provide the desired product. $^1$H NMR (300 MHz, dimethylsulfoxide-d$_6$) δ ppm 12.86 (s, 1H), 8.05 (m, 2H), 7.79 (d, 1H), 7.48 (m, 5H), 7.05 (d, 1H), 6.87 (d, 1H), 5.02 (s, 2H), 3.95 (t, 2H), 3.07 (m, 5H), 2.01 (s, 3H), 1.65 (m, 6H).

Example 184

6-[8-(1,3-benzothiazol-2-ylcarbamoyl)-3,4-dihydroisoquinolin-2(1H)-yl]-3-[1-(1-cyclohexyl-3-methoxypropyl)-5-methyl-1H-pyrazol-4-yl]pyridine-2-carboxylic acid

Example 184A 3-cyclohexyl-3-(1H-pyrazol-1-yl)propan-1-ol

To a solution of EXAMPLE 152A (2.42 g) in toluene (20 mL) diisobutylaluminum hydride (28.2 mL) was added at -78° C. The reaction mixture was stirred for 60 minutes. The reaction mixture was quenched with methanol (10 mL), 1M aqueous HCl (200 mL) and washed with saturated NaHCO$_3$. The organic layer was dried over magnesium sulfate, filtered and concentrated. The product was purified by flash chromotography (silica gel, 10-100% ethyl acetate/hexanes) to provide the title compound.

Example 184B 1-(1-cyclohexyl-3-methoxypropyl)-1H-pyrazole

To a solution of EXAMPLE 184A (0.23 g) in dry tetrahydrofuran (5 mL) was added sodium hydride (0.166 g) at 0° C. The reaction mixture was stirred for 60 minutes when methyl iodide (0.259 mL) was added and stirring was continued for 4 hours at room temperature. The reaction mixture was quenched with ammonium chloride solution (5 mL), and extracted with ethyl acetate. The organic layer was dried over magnesium sulfate, filtered and concentrated. The crude material was purified by flash chromatography on silica gel, and was eluted with 10-60% ethyl acetate/hexanes.

Example 184C 1-(1-cyclohexyl-3-methoxypropyl)-5-methyl-1H-pyrazole

The title compound was prepared by substituting EXAMPLE 184B for EXAMPLE 63A in EXAMPLE 63B.

Example 184D 4-bromo-1-(1-cyclohexyl-3-methoxypropyl)-5-methyl-1H-pyrazole

The title compound was prepared by substituting EXAMPLE 184C for EXAMPLE 63B in EXAMPLE 63C.

Example 184E tert-butyl 6-(8-(benzo[d]thiazol-2-ylcarbamoyl)-3,4-dihydroisoquinolin-2(1H)-yl)-3-(1-(1-cyclohexyl-3-methoxypropyl)-5-methyl-1H-pyrazol-4-yl)picolinate The title compound was prepared by substituting EXAMPLE 184D for EXAMPLE 77D in EXAMPLE 77E.

Example 184F

6-[8-(1,3-benzothiazol-2-ylcarbamoyl)-3,4-dihydroisoquinolin-2(1H)-yl]-3-[1-(1-cyclohexyl-3-methoxypropyl)-5-methyl-1H-pyrazol-4-yl]pyridine-2-carboxylic acid The title compound was prepared by substituting EXAMPLE 184E for EXAMPLE 1E in EXAMPLE 1F. $^1$H NMR (300 MHz, dimethylsulfoxide-d$_6$) δ ppm 12.85 (s, 1H), 8.04 (d, 1H), 7.79 (d, 1H), 7.62 (d, 1H), 7.52-7.40 (m, 3H), 7.41-7.29 (m, 3H), 6.95 (d, 1H), 4.95 (s, 2H), 3.97-3.84 (m, 4H), 3.15-3.07 (m, 1H), 3.10 (s, 3H), 3.01 (t, 2H), 2.64 (td, 1H), 2.16-2.05 (m, 1H), 2.04 (s, 3H), 2.00-1.82 (m, 2H), 1.81-1.65 (m, 2H), 1.65-1.50 (m, 2H), 1.29-0.75 (m, 6H).

Example 185

6-[8-(1,3-benzothiazol-2-ylcarbamoyl)-3,4-dihydroisoquinolin-2(1H)-yl]-3-[1-({3,3-dimethyl-1-[2-(methylamino)ethoxy]cyclohexyl}methyl)-5-methyl-1H-pyrazol-4-yl]pyridine-2-carboxylic acid Example 185A 3,3-dimethyl-1-((5-methyl-1H-pyrazol-1-yl)methyl)cyclohexanol To a cold (−78° C.) solution of nBuLi (12.48 mL) in tetrahydrofuran (40 mL) was added a solution of 1,5-dimethyl-1H-pyrazole (3.0 g) in tetrahydrofuran (3 mL) dropwise. After stirring for 1 hour, a solution of 3,3-dimethylcyclohexanone (3.94 g) in tetrahydrofuran (3 mL) was added dropwise, and the reaction was allowed to warm to 0° C. After stirring for 1 hour, the reaction mixture was diluted with ether (100 mL), washed with water (50 mL) and brine (50 mL), dried over magnesium sulfate, filtered, and concentrated. Purification of the residue by silica gel chromatography, eluting with a gradient of 3% to 25% ethyl acetate in hexanes, gave the title compound.

Example 185B 1-((4-bromo-5-methyl-1H-pyrazol-1-yl)methyl)-3,3-dimethylcyclohexanol The title compound was prepared by substituting EXAMPLE 185A for EXAMPLE 63B in EXAMPLE 63C.

Example 185C 1-((1-(allyloxy)-3,3-dimethylcyclohexyl)methyl)-4-bromo-5-methyl-1H-pyrazole To a cold (0° C.) solution of EXAMPLE 185B (3.63 g) in N,N-dimethylformamide (25 mL) was added NaH (0.964 g, 60% dispersion in mineral oil), and the reaction was stirred for 30 minutes. 3-Bromoprop-1-ene (1.529 mL) was added. The cooling bath was removed, and the reaction was warmed to room temperature. The reaction mixture was heated to 50° C., whereupon a significant evolution of gas occurred. After 2 hours, the reaction mixture was diluted with diethyl ether (75 mL), washed with water (2×50 mL) and brine (50 mL), dried over magnesium sulfate, filtered, and concentrated. Purification of the residue by silica gel chromatography, eluting with a gradient of 1.5% to 15% ethyl acetate in hexanes, gave the title compound.

Example 185D 2-(trimethylsilyl)ethyl (2-((1-((4-bromo-5-methyl-1H-pyrazol-1-yl)methyl)-3,3-dimethylcyclohexyl)oxy)ethyl)(methyl)carbamate To a solution of EXAMPLE 185C (0.93 g) in dioxane (9 mL) and water (3 mL) was added 2,6-dimethylpyridine (0.634 mL) and sodium periodate (2.331 g) followed by osmium tetroxide (0.277 mL, 2.5% solution in tert-butanol). The reaction mixture was stirred for 30 minutes at room temperature, whereupon a significant precipitate formed. The reaction mixture was stirred for an additional 1 hour, diluted with ether (100 mL), washed with water (50 mL) and brine (50 mL), dried over magnesium sulfate, filtered, and concentrated. To the residue dissolved in methanol (5 mL) was added methanamine (1.635 mL) and sodium cyanoborohydride (0.171 g). After 1 hour, the reaction mixture was diluted with ethyl acetate (50 mL), washed with water (50 mL), brine (50 mL), dried over magnesium sulfate and concentrated. The residue was dissolved in methylene chloride (5 mL), and 2,5-dioxopyrrolidin-1-yl 2-(trimethylsilyl)ethyl carbonate (0.848 g) was added. After 1 hour, the reaction was quenched by the addition of water. The layers were separated, and the organic layer was dried with magnesium sulfate, filtered and concentrated. The residue was purified by silica gel chromatography, eluting with hexane/ethyl acetate, to give the title product.

Example 185E

6-[8-(1,3-benzothiazol-2-ylcarbamoyl)-3,4-dihydroisoquinolin-2 (1H)-yl]-3-[1-({3,3-dimethyl-1-[2-(methylamino)ethoxy]cyclohexyl}methyl)-5-methyl-1H-pyrazol-4-yl]pyridine-2-carboxylic acid A mixture of EXAMPLE 30A (0.629 g), EXAMPLE 185D (0.430 g), 1,3,5,7-tetramethyl-6-phenyl-2,4,8-trioxa-6-phosphaadamantane (0.125 g), potassium phosphate (0.908 g) and tris(dibenzylideneacetone)dipalladium(0) chloroform adduct (0.089 g) was dissolved in tetrahydrofuran (3 mL) and water (1 mL). The reaction vessel was flushed with nitrogen and then heated under microwave conditions (Biotage) to 140° C. for 5 minutes. The reaction mixture was diluted with ether (25 mL), washed with saturated NH$_4$Cl solution (20 mL) and brine (20 mL), dried over magnesium sulfate, filtered, and concentrated. Purification of the residue by silica gel chromatography, eluting with a gradient of 5% to 100% ethyl acetate in hexanes, gave an intermediate ester. The residue was dissolved in methylene chloride (1 mL), and TFA (1 mL) was added. After stirring overnight, the reaction mixture was concentrated and purified by RP-HPLC, eluting with 10-80% acetonitrile in water containing 0.1% v/v TFA, to give the title compound. $^1$H NMR (300 MHz, dimethylsulfoxide-d$_6$) δ 12.85 (s, 1H), 8.70 (s, 2H), 8.03 (d, J=7.8, 1H), 7.79 (d, 1H), 7.62 (d, 1H), 7.54-7.41 (m, 4H), 7.36 (m, 2H), 6.97 (d, 1H), 4.97 (s, 2H), 4.06 (s, 2H), 3.90 (t, 2H), 3.74 (m, 2H), 3.12 (s, 2H), 3.02 (t, 2H), 2.65 (t, 3H), 2.14 (s, 3H), 1.35 (m, 8H), 0.97 (s, 3H), 0.86 (s, 3H).

Example 186

6-[8-(1,3-benzothiazol-2-ylcarbamoyl)-3,4-dihydroisoquinolin-2(1H)-yl]-3-{5-methyl-1-[(2,6,6-trimethyltetrahydro-2H-pyran-2-yl)methyl]-1H-pyrazol-4-yl}pyridine-2-carboxylic acid Example 186A 2,6-dimethyl-1-(5-methyl-1H-pyrazol-1-yl)hept-5-en-2-ol The title compound was prepared by substituting 6-methylhept-5-en-2-one for 3,3-dimethylcyclohexanone in EXAMPLE 185A.

Example 186B 5-methyl-1-((2,6,6-trimethyltetrahydro-2H-pyran-2-yl)methyl)-1H-pyrazole A mixture of EXAMPLE 186A (6.5 g) and formic acid (20 mL) was heated at 100° C. for 3 hours. The reaction mixture was concentrated, and the residue was purified by silica gel chromatography, eluting with 1% ethyl acetate in petroleum ether, to give the title product.

Example 186C 4-bromo-5-methyl-1-((2,6,6-trimethyltetrahydro-2H-pyran-2-yl)methyl)-1H-pyrazole The title compound was prepared by substituting EXAMPLE 186B for EXAMPLE 63B in EXAMPLE 63C.

Example 186D 5-methyl-4-(4,4,5,5-tetramethyl-1,3,2-dioxaborolan-2-yl)-1-((2,6,6-trimethyltetrahydro-2H-pyran-2-yl)methyl)-1H-pyrazole The title compound was prepared by substituting EXAMPLE 186C for EXAMPLE 84C in EXAMPLE 84D.

Example 186E tert-butyl 6-(8-(benzo[d]thiazol-2-ylcarbamoyl)-3,4-dihydroisoquinolin-2(1H)-yl)-3-(5-methyl-1-((2,6,6-trimethyltetrahydro-2H-pyran-2-yl)methyl)-1H-pyrazol-4-yl)picolinate The title compound was prepared by substituting EXAMPLE 186D for EXAMPLE 82D in EXAMPLE 82E.

Example 186F

6-[8-(1,3-benzothiazol-2-ylcarbamoyl)-3,4-dihydroisoquinolin-2(1H)-yl]-3-{5-methyl-1-[(2,6,6-trimethyltetrahydro-2H-pyran-2-yl)methyl]-1H-pyrazol-4-yl}pyridine-2-carboxylic acid The title compound was prepared by substituting EXAMPLE 186E for EXAMPLE 1E in EXAMPLE 1F. $^1$H NMR (400 MHz, dimethylsulfoxide-d$_6$) δ ppm 12.84 (v br s, 1H), 8.03 (d, 1H), 7.79 (d, 1H), 7.61 (d, 1H), 7.45 (m, 3H), 7.36 (m, 2H), 7.27 (s, 1H), 6.96 (d, 1H), 4.95 (s, 2H), 4.00 (d, 2H), 3.88 (br t, 2H), 3.01 (br t, 2H), 2.16 (s, 3H), 1.69 (m, 1H), 1.52 (m, 2H), 1.39 (m, 2H), 1.15 (s, 3H), 1.14 (s, 3H), 1.07 (m, 1H), 1.06 (s, 3H).

Example 187

6-[8-(1,3-benzothiazol-2-ylcarbamoyl)-3,4-dihydroisoquinolin-2(1H)-yl]-3-(1-benzyl-1H-indazol-4-yl)pyridine-2-carboxylic acid Example 187A 1-benzyl-4-(4,4,5,5-tetramethyl-1,3,2-dioxaborolan-2-yl)-1H-indazole The title compound was prepared by substituting 4-(4,4,5,5-tetramethyl-1,3,2-dioxaborolan-2-yl)-1H-indazole for 4-(4,4,5,5-tetramethyl-1,3,2-dioxaborolan-2-yl)-1H-pyrazole and benzyl bromide for EXAMPLE 4A in EXAMPLE 4B.

Example 187B tert-butyl 6-(8-(benzo[d]thiazol-2-ylcarbamoyl)-3,4-dihydroisoquinolin-2(1H)-yl)-3-(1-benzyl-1H-indazol-4-yl)picolinate The title compound was prepared by substituting EXAMPLE 187A for EXAMPLE 22A in EXAMPLE 22B.

Example 187C

6-[8-(1,3-benzothiazol-2-ylcarbamoyl)-3,4-dihydroisoquinolin-2(1H)-yl]-3-(1-benzyl-1H-indazol-4-yl)pyridine-2-carboxylic acid The title compound was prepared by substituting EXAMPLE 187B for EXAMPLE 1E in EXAMPLE 1F. $^1$H NMR (400 MHz, dimethylsulfoxide-$d_6$) δ ppm 12.89 (v br s, 1H), 8.03 (d, 1H), 7.87 (s, 1H), 7.78 (m, 2H), 7.64 (m, 2H), 7.46 (m, 2H), 7.40-7.20 (m, 8H), 7.04 (d, 1H), 6.99 (d, 1H), 5.66 (s, 2H), 5.02 (s, 2H), 3.95 (br t, 2H), 3.04 (br t, 2H).

Example 188

6-[8-(1,3-benzothiazol-2-ylcarbamoyl)-3,4-dihydroisoquinolin-2(1H)-yl]3-(1-benzyl-1H-pyrrolo[2,3-c]pyridin-3-yl)pyridine-2-carboxylic acid

Example 188A 1-benzyl-3-bromo-1H-pyrrolo[2,3-c]pyridine

The title compound was prepared by substituting 3-bromo-1H-pyrrolo[2,3-c]pyridine for 3-bromo-1H-pyrrolo[2,3-b]pyridine in EXAMPLE 141A.

Example 188B 1-benzyl-3-(4,4,5,5-tetramethyl-1,3,2-dioxaborolan-2-yl)-1H-pyrrolo[2,3-c]pyridine The title compound was prepared by substituting EXAMPLE 188A for EXAMPLE 84C in EXAMPLE 84D.

Example 188C tert-butyl 6-(8-(benzo[d]thiazol-2-ylcarbamoyl)-3,4-dihydroisoquinolin-2(1H)-yl)-3-(1-benzyl-1H-pyrrolo[2,3-c]pyridin-3-yl)picolinate The title compound was prepared by substituting EXAMPLE 188B for EXAMPLE 22A in EXAMPLE 22B.

Example 188D

6-[8-(1,3-benzothiazol-2-ylcarbamoyl)-3,4-dihydroisoquinolin-2(1H)-yl]-3-(1-benzyl-1H-pyrrolo[2,3-c]pyridin-3-yl)pyridine-2-carboxylic acid The title compound was prepared by substituting EXAMPLE 188C for EXAMPLE 8B in EXAMPLE 8C. $^1$H NMR (400 MHz, dimethylsulfoxide-$d_6$) δ ppm 9.42 (s, 1H), 8.47 (s, 1H), 8.32 (d, 1H), 8.04 (d, 1H), 7.89 (d, 1H), 7.79 (d, 1H), 7.76 (d, 1H), 7.64 (br d, 1H), 7.48 (m, 2H), 7.40-7.28 (m, 7H), 7.01 (d, 1H), 5.76 (s, 2H), 5.04 (s, 2H), 3.95 (br t, 2H), 3.05 (br t, 2H).

---

What is claimed is:

1. A compound or therapeutically acceptable salt thereof, wherein the compound is selected from the group consisting of 6-[8-(1,3-benzothiazol-2-ylcarbamoyl)-3,4-dihydroisoquinolin-2(1H)-yl]-3-(1-phenyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(4-phenoxyphenyl)pyridine-2-carboxylic acid;

6-[8-(1,3-benzothiazol-2-ylcarbamoyl)-3,4-dihydroisoquinolin-2(1H)-yl]-3-(3-phenoxyphenyl)pyridine-2-carboxylic acid;

6-[8-(1,3-benzothiazol-2-ylcarbamoyl)-3,4-dihydroisoquinolin-2(1H)-yl]-3-[3-(4-nitrophenoxy)phenyl]pyridine-2-carboxylic acid;

6-[8-(1,3-benzothiazol-2-ylcarbamoyl)-3,4-dihydroisoquinolin-2(1H)-yl]-3-[3-(4-chlorophenoxy)phenyl]pyridine-2-carboxylic acid;

6-[8-(1,3-benzothiazol-2-ylcarbamoyl)-3,4-dihydroisoquinolin-2(1H)-yl]-3-(3-benzylphenyl)pyridine-2-carboxylic acid;

6-[8-(1,3-benzothiazol-2-ylcarbamoyl)-3,4-dihydroisoquinolin-2(1H)-yl]-3-[3-(cyclohexylmethyl)-2-methylphenyl]pyridine-2-carboxylic acid;

6-[8-(1,3-benzothiazol-2-ylcarbamoyl)-3,4-dihydroisoquinolin-2(1H)-yl]-3-(4-methyl-3-phenoxyphenyl)pyridine-2-carboxylic acid;

6-[8-(1,3-benzothiazol-2-ylcarbamoyl)-3,4-dihydroisoquinolin-2(1H)-yl]-3-(2-methyl-5-phenoxyphenyl)pyridine-2-carboxylic acid;

6-[8-(1,3-benzothiazol-2-ylcarbamoyl)-3,4-dihydroisoquinolin-2(1H)-yl]-3-(2-methyl-3-phenoxyphenyl)pyridine-2-carboxylic acid;

6-[8-(1,3-benzothiazol-2-ylcarbamoyl)-3,4-dihydroisoquinolin-2(1H)-yl]-3-(2-methyl-4-phenoxyphenyl)pyridine-2-carboxylic acid;

6-[8-(1,3-benzothiazol-2-ylcarbamoyl)-3,4-dihydroisoquinolin-2(1H)-yl]-3-[3-(cyclohexylmethoxy)-2-methylphenyl]pyridine-2-carboxylic acid;

6-[8-(1,3-benzothiazol-2-ylcarbamoyl)-3,4-dihydroisoquinolin-2(1H)-yl]-3-[4-(cyclohexyloxy)-2-methylphenyl]pyridine-2-carboxylic acid;

6-[8-(1,3-benzothiazol-2-ylcarbamoyl)-3,4-dihydroisoquinolin-2(1H)-yl]-3-[3-(cyclohexyloxy)-2-methylphenyl]pyridine-2-carboxylic acid;

6-[8-(1,3-benzothiazol-2-ylcarbamoyl)-3,4-dihydroisoquinolin-2(1H)-yl]-3-[4-(cyclohexylmethoxy)-2-methylphenyl]pyridine-2-carboxylic acid;

6-[8-(1,3-benzothiazol-2-ylcarbamoyl)-3,4-dihydroisoquinolin-2(1H)-yl]-3-[2-cyano-3-(cyclohexyloxy)phenyl]pyridine-2-carboxylic acid;

6-[8-(1,3-benzothiazol-2-ylcarbamoyl)-3,4-dihydroisoquinolin-2(1H)-yl]-3-[2-chloro-3-(cyclohexyloxy)phenyl]pyridine-2-carboxylic acid;

6-[8-(1,3-benzothiazol-2-ylcarbamoyl)-3,4-dihydroisoquinolin-2(1H)-yl]-3-[3-(cyclohexylamino)-2-methylphenyl]pyridine-2-carboxylic acid;

6-[8-(1,3-benzothiazol-2-ylcarbamoyl)-3,4-dihydroisoquinolin-2(1H)-yl]-3-[3-(cyclohexyloxy)-2-fluorophenyl]pyridine-2-carboxylic acid;

6-[8-(1,3-benzothiazol-2-ylcarbamoyl)-3,4-dihydroisoquinolin-2(1H)-yl]-3-[3-(cyclohexyloxy)-2-(trifluoromethyl)phenyl]pyridine-2-carboxylic acid;

6-[8-(1,3-benzothiazol-2-ylcarbamoyl)-3,4-dihydroisoquinolin-2(1H)-yl]-3-{3-[(3,3-dimethylcyclohexyl)oxy]-2-methylphenyl}pyridine-2-carboxylic acid;

6-[8-(1,3-benzothiazol-2-ylcarbamoyl)-3,4-dihydroisoquinolin-2(1H)-yl]-3-{1-[(4-methylphenyl)sulfonyl]-1H-pyrrol-3-yl}pyridine-2-carboxylic acid;

6-[8-(1,3-benzothiazol-2-ylcarbamoyl)-3,4-dihydroisoquinolin-2(1H)-yl]-3-(1-benzoyl-1H-pyrrol-3-yl)pyridine-2-carboxylic acid;

6-[8-(1,3-benzothiazol-2-ylcarbamoyl)-3,4-dihydroisoquinolin-2(1H)-yl]-3-[1-(phenylsulfonyl)-1H-pyrrol-3-yl]pyridine-2-carboxylic acid;

6,6'-bis[8-(1,3-benzothiazol-2-ylcarbamoyl)-3,4-dihydroisoquinolin-2(1H)-yl]-3,3'-bipyridine-2,2'-dicarboxylic acid;

6-[8-(1,3-benzothiazol-2-ylcarbamoyl)-3,4-dihydroisoquinolin-2(1H)-yl]-3-(2-benzyl-1,2,3,4-tetrahydroisoquinolin-6-yl)pyridine-2-carboxylic acid;

6-[8-(1,3-benzothiazol-2-ylcarbamoyl)-3,4-dihydroisoquinolin-2(1H)-yl]-3-[2-(pyridin-2-ylmethyl)-1,2,3,4-tetrahydroisoquinolin-6-yl]pyridine-2-carboxylic acid;

6-[8-(1,3-benzothiazol-2-ylcarbamoyl)-3,4-dihydroisoquinolin-2(1H)-yl]-3-[2-(cyclohexylmethyl)-1,2,3,4-tetrahydroisoquinolin-6-yl]pyridine-2-carboxylic acid;

6-[8-(1,3-benzothiazol-2-ylcarbamoyl)-3,4-dihydroisoquinolin-2(1H)-yl]-2'-(cyclohexyloxy)-3'-methyl-3,4'-bipyridine-2-carboxylic acid;

6-[8-(1,3-benzothiazol-2-ylcarbamoyl)-3,4-dihydroisoquinolin-2(1H)-yl]-2'-(cyclohexyloxy)-3,4'-bipyridine-2-carboxylic acid;

6-[8-(1,3-benzothiazol-2-ylcarbamoyl)-3,4-dihydroisoquinolin-2(1H)-yl]-2'-phenoxy-3,4'-bipyridine-2-carboxylic acid;

6-[8-(1,3-benzothiazol-2-ylcarbamoyl)-3,4-dihydroisoquinolin-2(1H)-yl]-3-(1-benzyl-1H-pyrrolo[2,3-b]pyridin-3-yl)pyridine-2-carboxylic acid;

6-[8-(1,3-benzothiazol-2-ylcarbamoyl)-3,4-dihydroisoquinolin-2(1H)-yl]-3'-methyl-2'-phenoxy-3,4'-bipyridine-2-carboxylic acid;

6-[8-(1,3-benzothiazol-2-ylcarbamoyl)-3,4-dihydroisoquinolin-2(1H)-yl]-3'-methyl-2'-[methyl(phenyl)amino]-3,4'-bipyridine-2-carboxylic acid;

6-[8-(1,3-benzothiazol-2-ylcarbamoyl)-3,4-dihydroisoquinolin-2(1H)-yl]-3-(1-benzyl-1H-indazol-5-yl)pyridine-2-carboxylic acid;

6-[8-(1,3-benzothiazol-2-ylcarbamoyl)-3,4-dihydroisoquinolin-2(1H)-yl]-3-{2-methyl-3-[methyl(phenyl)amino]phenyl}pyridine-2-carboxylic acid;

6-[8-(1,3-benzothiazol-2-ylcarbamoyl)-3,4-dihydroisoquinolin-2(1H)-yl]-3-{3-[(3,3-dimethylcyclohexyl)(methyl)amino]-2-methylphenyl}pyridine-2-carboxylic acid;

6-[8-(1,3-benzothiazol-2-ylcarbamoyl)-3,4-dihydroisoquinolin-2(1H)-yl]-2'-[cyclohexyl(methyl)amino]-3'-methyl-3,4'-bipyridine-2-carboxylic acid;

6-[8-(1,3-benzothiazol-2-ylcarbamoyl)-3,4-dihydroisoquinolin-2(1H)-yl]-3'-cyano-2'-[cyclohexyl(methyl)amino]-3,4'-bipyridine-2-carboxylic acid;

6-[8-(1,3-benzothiazol-2-ylcarbamoyl)-3,4-dihydroisoquinolin-2(1H)-yl]-3-{3-[(cyclohexylcarbonyl)(methyl)amino]-2-methylphenyl}pyridine-2-carboxylic acid;

6-[8-(1,3-benzothiazol-2-ylcarbamoyl)-3,4-dihydroisoquinolin-2(1H)-yl]-3-(2-methyl-3-{methyl[(1-methylcyclohexyl)carbonyl]amino}phenyl)pyridine-2-carboxylic acid;

6-[8-(1,3-benzothiazol-2-ylcarbamoyl)-3,4-dihydroisoquinolin-2(1H)-yl]-3-{2-cyano-3-[(cyclohexylsulfonyl)(methyl)amino]phenyl}pyridine-2-carboxylic acid;

6-[8-(1,3-benzothiazol-2-ylcarbamoyl)-3,4-dihydroisoquinolin-2(1H)-yl]-3-{2-cyano-3-[2-(tricyclo[3.3.1.1$^{3,7}$]dec-1-yl)pyrrolidin-1-yl]phenyl}pyridine-2-carboxylic acid;

6-[8-(1,3-benzothiazol-2-ylcarbamoyl)-3,4-dihydroisoquinolin-2(1H)-yl]-3'-methyl-2'-(piperidin-1-yl)-3,4'-bipyridine-2-carboxylic acid;

6-[8-(1,3-benzothiazol-2-ylcarbamoyl)-3,4-dihydroisoquinolin-2(1H)-yl]-3-(1-benzyl-1H-indazol-4-yl)pyridine-2-carboxylic acid; and 6-[8-(1,3-benzothiazol-2-ylcarbamoyl)-3,4-dihydroisoquinolin-2(1H)-yl]-3-(1-benzyl-1H-pyrrolo[2,3-c]pyridin-3-yl)pyridine-2-carboxylic acid.

2. A composition comprising a pharmaceutically acceptable excipient and a therapeutically effective amount of the compound or therapeutically acceptable salt of claim 1.

* * * * *